US011254982B2

(12) United States Patent
Micura et al.

(10) Patent No.: US 11,254,982 B2
(45) Date of Patent: Feb. 22, 2022

(54) OSMIUMTETROXIDE-BASED CONVERSION OF RNA AND DNA CONTAINING THIOLATED NUCLEOTIDES

(71) Applicants: UNIVERSITY OF INNSBRUCK, Innsbruck (AT); MEDICAL UNIVERSITY OF INNSBRUCK, Innsbruck (AT)

(72) Inventors: Ronald Micura, Innsbruck (AT); Alexandra Lusser, Innsbruck (AT); Christian Riml, Innsbruck (AT); Thomas Amort, Innsbruck (AT); Catherina Gasser, Innsbruck (AT); Isabel Delazer, Innsbruck (AT)

(73) Assignees: UNIVERSITY OF INNSBRUCK, Innsbruck (AT); MEDICAL UNIVERSITY OF INNSBRUCK, Innsbruck (AT)

( * ) Notice: Subject to any disclaimer, the term of this patent is extended or adjusted under 35 U.S.C. 154(b) by 240 days.

(21) Appl. No.: 16/533,988

(22) Filed: Aug. 7, 2019

(65) Prior Publication Data

US 2020/0048700 A1   Feb. 13, 2020

Related U.S. Application Data

(60) Provisional application No. 62/715,366, filed on Aug. 7, 2018.

(51) Int. Cl.
*C12P 19/34*  (2006.01)
*C12Q 1/6869*  (2018.01)

(52) U.S. Cl.
CPC ..... *C12Q 1/6869* (2013.01); *C12Q 2600/156* (2013.01)

(58) Field of Classification Search
CPC .................................................... C12Q 1/6869
See application file for complete search history.

(56) References Cited

U.S. PATENT DOCUMENTS

5,217,863 A * 6/1993 Cotton ................. C12Q 1/6827 435/6.11
5,571,676 A * 11/1996 Shuber .................. C12Q 1/683 435/5

OTHER PUBLICATIONS

Burton, Biochemical Journal 104, 686-694 (1967). (Year: 1967).*
Herzog et al, "Thiol-Linked Alkylation for the Metabolic Sequencing of RNA," bioRxiv, Aug. 17, 2017; http://dx.doi.org/10.110/17742, pp. 1-40.
Muhar et al, "SLAM-seq Defines Direct Gene-Regulatory Functions of the BRD4-MYC Axis," Science, Apr. 5, 2018, pp. 1-10.
Riml et al., "Osmium-Mediated Transformation of 4-Thiouridine to Cytidine as Key to Study RNA Dynamics by Sequencing," Angew. Chem. Int. Ed. 2017, 56, 13479-13483.

* cited by examiner

*Primary Examiner* — Kenneth R Horlick
(74) *Attorney, Agent, or Firm* — Parker Highlander PLLC

(57) ABSTRACT

Provided are compositions and methods for the conversion of thiolated nucleotides, and subsequent detection of the converted nucleotides in RNA or DNA. Also provided herein are compositions and methods for the metabolic labeling of RNA and DNA by incorporation of thiolated nucleotides, and their subsequent conversion and detection.

20 Claims, 23 Drawing Sheets

Specification includes a Sequence Listing.

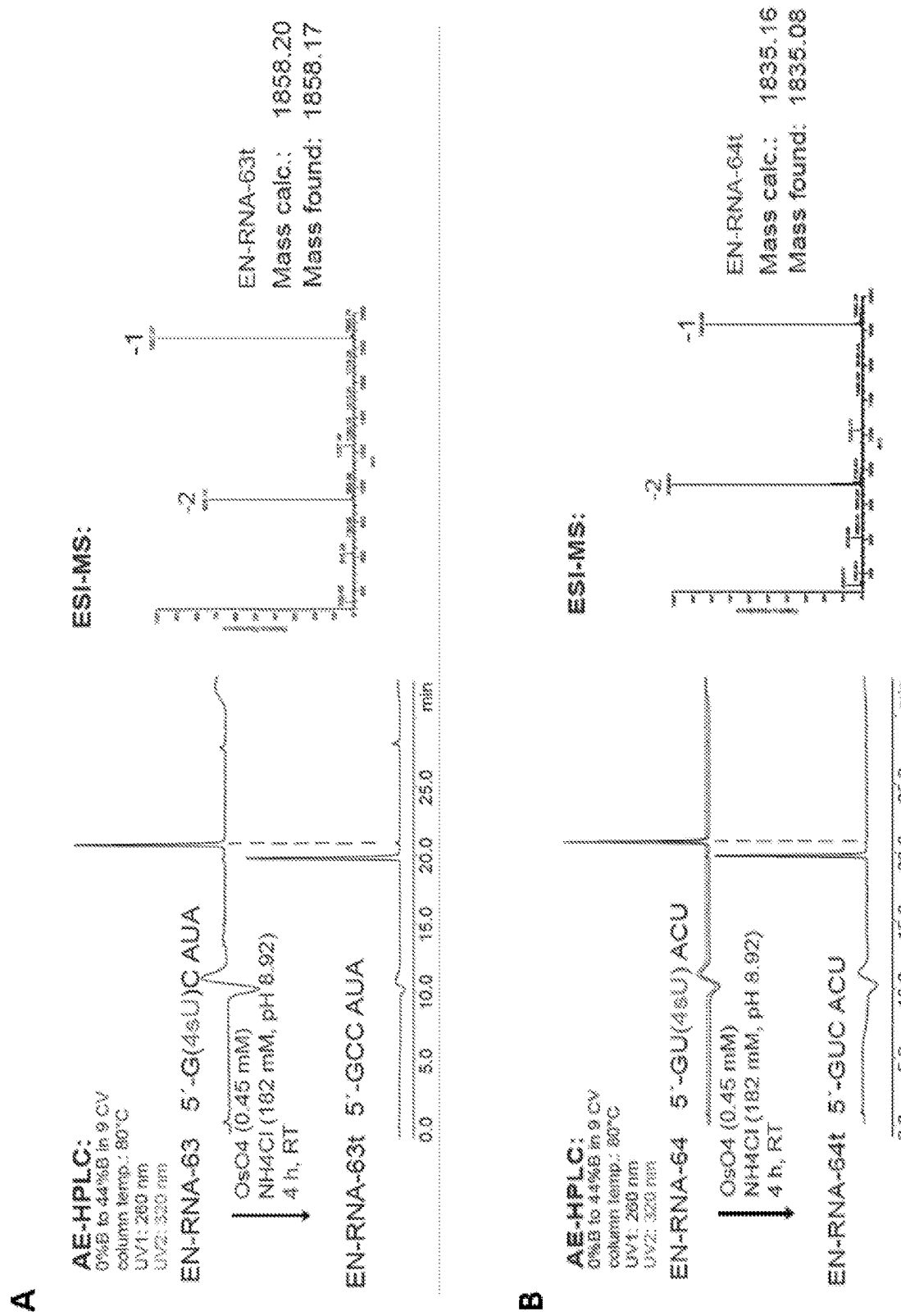
FIG. 26A-B

SEQUENCE LISTING

<160> NUMBER OF SEQ ID NOS: 30

<210> SEQ ID NO 1
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 1
ggtgggtgat gacgggatc                                              19

<210> SEQ ID NO 2
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 2
gttggctctg gtgcagggtc cgaggtattc gcaccagagc caacgggtga            50

<210> SEQ ID NO 3
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 3
gtgcagggtc cgaggt                                                 16

<210> SEQ ID NO 4
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 4
gtgatgacgg gatc                                                   14

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
agctggacgg cgacgtaaac                                             20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
cagggtcagc ttgccgtagg                                             20

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 7
gttgtctcct gcgacttcaa c					21

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
attgtcatac caggaaatga gc					22

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ccagaagtag cagagtttgt					20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
ttgaggagag aaacaccatg					20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
acatcgaagc atgctaagat					20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
ctatgcagca gattctccat					20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
gagggcagtt ttctaatgga					20

```
<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
atcaagggga gattgcattt                                                     20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
ctgatgaaga tgcacacaac                                                     20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
cttttgttgt tgtgggagtc                                                     20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
cttgagtggg gttatctctg                                                     20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
atattcagca ttgtgggagg                                                     20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
ccatcttctt caaggacgac                                                     20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 20
tacttgtaca gctcgtccat                                            20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
accaaaccag gagaaagttt                                            20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
tccttcttca tcctcgatct                                            20

<210> SEQ ID NO 23
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n = 4-thiothymidine

<400> SEQUENCE: 23
tagcacgngc taa                                                   13

<210> SEQ ID NO 24
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n = 2'-deoxy-5-methylcytidine

<400> SEQUENCE: 24
tagcacgngc taa                                                   13

<210> SEQ ID NO 25
<211> LENGTH: 17
<212> TYPE: RNA
<213> ORGANISM: Artificial sequence
<220> FEATURE:
<223> OTHER INFORMATION: Synthetic oligoribonucleotide
<220> FEATURE:
<221> NAME/KEY: misc_feature
<222> LOCATION: (14)..(14)
<223> OTHER INFORMATION: n = 4-thiouridine

<400> SEQUENCE: 25
gcgaaccugc gggnucg                                               17

<210> SEQ ID NO 26
```

```
<211> LENGTH: 42
<212> TYPE: RNA
<213> ORGANISM: Artificial sequence
<220> FEATURE:
<223> OTHER INFORMATION: Synthetic oligoribonucleotide
<220> FEATURE:
<221> NAME/KEY: misc_feature
<222> LOCATION: (13)..(13)
<223> OTHER INFORMATION: n = 4-thiouridine

<400> SEQUENCE: 26
agaacguuaa cuncaaauca gaucgacaga acuaacgauu cg          42

<210> SEQ ID NO 27
<211> LENGTH: 42
<212> TYPE: RNA
<213> ORGANISM: Artificial sequence
<220> FEATURE:
<223> OTHER INFORMATION: Synthetic oligoribonucleotide

<400> SEQUENCE: 27
agaacguuaa cuccaaauca gaucgacaga acuaacgauu cg          42

<210> SEQ ID NO 28
<211> LENGTH: 14
<212> TYPE: RNA
<213> ORGANISM: Artificial sequence
<220> FEATURE:
<223> OTHER INFORMATION: Synthetic oligoribonucleotide
<220> FEATURE:
<221> NAME/KEY: misc_feature
<222> LOCATION: (8)..(8)
<223> OTHER INFORMATION: n = 6-thioguanosine

<400> SEQUENCE: 28
uacccucnuc aucc          14

<210> SEQ ID NO 29
<211> LENGTH: 14
<212> TYPE: RNA
<213> ORGANISM: Artificial sequence
<220> FEATURE:
<223> OTHER INFORMATION: Synthetic oligoribonucleotide
<220> FEATURE:
<221> NAME/KEY: misc_feature
<222> LOCATION: (8)..(8)
<223> OTHER INFORMATION: n = 6-Thioguanosine oxidized at the position 6

<400> SEQUENCE: 29
uacccucnuc aucc          14

<210> SEQ ID NO 30
<211> LENGTH: 14
<212> TYPE: RNA
<213> ORGANISM: Artificial sequence
<220> FEATURE:
<223> OTHER INFORMATION: Synthetic oligoribonucleotide
<220> FEATURE:
<221> NAME/KEY: misc_feature
<222> LOCATION: (8)..(8)
<223> OTHER INFORMATION: n = 6'-hydrazino-2-aminopurine-ribonuceloside

<400> SEQUENCE: 30
uacccucnuc aucc          14
```

OSMIUMTETROXIDE-BASED CONVERSION OF RNA AND DNA CONTAINING THIOLATED NUCLEOTIDES

This application claims the benefit of U.S. Provisional Patent Application No. 62/715,366, filed Aug. 7, 2018, the entirety of which is incorporated herein by reference.

BACKGROUND OF THE INVENTION

1. Field of the Invention

The present invention relates generally to the fields of biology and molecular biology, and more particularly to RNA and DNA sequencing.

2. Description of Related Art

RNA is one of the central molecules in all kingdoms of life and exists in an astonishing variety of subtypes ranging from protein-encoding mRNA, to splicing and translation-mediating snRNAs, tRNAs and rRNAs and to many different kinds of long and small regulatory RNAs. In the cell, all RNAs are constantly processed, modified and turned-over, and are thus parts of the dynamic system that translates genotype into phenotype. To understand the various roles of RNA, it is essential to study the dynamics of production, processing and decay of the numerous subtypes of RNA. Thus, methods are required that are able to assess RNA dynamics in a way that perturbs cellular processes as little as possible, that enable analysis in an unbiased and reproducible manner, and that are technically straight-forward and robust to minimize methodologically introduced artifacts. In the past, different methods have been used to study the dynamics of RNA, in particular mRNA. Traditionally, these included transcriptional run-on assays or time course RNA analyses coupled to transcription inhibition by actinomycin D, 5,6-dichloro-1-b-dribofuranosylbenzimidazole (DRB) and a-amanitin or by inducible transcription mutants (Perez-Ortin et al., 2013; Tani and Akimitsu, 2012; Russo et al., 2017). However, inhibition of transcription is highly toxic for the cell and leads to pleiotropic responses affecting stability and localization of many transcripts, thus confounding the informative value of such experiments (Tani and Akimitsu, 2012; Balagopal et al., 2012).

The most commonly used method for assessing mRNA dynamics has been metabolic labeling with 4-thiouridine (4sU) followed by detection of labeled transcripts by affinity purification and hybridization to microarrays or by deep sequencing (Melvin et al., 1978; Cleary et al., 2005; Dolken et al., 2008). 4sU-labeling is only minimally disruptive to cell physiology (Russo et al., 2017; Martin and Coller, 2015), although this is dependent on the concentrations used and the time of application (Burger et al., 2013). Thiolation of uracil at the carbon atom in position 4 is a modification that occurs naturally on tRNAs in bacteria but has not been found in eukaryotes so far (Machnicka et al., 2014). Eukaryotic cells, however, readily take up 4sU and incorporate it into nascent RNA (Melvin et al., 1978). Consequently, thio-substituted uridine can be specifically tagged by a 2-pyridylthio-activated disulfide of biotin (HPDP-biotin), allowing enrichment of the tagged RNA by streptavidin affinity purification and subsequent sequencing (Cleary et al., 2005; Dolken et al., 2008). Recent improvements to this method includes 4sU biotinylation using methylthiosulfonate-activated biotin (MTS-biotin), which strongly enhances labeling efficiency (Duffy et al., 2015). 4sU pulse labeling and pulse-chase labeling approaches coupled to affinity purification techniques have been widely used to study various topics of mRNA dynamics, ranging from synthesis and decay rates (Dolken et al., 2008; Zeiner et al., 2008; Neymotin et al., 2014; Burow et al., 2015; Stubbs et al., 2015), to kinetics of splicing (Windhager et al., 2012; Barrass et al., 2015) and transcription elongation (Fuchs et al., 2014), polyadenylation of mRNA (Kuhn et al., 2017), protein—RNA binding kinetics (Wang et al., 2015) and miRNA (Duffy et al., 2015) as well as circRNA biogenesis (Zhang et al., 2016). Moreover, cell type-specific transcription can be assessed by in vivo labeling with 4-thiouracil in animals that have been genetically engineered to express the Toxoplasma gondii enzyme uracil phosphoribosyltransferase (UPRT) in a cell-type specific manner. This enzyme catalyzes the conversion of 4-thiouracil to 4-thiouridine monophosphate, which is incorporated into RNA (TU-tagging) (Zeiner et al., 2008; Miller et al., 2009).

Taken together, it is clear that 4sU labeling coupled to biotin-affinity purification is a powerful technique allowing for detailed analyses of RNA dynamics. Nevertheless, quantitative separation of 4sU-labeled RNA from pre-existing RNA is laborious and relies on efficient performance of several crucial steps: 1) the biotinylation reaction, 2) the binding to the streptavidin beads and 3) the recovery of the RNA. Slight variations in any of those steps may compromise reproducibility and validity of this method. Therefore, new methods which eliminate the need for tag-based separation of labeled and unlabeled RNA and allow for direct distinction of both species are highly desirable.

SUMMARY OF THE INVENTION

In some embodiments, the present disclosure provides methods for determining the presence of a thiolated nucleotide in a nucleic acid-containing sample comprising:
(a) providing a nucleic acid-containing sample;
(b) treating the nucleic acid-containing sample with osmium tetroxide and ammonium chloride to convert the thiolated nucleotide; and
(c) detecting the presence of a converted nucleotide in the nucleic acid-containing sample.

In some aspects, the nucleic acid-containing sample comprises RNA. In some aspects, the thiolated nucleotide is 4-thiouridine. In further aspects, 4-thiouridine is converted to cytidine. In some aspects, the thiolated nucleotide is 6-thioguanosine (or 6-selenoguanosine). In further aspects, the 6-thioguanosine is converted to 6-hydrazino-2aminopurine-ribonuceloside (6h2Ap). In some aspects, the RNA is total RNA. In some aspects, the RNA is tRNA, rRNA, siRNA, shRNA or miRNA. In some aspects, the RNA is mRNA. In some aspects, the nucleic acid-containing sample comprises DNA. In some aspects, wherein the thiolated nucleotide is 4-thiothymidine. In further aspects, the 4-thiothymidine is converted to 2'-deoxy-5-methylcytidine.

In some aspects, the nucleic acid-containing sample comprises DNA and RNA. In some aspects, the method further comprises purifying DNA and/or RNA from the sample. In some aspects, a portion of the DNA and/or RNA is biotinylated. In further aspects, the method further comprises purifying the biotinylated DNA and/or RNA. In some aspects, the nucleic acid-containing sample is synthetic. In other aspects, the nucleic acid-containing sample is isolated from an organism. In further aspects, the nucleic acid-containing sample is isolated from a prokaryotic cell. In other aspects, the nucleic acid-containing sample is isolated from a eukaryotic organism. In further aspects, the eukaryotic organism is mammalian. In still further aspects, the organism is human. In some aspects, the sample is from an organism that has been metabolically labeled. In some aspects, the nucleic acid-containing sample is isolated from a eukaryotic (e.g., human) cell culture.

In some aspects, the nucleic acid-containing sample is amplified prior to detecting. In further aspects, amplification is performed by PCR. In still further aspects, the PCR is reverse transcriptase PCR. In some aspects, determining the quantity of converted nucleic acids is calculated on a whole genome basis. In some aspects, determining the quantity of converted nucleic acids is calculated on an allele-specific basis. In some aspects, detecting is by sequencing. In further aspects, sequencing is Sanger sequencing. In other aspects, sequencing is next generation sequencing. In some aspects, detecting is by dynamic allele-specific hybridization. In some aspects, detecting is by hybridization of a molecular beacon. In some aspects, detecting is by microarray analysis. In some aspects, detecting is by restriction fragment length polymorphism analysis. In some aspects, detecting is by qPCR. In some aspects, detecting is by Flap endonuclease assay. In some aspects, detecting is by primer extension assay. In some aspects, detecting is by 5' nuclease assay. In some aspects, detecting is by high resolution melting analysis. In some aspects, the method does not comprise an enrichment step. In some aspects, the method does not comprise affinity tagging the nucleic acid sample. In some aspects, the method does not comprise biotinylating the sample.

In other embodiments, the present disclosure provides methods for detecting the presence of 4-thiouridine in a bacterial tRNA comprising:
(a) isolating total RNA from the bacteria;
(b) treating at least a portion of the isolated total RNA with osmium tetroxide and ammonium chloride to convert 4-thiouridine to cytidine;
(c) amplifying the tRNA of interest; and
(d) detecting the presence or absence of cytosine at the position of a 4-thiouridine in the amplified tRNA of interest.

In some aspects, the bacteria are metabolically labeled prior to step (a). In some aspects, the tRNA is amplified prior to detecting. In further aspects, amplification is performed by PCR. In still further aspects, the PCR is reverse transcriptase PCR. In some aspects, detecting is by sequencing. In further aspects, sequencing is Sanger sequencing. In other aspects, sequencing is next generation sequencing. In some aspects, detecting is by hybridization of a molecular beacon. In some aspects, detecting is by microarray analysis. In some aspects, detecting is by restriction fragment length polymorphism analysis. In some aspects, detecting is by qPCR. In some aspects, detecting is by Flap endonuclease assay. In some aspects, detecting is by primer extension assay. In some aspects, detecting is by 5' nuclease assay. In some aspects, detecting is by high resolution melting analysis. In some aspects, the method does not comprise an enrichment step. In some aspects, the method does not comprise affinity tagging the nucleic acid sample. In some aspects, the method does not comprise biotinylating the sample.

In other embodiments, the present disclosure provides methods for metabolic labelling of a nucleic acid-containing sample in a cell culture comprising:
(a) pulse-labeling a cell culture with a thiolated nucleotide;
(b) isolating a nucleic acid-containing sample from the cell culture;
(c) treating the nucleic acid-containing sample with osmium tetroxide and ammonium chloride to convert the thiolated nucleotide incorporated into the nucleic acid-containing sample into a converted nucleotide;
(d) detecting the converted nucleic acid-containing sample; and
(e) determining the quantity of converted nucleotides in the converted nucleic acid-containing sample.

In a further embodiment, the present disclosure provides methods for metabolic labelling of a nucleic acid-containing sample in a cell culture comprising:
(a) pulse-labeling a cell culture with a thiolated nucleotide;
(b) treating the nucleic acid-containing sample with osmium tetroxide and ammonium chloride to convert the thiolated nucleotide incorporated into the nucleic acid-containing sample into a converted nucleotide;
(c) isolating a nucleic acid-containing sample from the cell culture;
(d) detecting the converted nucleic acid-containing sample; and
(e) determining the quantity of converted nucleotides in the converted nucleic acid-containing sample.

In some aspects, the nucleic acid-containing sample comprises RNA. In some aspects, the thiolated nucleotide is 4-thiouridine. In further aspects, 4-thiouridine is converted to cytidine. In some aspects, the thiolated nucleotide is 6-thioguanosine. In further aspects, the 6-thioguanosine is converted to 6oxG, and the method further comprises treatment with hydrazine to convert the 6oxG groups to 6'-hydrazino-2-aminopurine-ribonuceloside (6h2Ap). In some aspects, the RNA is total RNA. In some aspects, the RNA is tRNA. In some aspects, the RNA is mRNA. In some aspects, the method further comprises a chase-labeling step between steps (a) and (b), wherein the chase labeling utilizes a second thiolated nucleotide. In some aspects, the first thiolated nucleotide is 4-thiouridine and the second thiolated nucleotide is 6-thioguanosine. In other aspects, the first thiolated nucleotide is 6-thioguanosine and the second thiolated nucleotide is 4-thiouridine. In some aspects, the method further comprises informatically separating the detected sequences into those having no conversions, those having conversions associated with the pulse label only, those having conversions associated with the second chase label only, or those having conversions associated with both pulses. In some aspects, the method further comprises determining the decay rate of the RNA from the group labeled with only the thiolated nucleotide from the first pulse-labeling step.

In some aspects, the nucleic acid sample comprises DNA. In some aspects, the thiolated nucleotide is 4-thiothymidine. In further aspects, the 4-thiothymidine is converted to 2'-deoxy-5-methylcytidine. In some aspects, the nucleic acid-containing sample comprises DNA and RNA. In some aspects, the nucleic acid-containing sample is synthetic. In other aspects, the nucleic acid-containing sample is isolated from an organism. In some aspects, the nucleic acid-containing sample is isolated from a eukaryotic organism. In further aspects, the eukaryotic organism is mammalian. In still further aspects, the organism is human. In some aspects, the nucleic acid-containing sample is isolated from a human cell culture. In some aspects, the nucleic acid-containing sample is amplified prior to detecting. In further aspects, amplification is performed by PCR. In still further aspects, the PCR is reverse transcriptase PCR. In some aspects, determining the quantity of converted nucleic acids is calculated on a whole genome basis. In some aspects, determining the quantity of converted nucleic acids is calculated on an allele-specific basis. In some aspects, detecting is by sequencing. In further aspects, sequencing is Sanger sequencing. In other aspects, sequencing is next generation sequencing. In some aspects, detecting is by microarray analysis. In some aspects, detecting is by qPCR. In some aspects, detecting is by high resolution melting analysis. In some aspects, the method does not comprise an enrichment step. In some aspects, the method does not comprise affinity tagging the nucleic acid-containing sample. In some aspects, the method does not comprise biotinylating the nucleic acid-containing sample.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 26A-D: HPLC studies are presented comparing TUC-Seq with TimeLapse nucleotide conversion.

DESCRIPTION OF ILLUSTRATIVE EMBODIMENTS

Figure 1:
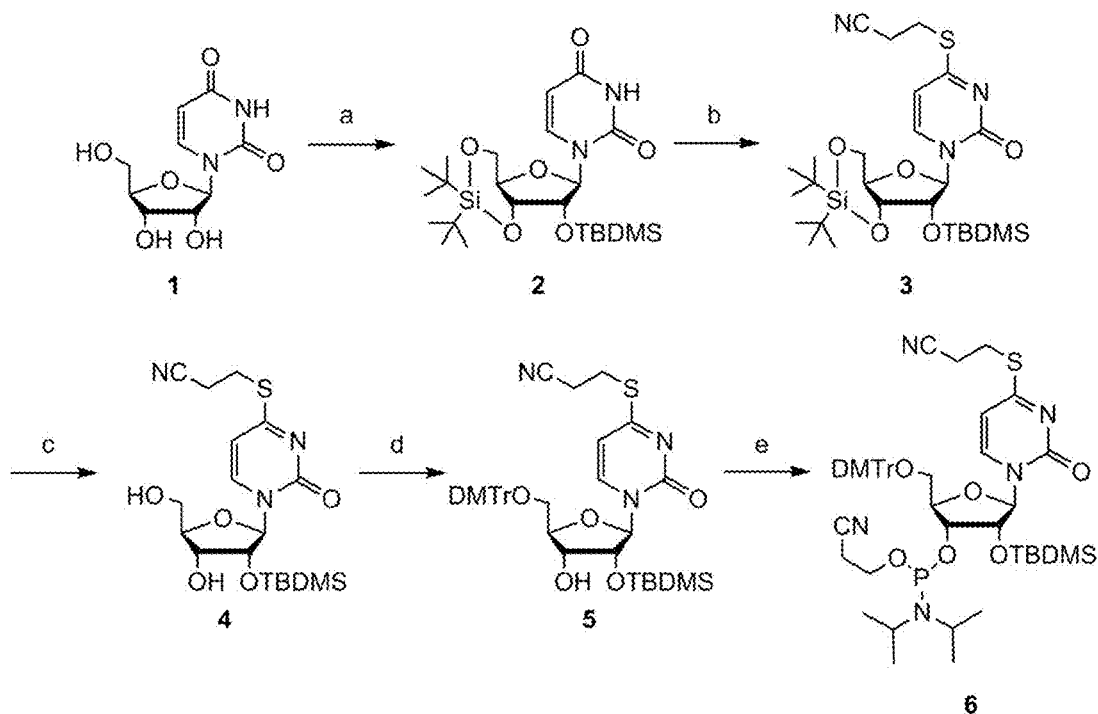
FIG. 1: Schematic of the synthesis of 5'-O-(4,4'-dimethoxytrityl)-2'-O-tert-butyldimethylsilyl-4-(2-cyanoethylthio)-uridine-3'-O-(2-cyanoethyl)-N,N-diisopropylphosphoramidite.

To understand the functional role of nucleic acids within a cell, it is essential to elucidate the dynamics of their production, processing, and decay. Prior methods have assessed mRNA dynamics by metabolic labeling with 4-thiouridine (4sU) followed by thio-selective attachment of affinity tags. Detection of labeled transcripts by affinity purification is time and labor intensive and lacks the accuracy of direct sequencing. Provided herein are compositions and methods for the metabolic labeling and detection of labeled transcripts by direct sequencing of nucleic acids.

In one aspect of the invention, methods are provided for the detection of thiolated nucleotides within a nucleic acid polymer such as DNA or RNA. 4-thiouridine (4sU) labeling of mRNA followed by detection of labeled transcripts by affinity purification and hybridization to microarrays or by deep sequencing has been a popular means by which to profile RNA dynamics, as it is only minimally disruptive to cellular physiology (Melvin et al., 1978; Cleary et al., 2005; Dolken et al., 2008 Russo et al., 2017; Martin and Coller, 2015). Consequently, thio-substituted uridine can be specifically tagged by a 2-pyridylthio-activated disulfide of biotin (HPDP-biotin), allowing enrichment of the tagged RNA by streptavidin affinity purification and subsequent sequencing (Cleary et al., 2005; Dolken et al., 2008). While 4sU labeling coupled to biotin-affinity purification is a powerful technique allowing for detailed analyses of RNA dynamics, quantitative separation of 4sU-labeled RNA from pre-existing RNA is laborious and relies on efficient performance of several crucial steps: 1) the biotinylation reaction, 2) the binding to the streptavidin beads and 3) the recovery of the RNA. Slight variations in any of those steps may compromise reproducibility and validity of this method.

Accordingly, the present disclosure overcomes challenges associated with the current technologies by providing methods and compositions for the metabolic labeling of nucleic acids and direct sequencing of thiolated nucleic acids. As mentioned above, 4-thiouridine labeling of RNA is a simple and well-known way to label mRNA, but nucleic acids can be metabolically labeled by the incorporation of a variety of thiolated nucleic acids. For instance, RNA may be labeled by the incorporation of 4-thiouridine (4sU) by the RNA polymerase, in place of uridine. Additionally, or alternatively, RNA may be labeled by the incorporation of 6-thioguanosine (6sG; or 6-selenoguanosine (6seG)) and/or Thioinosine (6sI). DNA may be labeled by the incorporation of 4-thiothymidine (4sT) in place of thymidine by a DNA polymerase. Additionally, or alternatively, DNA may be labeled by the incorporation of 6-thiodeoxyguanidine (6sG). Each of these nucleotides may be converted to a different nucleotide by treatment with osmium tetroxide. For example, OsO$_4$ treatment of 4sU results in the conversion of 4sU to C in the presence of a nucleophilic agent (in this case, a nitrogen donor reagent), such as NH$_4$Cl or hydrazine. OsO$_4$ treatment oxidizes 6sG into 6oxG (and likewise 6sI into 6oxI), which can then be converted to 6'-hydrazino-2-aminopurine (6h2Ap) (and likewise to 6'-hydrazino-purine (6hP)) by treatment with hydrazine. During sequencing, 6h2Ap (and 6hP) is read as an adenine. 4sT is converted to 5-methylcytidine (m$^5$C) following OsO$_4$/NH$_4$Cl treatment. Using the same treatment (OsO$_4$/NH$_4$Cl), 6sG can be converted into 2,6-diaminopurine (DAP) and 6sI can be converted into adenine (A). These conversions allow for the direct detection of labeled and unlabeled sequences by sequencing methods without the requirement for any physical separation.

In order to elucidate the dynamics of RNA production or decay, cells may be pulse labeled with a thiolated nucleoside, which is metabolized into the corresponding nucleotide in the cell and subsequently incorporated into the RNA strand during synthesis by the RNA polymerase. Following pulse labeling, RNA isolation may be performed. This RNA is then treated with OsO$_4$ and an NH$_4$ donor to convert the thiolated nucleotide. Detection of the converted nucleotide in a sequence indicates that the sequence was recently synthesized. Quantitative detection of the converted nucleotide and the wild type sequence can be used to understand the rate of synthesis and/or decay of a particular RNA.

Alternatively, following pulse labeling, a subset of cells may be treated as above to determine the quantity of nascent RNA, while the remainder of the cells may be washed and allowed to continue synthesis in the presence of an excess of native rNTPs. Synthesis may be stopped at any desired timepoint and, as above, the RNA can be treated to convert the thiolated ribonucleotide. The abundance of the converted ribonucleotide with respect to the wild type sequence in a sample can then be quantitated and compared between samples in order to determine the rate of decay of the RNA sequence. In some aspects, RNA may be labeled more than once, each time with a different labeled ribonucleotide, in order to more accurately distinguish between synthesis and decay rates of RNA. In some aspects, RNA is pulse labeled with a first thiolated nucleotide, such as 6sG, followed by a wash out and addition of a second thiolated nucleotide, such as 4sU, during the chase period. Following the chase period, the RNA is isolated and the thiolated nucleotides are converted by treatment with $OsO_4$. In the case of 6sG labeling, the RNA must then be treated with hydrazine to convert the 6oxG to 6h2Ap. Quantitative detection, such as by sequencing, will reveal four separate types of RNA: unlabeled RNA from the pool of preexisting RNA; 6sG labeled RNA characterized by a G-to-A mutation and identifying the RNA as synthesized during the pulse period; 6sG and 4sU labeled RNA characterized by G-to-A and U-to-C mutations which correspond to RNA synthesized during the chase labeling period; and RNA labeled with only 4sU, characterized by U-to-C mutations, corresponding to RNA synthesized late in the chase labeling period after 6sG was fully depleted. This method allows for the accurate determination of RNA decay rates by examining the group that only contains the G-to-A mutations, since it can be completely separated from the RNA synthesized in the chase period.

The methods detailed herein are superior to other possible analysis methods in that they can provide complete nucleotide conversion. Indeed, reverse transcriptases and polymerases in general are more prone to introduce errors in the nascent strand when the template contains non-natural nucleotides (products produced by methods such as the "TimeLapse-Seq method"). Studies presented below in Example 6, highlight these advantages. In particular, these data demonstrate the superiority of $OsO_4$-based conversion methods. Moreover, studies in subsequente Examples, show, that in the presence of $OsO_4$, $NH_4Cl$ treatment could be replaced with different nucleophilic agents (in this case, a nitrogen donor reagent), such as $NH_4Cl$, hydrazine or TFEA.

The thiolated nucleic acids may be treated with osmium tetroxide in combination with a nitrogen donor/nucleophilic agent, such as $NH_4Cl$, TFEA or hydrazine to convert the thiolated nucleotide into a different nucleotide. Additional nucleophilic agents that could be used include, for example, an alkylamine, which refers to the group $H_2NR$, in which R is an alkyl, as that term is defined above. Non-limiting examples include: $H_2NCH_3$ and $H_2NCH_2CH_3$. The term "dialkylamine" refers to the group HNRR', in which R and R' can be the same or different alkyl groups. Non-limiting examples of dialkylamino groups include: $HN(CH_3)_2$ and $HN(CH_3)(CH_2CH_3)$. The term "arylamine" when used without the "substituted" modifier, refers to a group defined as $H_2NR$, in which R is aryl. A non-limiting example of an arylamino group is $H_2NC_6H_5$. The term "diarylamino" refers to a group defined as $H_2NRR'$, in which R and R' are both aryl. In some aspects, the nucleophilic agent is TFEA. In other aspects the nucleophilic agent is any type of primary or secondary amine.

I. Definitions

The term "genome" or "genomic" as used herein is all the genetic material in the chromosomes of an organism. DNA derived from the genetic material in the chromosomes of a particular organism is genomic DNA.

The term "transcriptome" or "transcriptomic" as used herein is all of the expressed RNA in a cell or an organism.

"Amplification," as used herein, refers to any in vitro process for increasing the number of copies of a nucleotide sequence or sequences. Nucleic acid amplification results in the incorporation of nucleotides into DNA or RNA. As used herein, one amplification reaction may consist of many rounds of DNA replication. For example, one PCR reaction may consist of 30-100 "cycles" of denaturation and replication.

"Incorporating," as used herein, means becoming part of a nucleic acid polymer.

"Nucleotide," as used herein, is a term of art that refers to a base-sugar-phosphate combination. Nucleotides are the monomeric units of nucleic acid polymers, i.e., of DNA and RNA. The term includes ribonucleotide triphosphates, such as rATP, rCTP, rGTP, or rUTP, and deoxyribonucleotide triphosphates, such as dATP, dCTP, dUTP, dGTP, or dTTP.

A "nucleoside" is a base-sugar combination, i.e., a nucleotide lacking a phosphate. It is recognized in the art that there is a certain inter-changeability in usage of the terms nucleoside and nucleotide. For example, the nucleotide deoxyuridine triphosphate, dUTP, is a deoxyribonucleoside triphosphate. After incorporation into DNA, it serves as a DNA monomer, formally being deoxyuridylate, i.e., dUMP or deoxyuridine monophosphate. One may say that one incorporates dUTP into DNA even though there is no dUTP moiety in the resultant DNA. Similarly, one may say that one incorporates deoxyuridine into DNA even though that is only a part of the substrate molecule.

The term "nucleic acid" or "polynucleotide" will generally refer to at least one molecule or strand of DNA, RNA, DNA-RNA chimera or a derivative or analog thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "nucleic acid" encompasses the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially, or fully complementary to at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double-stranded nucleic acid by the prefix "ds", and a triple stranded nucleic acid by the prefix "ts."

A "nucleic acid molecule" or "nucleic acid target molecule" refers to any single-stranded or double-stranded nucleic acid molecule including standard canonical bases, hypermodified bases, non-natural bases, or any combination of the bases thereof. For example and without limitation, the nucleic acid molecule contains the four canonical DNA bases—adenine, cytosine, guanine, and thymine, and/or the four canonical RNA bases—adenine, cytosine, guanine, and uracil. Uracil can be substituted for thymine when the nucleoside contains a 2'-deoxyribose group. The nucleic acid molecule can be transformed from RNA into DNA and from DNA into RNA. For example, and without limitation, mRNA can be created into complementary DNA (cDNA) using reverse transcriptase and DNA can be created into RNA using RNA polymerase. A nucleic acid molecule can be of biological or synthetic origin. Examples of nucleic acid molecules include genomic DNA, cDNA, RNA, a DNA/RNA hybrid, amplified DNA, a pre-existing nucleic acid library, etc. A nucleic acid may be obtained from a human sample, such as blood, serum, plasma, cerebrospinal fluid, cheek scrapings, biopsy, semen, urine, feces, saliva, sweat, etc. A nucleic acid molecule may be subjected to various treatments, such as repair treatments and fragmenting treatments. Fragmenting treatments include chemical, mechanical, sonic, and hydrodynamic shearing. Repair treatments include nick repair via extension and/or ligation, polishing to create blunt ends, removal of damaged bases, such as deaminated, derivatized, abasic, or crosslinked nucleotides, etc. A nucleic acid molecule of interest may also be subjected to chemical modification (e.g., bisulfite conversion, methylation/demethylation), extension, amplification (e.g., PCR, isothermal, etc.), etc.

"Analogous" forms of purines and pyrimidines are well known in the art, and include, but are not limited to aziridinylcytosine, 4-acetylcytosine, 5-fluorouracil, 5-bromouracil, 5-carboxymthylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5-methoxyuracil, 2-methylthio-N6-isopentenyladenine, uracil-5-oxyacetic acid methylester, pseudouracil, queosine, 2-thiocytosine, 5-methyl-2-thiouracil, 2-thiouracil, 4-thiouracil, 4-thiothimidine, 6-thioguanosine, 6-thioinosine, 5-methyluracil, uracil-5-oxyacetic acid, and 2,6-diaminopurine. The nucleic acid molecule can also contain one or more hypermodified bases, for example and without limitation, 5-hydroxymethyluracil, 5-hydroxyuracil, a-putrescinylthymine, 5-hydroxymethylcytosine, 5-hydroxycytosine, 5-methylcytosine, ~-methyl cytosine, 2-aminoadenine, acarbamoylmethyladenine, N'-methyladenine, inosine, xanthine, hypoxanthine, 2,6-diaminpurine, and $N_7$-methylguanine. The nucleic acid molecule can also contain one or more non-natural bases, for example and without limitation, 7-deaza-7-hydroxymethyladenine, 7-deaza-7-hydroxymethylguanine, isocytosine (isoC), 5-methylisocytosine, and isoguanine (isoG). The nucleic acid molecule may contain canonical, hypermodified, non-natural bases, or any combinations the bases thereof. Nucleotide residues can be comprised of standard phosphodiester linkages, and in addition, may contain one or more modified linkages, for example and without limitation, substitution of the non-bridging oxygen atom with a nitrogen atom (i.e., a phosphoramidate linkage, a sulfur atom (i.e., a phosphorothioate linkage), or an alkyl or aryl group (i.e., alkyl or aryl phosphonates), substitution of the bridging oxygen atom with a sulfur atom (i.e., phosphorothiolate), substitution of the phosphodiester bond with a peptide bond (i.e., peptide nucleic acid or PNA), or formation of one or more additional covalent bonds (i.e., locked nucleic acid or LNA), which has an additional bond between the 2'-oxygen and the 4'-carbon of the ribose sugar.

It will also be recognized by a skilled worker that any nucleoside described here can be substituted with an analogous selenium substituted version. For example, 6-thioguanosine may also be 6-selenoguanosine and likewise 4-thiouridine can be 4-selenouridine. Thus, all reaction employing $OsO_4$ and nitrogen donor reagent also work for 4-selenouridine (4SeU), 6-selenoguanosine (6SeG), 4-selenothymidine (4SeT) and 6-seleno-2'deoxyguanosine (6SedG).

Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" may refer to nucleic acid(s) that are substantially complementary, as may be assessed by the same nucleotide comparison set forth above. The term "substantially complementary" may refer to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double-stranded nucleic acid molecule during hybridization. In certain embodiments, the term "substantially complementary" refers to at least one nucleic acid that may hybridize to at least one nucleic acid strand or duplex in stringent conditions. In certain embodiments, a "partially complementary" nucleic acid comprises at least one sequence that may hybridize in low stringency conditions to at least one single or double-stranded nucleic acid, or contains at least one sequence in which less than about 70% of the nucleobase sequence is capable of base-pairing with at least one single or double-stranded nucleic acid molecule during hybridization.

"Oligonucleotide," as used herein, refers collectively and interchangeably to two terms of art, "oligonucleotide" and "polynucleotide." Note that although oligonucleotide and polynucleotide are distinct terms of art, there is no exact dividing line between them and they are used interchangeably herein. The term "adaptor" may also be used interchangeably with the terms "oligonucleotide" and "polynucleotide."

The term "primer," as used herein, is meant to encompass any nucleic acid that is capable of priming the synthesis of a nascent nucleic acid in a template-dependent process, such as a single-stranded oligonucleotide or a single-stranded polynucleotide that is extended by covalent addition of nucleotide monomers during amplification. Often, nucleic acid amplification is based on nucleic acid synthesis by a nucleic acid polymerase. Many such polymerases require the presence of a primer that can be extended to initiate nucleic acid synthesis. Typically, primers are oligonucleotides from ten to twenty and/or thirty base pairs in length, but longer sequences may be employed. Primers may be provided in double-stranded and/or single-stranded form, although the single-stranded form is preferred.

The terms "hairpin," "stem-loop oligonucleotide," and "stem-loop nucleic acid" as used herein refer to a structure formed by an oligonucleotide comprised of 5' and 3' terminal regions, which are intramolecular inverted repeats that form a double-stranded stem, and a non-self-complementary central region, which forms a single-stranded loop.

The term "non-complementary" refers to nucleic acid sequence that lacks the ability to form at least one Watson-Crick base pair through specific hydrogen bonds.

"Sample" means a material obtained or isolated from a fresh or preserved biological sample or synthetically-created source that contains nucleic acids of interest. Samples can include at least one cell, fetal cell, cell culture, tissue specimen, blood, serum, plasma, saliva, urine, tear, vaginal secretion, sweat, lymph fluid, cerebrospinal fluid, mucosa secretion, peritoneal fluid, ascites fluid, fecal matter, body exudates, umbilical cord blood, chorionic villi, amniotic fluid, embryonic tissue, multicellular embryo, lysate, extract, solution, or reaction mixture suspected of containing immune nucleic acids of interest. Samples can also include non-human sources, such as non-human primates, rodents and other mammals, other animals, plants, fungi, bacteria, and viruses.

The term "array" or "microarray" as used herein refers to an intentionally created collection of molecules which can be prepared either synthetically or biosynthetically (e.g. Illumina HumanMethylation27 microarrays). The molecules in the array can be identical or different from each other. The array can assume a variety of formats, for example, libraries of soluble molecules; libraries of compounds tethered to resin beads, silica chips, or other solid supports.

The term "convert", "converted", or "conversion" as used herein generally refers to a chemical change in structure from one nucleotide to different nucleotide. Generally, a thiolated nucleotide will be converted to a non-thiolated nucleotide following chemical treatment, such as with osmium tetroxide ($OsO_4$) and ammonium chloride ($NH_4Cl$). In some aspects, the thiolated nucleotide may be 4-thiouridine. 4-thiouridine, when reverse transcribed is read as a thymidine. Following $OsO_4/NH_4Cl$ treatment, 4-thiouridine may be converted to a cytidine. In some aspects, the thiolated nucleotide may be 4-thiothymidine. 4-thiothymidine, when replicated is read as a thymidine, however following $OsO_4/NH_4Cl$ treatment, 4-thiothymidine is converted to 5-methylcytidine and is read as a cytidine during replication, transcription, and sequencing. In some aspects, the thiolated nucleotide may be 6-thioguanosine. 6-thioguanosine is read as a guanine during replication, transcription, reverse transcription, and sequencing. 6-thioguanosine may be treated with $OsO_4$, however, to generate 6-oxo-guanosine (6oxoG). 6oxoG can then be treated with hydrazine to generate 6'-hydrazino-2-aminopurine, which is read as an adenine during replication, transcription, reverse transcription and sequencing.

As used in this specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about", "approximately" or related terms are used to indicate that a value includes the inherent variation of error for the device, the method being employed to determine the value, or the variation that exists among the study subjects.

Any embodiment of any of the present methods, kits, and compositions may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

II. Metabolic Labeling

Metabolic labeling refers to methods in which the endogenous synthesis and modification machinery of living cells is used to incorporate detection or affinity tags into biomolecules. Typically, this is accomplished by culturing cells or organisms in media in which a specific natural molecular building block (e.g., amino acid, nucleotide, carbohydrate) has been supplemented with a tagged chemical analog, such as a thiolated nucleotide. Cells use the chemical analog instead of the natural biomolecule to synthesize labeled nucleotides or proteins, or modify proteins or nucleic acids. Metabolic labeling is a powerful strategy because it is simple to perform and enables measurement of metabolic rates and detection of biologically relevant interactions in vivo with minimal disruption to cellular processes. Common methods of metabolic labeling include incorporation of radiolabeled nucleic acids or amino acids, and incorporation of analogous nucleotides or amino acids, such as the incorporation of 4-thiouridine, 6-thioguanosine, 4-thiothymidine, 6sI, 6seG or 2'-deoxy-5-methylcytidine.

Radiolabeled isotopes can be substituted in biomolecule monomers without any changes to the chemical structure and are readily incorporated in vivo. Radiolabeled macromolecules are also easily detected by sensitive radiometric techniques such as liquid scintillation counting or positron emission tomography (PET) scanning. Examples of radioactive tracers and applications include $^3H$ thymidine uptake for cell proliferation assays, $^{35}S$ methionine labeling for protein synthesis determination, $^{32}P$ orthophosphate labeling for in vivo kinase assays, and $^{14}C$-labeled D-glucose update for determination of cellular metabolism rates. Although radioactive isotopes are easily detected and relatively inexpensive, there are some disadvantages including safety hazards, generation of radioactive waste, toxicity to organisms, and radioactive decay leading to loss of signal over time.

Metabolic RNA labeling approaches that employ nucleotide-analogs enable tracking of RNA species over time without interfering with cellular integrity. Historically, 4-thiouridine (4sU has been the most commonly used nucleotide-analog for studying the dynamics of RNA expression, particularly because of the opportunity to use thiol chemistry to attach affinity groups. Affinity-based RNA-purification upon 4sU-labeling has been successfully applied to cultured cells of diverse biological and organismal origin, as well as in vivo in yeast and metazoan model organisms, including insects and mammals, using either 4-thiouridine or 4-thiouracil upon metabolic activation by uracil phosphoribosyltransferase (UPRT). However, like any biochemical separation method, the underlying protocols are laborious, require ample starting material, and typically encounter the problem of low signal-to-noise performance, in part because of limited biotinylation efficiency. Further, analysis of labeled RNA species by sequencing requires extensive controls in order to provide integrative insights into gene expression dynamics.

III. RNA Sequencing

RNA sequencing (RNA-seq) is a well-established method for analyzing gene expression. A variety of methodologies for RNA-seq exist. See, for example, U.S. patent application Ser. No. 14/912,556, U.S. Pat. No. 5,962,272, both of which are incorporated herein by reference. Generally, methods for RNA-seq begin by generating a cDNA from the RNA by reverse transcription. In this process, a primer is hybridized to the 3' end of the RNA, and a reverse transcriptase extends from the primer, synthesizing complementary DNA. A second primer then hybridizes to the 3' end of the nascent cDNA, and either a DNA polymerase, or the same reverse transcriptase extends from the primer, and synthesizes a complementary strand, thereby generating double stranded DNA, after which logarithmic amplification can begin (i.e., PCR). Many methods of cDNA synthesis utilize the poly(A) tail of the mRNA as the starting point for cDNA synthesis and utilize a first primer which has a stretch of T nucleotides, complementary to the poly(A) tail. Some methods then use random primers as the other primers, though this has proved to cause consistent bias. As practiced in U.S. patent application Ser. No. 14/912,556 and U.S. Pat. No. 5,962,272, certain reverse transcriptases can add extra non-templated nucleotides to the end of a sequence, and then switch templates to a primer which binds there. This allows for the addition of the second primer, with very low bias.

IV. Reagents and Kits

Kits may comprise suitably aliquoted reagents for preforming assays of the present embodiments. For example, commercial kits might include single reagents or buffers, reagents and buffers assembled in a kit, software and algorithm for data analysis, optimized solutions including TUC-Seq library preparation and Tuc-seq analysis. In certain aspects, reagents are provided lyophilized or desiccated and need to be reconstituted with an appropriate solvent before the use. In certain embodiments reagents can be provided in a container under vacuum, or in an atmosphere containing argon, nitrogen, or one or more inert gas. In certain embodiments reagents are kept refrigerated or frozen after reconstitution. In other commercial embodiments the reagents are provided aliquoted (in a liquid or solid format) and each aliquot is sufficient to perform 1, 2, 3, 4, 5, 6, 7, 8, 9, 10 or more TUC-Seq reactions. In certain commercial embodiments reagents and kits can be stored and shipped at temperatures ranging from −80° C. to ambient temperature. In some aspects, reagents and kits will be stored and shipped at temperature between −20° C. to ambient temperature. An exemplary 50 prep kit could include one or more of the following components:

Component 1: $OsO_4$ in a solid, or a liquid format in a concentration range between 1 µM and 10 M. Other compounds and salts containing $Os^{8+}$, $Os^{6+}$ (e.g. potassium osmate (VI) dihydrate ($K_2OsO_4.2H_2O$)), or other transition metal (in particular those belonging to the groups 6, 7, 8, 9, and 10 in the periodic table of elements) can be used instead of Component 1.

Component 2: $NH_4Cl$ in a solid or a liquid format in a concentration range between 1 µM and 7 M. Ammonium acetate, ammonium nitrate, ammonium sulfate, and other ammonium salts can be used instead of $NH_4Cl$ for Component 2. In further aspects, a different nucleophilic agent, such an alkylamine or TFEA may be included as the component 2.

Component 3: Hydrazine, pure, diluted, or on in a salt format (e.g. hydrazine chloride, sulfate, etc, . . . ). Hydroxylamine, methylhydrazine, dimethylhydrazine, and other amino, and hydrazine derivates can be used instead of hydrazine for Component 3.

Component 4: One or more nucleotides (4-thiouridine, 6-thioguanosine, 6seG, 4-thiothymidine, 6-thio-2'-deoxyguanosine, 6-thioinosine, 2-thiouridine, 2-thiocytidine, 5-methyl-4-thiouridine, as well as un-modified ribonucleotides triphosphate and deoxyribonucleotides triphosphate) in a solid format, or at a concentration range between 100 µM and 1 M.

Component 5: One or more solvent and buffer (DMSO, ethanol or other alcohols, water, ammonium hydroxide, TE-buffer, PBS-buffer, Tris-HCl buffer, citrate-buffer, HEPES-buffer, MOPS buffer).

Component 6: RNA and/or DNA Standards and control samples, that may contain one or more modified nucleobase.

Component 7: One or more nucleic acid purification system based on silica columns, guanidinium reagents, magnetic beads, or a filtration/size exclusion approaches.

Component 8: Oligonucleotides, including a first strand synthesis primer (with or without a polyT annealing region and a specifically designed identifier sequence), a second strand synthesis primer that may contain one random annealing sequence, and adaptors for sequencing containing or not unique indexes for sequencing library de-multiplexing.

Component 9: One, or mole enzymes, including DNA polymerases, Reverse transcriptases, DNA ligases, nucleases).

Component 10: One or more tool, software, and algorithm for the TUC-Seq data analysis.

Optional Components: These may include components for cell and tissue culture (FBS, serum replacement components, cell culture supplements, matrixes), enzymes (accutase, trypsin, uracil-DNA glycosylase, alkaline phosphatases, kinases, glycosylases, glycosyltransferases, cellulases, macerozyme, pectolase, zymolase, chitinase), and components to determine the efficiency of nucleic acids labeling during TUC-Seq procedure.

Additional components that may be included in a kit according to the embodiments include, but are not limited to, reagents for nucleic acid purification, one or more wash buffer including a magnetic bead (i.e., magnetic beads such as MagBinding Beads), Pre-wash buffer, an elution buffer, a proteinase composition, DNase and/or RNase inhibitors, DNase or RNase enzymes, oligonucleotide primers, reference samples (e.g., samples comprising known amounts of DNA or RNA), distilled water, DEPC-treated water, probes, sample vials, polymerase, magnetic binding beads (e.g., magnetic silica beads such as MagBinding Beads), 96-well silica plates, 96-well collection plates, cover foils for 96 well plates and instructions for nucleic acid purification. In certain further aspects, additional reagents for DNA and/or RNA clean-up may be included.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing reagent containers in close confinement for commercial sale. Such containers may include cardboard containers or injection or blow-molded plastic containers into which the desired vials are retained.

When the components of the kit are provided in one or more liquid solutions, the liquid solution is an aqueous solution, with a sterile aqueous solution being preferred. However, the components of the kit may be provided as dried powder(s). When reagents and/or components are provided as a dry powder, the powder can be reconstituted by the addition of a suitable solvent. It is envisioned that the solvent may also be provided in another container means.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Synthesis of 4-thiouridine phosphoramidite. The synthesis of 4-thiouridine phosphoramidite from uridine was elaborated by taking into account work by Beigelman, Adams, and McGregor (Serebryany and Biegelman, 2002; Adams et al., 1994; McGregor et al., 1996). The complete reaction scheme is pictured in FIG. 1, and individual reactions are shown in FIGS. 2, 5, 8, 11, and 14.

Figure 2:
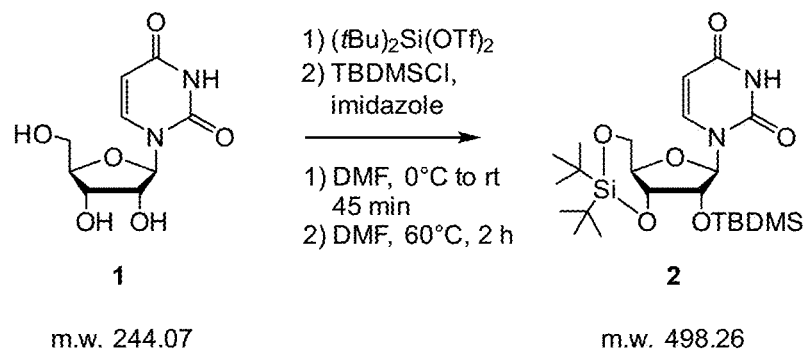
FIG. 2: Schematic of the synthesis of compound 2 from uridine. This step corresponds to step a of FIG. 1.
Figure 3:
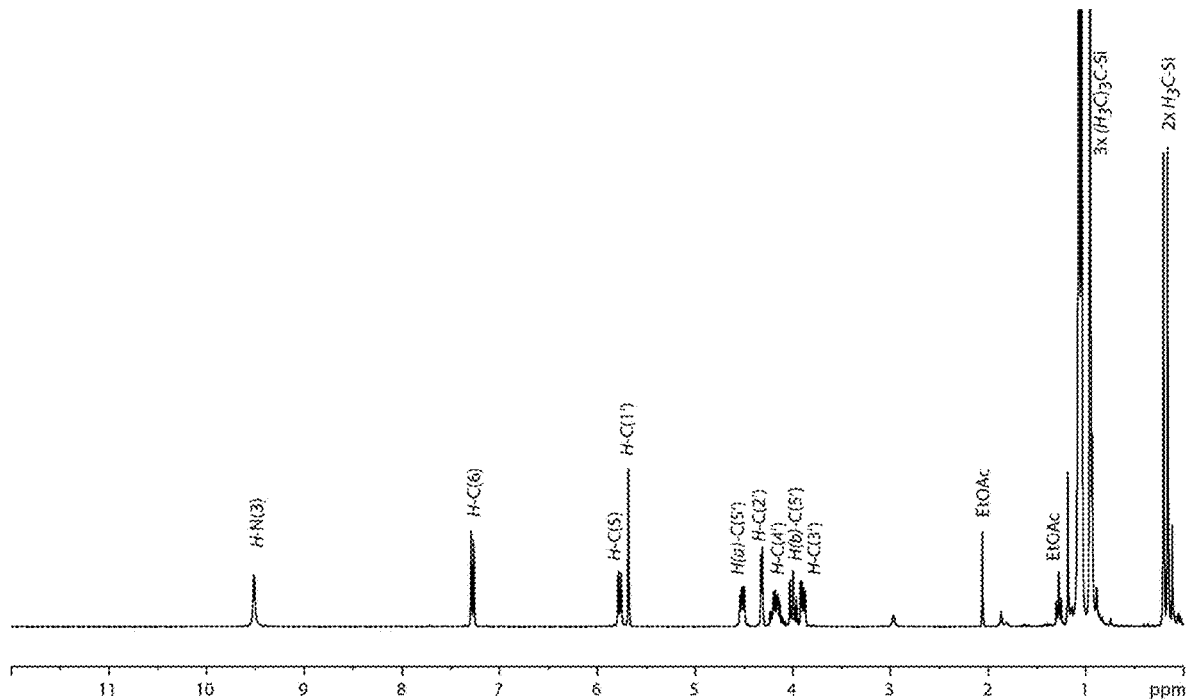
FIG. 3: $^1$H NMR (300 MHz, CDCl$_3$) spectra of compound 2.
Figure 4:
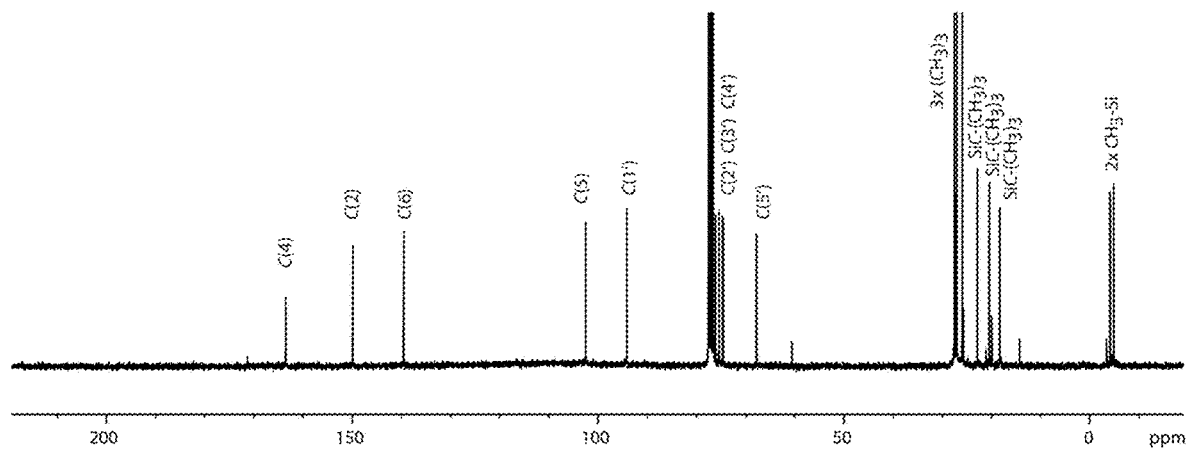
FIG. 4: $^{13}$C NMR (75 MHz, CDCl$_3$) spectra of compound 2.

First, 2'-O-(tert-butyldimethylsilyl)-3',5'-O-(di-tert-butylsilylene)-uridine was synthesized from uridine (FIG. 2). Briefly, 2.0 g of uridine (compound 1) was dissolved in 10 ml of dry DMF and stirred at 0° C. Then di-tert-butylsilyl bis(trifluoromethanesulfonate) (3.2 ml; 4.4 g, 9.9 mmol, 1.2 eq.) was added dropwise. After 45 minutes, imidazole (2.8 g, 41 mmol, 5.0 eq.) was added and the reaction was warmed to room temperature over a period of 30 min. Then, tert-butyldimethylsilyl chloride (1.5 g, 9.9 mmol, 1.2 eq.) was added and the reaction was heated to 60° C. for 2 h. Subsequently, the reaction mixture was diluted with EtOAc (200 ml) and extracted twice with saturated NaHCO$_3$ (200 ml) and water (200 ml). The organic layer was dried over Na$_2$SO$_4$ and evaporated. The crude 2'-O-(tert-butyldimethylsilyl)-3',5'-O-(di-tert-butylsilylene)-uridine product was purified by SiO$_2$ column chromatography (30% EtOAc in hexanes) (FIG. 2, compound 2). The identity of the compound was confirmed by $^1$H and $^{13}$C NMR and ESI mass spectrometry (FIGS. 3 and 4).

Figure 5:
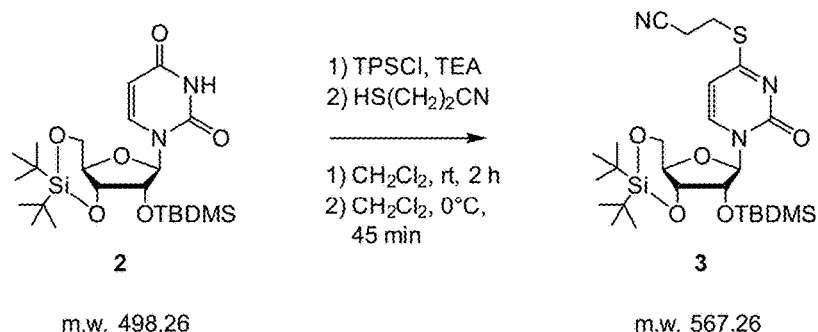
FIG. 5: Schematic of the synthesis of compound 3 from compound 2. This step corresponds to step b of FIG. 1.
Figure 6:
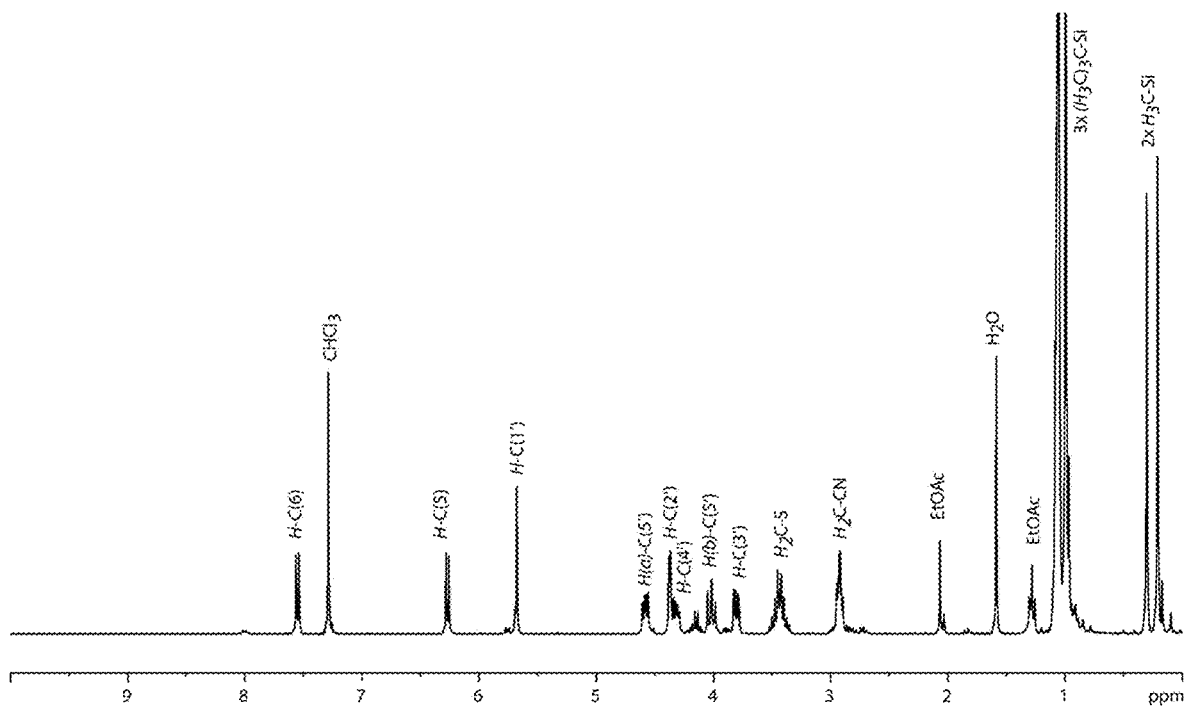
FIG. 6: $^1$H NMR (300 MHz, CDCl$_3$) spectra of compound 3.
Figure 7:
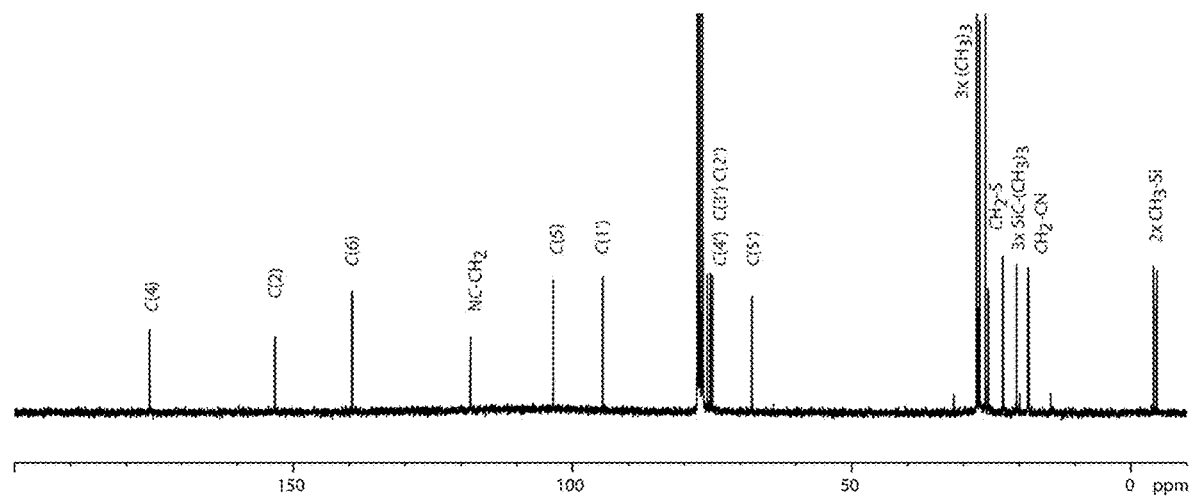
FIG. 7: $^{13}$C NMR (75 MHz, CDCl$_3$) spectra of compound 3.

Next, 2'-O-(tert-butyldimethylsilyl)-3',5'-O-(di-tert-butylsilylene)-4-(2-cyanoethylthio)-uridine was synthesized from 2'-O-(tert-butyldimethylsilyl)-3',5'-O-(di-tert-butylsilylene)-uridine (FIG. 5). First, 3-mercaptonitrile was prepared from 3,3'-dithiobis(propionitrile). 1.29 g of 3,3'-dithiobis(propionitrile) was suspended in 25 mL of 2 M hydrogen chloride. 1.3 g zinc powder was added slowly to the suspension and it was stirred for 1 hour at room temperature. The aqueous phase was extracted with 30 mL of CH$_2$Cl$_2$, dried over Na$_2$SO$_4$ and the solvent was evaporated. 3-mercaptonitrile was received as a colourless liquid. Next, 750 mg (1.5 mmol) of compound 2 were dissolved in 5 mL dry CH$_2$Cl$_2$. Then 1 mL of triethylamine (7.5 mmol, 5.0 eq.), 3 mg of 4-(dimethylamino)-pyridine and 498 mg (1.65 mmol, 1.1 eq.) of 2,4,6-triisopropylbenzenesulfonyl chloride were added. The solution was stirred for 2 hours. After control by thin layer chromatography, 1.57 mL (15.0 mmol, 10 eq.) of N-methyl-pyrrolidine and 1.29 g (7.5 mmol, 5 eq.) of freshly prepared 3-mercaptopropionitrile in 5 mL CH$_2$Cl$_2$ were added to the solution. The solution was stirred for 45 min at 0° C. Then the reaction mixture was diluted with CH$_2$Cl$_2$ and extracted with saturated NaHCO$_3$ solution. The organic layer was dried over Na$_2$SO$_4$ and the residual 3-mercaptopropionitrile was evaporated under high vacuum. The crude 2'-O-(tert-butyldimethylsilyl)-3',5'-O-(di-tert-butylsilylene)-4-(2-cyanoethylthio)-uridine (compound 3) product was purified by silica gel column chromatography (15-25% EtOAc in hexanes) and analyzed by $^1$H and $^{13}$C NMR and ESI mass spectrometry (FIGS. 6 and 7).

Figure 8:
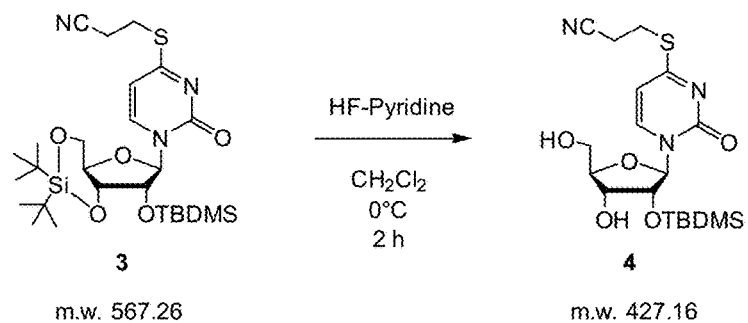
FIG. 8: Schematic of the synthesis of compound 4 from compound 3. This step corresponds to step c of FIG. 1.
Figure 9:
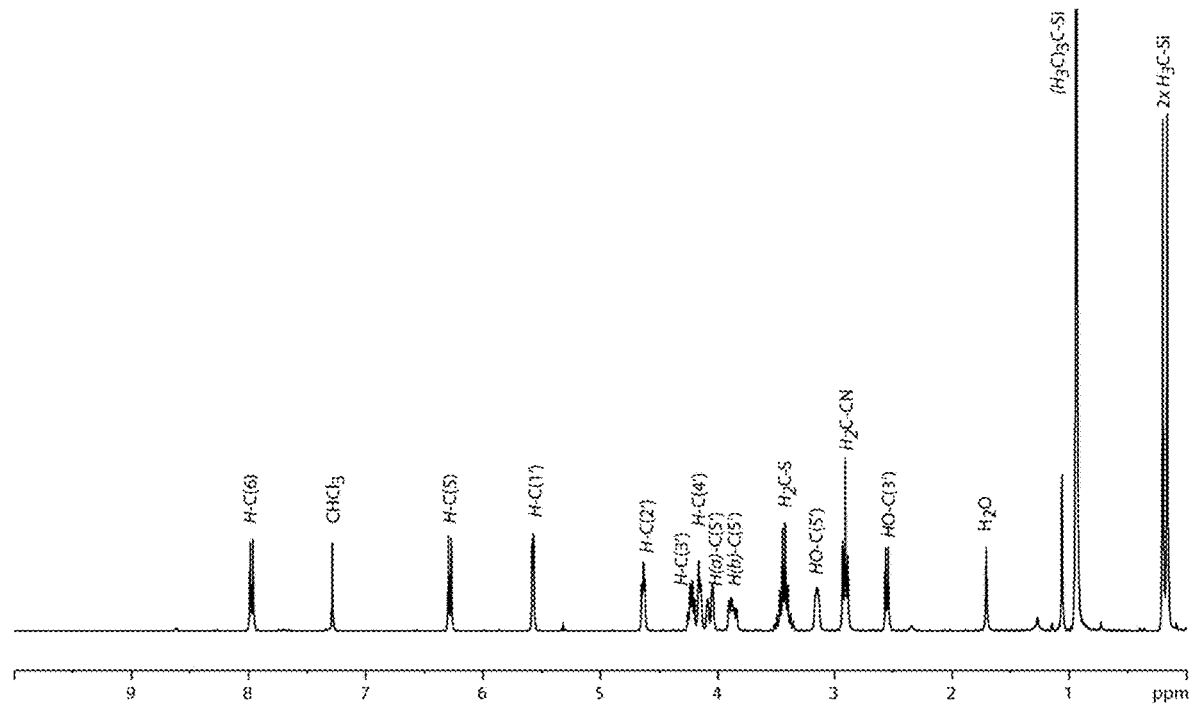
FIG. 9: $^1$H NMR (300 MHz, CDCl$_3$) spectra of compound 4.
Figure 10:
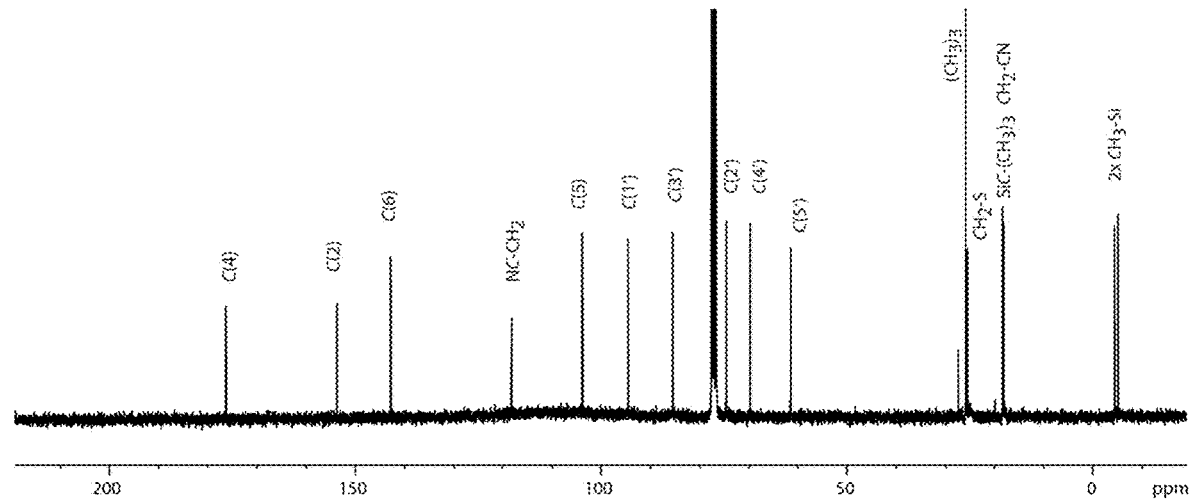
FIG. 10: $^{13}$C NMR (75 MHz, CDCl$_3$) spectra of compound 4.

To prepare 2'-O-(tert-butyldimethylsilyl)-4-(2-cyanoethylthio)-uridine (compound 4) 600 mg (1.05 mmol) of 2'-O-(tert-butyldimethylsilyl)-3', 5'-O-(di-tert-butylsilylene)-4-(2-cyanoethylthio)-uridine (compound 3) was dissolved in 5 mL dry CH$_2$Cl$_2$, and 109 µL of hydrogen fluoride pyridine complex (4.2 mmol, 4.0 eq.) in 650 µL of pyridine were added (FIG. 8). The solution was stirred for 2 hours at 0° C. Then the reaction mixture was diluted with CH$_2$Cl$_2$ and extracted with saturated NaHCO3 solution. The organic layer was dried over Na$_2$SO$_4$ and evaporated. The crude 2'-O-(tert-butyldimethylsilyl)-4-(2-cyanoethylthio)-uridine (compound 4) product was purified by silica gel column chromatography (1-3% MeOH in CH$_2$Cl$_2$), and then analyzed by $^1$H and $^{13}$C NMR and ESI mass spectrometry (FIGS. 9 and 10).

Figure 11:
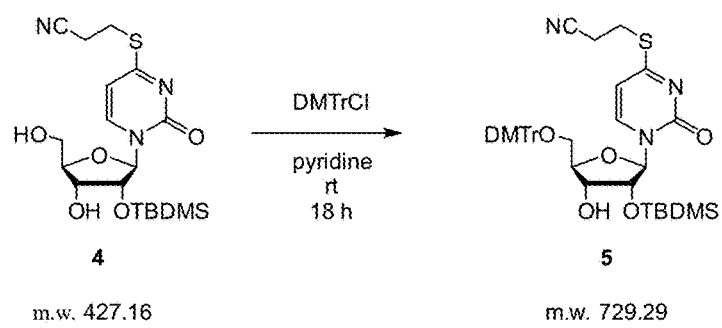
FIG. 11: Schematic of the synthesis of compound 5 from compound 4. This step corresponds to step d of FIG. 1.
Figure 12:
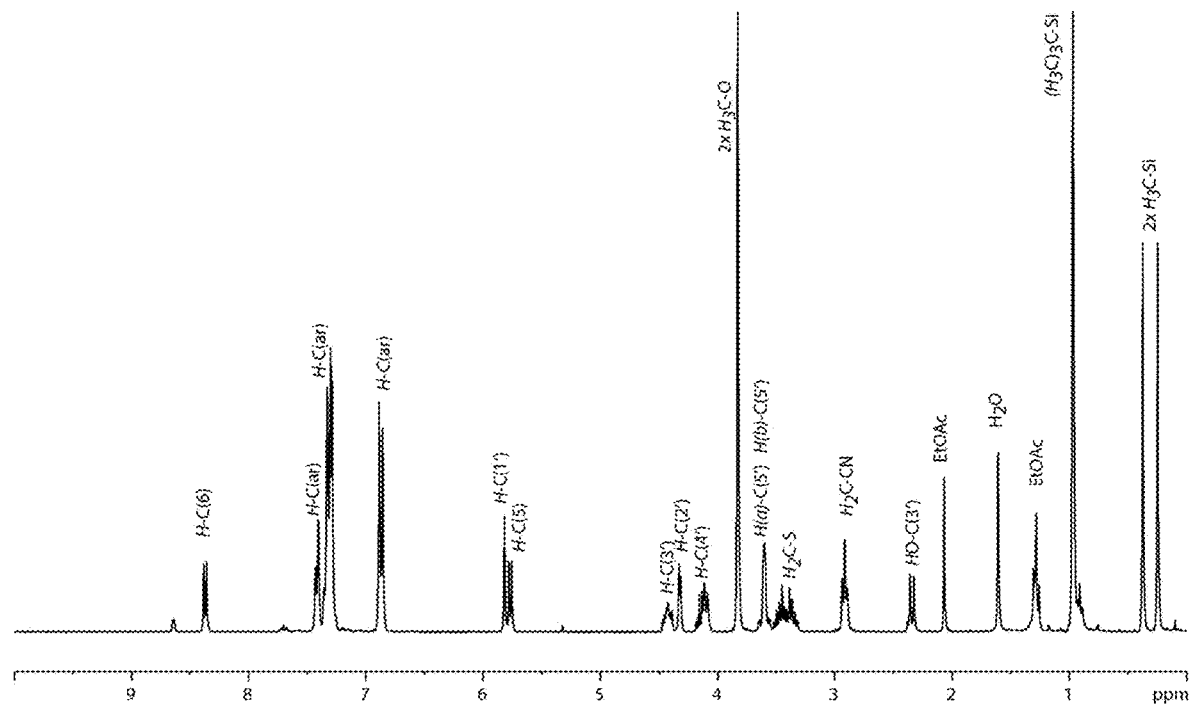
FIG. 12: $^1$H NMR (300 MHz, CDCl$_3$) spectra of compound 5.
Figure 13:
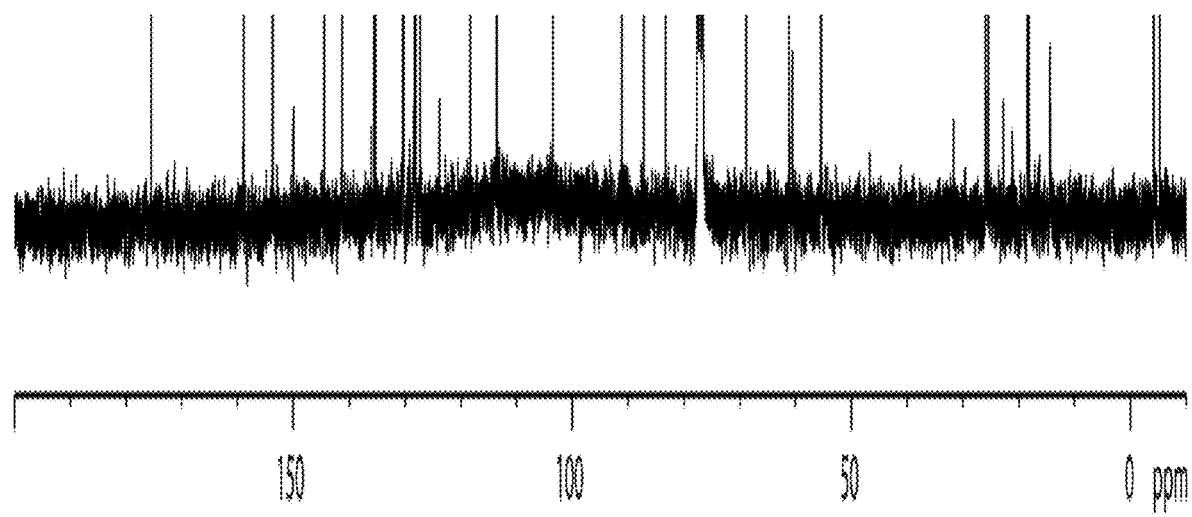
FIG. 13: $^{13}$C NMR (75 MHz, CDCl$_3$) spectra of compound 5.

5'-O-(4,4'-dimethoxytrityl)-2'-O-(tert-butyldimethylsilyl)-4-(2-cyanoethylthio)-uridine (compound 5) was prepared as follows: 350 mg (0.82 mmol) of 2'-O-(tert-butyldimethylsilyl)-4-(2-cyanoethylthio)-uridine (compound 4) was dissolved in 5 mL dry pyridine (FIG. 11). Then 360 mg (1.07 mmol, 1.3 eq.) of 4,4'-dimethoxytriphenylmethylchlorid were added to the solution (FIG. 11). The reaction mixture was stirred for 18 hours at rt. Then the reaction was quenched with 500 µL MeOH and diluted with CH$_2$Cl$_2$ (200 mL). The organic phase was extracted twice with 5% citric acid and with saturated NaHCO$_3$ solution. The organic layer was dried over Na$_2$SO$_4$ and evaporated. The crude 5'-O-(4,4'-dimethoxytrityl)-2'-O-(tert-butyldimethylsilyl)-4-(2-cyanoethylthio)-uridine product was purified by silica gel column chromatography (25-45% EtOAc in Hexanes) and analyzed by $^1$H and $^{13}$C NMR and ESI mass spectrometry (FIGS. 12 and 13).

Figure 14:
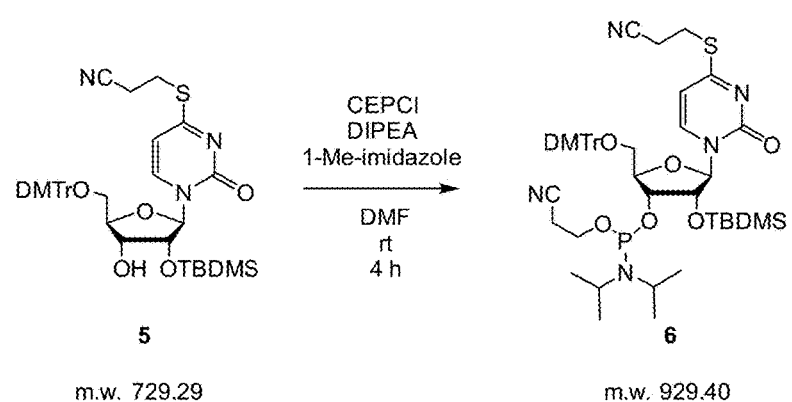
FIG. 14: Schematic of synthesis of compound 6 from compound 5. This step corresponds to step e of FIG. 1.
Figure 15:
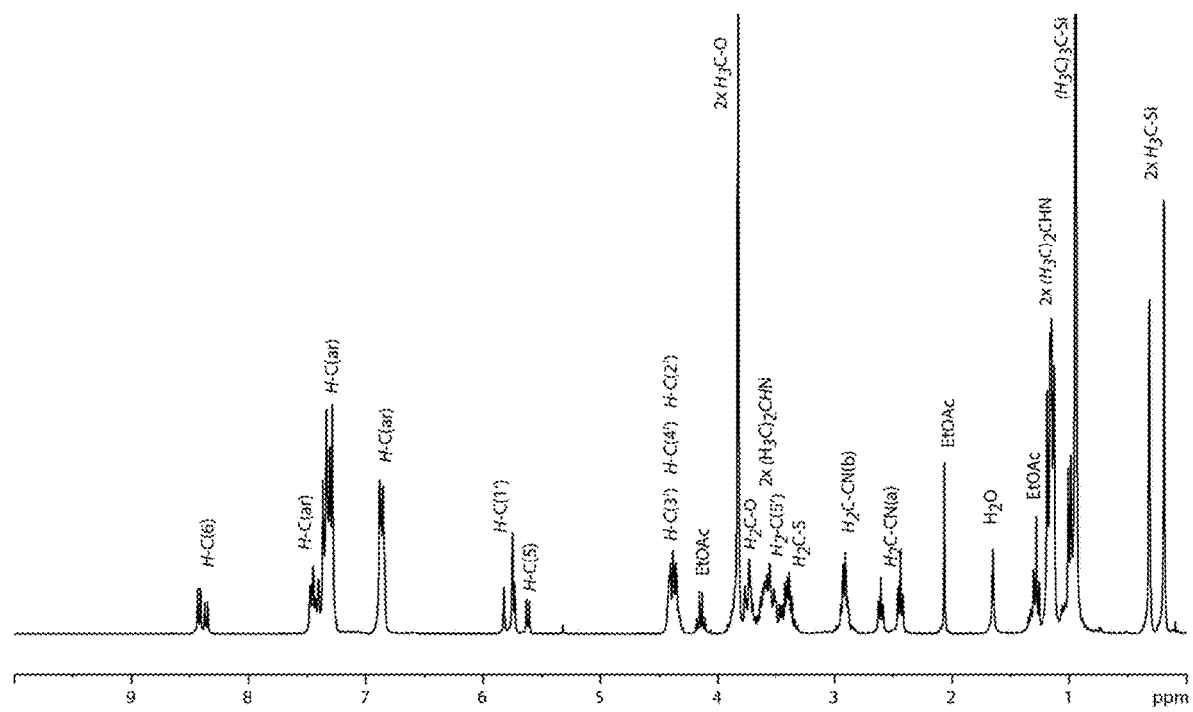
FIG. 15: $^1$H NMR (300 MHz, CDCl$_3$) spectra of compound 6.
Figure 16:
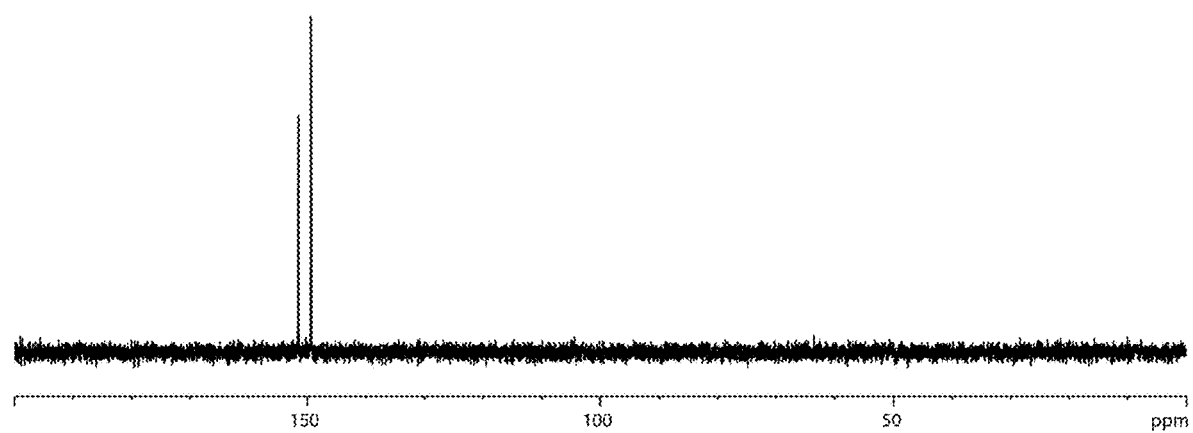
FIG. 16: $^{31}$P NMR (121 MHz, CDCl$_3$) spectra of compound 6.

Finally, 5'-O-(4,4'-dimethoxytrityl)-2'-O-tert-butyldimethylsilyl-4-(2-cyanoethylthio)-uridine-3'-O-2-cyanoethyl-N,N-diisopropylphosphoramidite (4-thiouridine phosphoramidite) was prepared from 5'-O-(4,4'-dimethoxytrityl)-2'-O-(tert-butyldimethylsilyl)-4-(2-cyanoethylthio)-uridine as follows: 450 mg (0.62 mmol) of 5'-O-(4,4'-dimethoxytrityl)-2'-O-(tert-butyldimethylsilyl)-4-(2-cyanoethylthio)-uridine (compound 5) was dissolved in 10 mL dry CH$_2$Cl$_2$. Then 26 µL (0.31 mmol, 0.5 eq.) of 1-Me-imidazole, 644 µL (3.7 mmol, 6 eq.) of diisopropylethylamine and 276 µL (1.24 mmol, 2 eq.) of 2-cyanoethyl-N,N-diisopropylchlorophosphoramidite were added to the solution (FIG. 14). The reaction mixture was stirred for 4 hours at room temperature. Then the reaction was diluted with CH$_2$Cl$_2$ (200 mL) and extracted with saturated NaHCO$_3$ solution. The organic layer was dried over Na$_2$SO$_4$ and evaporated. The crude 5'-O-(4,4'-dimethoxytrityl)-2'-O-tert-butyldimethylsilyl-4-(2-cyanoethylthio)-uridine-3'-O-2-cyanoethyl-N,N-diisopropylphosphoramidite (compound 6) product was purified by silica gel column chromatography (35% EtOAc in Hexanes, 0.5% TEA) and analyzed analyzed by $^1$H and $^{31}$P NMR and ESI mass spectrometry (FIGS. 15 and 16).

RNA solid-phase synthesis and deprotection. RNA synthesis was performed by standard methods of automated oligonucleotide synthesis using commercially available 2'-O-TOM RNA phosphoramidites (ChemGenes, Wilmington, Mass.) in combination with the 4sU phosphoramidite building block compound 6. After synthesis, the solid support was treated with 1,8-diazabicyclo[5.4.0]undec-7-en (DBU) in anhydrous acetonitrile (10 mL, 1 M) for two hours at room temperature and washed with dry acetonitrile (50 mL) to remove residual DBU. Cleavage of the solid support and base deprotection of the oligonucleotides were performed by treatment of the solid support with tert-butylamine/MeOH/H$_2$O (1 mL, 1:1:2, v/v/v) containing NaSH (50 mM) for 4 hours at 55° C. Subsequently, the solid support was filtered off, the solvents were evaporated under reduced pressure and the oligonucleotides were desalted by size exclusion chromatography (GE Healthcare, HiPrep™ 26/10 Desalting; 2.6×10 cm, Sephadex G25) eluting with H$_2$O, and the collected fraction was evaporated to dryness. Removal of the 2'-O protecting groups was achieved by treatment of the oligonucleotides with tetrabutylammonium fluoride trihydrate (TBAF.3H$_2$O) in THF (1 M, 1 mL) at 37° C. overnight. The reaction was quenched by the addition of triethylammonium acetate (TEAA) (1 M, pH 7.4, 1 mL). The volume of the solution was reduced, and the solution was desalted with a size-exclusion column (GE Healthcare, HiPrep™ 26/10 Desalting; 2.6×10 cm, Sephadex G25) eluting with H$_2$O, and the collected fraction was evaporated to dryness and dissolved in H$_2$O (1 mL). Analysis of the crude RNA after deprotection was performed by anion-exchange chromatography on a Dionex DNAPac PA-100 column (4 mm×250 mm) at 80° C.; injection: 200 pmol of crude RNA in 100 µL of H$_2$O; flow rate: 1 mL/min; eluent A: 25 mM Tris·HCl (pH 8.0), 6 M urea; eluent B: Tris·HCl (25 mM) (pH 8.0), NaCl$_4$ (0.5 M), urea (6 M); gradient: 0-60% B in A within 45 min and UV detection at 260 nm.

Purification of RNA oligonucleotides. Crude RNA products were purified on a semipreparative Dionex DNAPac PA-100 column (9 mm×250 mm) at 80° C. with a flow rate of 2 mL/min; injection: 10-40 nmol of crude RNA in 100 µL of H$_2$O; eluent A: 25 mM Tris·HCl (pH 8.0), 6 M urea; eluent B: Tris·HCl (25 mM) (pH 8.0), NaClO4 (0.5 M), urea (6 M); gradient (for target RNA between 25 and 30 nt in length): 30-45% B in A within 20 min; UV detection at 260 nm. Fractions containing RNA were loaded on a C18 SepPak Plus cartridge (Waters/Millipore), washed with (Et$_3$NH)+HCO$_3$-(0.1 M) and H$_2$O, and eluted with H$_2$O/MeCN (1:1). RNA-containing fractions were evaporated to dryness and dissolved in H$_2$O (1 mL). Analysis of the quality of purified RNA was performed by anion-exchange chromatography under the same conditions as utilized for crude RNA; the molecular weight was confirmed by LC-ESI mass spectrometry. Yield determination was performed by UV photometrical analysis of oligonucleotide solutions.

Mass spectrometry of RNA oligonucleotides. All experiments were performed on a Finnigan LCQ Advantage MAX ion trap instrument connected to an Amersham Ettan micro LC system. RNA sequences were analyzed in the negative-ion mode with a potential of −4 kV applied to the spray needle. LC: Sample (200 pmol RNA dissolved in 30 µL of 20 mM EDTA solution; average injection volume: 30 µL), column (Waters XTerra®MS, C18 2.5 µm; 2.1×50 mm) at 21° C.; flow rate: 30 µL/min; eluent A: Et$_3$N (8.6 mM), 1,1,1,3,3,3-hexafluoroisopropanol (100 mM) in H$_2$O (pH 8.0); eluent B: MeOH; gradient: 0-100% B in A within 30 min; UV detection at 254 nm.

Metabolic labeling of HEK293 cells. HEK293 cells (293-HA-StrepIII-eGFP; Glatter et al., 2009) containing a single integrated copy of eGFP controlled by an inducible CMV promoter were seeded into 6-well plates at 5×10$^5$ cells/well and grown overnight at 37° C. and 5% CO$_2$ in DMEM medium (Gibco). Medium was replaced with DMEM supplemented with 0.05 mM or 0.1 mM 4-thiouridine (4sU; Jena Bioscience), respectively, cells were labeled for 1 hour and subsequently harvested. After 30 min of labeling, transcription of eGFP was induced by addition of 1 µg/ml doxycycline.

Total RNA isolation from E. coli and HEK293 cells. Total RNA from E. coli DH5α cells (grown overnight in 3 ml standard Luria Bertani (LB) medium) and HEK293 cells was isolated using TRIzol (Sigma-Aldrich) following the manufacturer's protocol, digested with DNase I (NEB) and purified using phenol-chloroform extraction and precipitation with 0.3 M NaAc pH 5.2.

Quantitative Reverse Transcriptase PCR To determine the relative expression levels of eGFP, RNA was isolated from Dox-treated and untreated cells, reverse transcribed as above and subjected to real-time PCR using POWER SYBR Green PCR mastermix (Applied Biosystems) with 1.25 ng/ml cDNA and 0.8 mM eGFP-specific primers in a StepONE Plus Instrument (Applied Biosystems). Data were normalized against glyceraldehyde 3-phosphate dehydrogenase (GAPDH; Table 1) and differences between induced and non-induced samples were calculated using the ΔΔCT method.

TABLE 1

| oligonucleotide sequences | |
|---|---|
| E. coli tRNA$^{Val}$ | |
| tRNA$^{Val}$ reverse transcription primer | 5'-GGTGGGTGATGACGGGATC (SEQ ID NO: 1) |
| Stemloop primer* | 5'-GTTGGCTCTGGTGCAGGGTCCGAGGTATTC GCACCAGAGCCAAC GGGTGA (SEQ ID NO: 2) |
| Stemloop_PCR_ Primer_forward | 5'-GTGCAGGGTCCGAGGT (SEQ ID NO: 3) |
| PCR_Primer_ reverse | 5'-GTGATGACGGGATC (SEQ ID NO: 4) |
| eGFP expression (qPCR) | |
| eGFP_qPCR_ forward | 5'-AGCTGGACGGCGACGTAAAC (SEQ ID NO: 5) |
| eGFP_qPCR_ reverse | 5'-CAGGGTCAGCTTGCCGTAGG (SEQ ID NO: 6) |
| GAPHD_qPCR_ forward | 5'-GTTGTCTCCTGCGACTTCAAC (SEQ ID NO: 7) |

TABLE 1-continued oligonucleotide sequences

| | | |
|---|---|---|
| GAPHD_qPCR_reverse | 5'-ATTGTCATACCAGGAAATGAGC (SEQ ID NO: 8) | |

Amplicon Sequencing

| | | |
|---|---|---|
| CcnA2_fw | 5'-CCAGAAGTAGCAGAGTTTGT (SEQ ID NO: 9) | |
| CcnA2_rv | 5'-TTGAGGAGAGAAACACCATG (SEQ ID NO: 10) | |
| CcnB1_fw | 5'-ACATCGAAGCATGCTAAGAT (SEQ ID NO: 11) | |
| CcnB1_rv | 5'-CTATGCAGCAGATTCTCCAT (SEQ ID NO: 12) | |
| CcnD1_fw | 5'-GAGGGCAGTTTTCTAATGGA (SEQ ID NO: 13) | |
| CcnD1_rv | 5'-ATCAAGGGGAGATTGCATTT (SEQ ID NO: 14) | |
| CcnE1_fw | 5'-CTGATGAAGATGCACACAAC (SEQ ID NO: 15) | |
| CcnE1_rv | 5'-CTTTTGTTGTTGTGGGAGTC (SEQ ID NO: 16) | |
| p21/Cdkn1A_fw | 5'-CTTGAGTGGGGTTATCTCTG (SEQ ID NO: 17) | |
| p21/Cdkn1A_rv | 5'-ATATTCAGCATTGTGGGAGG (SEQ ID NO: 18) | |
| eGFP_fw | 5'-CCATCTTCTTCAAGGACGAC (SEQ ID NO: 19) | |
| eGFP_rv | 5'-TACTTGTACAGCTCGTCCAT (SEQ ID NO: 20) | |
| PCNA_fw | 5'-ACCAAACCAGGAGAAAGTTT (SEQ ID NO: 21) | |
| PCNA_rv | 5'-TCCTTCTTCATCCTCGATCT (SEQ ID NO: 22) | |

4-thiothymidine conversion oligonucleotides

| | |
|---|---|
| CR042 | 5'-TAGCACG4sT GCTAA-3' (SEQ ID NO: 23) |
| Converted CR042 | 5'-TAGCACGm5CGCTAA-3' (SEQ ID NO: 24) |

*underlined sequence is complementary to the 5' end of tRNAVal

4sU-to-C conversion reaction. To convert 4sU to C, an $OsO_4$ solution (1 mM) was freshly prepared from aqueous $OsO_4$ stock solution (1 mL; 100 mM) stored at −20° C. $NH_4Cl$ solution (2 M) was prepared by dissolving $NH_4Cl$ (10.7 g) in $H_2O$ (100 mL) and adjusting pH to 8.88 by the addition of ammoniumhydroxide solution (2.0 M). Synthetic lyophilized RNA (1 nmol) was dissolved in $H_2O$ (10 mL). $NH_4Cl$ solution (2 mL; 2 M, pH 8.88) and $OsO_4$ solution (10 mL; 1 mM) were added to the dissolved RNA to give final concentrations of 0.45 mM $OsO_4$ and 180 mM $NH_4Cl$ in a total volume of 22 μL. The reactions were mixed and incubated for 4 hours at room temperature.

Procedure for total RNA from *E. coli* or HEK293 cells. Purified total RNA (10 mg) was dissolved in RNase free $H_2O$ (20 mL). Following dissolution, $NH_4Cl$ solution (4 mL; 2 M, pH 8.88) and aqueous $OsO_4$ solution (20 mL; 1 mM) were added to give final concentrations of 0.45 mM $OsO_4$ and 180 mM $NH_4Cl$ in a total volume of 44 μL. The reaction mixture was then incubated for 3 hours at room temperature or at 50° C., respectively. In one case, the RNA was denatured at 92° C. for 2 minutes before treatment with $OsO_4$ in order to test the effect of denaturation on the reaction. To remove $OsO_4/NH_4Cl$ following the reaction, the reaction mixture was transferred into Vivaspin 500 (MWCO 3000, PES) centrifugal concentrators (Sartorius, Göttingen, Germany), washed 4 times with $H_2O$ (500 mL), and the concentrate was either lyophilized or directly used in the next step.

Reverse transcription, cloning and sequencing of *E. coli* $tRNA^{Val}$. Osmium tetroxide-treated or untreated and purified RNA was reverse transcribed using GoScript™ Reverse Transcriptase (Promega) with a specific primer for $tRNA^{Val}$ according to the manufacturer's instructions. A stem-loop primer corresponding to the 5' end of $tRNA^{Val}$ was annealed to the cDNA by incubation at 65° C. for 5 minutes, followed by 10 minutes at 25° C. and immediate transfer to ice. Second strand synthesis was performed by adding 5 mM dNTPs, 0.25 units of Taq polymerase and Taq buffer in a final volume of 10 μl, and incubation at 25° C., 60° C. and 72° C. for 2 minutes each. Five μl of the second strand synthesis reaction was used as a template for subsequent PCR amplification of $tRNA^{Val}$ employing primers specific for the stem-loop sequence and the 3' end of $tRNA^{Val}$. PCR products were separated on a 2% agarose/TBE gel, excised, purified, and subcloned into a pGEM-T-Vector (Promega). A total of 40 individual clones were used for sequencing of the plasmid DNA. All primers are listed in Table 1.

Amplicon sequencing of metabolically labeled transcripts from HEK293 cells. RNA from labeled and unlabeled cells was isolated and treated with $OsO_4$ as described above for 3 h at room temperature. After purification and reverse transcription using GoScript™ Reverse Transcriptase (Promega®) and random hexamer primers, selected targets were amplified with specific primers containing barcode overhangs using standard PCR conditions (primer sequences without barcodes are listed in Table 1). The products were separated on a 2% agarose gel, purified from the gel and pooled at equimolar ratio. Library preparation from the amplicon pool and sequencing using the Illumina® HiSeq® platform was performed by GATC Biotech.

Sequencing data analysis. The multiplexed sequencing read data were split into single sample files according to the sample-specific forward and reverse barcodes using flexbar version 2.5 (Dodt et al., 2012). The sample-specific sequencing reads were aligned to the amplicon-specific reference sequences by running Bowtie 2, version 2.2.9 (Langmead et al., 2009), in a first round in "end-to-end" mode. Reads that failed to align in "end-to-end" mode were then aligned in a second round by using the "local" mode. Amplicon positions with U-to-C conversions were called using VarScan2 version 2.4.3 (Koboldt et al., 2012). The maximum depth was set to $1e^6$ and the minimum base call quality score was set to 30. Only U positions with a minimum conversion frequency of $1e^{-4}$ were considered further. For identifying the background/baseline mutation/error frequency all non U-to-C changes were analyzed according to the same criteria as used for U-to-C conversions. In order to minimize errors from potentially misaligned reads only positions on the amplicons which were at maximum 146 bases distant from the amplicon ends were considered. To quantify the number of reads with U-to-C conversions, sam2tsv (Lindenbaum, 2015) was used, along with a custom written perl script to analyze each aligned read and count the U-to-C conversions and the read specific conversion frequency. Again, only sequence read bases with a minimum base call quality score of 30, and a maximum amplicon end distance of 146 were considered in these analyses.

Statistical analyses. To determine the statistical significance of differences of U-to-C mutation frequencies of 4sU-labeled and OsO$_4$-treated versus unlabeled and untreated, and 4sU labeled but not OsO$_4$-treated samples, and of differences between U-to-C mutation frequencies versus A-, C-, or G-to-N mutation frequencies, Chi-Square analyses with Yates' correction were performed using GraphPad Prism v.7. Statistical significance was set to p<0.05.

Example 2

Synthesis of 4-Thiouridine Phosphoramidite

Synthesis of compound 2. 2'-O-(tert-butyldimethylsilyl)-3',5'-O-(di-tert-butylsilylene)-uridine was synthesized from uridine as described above and shown in FIG. 2. This process yielded 3.8 g (7.6 mmol), with 93% as white foam. The identity of the product was first confirmed by thin layer chromatography using a 1:1 v:v mix of EtOAc:hexane and was found to have a retention factor (Rf) of 0.65. The identity was further confirmed by $^1$H NMR and $^{13}$C NMR with the following results:

$^1$H NMR (300 MHz, CDCl$_3$): δ 0.16 (s, 3H, H$_3$C—Si); 0.20 (s, 3H, H$_3$C—Si); 0.95 (s, 9H, (H$_3$C)$_3$—C); 1.04 (s, 9H, (H$_3$C)$_3$—C); 1.07 (s, 9H, (H$_3$C)$_3$—C); 3.87-3.91 (dd, 1H, H—C(3'), J$_1$=5 Hz, J$_2$=4 Hz); 3.96-4.02 (d, 1H, H(b)-C(5'), J=10 Hz); 4.17 (m, 1H, H—C(4'), J$_1$=5 Hz J$_2$=4.5 Hz); 4.30-4.32 (d, 1H, H—C(2'), J=4 Hz); 4.49-4.54 (dd, 1H, H(a)-C(5'), J$_1$=10 Hz, J$_2$=4.5 Hz); 5.68 (s, 1H, H—C(1')); 5.72-5.75 (d, 1H, H—C(5), J=7 Hz); 7.23-7.26 (d, 1H, H—C(6) J=7 Hz); 9.48 (s, 1H, H-N) ppm. See FIG. 3 for the image of the spectra.

$^{13}$C NMR (75 MHz, CDCl$_3$): δ−4.91,-4.17 (2×CH$_3$—Si); 18.37, 20.47, 22.90 (3×C(CH$_3$)$_3$); 25.97, 27.10, 27.60 (9×CH$_3$—C—Si); 67.70 (C(5'); 74.67 (C(4')); 75.47 (C(2')); 76.19 (C(3')); 94.14 (C(1')); 102.51 (C(5)); 139.44 (C(6)); 149.89 (C(2)); 163.50 (C(4)) ppm. See FIG. 4 for the image of the spectra.

Electrospray ionization mass spectrometry (ESI-MS) was also performed. The ESI-MS [MH+] for C$_{23}$H$_{42}$N$_2$O$_6$Si$_2$ was calculated to be 499.27, and observed to be 499.29.

Synthesis of compound 3. 2'-O-(tert-butyldimethylsilyl)-3', 5'-O-(di-tert-butylsilylene)-4-(2-cyanoethylthio)-uridine (compound 3) was synthesized from 2'-O-(tert-butyldimethylsilyl)-3',5'-O-(di-tert-butylsilylene)-uridine (compound 2) as described above and shown in FIG.5. This process yielded 600 mg of product, 70% as white foam. To confirm the product, thin layer chromatography was performed with a 1:1 mixture of EtOAc:hexane which yielded a retention factor of 0.65. The identity was further confirmed by $^1$H NMR and $^{13}$C NMR with the following results:

$^1$H NMR (300 MHz, CDCl$_3$): δ 0.20 (s, 3H, H$_3$C—Si); 0.29 (s, 3H, H$_3$C—Si); 0.98 (s, 9H, (H$_3$C)$_3$—C); 1.04 (s, 18H, (H$_3$C)$_3$—C); 2.91-2.92 (m, 2H, H$_2$C—CN); 3.41-3.44 (m, 2H, H$_2$C—S); 3.78-3.82 (dd, 1H, H—C(3'), J$_1$=5 Hz, J$_2$=4 Hz); 3.98-4.04 (d, 1H, H(b)-C(5'), J=10 Hz); 4.17 (m, 1H, H—C(4'), J$_1$=5 Hz J$_2$=4.5 Hz); 4.28-4.33 (d, 1H, H—C(2'), J=4 Hz); 4.55-4.60 (dd, 1H, H(a)-C(5'), J$_1$=10 Hz, J$_2$=4.5 Hz); 5.67 (s, 1H, H—C(1')); 6.26-6.28 (d, 1H, H—C(5), J=7 Hz); 7.53-7.56 (d, 1H, H—C(6) J=7 Hz) ppm. See FIG. 6 for the associated spectra.

$^{13}$C NMR (75 MHz, CDCl$_3$): δ−4.69,-4.14 (2×CH$_3$—Si); 18.44 (CH$_2$—CN); 18.33, 20.47, 22.91 (3× C(CH$_3$)$_3$); 25.53 (CH$_2$-S); 26.04, 27.08, 27.61 (9× CH$_3$—C—Si); 67.80 (C(5'); 74.94 (C(4')); 75.33 (C(2')); 75.86 (C(3')); 94.56 (C(1')); 103.42 (C(5)); 118.20 (CN); 139.47 (C(6)); 153.28 (C(2)); 175.80 (C(4)) ppm. See FIG. 7 for the associated spectra.

To further characterize compound 3, electrospray ionization mass spectrometry was performed. The mass of C$_{26}$H$_{45}$N$_3$O$_5$SSi$_2$ was calculated to be [MH$^+$]568.27 and ESI-MS found it to be 567.95.

Synthesis of compound 4. Synthesis of 2'-O-(tert-butyldimethylsilyl)-4-(2-cyanoethylthio)-uridine (compound 4) was performed as described above and shown in FIG. 8. Following purification the process yielded 370 mg (0.87 mmol), of which 83% was as white foam. Thin Layer Chromatography was performed with a 95:5 v:v ratio of CH$_2$Cl$_2$: MeOH and was found to have a retention factor of 0.45. The identity was further confirmed by $^1$H NMR and $^{13}$C NMR with the following results:

$^1$H NMR (300 MHz, CDCl$_3$): δ 0.14 (s, 3H, H$_3$C—Si); 0.17 (s, 3H, H$_3$C—Si); 0.91 (s, 9H, (H$_3$C)$_3$—C); 2.52-2.54 (d, 1H, HO—C(3'), J=7 Hz); 2.86-2.90 (t, 2H, H$_2$C—CN); 3.12-3.13 (t, 1H, HO—C(5')) 3.39-3.42 (m, 2H, H$_2$C—S); 3.82-3.88 (dd, 1H, H(b)-C(5')) 4.02-4.06 (d, 1H, dd, 1H, H(a)-C(5')); 4.14 (m, 1H, H—C(4')); 4.20 (m, 1H, H—C (3')), 4.59-4.62 (m, 1H, H-C(2')); 5.54-5.55 (d, 1H, H—C (1'), J=3 Hz); 6.25-6.27 (d, 1H, H—C(5), J=7 Hz); 7.94-7.96 (d, 1H, H—C(6) J=7 Hz) ppm. See FIG. 9 for the associated NMR spectra.

$^{13}$C NMR (75 MHz, CDCl$_3$): δ−5.14,-4.47 (2× CH$_3$-Si); 18.14 (C(CH$_3$)$_3$); 18.39 (CH$_2$-CN); 25.55 (CH$_2$-S); 25.90 (3× CH$_3$—C—Si); 61.39 (C(5'); 69.76 (C(3')); 74.63 (C(2')); 85.43 (C(4')); 94.52 (C(1')); 103.79 (C(5)); 118.15 (CN); 142.79 (C(6)); 153.72 (C(2)); 176.24 (C(4)) ppm. See FIG. 10 for the associated NMR spectra.

To further characterize compound 4, electrospray ionization mass spectrometry was performed. The calculated mass for C$_{18}$H$_{29}$N$_3$O$_5$SSi was [MH$^-$]428.17, while the mass was actually found to be 428.03.

Synthesis of compound 5. 5'-O-(4,4'-dimethoxytrityl)-2'-O-(tert-butyldimethylsilyl)-4-(2-cyanoethylthio)-uridine was synthesized from compound 4 as described above and shown in FIG. 11. The synthesis yielded 480 mg (0.65 mmol) of compound 5, 80% of which was as white foam. Thin layer chromatography was performed on compound 5 using a mix of 1:1 v:v EtOAc:hexane and yielded a retention factor of 0.60. The identity of compound 5 was further confirmed by $^1$H NMR and $^{13}$C NMR, the results of which are listed below:

$^1$H NMR (300 MHz, CDCl$_3$): δ 0.24 (s, 3H, H$_3$C—Si); 0.37 (s, 3H, H$_3$C—Si); 0.96 (s, 9H, (H$_3$C)$_3$—C); 2.33-2.37 (d, 1H, HO—C(3'), J=10 Hz); 2.89-2.93 (t, 2H, H$_2$C—CN); 3.31-3.51 (m, 2H, H$_2$C—S); 3.60 (m, 2H, H$_2$—C(5')) 3.83 (s, 6H, H$_3$CO); 4.12 (m, 1H, H—C(4')); 4.33 (m, 1H, H—C(2')), 4.43 (m, 1H, H—C(3')); 5.75-5.78 (d, 1H, H—C (5), J=7 Hz); 5.81 (s, 1H, H—C(1')); 6.85-6.88 (m, 4H, H—C(ar)); 7.30-7.41 (m, 9H, H—C(ar)); 8.36-8.38 (d, 1H, H—C(6) J=7 Hz) ppm. The associated $^1$H NMR spectra is shown in FIG. 12.

$^{13}$C NMR (75 MHz, CDCl$_3$): δ−5.26, −4.20 (2× CH$_3$—Si); 18.22 (C(CH$_3$)$_3$); 18.48 (CH$_2$—CN); 25.45 (CH$_2$—S); 26.00 (3× CH$_3$—C—Si); 55.41 (2× OCH$_3$) 61.10 (C(5'); 68.88 (C(3')); 76.55 (C(2')); 83.27 (C(4')); 87.23 (tert-C (DMT)); 91.13 (C(1')); 103.45 (C(5)); 113.46 (C(ar)); 118.25 (CN); 127.29 (C(ar)); 128.16 (C(ar)); 128.35 (C(ar)); 130.28 (C(ar)); 130.32 (C(ar)); 135.28 (C(ar)); 135.54 (C(ar)); 141.26 (C(ar)); 144.42 (C(6)); 153.69 (C(2));

158.89 (C(ar)); 175.53 (C(4)) ppm. The associated $^{13}$C NMR spectra is shown in FIG. 13.

Compound 5 was then analyzed by mass spectrometry to confirm its identity. The expected mass for compound 5 ($C_{39}H_{47}N_3O_7SSi$) was calculated to be 730.30, and the mass was found to be 729.79 by ESI-MS.

Synthesis of compound 6. 5'-O-(4,4'-dimethoxytrityl)-2'-O-tert-butyldimethylsilyl-4-(2-cyanoethylthio)-uridine-3'-O-2-cyanoethyl-N,N-diisopropylphosphoramidite was synthesized from compound 5 as described above and shown in FIG. 14. Synthesis and purification yielded 500 mg (0.53 mmol) of product, 87% as white foam. Thin layer chromatography was performed with a 1:1 v:v ratio of EtOAc:hexane and compound 6 was shown to have a retention factor of 0.50. To confirm its identity, compound 6 was analyzed by $^1$H and $^{31}$P NMR. The results are listed below:

$^1$H NMR (300 MHz, CDCl$_3$): δ 0.19 (s, 3H, H$_3$C—Si); 0.31 (s, 3H, H$_3$C—Si); 0.94 (s, 9H, (H$_3$C)$_3$—C); 0.98-1.15 (m, 12H, 2× (H$_3$C)$_2$CHN); 2.44-2.61 (m, 2H, H$_2$C—CN(a)); 2.91 (m, 2H, H$_2$C—CN(b)); 3.39 (m, 2H, H$_2$C—S); 3.55 (m, 4H, H$_2$-C(5') +2× (H$_3$C)$_2$CHN); 3.73 (m, 2H, H$_2$C—O); 3.83 (s, 6H, H$_3$CO); 4.38 (m, 3H, H—C(4') +H—C(2') +H—C(3')); 5.60-5.73 (d, 1H, H-C(5)); 5.75-5.82 (s, 1H, H—C(1')); 6.86-6.88 (m, 4H, H—C(ar)); 7.29-7.45 (m, 9H, H—C(ar)); 8.35-8.43 (d, 1H, H—C(6)) ppm. The associated NMR spectra is shown in FIG. 15

$^{31}$P NMR (121 MHz, CDCl$_3$): δ 149.34, 151.48 ppm. The associated NMR spectra is shown in FIG. 16.

Finally, the identity of compound 6 was confirmed by mass spectrometry. The mass of $C_{48}H_{64}N_5O_8PSSi$ was calculated to be 930.40, and found by ESI-MS to be 929.92.

Example 3

Development of TUC-Seq

Figure 17:
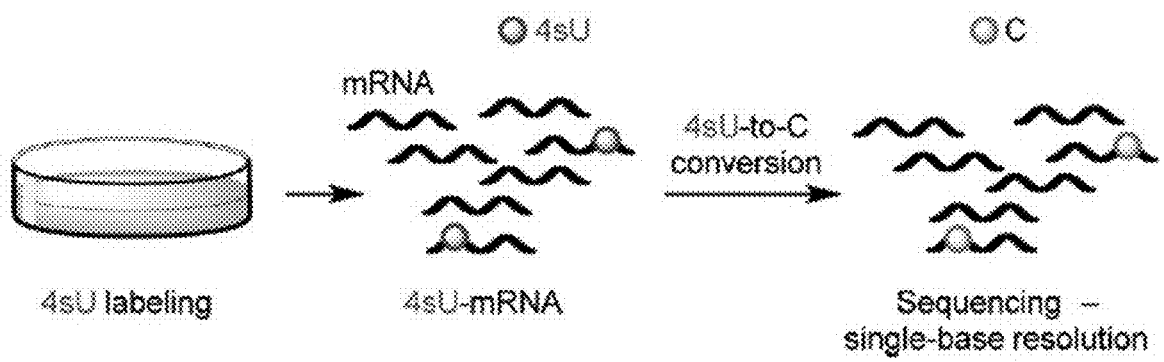
FIG. 17: Schematic of labelling and analysis of 4sU treated RNA. Cells are treated with 4sU and total RNA is isolated. RNA transcribed during treatment will be 4sU labeled, whereas previously transcribed RNA will be unlabeled. Total RNA (unlabeled and 4sU-labeled) is then chemically treated with OsO$_4$/NH$_4$Cl to convert 4sU into C, and subjected to RNA sequencing to achieve single molecule resolution for comparative sequence analysis.

Given the difficulties associated with modern RNA profiling using metabolic labelling techniques, the inventors sought to eliminate the need for tag-based separation of labeled and unlabeled RNA and allow direct distinction from both species by sequencing by utilizing thiouridine conversion to cytosine by OsO$_4$ followed by sequencing (TUC-seq). The conversion of thiouridine to cytidine at the nucleoside level by OsO$_4$ and aqueous ammonia has previously been described (Burton, 1967). However, its potential for modern sequencing techniques had not been explored. Therefore, it was investigated whether OsO$_4$ treatment of 4sU-containing RNA can be used as key reaction for a comparative sequencing approach. In untreated RNA, 4sU would be read as T, while for OsO$_4$ treated RNA, 4sU should be read as C (FIG. 17).

Considering that during metabolic labeling 4sU is randomly and sparsely incorporated into nascent RNA, the conversion reaction has to be highly efficient to ensure sufficient sensitivity upon sequencing. Thus, reaction conditions were first established allowing optimal conversion coupled to low RNA degradation using a short oligoribonucleotide. Oligonucleotides were thus synthesized with a mixture of commercially available 2'-O-TOM RNA phosphoramidites as well as the 4sU phosphoramidite building block compound 6, synthesized in Example 2 (5'-O-(4,4'-dimethoxytrityl)-2'-O-tert-butyldimethylsilyl-4-(2-cyanoethylthio)-uridine-3'-O-2-cyanoethyl-N,N-diisopropylphosphoramidite), using standard automated synthesis methods.

Figure 18:
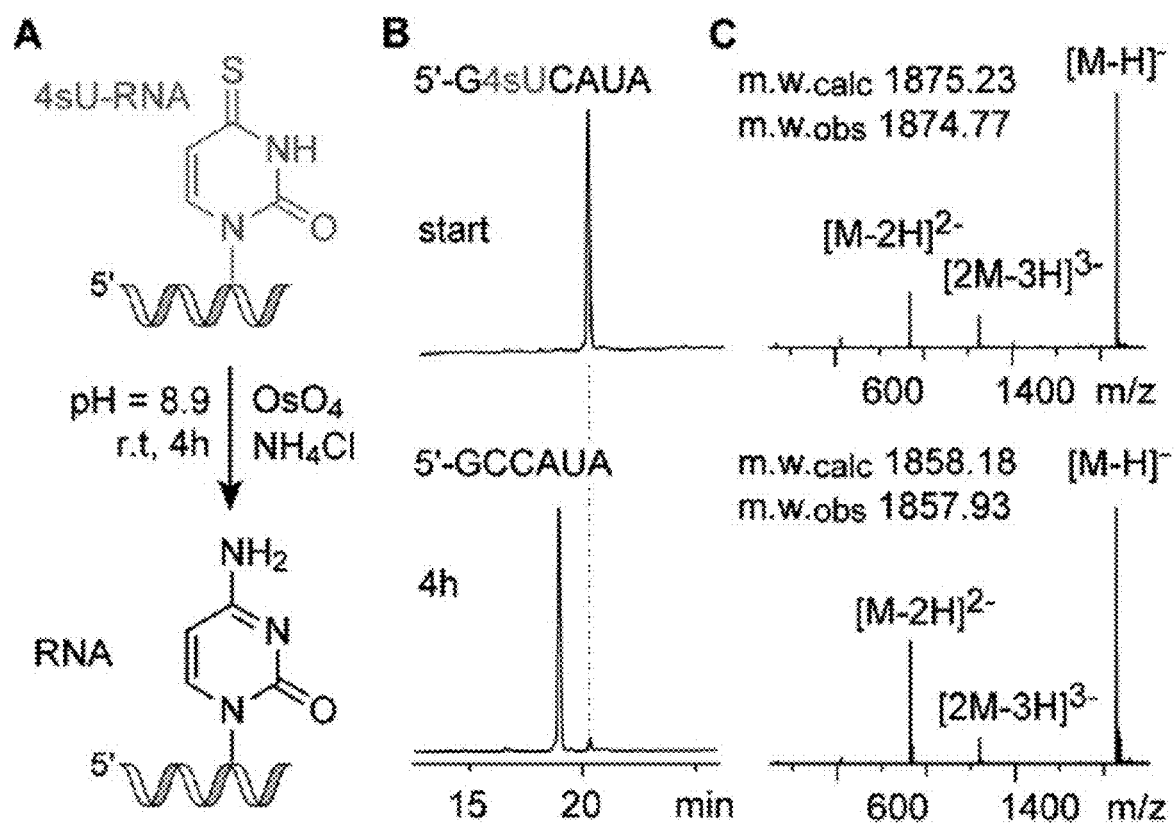
FIG. 18: Transformation of 4-thiouridine to cytidine in short RNA. (A) Chemical structures of 4sU-labeled and converted RNA; reaction conditions as indicated. (B) Anion exchange chromatography trace depicting conversion of 4sU-labeled RNA by OsO$_4$/NH$_4$Cl. (C) Verification of the molecular weights of starting material and product RNA by LC-ESI mass spectrometry.
Figure 19:
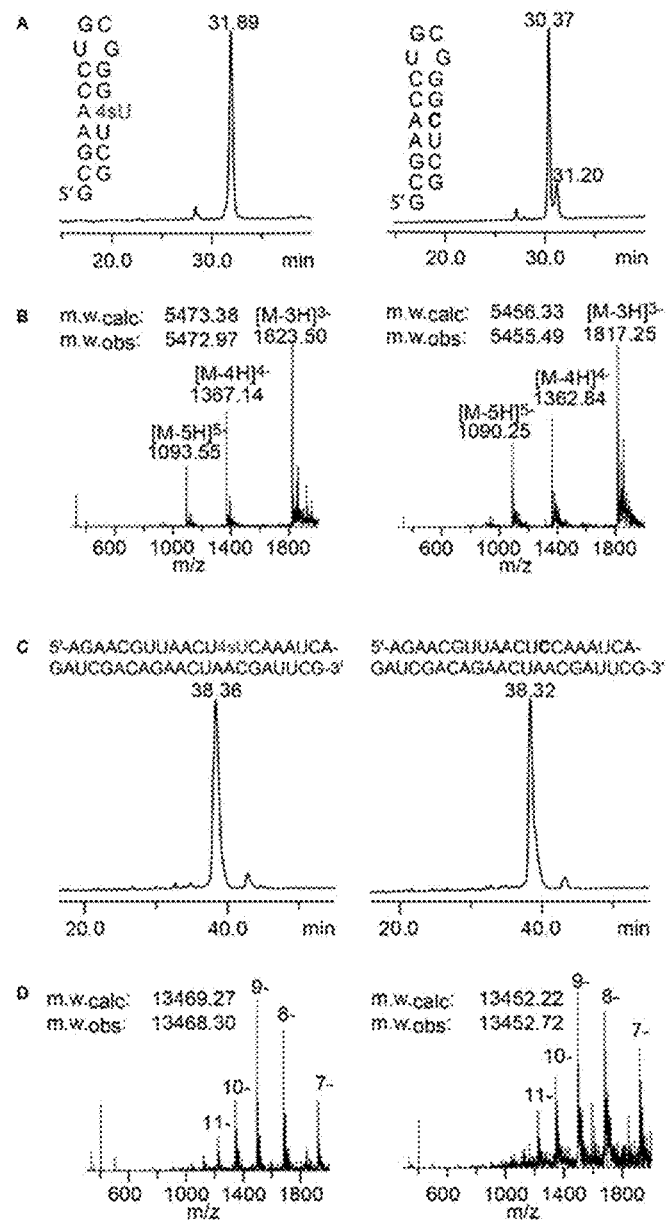
FIG. 19: Anion exchange traces and LC-ESI mass spectra of 17 nt hairpin and 42 nt oligonucleotides. (A) Anion exchange chromatograms of a 17 nt hairpin oligoribonucleotide (5'-GCGAACCUGCGGG(4sU)UCG-3' (SEQ ID NO: 25) before (left) and after (right) treatment with OsO4 (450 µM) in ammonium chloride buffer (180 mM). (B) LC-ESI mass spectra of the corresponding 17 nt hairpin oligoribonucleotide prior (left) and after (right) conversion. (C) Anion exchange chromatograms of a 42 nt oligoribonucleotide (5'-AGAACGUUAACU(4sU)C-AAAUCAGAUCGACA-GAACUAACGAUUCG-3' (SEQ ID NO: 26)) prior (left) and after (right; 5'-AGAACGUUAACUCC-AAAU-CAGAUCGACAGAACUAACGAUUCG-3' (SEQ ID NO: 27)) treatment with OsO$_4$ (450 µM) in ammonium chloride buffer (180 mM). (D) LC-ESI mass spectra of the corresponding 42 nt oligoribonucleotide prior (left) and after (right) conversion.

Treatment of chemically synthesized 5'-G4sUCAUA with a modestly basic aqueous solution of osmium tetroxide and ammonium chloride for four hours at room temperature resulted in nearly quantitative 4sU-to-C conversion (>98%) without degradation of the RNA (FIGS. 18A-18B). The corresponding molecular weights of starting material and product RNA were confirmed by LC-ESI mass spectrometry (FIG. 18C). Almost the same reaction efficiency was obtained using larger (chemically synthesized) 4sU-containing RNAs with up to 42 nt (FIG. 19).

Figure 20:
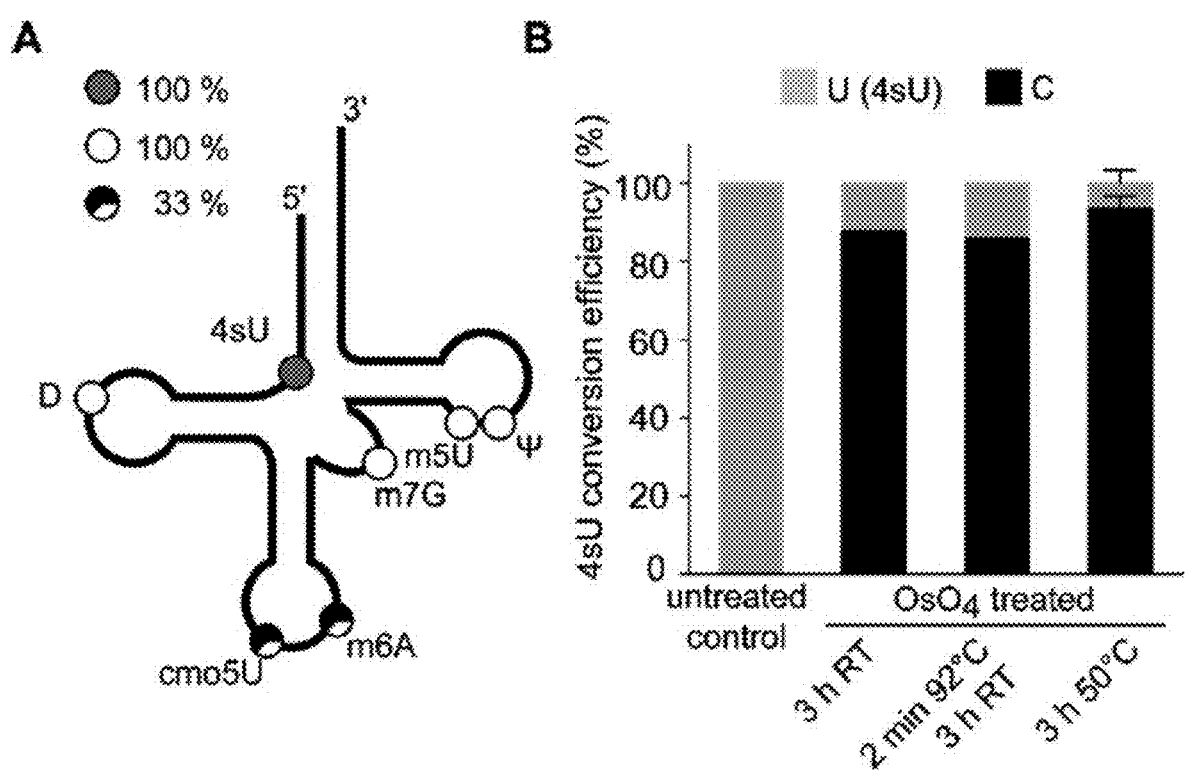
FIG. 20: Detection of natural 4-thiouridine on E. coli tRNA$^{Val}$. (A) Schematic depiction of the tRNA$^{Val}$ secondary structure. Known modifications are shown as circles and the degree of modification is symbolized by color as indicated in the figure legend. 4sU, 4-thiouridine, ψ, pseudouridine; m$^5$U, 5-methyluridine, m$^7$G, 7-methylguanosine; m$^6$A, N$^6$-methyladenosine, cmo5U, uridine 5-oxyacetic acid, D, dihydrouridine. (B) Quantification of 4sU (gray) and C (black) bases at tRNA position 8 in sequencing products of tRNA$^{Val}$ (n=10; mean and SEM values of three independent experiments are shown for the 3 h/50° C. condition). Samples were either untreated or subjected to the indicated reaction conditions.

The performance of the method was then tested on a complex mixture of natural RNA. While 4sU has not yet been detected in eukaryotic species, it is well established that in bacteria, the uridine at either position 8 or 9 of several tRNAs (Čavužić and Liu, 2017) is fully thiolated (FIG. 20A). Therefore, total RNA was isolated from E. coli and subjected to three different OsO$_4$-reaction conditions (FIG. 20B). Using a stem loop primer, tRNA$^{Val}$ was specifically reverse transcribed and amplified by polymerase chain reaction (PCR). The amplification products were subcloned, and a set of 10 clones for each condition was sequenced. These experiments revealed 93% 4sU-to-C conversion efficiency of the naturally occurring 4sU in tRNA$^{Val}$ when treated with OsO$_4$ at room temperature, independent of prior RNA denaturation at 92° C. for 2 minutes. However, when the reaction temperature was increased to 50° C. nearly quantitative conversion was observed (FIG. 20B).

Figure 21:
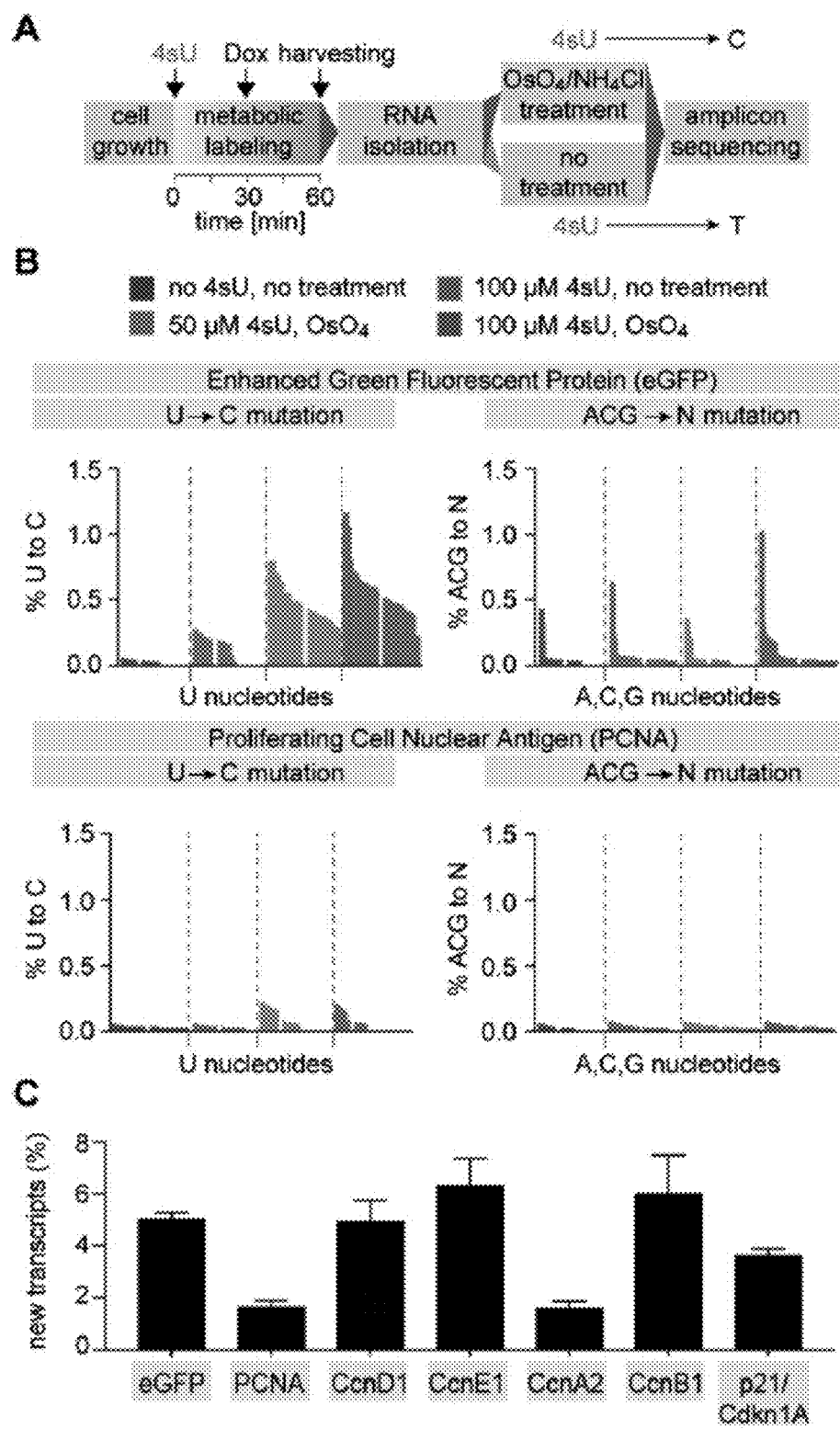
FIG. 21: TUC-seq allows for efficient detection of new transcripts in pulse-labeled samples. (A) Schematic of experimental design. Briefly, eGFP-inducible cells were grown, and treated for 1 hour with 4sU. 30 min into the 4sU treatment, eGFP expression was induced by treatment with doxycycline. The cells were then harvested after completion of the 4sU and doxycycline treatment. (B) Graphs on the left: U-to-C mutation frequencies for individual U positions in amplicon sequencing reads of the indicated transcripts. Each U position for which a C exchange was observed is shown as vertical line and the four different labeling conditions (see legend) were combined into one graph. Because labeling occurs randomly, there are different numbers of lines present in the different conditions. Converted Us are ordered according to their mutation frequency in a descending manner. Graphs on the right: Background mutation frequencies of A, C and G into any nucleotide (ACG-to-N) are shown in the same manner as described for the graphs on the left. Median mutation frequencies are indicated as white lines. (C) Relative contribution of labeled transcripts to the total pool of the indicated transcripts. Values were corrected for random mutation using values derived from the unlabeled (no 4sU, no OsO$_4$) sample. Mean values +/− SEM of three biological replicates are shown.

These results show that OsO$_4$/NH$_4$Cl is suitable to react on 4sU in complex RNA mixtures, and that it can be used for the detection and identification of naturally occurring 4sU sites in bacterial RNA in combination with sequencing techniques. Next, the potential of OsO$_4$/NH$_4$Cl for selective detection of transcripts metabolically labeled by 4sU in eukaryotic cells was investigated. To this end, HEK293 cells were incubated for 1 h with 4sU (50 μM or 100 μM) or without 4sU before harvesting the cells, isolation and OsO$_4$ treatment of total RNA (FIG. 4A). A cell line that bears a stable integration of an inducible enhanced green fluorescence protein (eGFP) gene was used, so eGFP transcription was activated by addition of doxycycline (Dox) 30 minutes after the start of labeling. To determine the relative amount of newly synthesized (and thus labeled) mRNA, transcripts of eGFP as well as of six endogenous target genes were amplified by PCR from OsO$_4$-treated and untreated RNA samples and subjected to amplicon sequencing using the Illumina platform (FIG. 21A). For each individual target, coverage of approximately 52000-251000 reads was obtained.

Next, the frequency of U-to-C conversion for every possible U for the unlabeled, the 4sU-labeled, and the 4sU-labeled/OsO4-treated samples was determined (Tables 2-5). The mutation frequencies of A, C and G into any base (N) were also calculated to determine the background mutation rate, which may be caused by polymerase errors introduced during reverse transcription, PCR or sequencing (Tables 6-9).

TABLE 2

T-to-C mutation frequencies in amplicon sequences: no 4sU labeling, no OsO$_4$//NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| A2_CcnA2 | 354 | T | C | 97645 | 42 | 0.04% | 1.74E−06 | 39 | 38 |
| A2_CcnA2 | 365 | T | C | 97123 | 37 | 0.04% | 1.09E−07 | 39 | 37 |
| A2_CcnA2 | 93 | T | C | 105004 | 33 | 0.03% | 3.01E−10 | 40 | 39 |
| A2_CcnA2 | 94 | T | C | 104661 | 24 | 0.02% | 2.25E−13 | 40 | 39 |
| A2_CcnA2 | 116 | T | C | 96910 | 19 | 0.02% | 7.12E−14 | 39 | 36 |
| A2_CcnA2 | 120 | T | C | 95399 | 15 | 0.02% | 1.05E−15 | 39 | 35 |
| A2_CcnA2 | 139 | T | C | 96387 | 15 | 0.02% | 6.08E−16 | 39 | 38 |
| A2_CcnA2 | 124 | T | C | 96369 | 11 | 0.01% | 2.11E−18 | 39 | 38 |
| A2_CcnA2 | 125 | T | C | 97287 | 10 | 0.01% | 2.36E−19 | 39 | 39 |
| A2_CcnA2 | 143 | T | C | 94210 | 13 | 0.01% | 1.27E−16 | 39 | 37 |
| A2_CcnA2 | 324 | T | C | 86974 | 13 | 0.01% | 1.13E−14 | 39 | 36 |
| B1_CcnB1 | 366 | T | C | 99994 | 45 | 0.04% | 2.84E−06 | 40 | 39 |
| B1_CcnB1 | 376 | T | C | 99730 | 35 | 0.04% | 1.43E−08 | 40 | 38 |
| B1_CcnB1 | 354 | T | C | 98147 | 27 | 0.03% | 5.82E−11 | 39 | 37 |
| B1_CcnB1 | 368 | T | C | 100799 | 32 | 0.03% | 1.20E−09 | 40 | 38 |
| B1_CcnB1 | 38 | T | C | 104632 | 22 | 0.02% | 2.99E−14 | 40 | 39 |
| B1_CcnB1 | 98 | T | C | 98238 | 15 | 0.02% | 2.01E−16 | 39 | 39 |
| B1_CcnB1 | 129 | T | C | 96353 | 16 | 0.02% | 2.15E−15 | 39 | 37 |
| B1_CcnB1 | 345 | T | C | 97628 | 19 | 0.02% | 4.25E−14 | 39 | 39 |
| B1_CcnB1 | 346 | T | C | 94406 | 17 | 0.02% | 2.10E−14 | 39 | 38 |
| B1_CcnB1 | 351 | T | C | 99013 | 15 | 0.02% | 1.16E−16 | 39 | 39 |
| B1_CcnB1 | 353 | T | C | 97933 | 15 | 0.02% | 3.50E−16 | 39 | 39 |
| B1_CcnB1 | 372 | T | C | 100291 | 19 | 0.02% | 8.93E−15 | 40 | 38 |
| B1_CcnB1 | 373 | T | C | 101273 | 16 | 0.02% | 1.41E−16 | 40 | 39 |
| B1_CcnB1 | 421 | T | C | 101552 | 19 | 0.02% | 5.29E−15 | 40 | 40 |
| B1_CcnB1 | 20 | T | C | 104930 | 11 | 0.01% | 1.87E−20 | 40 | 39 |
| B1_CcnB1 | 42 | T | C | 106563 | 12 | 0.01% | 2.83E−20 | 40 | 40 |
| B1_CcnB1 | 92 | T | C | 103878 | 14 | 0.01% | 3.13E−18 | 40 | 40 |
| B1_CcnB1 | 108 | T | C | 87438 | 11 | 0.01% | 3.97E−16 | 38 | 37 |
| B1_CcnB1 | 123 | T | C | 97722 | 12 | 0.01% | 5.39E−18 | 39 | 39 |
| B1_CcnB1 | 137 | T | C | 89863 | 10 | 0.01% | 2.71E−17 | 39 | 39 |
| B1_CcnB1 | 332 | T | C | 92940 | 12 | 0.01% | 9.60E−17 | 39 | 37 |
| B1_CcnB1 | 334 | T | C | 93576 | 12 | 0.01% | 5.41E−17 | 39 | 38 |
| B1_CcnB1 | 405 | T | C | 100977 | 15 | 0.01% | 6.64E−17 | 40 | 37 |
| B1_CcnB1 | 422 | T | C | 99324 | 11 | 0.01% | 3.61E−19 | 40 | 40 |
| D1_CcnD1 | 41 | T | C | 143163 | 64 | 0.04% | 2.02E−08 | 40 | 38 |
| D1_CcnD1 | 61 | T | C | 138579 | 50 | 0.04% | 4.99E−11 | 40 | 39 |
| D1_CcnD1 | 104 | T | C | 66194 | 25 | 0.04% | 1.01E−05 | 35 | 36 |
| D1_CcnD1 | 311 | T | C | 132200 | 55 | 0.04% | 8.58E−09 | 40 | 38 |
| D1_CcnD1 | 126 | T | C | 112432 | 34 | 0.03% | 3.17E−11 | 38 | 37 |
| D1_CcnD1 | 99 | T | C | 67967 | 11 | 0.02% | 3.02E−11 | 34 | 35 |
| D1_CcnD1 | 106 | T | C | 88115 | 13 | 0.01% | 3.70E−15 | 35 | 39 |
| D1_CcnD1 | 107 | T | C | 106989 | 13 | 0.01% | 7.33E−20 | 36 | 36 |
| D1_CcnD1 | 283 | T | C | 122566 | 13 | 0.01% | 1.10E−23 | 39 | 39 |
| D1_CcnD1 | 386 | T | C | 138232 | 17 | 0.01% | 4.72E−25 | 40 | 37 |
| D1_CcnE1 | 43 | T | C | 47494 | 18 | 0.04% | 2.10E−04 | 40 | 39 |
| D1_CcnE1 | 47 | T | C | 46786 | 19 | 0.04% | 5.43E−04 | 40 | 40 |
| D1_CcnE1 | 86 | T | C | 45453 | 19 | 0.04% | 7.78E−04 | 39 | 39 |
| D1_CcnE1 | 95 | T | C | 46667 | 21 | 0.04% | 1.53E−03 | 40 | 40 |
| D1_CcnE1 | 101 | T | C | 44458 | 17 | 0.04% | 3.63E−04 | 39 | 40 |
| D1_CcnE1 | 102 | T | C | 43883 | 18 | 0.04% | 9.31E−04 | 39 | 37 |
| D1_CcnE1 | 107 | T | C | 45371 | 17 | 0.04% | 2.47E−04 | 39 | 39 |
| D1_CcnE1 | 116 | T | C | 39871 | 14 | 0.04% | 4.00E−04 | 39 | 39 |
| D1_CcnE1 | 351 | T | C | 32357 | 12 | 0.04% | 1.82E−03 | 37 | 38 |
| D1_CcnE1 | 48 | T | C | 47602 | 13 | 0.03% | 6.04E−06 | 40 | 40 |
| D1_CcnE1 | 82 | T | C | 44089 | 14 | 0.03% | 5.00E−05 | 39 | 39 |
| D1_CcnE1 | 104 | T | C | 45902 | 12 | 0.03% | 6.53E−06 | 39 | 38 |
| D1_CcnE1 | 109 | T | C | 44500 | 13 | 0.03% | 2.34E−05 | 39 | 37 |
| D1_CcnE1 | 143 | T | C | 29182 | 9 | 0.03% | 8.26E−04 | 37 | 38 |
| D1_CcnE1 | 346 | T | C | 35781 | 9 | 0.03% | 5.28E−05 | 37 | 37 |
| D1_CcnE1 | 354 | T | C | 29441 | 9 | 0.03% | 8.26E−04 | 36 | 35 |
| D1_CcnE1 | 368 | T | C | 39236 | 12 | 0.03% | 9.86E−05 | 38 | 38 |
| D1_CcnE1 | 22 | T | C | 48674 | 8 | 0.02% | 2.33E−08 | 40 | 41 |
| D1_CcnE1 | 42 | T | C | 47953 | 8 | 0.02% | 4.00E−08 | 40 | 41 |
| D1_CcnE1 | 52 | T | C | 47704 | 10 | 0.02% | 3.73E−07 | 40 | 40 |
| D1_CcnE1 | 79 | T | C | 46109 | 8 | 0.02% | 6.87E−08 | 39 | 38 |
| D1_CcnE1 | 81 | T | C | 43413 | 8 | 0.02% | 3.41E−07 | 39 | 38 |
| D1_CcnE1 | 84 | T | C | 43681 | 9 | 0.02% | 1.01E−06 | 39 | 39 |
| D1_CcnE1 | 340 | T | C | 35925 | 6 | 0.02% | 2.42E−06 | 37 | 36 |
| D1_CcnE1 | 357 | T | C | 34449 | 8 | 0.02% | 3.42E−05 | 37 | 36 |
| D1_CcnE1 | 362 | T | C | 29709 | 6 | 0.02% | 5.82E−05 | 37 | 38 |
| D1_CcnE1 | 363 | T | C | 32144 | 5 | 0.02% | 3.69E−06 | 37 | 36 |
| D1_CcnE1 | 372 | T | C | 37340 | 9 | 0.02% | 2.02E−05 | 38 | 39 |
| D1_CcnE1 | 385 | T | C | 42093 | 7 | 0.02% | 1.80E−07 | 39 | 38 |
| D1_CcnE1 | 431 | T | C | 44046 | 9 | 0.02% | 6.06E−07 | 39 | 38 |
| D1_CcnE1 | 341 | T | C | 35495 | 4 | 0.01% | 1.67E−07 | 37 | 40 |

TABLE 2-continued

T-to-C mutation frequencies in amplicon sequences: no 4sU labeling, no OsO$_4$//NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| D1_CcnE1 | 343 | T | C | 37320 | 4 | 0.01% | 5.09E−08 | 37 | 35 |
| D1_CcnE1 | 344 | T | C | 35661 | 4 | 0.01% | 1.67E−07 | 37 | 36 |
| D1_CcnE1 | 347 | T | C | 33912 | 5 | 0.01% | 2.12E−06 | 37 | 40 |
| D1_CcnE1 | 367 | T | C | 36379 | 4 | 0.01% | 9.22E−08 | 38 | 38 |
| D1_CcnE1 | 398 | T | C | 40380 | 5 | 0.01% | 3.91E−08 | 39 | 40 |
| D1_CcnE1 | 423 | T | C | 44000 | 6 | 0.01% | 1.61E−08 | 40 | 39 |
| D1_CcnE1 | 438 | T | C | 44033 | 6 | 0.01% | 1.61E−08 | 40 | 38 |
| D1_CcnE1 | 444 | T | C | 44519 | 5 | 0.01% | 3.77E−09 | 40 | 40 |
| eGFP | 118 | T | C | 36381 | 14 | 0.04% | 1.30E−03 | 38 | 34 |
| eGFP | 67 | T | C | 45272 | 13 | 0.03% | 1.50E−05 | 40 | 39 |
| eGFP | 133 | T | C | 35408 | 9 | 0.03% | 5.28E−05 | 37 | 39 |
| eGFP | 313 | T | C | 31574 | 10 | 0.03% | 7.23E−04 | 38 | 37 |
| eGFP | 46 | T | C | 40008 | 9 | 0.02% | 4.60E−06 | 39 | 39 |
| eGFP | 51 | T | C | 44054 | 7 | 0.02% | 6.01E−08 | 39 | 39 |
| eGFP | 79 | T | C | 41800 | 8 | 0.02% | 9.76E−07 | 39 | 38 |
| eGFP | 85 | T | C | 43715 | 7 | 0.02% | 1.04E−07 | 39 | 37 |
| eGFP | 100 | T | C | 40315 | 10 | 0.02% | 1.19E−05 | 38 | 38 |
| eGFP | 324 | T | C | 28773 | 7 | 0.02% | 2.53E−04 | 37 | 39 |
| eGFP | 27 | T | C | 46537 | 5 | 0.01% | 1.15E−09 | 40 | 41 |
| eGFP | 52 | T | C | 45015 | 5 | 0.01% | 2.09E−09 | 39 | 39 |
| eGFP | 99 | T | C | 42819 | 5 | 0.01% | 1.22E−08 | 39 | 41 |
| eGFP | 359 | T | C | 38681 | 4 | 0.01% | 2.81E−08 | 39 | 38 |
| eGFP | 364 | T | C | 38473 | 4 | 0.01% | 2.81E−08 | 39 | 41 |
| eGFP | 370 | T | C | 39262 | 5 | 0.01% | 6.98E−08 | 39 | 37 |
| p21_Cdkn1A | 436 | T | C | 87133 | 49 | 0.06% | 7.06E−04 | 40 | 40 |
| p21_Cdkn1A | 51 | T | C | 81808 | 37 | 0.05% | 3.13E−05 | 40 | 40 |
| p21_Cdkn1A | 131 | T | C | 58885 | 30 | 0.05% | 1.87E−03 | 37 | 38 |
| p21_Cdkn1A | 378 | T | C | 74983 | 34 | 0.05% | 5.33E−05 | 39 | 37 |
| p21_Cdkn1A | 23 | T | C | 82214 | 32 | 0.04% | 1.56E−06 | 40 | 40 |
| p21_Cdkn1A | 2 | T | C | 84308 | 25 | 0.03% | 6.02E−09 | 40 | 40 |
| p21_Cdkn1A | 132 | T | C | 57163 | 15 | 0.03% | 3.25E−07 | 37 | 39 |
| p21_Cdkn1A | 349 | T | C | 73510 | 20 | 0.03% | 1.45E−08 | 38 | 36 |
| p21_Cdkn1A | 369 | T | C | 81833 | 22 | 0.03% | 2.01E−09 | 39 | 40 |
| p21_Cdkn1A | 385 | T | C | 78910 | 23 | 0.03% | 1.76E−08 | 39 | 37 |
| p21_Cdkn1A | 76 | T | C | 77855 | 12 | 0.02% | 4.46E−13 | 39 | 39 |
| p21_Cdkn1A | 121 | T | C | 55647 | 12 | 0.02% | 5.09E−08 | 37 | 37 |
| p21_Cdkn1A | 356 | T | C | 70015 | 16 | 0.02% | 1.59E−09 | 38 | 37 |
| p21_Cdkn1A | 361 | T | C | 66670 | 13 | 0.02% | 5.33E−10 | 38 | 36 |
| p21_Cdkn1A | 431 | T | C | 86563 | 21 | 0.02% | 7.91E−11 | 40 | 41 |
| p21_Cdkn1A | 7 | T | C | 74042 | 10 | 0.01% | 1.62E−13 | 37 | 32 |
| p21_Cdkn1A | 45 | T | C | 61090 | 7 | 0.01% | 3.65E−12 | 37 | 36 |
| PCNA | 126 | T | C | 103199 | 40 | 0.04% | 6.80E−08 | 39 | 39 |
| PCNA | 112 | T | C | 99076 | 28 | 0.03% | 8.48E−11 | 39 | 39 |
| PCNA | 116 | T | C | 103463 | 30 | 0.03% | 7.17E−11 | 39 | 38 |
| PCNA | 136 | T | C | 95072 | 28 | 0.03% | 5.02E−10 | 38 | 38 |
| PCNA | 348 | T | C | 87785 | 30 | 0.03% | 6.35E−08 | 38 | 37 |
| PCNA | 370 | T | C | 98752 | 30 | 0.03% | 6.38E−10 | 39 | 38 |
| PCNA | 33 | T | C | 114580 | 21 | 0.02% | 5.69E−17 | 40 | 40 |
| PCNA | 38 | T | C | 102223 | 17 | 0.02% | 2.88E−16 | 39 | 39 |
| PCNA | 42 | T | C | 109652 | 23 | 0.02% | 6.82E−15 | 40 | 40 |
| PCNA | 46 | T | C | 105589 | 18 | 0.02% | 1.95E−16 | 39 | 40 |
| PCNA | 47 | T | C | 108207 | 24 | 0.02% | 3.14E−14 | 40 | 39 |
| PCNA | 48 | T | C | 110748 | 20 | 0.02% | 1.47E−16 | 40 | 39 |
| PCNA | 52 | T | C | 114819 | 24 | 0.02% | 1.56E−15 | 40 | 39 |
| PCNA | 64 | T | C | 110537 | 22 | 0.02% | 1.41E−15 | 40 | 38 |
| PCNA | 69 | T | C | 114509 | 22 | 0.02% | 1.78E−16 | 40 | 40 |
| PCNA | 70 | T | C | 111730 | 21 | 0.02% | 2.75E−16 | 40 | 40 |
| PCNA | 91 | T | C | 107755 | 18 | 0.02% | 6.63E−17 | 40 | 40 |
| PCNA | 93 | T | C | 105087 | 16 | 0.02% | 1.55E−17 | 39 | 40 |
| PCNA | 102 | T | C | 109555 | 25 | 0.02% | 5.18E−14 | 40 | 39 |
| PCNA | 106 | T | C | 105851 | 23 | 0.02% | 5.08E−14 | 39 | 39 |
| PCNA | 107 | T | C | 102835 | 20 | 0.02% | 9.66E−15 | 39 | 39 |
| PCNA | 118 | T | C | 107257 | 20 | 0.02% | 7.14E−16 | 39 | 40 |
| PCNA | 124 | T | C | 103079 | 21 | 0.02% | 1.72E−14 | 40 | 40 |
| PCNA | 128 | T | C | 104477 | 21 | 0.02% | 1.03E−14 | 39 | 39 |
| PCNA | 138 | T | C | 92980 | 16 | 0.02% | 1.86E−14 | 39 | 38 |
| PCNA | 326 | T | C | 80293 | 20 | 0.02% | 5.52E−10 | 37 | 35 |
| PCNA | 343 | T | C | 83826 | 14 | 0.02% | 2.08E−13 | 38 | 38 |
| PCNA | 352 | T | C | 91224 | 15 | 0.02% | 9.37E−15 | 39 | 38 |
| PCNA | 390 | T | C | 103227 | 20 | 0.02% | 5.75E−15 | 40 | 40 |
| PCNA | 434 | T | C | 105928 | 19 | 0.02% | 6.43E−16 | 40 | 39 |
| PCNA | 437 | T | C | 105516 | 19 | 0.02% | 6.43E−16 | 40 | 40 |
| PCNA | 26 | T | C | 112747 | 15 | 0.01% | 7.73E−20 | 40 | 40 |
| PCNA | 28 | T | C | 113841 | 17 | 0.01% | 6.88E−19 | 40 | 40 |
| PCNA | 39 | T | C | 104471 | 14 | 0.01% | 1.77E−18 | 39 | 39 |
| PCNA | 55 | T | C | 110168 | 13 | 0.01% | 1.28E−20 | 40 | 39 |

TABLE 2-continued

T-to-C mutation frequencies in amplicon sequences: no 4sU labeling, no $OsO_4//NH_4Cl$ treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| PCNA | 63 | T | C | 111330 | 16 | 0.01% | 5.48E−19 | 40 | 40 |
| PCNA | 83 | T | C | 90734 | 13 | 0.01% | 1.21E−15 | 38 | 38 |
| PCNA | 89 | T | C | 107922 | 16 | 0.01% | 5.12E−18 | 40 | 40 |
| PCNA | 96 | T | C | 107468 | 16 | 0.01% | 5.12E−18 | 39 | 38 |
| PCNA | 109 | T | C | 106905 | 16 | 0.01% | 8.92E−18 | 39 | 39 |
| PCNA | 117 | T | C | 107868 | 16 | 0.01% | 5.12E−18 | 39 | 39 |
| PCNA | 331 | T | C | 89871 | 11 | 0.01% | 1.25E−16 | 38 | 40 |
| PCNA | 350 | T | C | 91070 | 11 | 0.01% | 3.91E−17 | 38 | 39 |
| PCNA | 360 | T | C | 99533 | 12 | 0.01% | 1.69E−18 | 39 | 39 |
| PCNA | 384 | T | C | 99177 | 11 | 0.01% | 3.61E−19 | 39 | 40 |
| PCNA | 393 | T | C | 103543 | 12 | 0.01% | 1.64E−19 | 40 | 39 |
| PCNA | 401 | T | C | 105686 | 12 | 0.01% | 5.09E−20 | 40 | 40 |
| PCNA | 415 | T | C | 104562 | 11 | 0.01% | 1.87E−20 | 40 | 40 |
| PCNA | 417 | T | C | 104499 | 12 | 0.01% | 9.15E−20 | 40 | 40 |
| PCNA | 442 | T | C | 104153 | 12 | 0.01% | 9.15E−20 | 40 | 40 |

TABLE 3

T-to-C mutation frequencies in amplicon sequences: 100 µM 4sU labeling, no $OsO_4/NH_4Cl$ treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| A2_CcnA2 | 40 | T | C | 88036 | 41 | 0.05% | 2.12E−05 | 40 | 36 |
| A2_CcnA2 | 93 | T | C | 89154 | 34 | 0.04% | 3.68E−07 | 40 | 40 |
| A2_CcnA2 | 352 | T | C | 75045 | 33 | 0.04% | 3.26E−05 | 40 | 38 |
| A2_CcnA2 | 359 | T | C | 62237 | 25 | 0.04% | 4.51E−05 | 38 | 35 |
| A2_CcnA2 | 342 | T | C | 68133 | 20 | 0.03% | 1.37E−07 | 38 | 37 |
| A2_CcnA2 | 365 | T | C | 73956 | 21 | 0.03% | 3.30E−08 | 39 | 38 |
| A2_CcnA2 | 376 | T | C | 74266 | 23 | 0.03% | 1.00E−07 | 39 | 39 |
| A2_CcnA2 | 33 | T | C | 91015 | 16 | 0.02% | 3.18E−14 | 40 | 39 |
| A2_CcnA2 | 36 | T | C | 89460 | 18 | 0.02% | 8.78E−13 | 39 | 38 |
| A2_CcnA2 | 72 | T | C | 83802 | 16 | 0.02% | 2.17E−12 | 39 | 40 |
| A2_CcnA2 | 78 | T | C | 86326 | 14 | 0.02% | 4.08E−14 | 39 | 39 |
| A2_CcnA2 | 94 | T | C | 89109 | 17 | 0.02% | 2.91E−13 | 40 | 40 |
| A2_CcnA2 | 96 | T | C | 90909 | 15 | 0.02% | 1.61E−14 | 40 | 40 |
| A2_CcnA2 | 139 | T | C | 85240 | 15 | 0.02% | 2.38E−13 | 39 | 37 |
| A2_CcnA2 | 366 | T | C | 76307 | 13 | 0.02% | 2.69E−12 | 40 | 38 |
| A2_CcnA2 | 56 | T | C | 88434 | 9 | 0.01% | 9.85E−18 | 39 | 40 |
| A2_CcnA2 | 57 | T | C | 89303 | 9 | 0.01% | 5.41E−18 | 40 | 39 |
| A2_CcnA2 | 74 | T | C | 87274 | 10 | 0.01% | 8.79E−17 | 40 | 40 |
| A2_CcnA2 | 79 | T | C | 89354 | 9 | 0.01% | 5.41E−18 | 40 | 40 |
| A2_CcnA2 | 126 | T | C | 85318 | 9 | 0.01% | 5.89E−17 | 39 | 38 |
| A2_CcnA2 | 330 | T | C | 61303 | 9 | 0.01% | 6.35E−11 | 38 | 39 |
| A2_CcnA2 | 441 | T | C | 79780 | 8 | 0.01% | 4.12E−16 | 40 | 38 |
| B1_CncB1 | 29 | T | C | 153316 | 98 | 0.06% | 3.11E−04 | 40 | 39 |
| B1_CncB1 | 38 | T | C | 151977 | 92 | 0.06% | 7.35E−05 | 40 | 39 |
| B1_CncB1 | 43 | T | C | 154533 | 90 | 0.06% | 2.49E−05 | 40 | 40 |
| B1_CncB1 | 117 | T | C | 147433 | 86 | 0.06% | 3.86E−05 | 39 | 39 |
| B1_CncB1 | 368 | T | C | 137933 | 76 | 0.06% | 1.34E−05 | 39 | 38 |
| B1_CncB1 | 440 | T | C | 125150 | 72 | 0.06% | 9.70E−05 | 38 | 40 |
| B1_CncB1 | 422 | T | C | 142706 | 66 | 0.05% | 7.23E−08 | 40 | 40 |
| B1_CncB1 | 72 | T | C | 147245 | 52 | 0.04% | 5.31E−12 | 39 | 38 |
| B1_CncB1 | 83 | T | C | 148971 | 53 | 0.04% | 4.63E−12 | 40 | 40 |
| B1_CncB1 | 85 | T | C | 151952 | 57 | 0.04% | 1.80E−11 | 40 | 38 |
| B1_CncB1 | 108 | T | C | 129516 | 53 | 0.04% | 8.38E−09 | 38 | 39 |
| B1_CncB1 | 144 | T | C | 118409 | 48 | 0.04% | 2.71E−08 | 38 | 37 |
| B1_CncB1 | 334 | T | C | 136225 | 51 | 0.04% | 2.01E−10 | 39 | 38 |
| B1_CncB1 | 351 | T | C | 134874 | 60 | 0.04% | 5.61E−08 | 39 | 37 |
| B1_CncB1 | 352 | T | C | 140293 | 63 | 0.04% | 3.34E−08 | 40 | 38 |
| B1_CncB1 | 354 | T | C | 139808 | 57 | 0.04% | 2.14E−09 | 39 | 39 |
| B1_CncB1 | 372 | T | C | 139374 | 52 | 0.04% | 1.18E−10 | 39 | 38 |
| B1_CncB1 | 436 | T | C | 139908 | 49 | 0.04% | 1.77E−11 | 39 | 37 |
| B1_CncB1 | 60 | T | C | 150309 | 47 | 0.03% | 4.78E−14 | 40 | 40 |
| B1_CncB1 | 61 | T | C | 153142 | 53 | 0.03% | 9.46E−13 | 40 | 39 |
| B1_CncB1 | 89 | T | C | 152466 | 45 | 0.03% | 4.40E−15 | 40 | 39 |
| B1_CncB1 | 103 | T | C | 144952 | 44 | 0.03% | 6.54E−14 | 39 | 40 |
| B1_CncB1 | 345 | T | C | 126378 | 34 | 0.03% | 6.16E−14 | 38 | 38 |
| B1_CncB1 | 377 | T | C | 142926 | 38 | 0.03% | 1.24E−15 | 40 | 39 |
| B1_CncB1 | 405 | T | C | 143488 | 44 | 0.03% | 1.00E−13 | 40 | 38 |
| B1_CncB1 | 418 | T | C | 145502 | 49 | 0.03% | 1.59E−12 | 40 | 38 |
| B1_CncB1 | 15 | T | C | 156103 | 28 | 0.02% | 4.72E−23 | 40 | 37 |
| B1_CncB1 | 20 | T | C | 152276 | 34 | 0.02% | 2.53E−19 | 40 | 40 |
| B1_CncB1 | 42 | T | C | 155498 | 30 | 0.02% | 7.97E−22 | 40 | 39 |

TABLE 3-continued

T-to-C mutation frequencies in amplicon sequences: 100 μM 4sU labeling, no OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| B1_CncB1 | 54 | T | C | 150059 | 31 | 0.02% | 3.10E−20 | 40 | 39 |
| B1_CncB1 | 74 | T | C | 150043 | 33 | 0.02% | 2.48E−19 | 40 | 40 |
| B1_CncB1 | 129 | T | C | 140904 | 23 | 0.02% | 5.73E−22 | 39 | 40 |
| B1_CncB1 | 341 | T | C | 123169 | 22 | 0.02% | 1.57E−18 | 38 | 37 |
| B1_CncB1 | 346 | T | C | 120553 | 20 | 0.02% | 6.95E−19 | 38 | 38 |
| B1_CncB1 | 353 | T | C | 138123 | 30 | 0.02% | 4.58E−18 | 39 | 38 |
| B1_CncB1 | 356 | T | C | 131899 | 25 | 0.02% | 7.50E−19 | 39 | 37 |
| B1_CncB1 | 358 | T | C | 129889 | 27 | 0.02% | 1.86E−17 | 38 | 39 |
| B1_CncB1 | 367 | T | C | 142985 | 30 | 0.02% | 3.72E−19 | 40 | 38 |
| B1_CncB1 | 382 | T | C | 142248 | 28 | 0.02% | 7.16E−20 | 40 | 38 |
| B1_CncB1 | 386 | T | C | 143281 | 27 | 0.02% | 1.39E−20 | 40 | 38 |
| B1_CncB1 | 399 | T | C | 141868 | 23 | 0.02% | 3.33E−22 | 40 | 40 |
| B1_CncB1 | 417 | T | C | 145889 | 30 | 0.02% | 1.35E−19 | 40 | 38 |
| B1_CncB1 | 50 | T | C | 149621 | 21 | 0.01% | 2.82E−25 | 39 | 40 |
| B1_CncB1 | 328 | T | C | 106053 | 11 | 0.01% | 5.69E−21 | 37 | 33 |
| B1_CncB1 | 366 | T | C | 142510 | 20 | 0.01% | 3.63E−24 | 40 | 35 |
| B1_CncB1 | 396 | T | C | 131924 | 14 | 0.01% | 2.66E−25 | 39 | 37 |
| D1_CncD1 | 61 | T | C | 158107 | 89 | 0.06% | 6.65E−06 | 39 | 39 |
| D1_CncD1 | 311 | T | C | 127735 | 79 | 0.06% | 5.03E−04 | 39 | 38 |
| D1_CncD1 | 104 | T | C | 80529 | 44 | 0.05% | 7.79E−04 | 35 | 39 |
| D1_CncD1 | 294 | T | C | 111677 | 51 | 0.05% | 1.38E−06 | 38 | 39 |
| D1_CncD1 | 333 | T | C | 126711 | 64 | 0.05% | 4.01E−06 | 39 | 39 |
| D1_CncD1 | 82 | T | C | 154958 | 62 | 0.04% | 1.11E−10 | 39 | 40 |
| D1_CncD1 | 287 | T | C | 99960 | 37 | 0.04% | 5.08E−08 | 37 | 37 |
| D1_CncD1 | 309 | T | C | 133248 | 57 | 0.04% | 1.74E−08 | 40 | 37 |
| D1_CncD1 | 377 | T | C | 139410 | 56 | 0.04% | 1.23E−09 | 40 | 37 |
| D1_CncD1 | 33 | T | C | 165938 | 45 | 0.03% | 1.33E−17 | 40 | 39 |
| D1_CncD1 | 74 | T | C | 161419 | 43 | 0.03% | 1.49E−17 | 40 | 40 |
| D1_CncD1 | 84 | T | C | 156717 | 41 | 0.03% | 2.63E−15 | 39 | 40 |
| D1_CncD1 | 93 | T | C | 134707 | 38 | 0.03% | 4.66E−14 | 38 | 40 |
| D1_CncD1 | 99 | T | C | 79545 | 21 | 0.03% | 2.15E−09 | 35 | 39 |
| D1_CncD1 | 120 | T | C | 137591 | 43 | 0.03% | 6.15E−13 | 38 | 39 |
| D1_CncD1 | 142 | T | C | 141426 | 42 | 0.03% | 5.14E−14 | 39 | 39 |
| D1_CncD1 | 296 | T | C | 114275 | 30 | 0.03% | 4.89E−13 | 38 | 36 |
| D1_CncD1 | 339 | T | C | 131059 | 39 | 0.03% | 3.90E−13 | 39 | 39 |
| D1_CncD1 | 359 | T | C | 138754 | 39 | 0.03% | 1.76E−14 | 40 | 39 |
| D1_CncD1 | 392 | T | C | 139924 | 35 | 0.03% | 3.52E−16 | 40 | 40 |
| D1_CncD1 | 26 | T | C | 163895 | 30 | 0.02% | 1.22E−23 | 40 | 40 |
| D1_CncD1 | 27 | T | C | 162664 | 26 | 0.02% | 1.60E−25 | 40 | 39 |
| D1_CncD1 | 35 | T | C | 164765 | 31 | 0.02% | 2.28E−23 | 40 | 40 |
| D1_CncD1 | 41 | T | C | 163963 | 25 | 0.02% | 2.53E−26 | 40 | 39 |
| D1_CncD1 | 44 | T | C | 166036 | 34 | 0.02% | 2.25E−22 | 40 | 40 |
| D1_CncD1 | 45 | T | C | 161983 | 33 | 0.02% | 5.89E−22 | 40 | 40 |
| D1_CncD1 | 48 | T | C | 163480 | 34 | 0.02% | 1.03E−21 | 40 | 40 |
| D1_CncD1 | 62 | T | C | 146877 | 25 | 0.02% | 2.67E−22 | 39 | 40 |
| D1_CncD1 | 72 | T | C | 145658 | 34 | 0.02% | 7.80E−18 | 38 | 39 |
| D1_CncD1 | 87 | T | C | 142285 | 24 | 0.02% | 6.74E−22 | 38 | 40 |
| D1_CncD1 | 106 | T | C | 131268 | 31 | 0.02% | 3.86E−16 | 38 | 39 |
| D1_CncD1 | 116 | T | C | 155287 | 26 | 0.02% | 7.16E−24 | 40 | 40 |
| D1_CncD1 | 126 | T | C | 144717 | 28 | 0.02% | 2.55E−20 | 39 | 40 |
| D1_CncD1 | 143 | T | C | 135467 | 28 | 0.02% | 2.57E−18 | 38 | 39 |
| D1_CncD1 | 274 | T | C | 107561 | 19 | 0.02% | 2.22E−16 | 37 | 37 |
| D1_CncD1 | 282 | T | C | 104748 | 19 | 0.02% | 1.09E−15 | 37 | 37 |
| D1_CncD1 | 292 | T | C | 115091 | 25 | 0.02% | 2.66E−15 | 38 | 36 |
| D1_CncD1 | 310 | T | C | 133079 | 20 | 0.02% | 5.56E−22 | 39 | 39 |
| D1_CncD1 | 320 | T | C | 135294 | 21 | 0.02% | 6.86E−22 | 40 | 39 |
| D1_CncD1 | 325 | T | C | 136661 | 26 | 0.02% | 1.72E−19 | 40 | 36 |
| D1_CncD1 | 334 | T | C | 131216 | 23 | 0.02% | 7.30E−20 | 39 | 39 |
| D1_CncD1 | 340 | T | C | 136520 | 23 | 0.02% | 5.00E−21 | 40 | 39 |
| D1_CncD1 | 346 | T | C | 132259 | 26 | 0.02% | 1.37E−18 | 39 | 39 |
| D1_CncD1 | 353 | T | C | 136802 | 33 | 0.02% | 2.31E−16 | 39 | 41 |
| D1_CncD1 | 355 | T | C | 135362 | 26 | 0.02% | 2.89E−19 | 39 | 39 |
| D1_CncD1 | 357 | T | C | 136498 | 25 | 0.02% | 5.46E−20 | 40 | 39 |
| D1_CncD1 | 358 | T | C | 134523 | 29 | 0.02% | 1.21E−17 | 40 | 38 |
| D1_CncD1 | 361 | T | C | 131288 | 27 | 0.02% | 6.75E−18 | 38 | 39 |
| D1_CncD1 | 371 | T | C | 113056 | 26 | 0.02% | 1.95E−14 | 39 | 40 |
| D1_CncD1 | 373 | T | C | 138643 | 21 | 0.02% | 1.31E−22 | 40 | 39 |
| D1_CncD1 | 374 | T | C | 132164 | 32 | 0.02% | 6.15E−16 | 40 | 40 |
| D1_CncD1 | 391 | T | C | 128678 | 31 | 0.02% | 1.64E−15 | 39 | 40 |
| D1_CncD1 | 395 | T | C | 140603 | 27 | 0.02% | 6.61E−20 | 40 | 40 |
| D1_CncD1 | 17 | T | C | 166941 | 22 | 0.01% | 7.57E−29 | 40 | 37 |
| D1_CncD1 | 22 | T | C | 162365 | 21 | 0.01% | 1.75E−28 | 40 | 41 |
| D1_CncD1 | 47 | T | C | 162544 | 24 | 0.01% | 1.17E−26 | 40 | 40 |
| D1_CncD1 | 49 | T | C | 165646 | 22 | 0.01% | 1.34E−28 | 40 | 39 |
| D1_CncD1 | 63 | T | C | 163953 | 18 | 0.01% | 1.00E−30 | 40 | 40 |
| D1_CncD1 | 108 | T | C | 147555 | 18 | 0.01% | 1.16E−26 | 38 | 39 |

TABLE 3-continued

T-to-C mutation frequencies in amplicon sequences: 100 μM 4sU labeling, no OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| D1_CncD1 | 141 | T | C | 136262 | 20 | 0.01% | 1.05E−22 | 39 | 37 |
| D1_CncD1 | 273 | T | C | 117416 | 13 | 0.01% | 2.11E−22 | 38 | 36 |
| D1_CncD1 | 275 | T | C | 115070 | 13 | 0.01% | 6.84E−22 | 38 | 39 |
| D1_CncD1 | 276 | T | C | 118522 | 12 | 0.01% | 2.30E−23 | 39 | 39 |
| D1_CncD1 | 285 | T | C | 117888 | 17 | 0.01% | 7.40E−20 | 38 | 39 |
| D1_CncD1 | 288 | T | C | 106141 | 15 | 0.01% | 2.31E−18 | 38 | 40 |
| D1_CncD1 | 312 | T | C | 134499 | 18 | 0.01% | 2.02E−23 | 40 | 37 |
| D1_CncD1 | 332 | T | C | 133915 | 19 | 0.01% | 1.44E−22 | 40 | 39 |
| D1_CncD1 | 336 | T | C | 133557 | 19 | 0.01% | 1.44E−22 | 39 | 39 |
| D1_CncD1 | 386 | T | C | 138642 | 18 | 0.01% | 2.06E−24 | 40 | 40 |
| D1_CncD1 | 388 | T | C | 134578 | 18 | 0.01% | 2.02E−23 | 39 | 40 |
| D1_CncD1 | 406 | T | C | 101210 | 11 | 0.01% | 1.11E−19 | 38 | 37 |
| E1_CncE1 | 342 | T | C | 57743 | 24 | 0.04% | 1.58E−04 | 39 | 37 |
| E1_CncE1 | 22 | T | C | 69866 | 19 | 0.03% | 3.88E−08 | 40 | 39 |
| E1_CncE1 | 347 | T | C | 40803 | 11 | 0.03% | 2.84E−05 | 37 | 38 |
| E1_CncE1 | 380 | T | C | 55923 | 19 | 0.03% | 1.68E−05 | 38 | 37 |
| E1_CncE1 | 143 | T | C | 52016 | 12 | 0.02% | 2.27E−07 | 38 | 40 |
| E1_CncE1 | 354 | T | C | 53777 | 11 | 0.02% | 4.99E−08 | 38 | 37 |
| E1_CncE1 | 438 | T | C | 58077 | 13 | 0.02% | 3.11E−08 | 38 | 33 |
| E1_CncE1 | 101 | T | C | 66342 | 8 | 0.01% | 8.93E−13 | 40 | 38 |
| E1_CncE1 | 124 | T | C | 62390 | 8 | 0.01% | 9.03E−12 | 39 | 38 |
| E1_CncE1 | 351 | T | C | 53344 | 7 | 0.01% | 3.80E−10 | 38 | 39 |
| E1_CncE1 | 364 | T | C | 28994 | 3 | 0.01% | 2.31E−06 | 36 | 33 |
| E1_CncE1 | 365 | T | C | 38213 | 5 | 0.01% | 1.24E−07 | 36 | 41 |
| E1_CncE1 | 398 | T | C | 49318 | 7 | 0.01% | 3.70E−09 | 38 | 38 |
| eGFP | 138 | T | C | 30631 | 77 | 0.25% | 3.08E−06 | 34 | 37 |
| eGFP | 379 | T | C | 60033 | 133 | 0.22% | 7.70E−08 | 38 | 39 |
| eGFP | 397 | T | C | 66497 | 148 | 0.22% | 1.02E−08 | 38 | 40 |
| eGFP | 309 | T | C | 58325 | 117 | 0.20% | 4.77E−06 | 38 | 37 |
| eGFP | 295 | T | C | 55806 | 109 | 0.19% | 1.48E−05 | 38 | 39 |
| eGFP | 359 | T | C | 66174 | 124 | 0.19% | 1.53E−05 | 38 | 40 |
| eGFP | 67 | T | C | 96636 | 176 | 0.18% | 6.94E−07 | 39 | 40 |
| eGFP | 99 | T | C | 93645 | 155 | 0.17% | 4.92E−05 | 39 | 40 |
| eGFP | 100 | T | C | 84304 | 144 | 0.17% | 4.23E−05 | 38 | 39 |
| eGFP | 324 | T | C | 61012 | 104 | 0.17% | 5.04E−04 | 38 | 39 |
| eGFP | 364 | T | C | 72132 | 120 | 0.17% | 3.25E−04 | 39 | 40 |
| eGFP | 79 | T | C | 90349 | 143 | 0.16% | 3.11E−04 | 39 | 40 |
| eGFP | 144 | T | C | 61919 | 101 | 0.16% | 1.39E−03 | 37 | 38 |
| eGFP | 51 | T | C | 90733 | 139 | 0.15% | 7.25E−04 | 38 | 39 |
| eGFP | 46 | T | C | 85309 | 123 | 0.14% | 5.04E−03 | 38 | 40 |
| eGFP | 70 | T | C | 83413 | 117 | 0.14% | 9.66E−03 | 38 | 39 |
| eGFP | 382 | T | C | 78704 | 44 | 0.06% | 1.33E−03 | 40 | 39 |
| eGFP | 9 | T | C | 103516 | 11 | 0.01% | 3.39E−20 | 40 | 39 |
| p21_Cdkn1A | 454 | T | C | 69906 | 193 | 0.28% | 8.34E−15 | 39 | 40 |
| p21_Cdkn1A | 98 | T | C | 68451 | 182 | 0.27% | 1.64E−13 | 39 | 39 |
| p21_Cdkn1A | 76 | T | C | 69121 | 180 | 0.26% | 6.38E−13 | 40 | 40 |
| p21_Cdkn1A | 131 | T | C | 55788 | 121 | 0.22% | 3.53E−07 | 38 | 37 |
| p21_Cdkn1A | 37 | T | C | 72258 | 122 | 0.17% | 2.02E−04 | 40 | 39 |
| p21_Cdkn1A | 136 | T | C | 60548 | 101 | 0.17% | 7.64E−04 | 37 | 38 |
| p21_Cdkn1A | 137 | T | C | 55625 | 93 | 0.17% | 1.11E−03 | 37 | 37 |
| p21_Cdkn1A | 406 | T | C | 57010 | 91 | 0.16% | 3.22E−03 | 38 | 40 |
| p21_Cdkn1A | 374 | T | C | 68518 | 102 | 0.15% | 5.55E−03 | 39 | 39 |
| p21_Cdkn1A | 2 | T | C | 73480 | 26 | 0.04% | 1.23E−06 | 40 | 40 |
| p21_Cdkn1A | 385 | T | C | 60549 | 25 | 0.04% | 9.29E−05 | 38 | 37 |
| p21_Cdkn1A | 436 | T | C | 74473 | 29 | 0.04% | 5.32E−06 | 40 | 34 |
| p21_Cdkn1A | 387 | T | C | 62666 | 18 | 0.03% | 4.04E−07 | 38 | 36 |
| p21_Cdkn1A | 13 | T | C | 71948 | 12 | 0.02% | 1.18E−11 | 39 | 35 |
| p21_Cdkn1A | 15 | T | C | 73165 | 11 | 0.02% | 1.11E−12 | 40 | 37 |
| p21_Cdkn1A | 351 | T | C | 63139 | 10 | 0.02% | 7.68E−11 | 38 | 38 |
| p21_Cdkn1A | 354 | T | C | 63118 | 13 | 0.02% | 2.50E−09 | 39 | 39 |
| p21_Cdkn1A | 384 | T | C | 69263 | 13 | 0.02% | 1.12E−10 | 39 | 38 |
| p21_Cdkn1A | 49 | T | C | 69003 | 10 | 0.01% | 2.74E−12 | 39 | 38 |
| p21_Cdkn1A | 349 | T | C | 61597 | 9 | 0.01% | 6.35E−11 | 38 | 35 |
| p21_Cdkn1A | 446 | T | C | 63508 | 7 | 0.01% | 1.12E−12 | 38 | 39 |
| p21_Cdkn1A | 457 | T | C | 72864 | 8 | 0.01% | 2.65E−14 | 40 | 37 |
| PCNA | 350 | T | C | 130542 | 49 | 0.04% | 5.79E−10 | 38 | 38 |
| PCNA | 64 | T | C | 190626 | 48 | 0.03% | 1.73E−21 | 40 | 40 |
| PCNA | 107 | T | C | 179080 | 46 | 0.03% | 4.97E−20 | 39 | 39 |
| PCNA | 116 | T | C | 182831 | 56 | 0.03% | 4.79E−17 | 40 | 39 |
| PCNA | 360 | T | C | 163315 | 56 | 0.03% | 1.28E−13 | 39 | 37 |
| PCNA | 366 | T | C | 153009 | 47 | 0.03% | 1.33E−14 | 39 | 39 |
| PCNA | 390 | T | C | 159604 | 40 | 0.03% | 2.65E−18 | 39 | 40 |
| PCNA | 442 | T | C | 141429 | 43 | 0.03% | 1.11E−13 | 39 | 40 |
| PCNA | 26 | T | C | 192895 | 29 | 0.02% | 5.42E−31 | 40 | 39 |
| PCNA | 69 | T | C | 193335 | 40 | 0.02% | 1.53E−25 | 40 | 40 |
| PCNA | 70 | T | C | 188365 | 34 | 0.02% | 2.46E−27 | 39 | 39 |

TABLE 3-continued

T-to-C mutation frequencies in amplicon sequences: 100 μM 4sU labeling, no OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| PCNA | 112 | T | C | 177487 | 34 | 0.02% | 7.87E−25 | 39 | 39 |
| PCNA | 329 | T | C | 142706 | 25 | 0.02% | 2.27E−21 | 38 | 37 |
| PCNA | 352 | T | C | 132421 | 23 | 0.02% | 4.28E−20 | 38 | 39 |
| PCNA | 376 | T | C | 169446 | 36 | 0.02% | 4.11E−22 | 40 | 39 |
| PCNA | 382 | T | C | 169810 | 30 | 0.02% | 5.11E−25 | 40 | 37 |
| PCNA | 384 | T | C | 151558 | 24 | 0.02% | 5.06E−24 | 38 | 39 |
| PCNA | 393 | T | C | 166445 | 26 | 0.02% | 1.79E−26 | 39 | 39 |
| PCNA | 394 | T | C | 174327 | 31 | 0.02% | 1.18E−25 | 40 | 39 |
| PCNA | 28 | T | C | 188809 | 23 | 0.01% | 1.07E−33 | 40 | 40 |
| PCNA | 42 | T | C | 191224 | 28 | 0.01% | 2.47E−31 | 40 | 39 |
| PCNA | 46 | T | C | 173747 | 19 | 0.01% | 1.36E−32 | 39 | 39 |
| PCNA | 83 | T | C | 157730 | 21 | 0.01% | 3.04E−27 | 38 | 39 |
| PCNA | 89 | T | C | 187523 | 20 | 0.01% | 1.74E−35 | 40 | 39 |
| PCNA | 91 | T | C | 185058 | 27 | 0.01% | 1.81E−30 | 40 | 39 |
| PCNA | 93 | T | C | 181409 | 23 | 0.01% | 6.06E−32 | 39 | 40 |
| PCNA | 348 | T | C | 141999 | 17 | 0.01% | 4.64E−26 | 38 | 37 |
| PCNA | 353 | T | C | 148838 | 16 | 0.01% | 2.86E−28 | 38 | 37 |
| PCNA | 370 | T | C | 162447 | 22 | 0.01% | 7.37E−28 | 39 | 39 |
| PCNA | 372 | T | C | 167176 | 21 | 0.01% | 9.89E−30 | 39 | 39 |
| PCNA | 374 | T | C | 164677 | 23 | 0.01% | 9.69E−28 | 39 | 39 |
| PCNA | 409 | T | C | 158353 | 18 | 0.01% | 1.90E−29 | 39 | 40 |
| PCNA | 417 | T | C | 157874 | 20 | 0.01% | 7.11E−28 | 39 | 40 |
| PCNA | 431 | T | C | 168419 | 19 | 0.01% | 2.59E−31 | 39 | 40 |

TABLE 4

T-to-C mutation frequencies in amplicon sequences: 50 μM 4sU WITH OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| A2_CcnA2 | 314 | T | C | 16003 | 67 | 0.42% | 6.67E−09 | 34 | 37 |
| A2_CcnA2 | 359 | T | C | 81930 | 154 | 0.19% | 1.59E−06 | 39 | 40 |
| A2_CcnA2 | 93 | T | C | 98545 | 174 | 0.18% | 2.34E−06 | 40 | 40 |
| A2_CcnA2 | 429 | T | C | 86785 | 145 | 0.17% | 6.21E−05 | 40 | 40 |
| A2_CcnA2 | 33 | T | C | 100119 | 137 | 0.14% | 9.55E−03 | 40 | 40 |
| A2_CcnA2 | 36 | T | C | 99982 | 142 | 0.14% | 4.11E−03 | 40 | 40 |
| A2_CcnA2 | 128 | T | C | 94627 | 132 | 0.14% | 6.81E−03 | 39 | 39 |
| A2_CcnA2 | 430 | T | C | 86662 | 124 | 0.14% | 5.23E−03 | 40 | 40 |
| A2_CcnA2 | 72 | T | C | 95142 | 54 | 0.06% | 4.89E−04 | 39 | 39 |
| A2_CcnA2 | 79 | T | C | 99815 | 55 | 0.06% | 2.44E−04 | 40 | 40 |
| A2_CcnA2 | 77 | T | C | 97533 | 51 | 0.05% | 9.66E−05 | 40 | 40 |
| A2_CcnA2 | 108 | T | C | 92773 | 50 | 0.05% | 2.66E−04 | 39 | 39 |
| A2_CcnA2 | 406 | T | C | 85534 | 47 | 0.05% | 5.95E−04 | 40 | 40 |
| A2_CcnA2 | 56 | T | C | 100315 | 42 | 0.04% | 6.16E−07 | 40 | 39 |
| A2_CcnA2 | 441 | T | C | 88574 | 20 | 0.02% | 1.15E−11 | 40 | 40 |
| A2_CcnA2 | 20 | T | C | 100970 | 14 | 0.01% | 1.71E−17 | 40 | 40 |
| B1_CncB1 | 336 | T | C | 87096 | 550 | 0.63% | 1.03E−83 | 39 | 39 |
| B1_CncB1 | 372 | T | C | 94483 | 551 | 0.58% | 1.50E−79 | 40 | 40 |
| B1_CncB1 | 373 | T | C | 95486 | 548 | 0.57% | 2.54E−78 | 40 | 40 |
| B1_CncB1 | 97 | T | C | 100842 | 551 | 0.54% | 2.05E−76 | 40 | 39 |
| B1_CncB1 | 380 | T | C | 91864 | 503 | 0.54% | 5.14E−70 | 39 | 40 |
| B1_CncB1 | 333 | T | C | 87675 | 458 | 0.52% | 8.78E−62 | 39 | 39 |
| B1_CncB1 | 376 | T | C | 94155 | 491 | 0.52% | 2.83E−66 | 40 | 40 |
| B1_CncB1 | 422 | T | C | 94046 | 495 | 0.52% | 3.51E−67 | 40 | 40 |
| B1_CncB1 | 334 | T | C | 88815 | 451 | 0.51% | 1.02E−59 | 39 | 39 |
| B1_CncB1 | 348 | T | C | 92612 | 477 | 0.51% | 1.31E−63 | 39 | 39 |
| B1_CncB1 | 399 | T | C | 95084 | 469 | 0.49% | 7.36E−61 | 40 | 40 |
| B1_CncB1 | 128 | T | C | 101356 | 489 | 0.48% | 1.84E−62 | 39 | 39 |
| B1_CncB1 | 345 | T | C | 92259 | 448 | 0.48% | 1.27E−57 | 39 | 39 |
| B1_CncB1 | 43 | T | C | 107880 | 507 | 0.47% | 3.51E−63 | 40 | 40 |
| B1_CncB1 | 368 | T | C | 95050 | 448 | 0.47% | 3.13E−56 | 40 | 39 |
| B1_CncB1 | 366 | T | C | 94392 | 436 | 0.46% | 4.54E−54 | 40 | 39 |
| B1_CncB1 | 42 | T | C | 107949 | 477 | 0.44% | 1.05E−56 | 40 | 40 |
| B1_CncB1 | 367 | T | C | 95590 | 421 | 0.44% | 5.85E−50 | 40 | 39 |
| B1_CncB1 | 382 | T | C | 94088 | 418 | 0.44% | 3.47E−50 | 40 | 40 |
| B1_CncB1 | 426 | T | C | 95359 | 425 | 0.44% | 3.01E−51 | 40 | 40 |
| B1_CncB1 | 50 | T | C | 105162 | 450 | 0.43% | 2.94E−52 | 40 | 40 |
| B1_CncB1 | 421 | T | C | 95776 | 416 | 0.43% | 6.76E−49 | 40 | 40 |
| B1_CncB1 | 61 | T | C | 107000 | 456 | 0.42% | 1.12E−52 | 40 | 40 |
| B1_CncB1 | 354 | T | C | 92934 | 388 | 0.42% | 2.89E−44 | 39 | 39 |
| B1_CncB1 | 433 | T | C | 94693 | 396 | 0.42% | 4.14E−45 | 40 | 40 |
| B1_CncB1 | 60 | T | C | 106200 | 434 | 0.41% | 1.70E−48 | 40 | 40 |

TABLE 4-continued

T-to-C mutation frequencies in amplicon sequences: 50 μM 4sU WITH OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| B1_CncB1 | 144 | T | C | 82948 | 340 | 0.41% | 2.20E−38 | 38 | 39 |
| B1_CncB1 | 374 | T | C | 95278 | 390 | 0.41% | 7.36E−44 | 40 | 40 |
| B1_CncB1 | 83 | T | C | 100810 | 406 | 0.40% | 9.75E−45 | 39 | 40 |
| B1_CncB1 | 98 | T | C | 99663 | 404 | 0.40% | 9.97E−45 | 40 | 39 |
| B1_CncB1 | 377 | T | C | 95182 | 384 | 0.40% | 1.28E−42 | 40 | 40 |
| B1_CncB1 | 54 | T | C | 104589 | 405 | 0.39% | 2.40E−43 | 40 | 40 |
| B1_CncB1 | 330 | T | C | 85719 | 338 | 0.39% | 9.00E−37 | 39 | 39 |
| B1_CncB1 | 407 | T | C | 97094 | 385 | 0.39% | 5.03E−42 | 40 | 40 |
| B1_CncB1 | 418 | T | C | 97319 | 383 | 0.39% | 1.29E−41 | 40 | 40 |
| B1_CncB1 | 89 | T | C | 106152 | 395 | 0.37% | 1.42E−40 | 40 | 40 |
| B1_CncB1 | 362 | T | C | 91507 | 343 | 0.37% | 7.49E−36 | 39 | 39 |
| B1_CncB1 | 20 | T | C | 106250 | 387 | 0.36% | 5.46E−39 | 40 | 40 |
| B1_CncB1 | 62 | T | C | 108326 | 394 | 0.36% | 1.24E−39 | 40 | 40 |
| B1_CncB1 | 116 | T | C | 101343 | 368 | 0.36% | 4.38E−37 | 39 | 39 |
| B1_CncB1 | 111 | T | C | 101997 | 346 | 0.34% | 1.79E−32 | 39 | 39 |
| B1_CncB1 | 123 | T | C | 99184 | 342 | 0.34% | 9.52E−33 | 39 | 39 |
| B1_CncB1 | 416 | T | C | 97612 | 329 | 0.34% | 5.88E−31 | 40 | 40 |
| B1_CncB1 | 440 | T | C | 97200 | 330 | 0.34% | 3.79E−31 | 40 | 40 |
| B1_CncB1 | 90 | T | C | 105159 | 348 | 0.33% | 7.80E−32 | 40 | 40 |
| B1_CncB1 | 103 | T | C | 99730 | 335 | 0.33% | 4.51E−31 | 39 | 39 |
| B1_CncB1 | 117 | T | C | 102205 | 342 | 0.33% | 1.03E−31 | 39 | 39 |
| B1_CncB1 | 27 | T | C | 105183 | 341 | 0.32% | 1.58E−30 | 40 | 40 |
| B1_CncB1 | 369 | T | C | 95592 | 311 | 0.32% | 3.05E−28 | 40 | 39 |
| B1_CncB1 | 415 | T | C | 96094 | 305 | 0.32% | 8.32E−27 | 40 | 40 |
| B1_CncB1 | 386 | T | C | 95492 | 297 | 0.31% | 1.16E−25 | 40 | 39 |
| B1_CncB1 | 387 | T | C | 94750 | 298 | 0.31% | 7.60E−26 | 40 | 40 |
| B1_CncB1 | 113 | T | C | 104638 | 318 | 0.30% | 1.20E−26 | 40 | 40 |
| B1_CncB1 | 129 | T | C | 97766 | 299 | 0.30% | 4.34E−25 | 39 | 38 |
| B1_CncB1 | 139 | T | C | 91557 | 276 | 0.30% | 4.02E−23 | 39 | 39 |
| B1_CncB1 | 341 | T | C | 87471 | 261 | 0.30% | 1.15E−21 | 39 | 39 |
| B1_CncB1 | 349 | T | C | 94129 | 286 | 0.30% | 5.44E−24 | 39 | 39 |
| B1_CncB1 | 436 | T | C | 95801 | 288 | 0.30% | 9.74E−24 | 40 | 40 |
| B1_CncB1 | 332 | T | C | 88567 | 260 | 0.29% | 3.43E−21 | 39 | 38 |
| B1_CncB1 | 346 | T | C | 90027 | 261 | 0.29% | 8.91E−21 | 39 | 39 |
| B1_CncB1 | 92 | T | C | 105410 | 297 | 0.28% | 1.14E−22 | 40 | 40 |
| B1_CncB1 | 352 | T | C | 94168 | 261 | 0.28% | 1.22E−19 | 39 | 39 |
| B1_CncB1 | 417 | T | C | 97534 | 275 | 0.28% | 3.54E−21 | 40 | 40 |
| B1_CncB1 | 29 | T | C | 108103 | 298 | 0.27% | 5.31E−22 | 40 | 40 |
| B1_CncB1 | 353 | T | C | 92863 | 254 | 0.27% | 9.75E−19 | 39 | 39 |
| B1_CncB1 | 356 | T | C | 91559 | 245 | 0.27% | 8.82E−18 | 39 | 39 |
| B1_CncB1 | 396 | T | C | 93998 | 250 | 0.27% | 8.31E−18 | 40 | 40 |
| B1_CncB1 | 328 | T | C | 75151 | 194 | 0.26% | 1.21E−13 | 37 | 37 |
| B1_CncB1 | 108 | T | C | 89446 | 225 | 0.25% | 4.63E−15 | 38 | 40 |
| B1_CncB1 | 137 | T | C | 91781 | 218 | 0.24% | 1.70E−13 | 39 | 39 |
| B1_CncB1 | 358 | T | C | 89479 | 215 | 0.24% | 1.66E−13 | 39 | 39 |
| B1_CncB1 | 53 | T | C | 105908 | 245 | 0.23% | 3.99E−14 | 40 | 40 |
| B1_CncB1 | 405 | T | C | 95874 | 222 | 0.23% | 5.84E−13 | 40 | 39 |
| B1_CncB1 | 408 | T | C | 96799 | 219 | 0.23% | 2.63E−12 | 40 | 40 |
| B1_CncB1 | 115 | T | C | 102051 | 222 | 0.22% | 1.10E−11 | 39 | 39 |
| B1_CncB1 | 38 | T | C | 106129 | 221 | 0.21% | 9.20E−11 | 40 | 40 |
| B1_CncB1 | 338 | T | C | 84482 | 179 | 0.21% | 2.27E−09 | 39 | 39 |
| B1_CncB1 | 72 | T | C | 102692 | 210 | 0.20% | 4.60E−10 | 39 | 40 |
| B1_CncB1 | 454 | T | C | 97751 | 193 | 0.20% | 8.86E−09 | 40 | 40 |
| B1_CncB1 | 45 | T | C | 108167 | 197 | 0.18% | 1.92E−07 | 40 | 40 |
| B1_CncB1 | 102 | T | C | 96984 | 171 | 0.18% | 3.58E−06 | 39 | 39 |
| B1_CncB1 | 351 | T | C | 93942 | 145 | 0.15% | 5.83E−04 | 39 | 40 |
| B1_CncB1 | 409 | T | C | 96672 | 145 | 0.15% | 9.57E−04 | 40 | 40 |
| D1_CncD1 | 377 | T | C | 110677 | 352 | 0.32% | 1.31E−30 | 40 | 40 |
| D1_CncD1 | 99 | T | C | 63809 | 197 | 0.31% | 2.92E−17 | 35 | 39 |
| D1_CncD1 | 141 | T | C | 71007 | 218 | 0.31% | 7.08E−19 | 36 | 39 |
| D1_CncD1 | 392 | T | C | 112954 | 348 | 0.31% | 2.98E−29 | 40 | 40 |
| D1_CncD1 | 336 | T | C | 108258 | 317 | 0.29% | 2.91E−25 | 40 | 40 |
| D1_CncD1 | 333 | T | C | 106976 | 302 | 0.28% | 5.86E−23 | 40 | 40 |
| D1_CncD1 | 33 | T | C | 130459 | 350 | 0.27% | 1.09E−24 | 40 | 40 |
| D1_CncD1 | 45 | T | C | 129191 | 331 | 0.26% | 7.24E−22 | 40 | 40 |
| D1_CncD1 | 332 | T | C | 106626 | 279 | 0.26% | 2.15E−19 | 40 | 40 |
| D1_CncD1 | 292 | T | C | 98825 | 248 | 0.25% | 3.26E−16 | 39 | 39 |
| D1_CncD1 | 361 | T | C | 104405 | 261 | 0.25% | 5.04E−17 | 38 | 40 |
| D1_CncD1 | 395 | T | C | 112640 | 279 | 0.25% | 6.99E−18 | 40 | 40 |
| D1_CncD1 | 61 | T | C | 127064 | 309 | 0.24% | 6.44E−19 | 40 | 40 |
| D1_CncD1 | 106 | T | C | 78877 | 178 | 0.23% | 2.93E−10 | 35 | 39 |
| D1_CncD1 | 329 | T | C | 108124 | 250 | 0.23% | 2.04E−14 | 40 | 39 |
| D1_CncD1 | 334 | T | C | 108151 | 251 | 0.23% | 1.45E−14 | 40 | 40 |
| D1_CncD1 | 393 | T | C | 113080 | 259 | 0.23% | 1.24E−14 | 40 | 40 |
| D1_CncD1 | 35 | T | C | 129769 | 282 | 0.22% | 2.52E−14 | 40 | 40 |

TABLE 4-continued

T-to-C mutation frequencies in amplicon sequences: 50 μM
4sU WITH OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| D1_CncD1 | 276 | T | C | 90624 | 196 | 0.22% | 1.64E-10 | 39 | 39 |
| D1_CncD1 | 320 | T | C | 107558 | 233 | 0.22% | 3.37E-12 | 40 | 40 |
| D1_CncD1 | 340 | T | C | 109260 | 240 | 0.22% | 9.12E-13 | 40 | 40 |
| D1_CncD1 | 22 | T | C | 128521 | 274 | 0.21% | 1.26E-13 | 40 | 40 |
| D1_CncD1 | 48 | T | C | 131552 | 275 | 0.21% | 3.54E-13 | 40 | 40 |
| D1_CncD1 | 285 | T | C | 93900 | 197 | 0.21% | 7.41E-10 | 39 | 39 |
| D1_CncD1 | 287 | T | C | 98102 | 206 | 0.21% | 2.71E-10 | 39 | 38 |
| D1_CncD1 | 357 | T | C | 111252 | 236 | 0.21% | 8.23E-12 | 40 | 40 |
| D1_CncD1 | 27 | T | C | 130648 | 257 | 0.20% | 5.00E-11 | 40 | 40 |
| D1_CncD1 | 273 | T | C | 94820 | 192 | 0.20% | 5.19E-09 | 38 | 38 |
| D1_CncD1 | 358 | T | C | 110958 | 217 | 0.20% | 2.43E-09 | 40 | 40 |
| D1_CncD1 | 362 | T | C | 113430 | 224 | 0.20% | 7.23E-10 | 39 | 40 |
| D1_CncD1 | 26 | T | C | 129670 | 250 | 0.19% | 2.48E-10 | 40 | 40 |
| D1_CncD1 | 62 | T | C | 128575 | 241 | 0.19% | 2.06E-09 | 40 | 40 |
| D1_CncD1 | 63 | T | C | 129089 | 250 | 0.19% | 2.48E-10 | 40 | 40 |
| D1_CncD1 | 296 | T | C | 94400 | 182 | 0.19% | 6.32E-08 | 38 | 39 |
| D1_CncD1 | 359 | T | C | 112064 | 216 | 0.19% | 4.78E-09 | 40 | 39 |
| D1_CncD1 | 388 | T | C | 113141 | 210 | 0.19% | 3.63E-08 | 40 | 40 |
| D1_CncD1 | 391 | T | C | 112678 | 212 | 0.19% | 1.46E-08 | 40 | 40 |
| D1_CncD1 | 17 | T | C | 133044 | 234 | 0.18% | 7.38E-08 | 40 | 40 |
| D1_CncD1 | 25 | T | C | 126391 | 225 | 0.18% | 6.89E-08 | 40 | 40 |
| D1_CncD1 | 82 | T | C | 120157 | 221 | 0.18% | 2.41E-08 | 39 | 40 |
| D1_CncD1 | 116 | T | C | 108556 | 192 | 0.18% | 6.99E-07 | 39 | 39 |
| D1_CncD1 | 283 | T | C | 100440 | 185 | 0.18% | 2.65E-07 | 39 | 39 |
| D1_CncD1 | 325 | T | C | 108514 | 201 | 0.18% | 6.61E-08 | 40 | 40 |
| D1_CncD1 | 44 | T | C | 130699 | 220 | 0.17% | 8.53E-07 | 40 | 40 |
| D1_CncD1 | 104 | T | C | 59491 | 103 | 0.17% | 3.38E-04 | 35 | 40 |
| D1_CncD1 | 107 | T | C | 97095 | 167 | 0.17% | 9.65E-06 | 36 | 38 |
| D1_CncD1 | 142 | T | C | 84741 | 143 | 0.17% | 5.39E-05 | 36 | 38 |
| D1_CncD1 | 143 | T | C | 91247 | 156 | 0.17% | 2.09E-05 | 37 | 37 |
| D1_CncD1 | 288 | T | C | 97960 | 164 | 0.17% | 2.69E-05 | 39 | 39 |
| D1_CncD1 | 295 | T | C | 96841 | 166 | 0.17% | 1.23E-05 | 39 | 39 |
| D1_CncD1 | 327 | T | C | 108978 | 191 | 0.17% | 1.25E-06 | 40 | 40 |
| D1_CncD1 | 386 | T | C | 112850 | 192 | 0.17% | 3.51E-06 | 40 | 40 |
| D1_CncD1 | 39 | T | C | 126767 | 200 | 0.16% | 2.43E-05 | 40 | 40 |
| D1_CncD1 | 49 | T | C | 131974 | 210 | 0.16% | 1.44E-05 | 40 | 40 |
| D1_CncD1 | 87 | T | C | 123830 | 201 | 0.16% | 1.13E-05 | 39 | 40 |
| D1_CncD1 | 275 | T | C | 91144 | 144 | 0.16% | 3.28E-04 | 39 | 39 |
| D1_CncD1 | 294 | T | C | 96721 | 151 | 0.16% | 2.79E-04 | 39 | 39 |
| D1_CncD1 | 311 | T | C | 108131 | 178 | 0.16% | 2.05E-05 | 40 | 39 |
| D1_CncD1 | 346 | T | C | 108973 | 171 | 0.16% | 1.25E-04 | 40 | 40 |
| D1_CncD1 | 353 | T | C | 110139 | 175 | 0.16% | 6.99E-05 | 40 | 40 |
| D1_CncD1 | 355 | T | C | 111375 | 181 | 0.16% | 2.47E-05 | 40 | 40 |
| D1_CncD1 | 126 | T | C | 102037 | 149 | 0.15% | 1.79E-03 | 38 | 38 |
| D1_CncD1 | 371 | T | C | 110305 | 165 | 0.15% | 5.42E-04 | 40 | 40 |
| D1_CncD1 | 108 | T | C | 108098 | 147 | 0.14% | 8.55E-03 | 37 | 38 |
| D1_CncD1 | 272 | T | C | 93664 | 134 | 0.14% | 3.88E-03 | 38 | 38 |
| D1_CncD1 | 274 | T | C | 95252 | 136 | 0.14% | 4.16E-03 | 38 | 38 |
| D1_CncD1 | 84 | T | C | 122240 | 46 | 0.04% | 1.94E-09 | 39 | 39 |
| E1_CncE1 | 364 | T | C | 28552 | 512 | 1.76% | 1.88E-116 | 37 | 39 |
| E1_CncE1 | 121 | T | C | 31970 | 370 | 1.14% | 1.01E-74 | 38 | 39 |
| E1_CncE1 | 362 | T | C | 26238 | 268 | 1.01% | 2.39E-52 | 37 | 39 |
| E1_CncE1 | 124 | T | C | 32565 | 306 | 0.93% | 7.91E-58 | 39 | 39 |
| E1_CncE1 | 347 | T | C | 29079 | 265 | 0.90% | 2.27E-49 | 37 | 38 |
| E1_CncE1 | 363 | T | C | 28122 | 247 | 0.87% | 1.92E-45 | 37 | 39 |
| E1_CncE1 | 410 | T | C | 34880 | 308 | 0.87% | 3.23E-56 | 39 | 40 |
| E1_CncE1 | 351 | T | C | 28098 | 234 | 0.83% | 3.99E-42 | 37 | 39 |
| E1_CncE1 | 47 | T | C | 38304 | 316 | 0.82% | 3.33E-56 | 40 | 40 |
| E1_CncE1 | 423 | T | C | 36584 | 298 | 0.81% | 5.54E-53 | 40 | 40 |
| E1_CncE1 | 417 | T | C | 33239 | 237 | 0.71% | 1.15E-39 | 39 | 39 |
| E1_CncE1 | 101 | T | C | 36516 | 250 | 0.68% | 4.97E-41 | 39 | 39 |
| E1_CncE1 | 366 | T | C | 31509 | 216 | 0.68% | 1.00E-35 | 38 | 40 |
| E1_CncE1 | 79 | T | C | 37597 | 244 | 0.64% | 5.55E-39 | 39 | 40 |
| E1_CncE1 | 441 | T | C | 37387 | 241 | 0.64% | 2.93E-38 | 40 | 40 |
| E1_CncE1 | 367 | T | C | 30876 | 187 | 0.60% | 9.38E-29 | 38 | 39 |
| E1_CncE1 | 357 | T | C | 29463 | 176 | 0.59% | 3.01E-27 | 37 | 38 |
| E1_CncE1 | 368 | T | C | 33124 | 198 | 0.59% | 2.95E-30 | 39 | 39 |
| E1_CncE1 | 343 | T | C | 31342 | 176 | 0.56% | 3.55E-26 | 37 | 38 |
| E1_CncE1 | 86 | T | C | 37255 | 202 | 0.54% | 4.43E-29 | 39 | 39 |
| E1_CncE1 | 339 | T | C | 29576 | 152 | 0.51% | 1.11E-21 | 37 | 38 |
| E1_CncE1 | 354 | T | C | 26010 | 127 | 0.49% | 1.64E-17 | 37 | 38 |
| E1_CncE1 | 445 | T | C | 36811 | 176 | 0.48% | 1.07E-23 | 40 | 39 |
| E1_CncE1 | 95 | T | C | 38264 | 172 | 0.45% | 6.55E-22 | 40 | 39 |
| E1_CncE1 | 340 | T | C | 30601 | 133 | 0.43% | 5.12E-17 | 37 | 37 |
| E1_CncE1 | 355 | T | C | 28229 | 121 | 0.43% | 2.59E-15 | 37 | 38 |

TABLE 4-continued

T-to-C mutation frequencies in amplicon sequences: 50 μM
4sU WITH OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| E1_CncE1 | 431 | T | C | 36833 | 154 | 0.42% | 6.34E−19 | 40 | 40 |
| E1_CncE1 | 385 | T | C | 35068 | 140 | 0.40% | 2.07E−16 | 39 | 39 |
| E1_CncE1 | 109 | T | C | 36596 | 139 | 0.38% | 8.19E−16 | 39 | 40 |
| E1_CncE1 | 450 | T | C | 37569 | 142 | 0.38% | 4.90E−16 | 40 | 39 |
| E1_CncE1 | 346 | T | C | 30403 | 109 | 0.36% | 4.68E−12 | 37 | 38 |
| E1_CncE1 | 42 | T | C | 39219 | 138 | 0.35% | 1.68E−14 | 40 | 40 |
| E1_CncE1 | 365 | T | C | 30454 | 103 | 0.34% | 6.95E−11 | 38 | 39 |
| E1_CncE1 | 84 | T | C | 36119 | 121 | 0.33% | 2.86E−12 | 39 | 40 |
| E1_CncE1 | 372 | T | C | 31722 | 99 | 0.31% | 8.58E−10 | 38 | 39 |
| E1_CncE1 | 102 | T | C | 36044 | 98 | 0.27% | 3.95E−08 | 39 | 39 |
| E1_CncE1 | 104 | T | C | 37642 | 93 | 0.25% | 4.75E−07 | 39 | 40 |
| E1_CncE1 | 337 | T | C | 29997 | 76 | 0.25% | 4.47E−06 | 38 | 37 |
| E1_CncE1 | 49 | T | C | 39166 | 96 | 0.24% | 4.93E−07 | 40 | 40 |
| E1_CncE1 | 344 | T | C | 30046 | 71 | 0.24% | 2.73E−05 | 37 | 37 |
| E1_CncE1 | 438 | T | C | 36679 | 86 | 0.23% | 3.40E−06 | 40 | 40 |
| E1_CncE1 | 22 | T | C | 39960 | 90 | 0.22% | 6.75E−06 | 40 | 40 |
| E1_CncE1 | 52 | T | C | 39186 | 85 | 0.22% | 2.18E−05 | 40 | 40 |
| E1_CncE1 | 361 | T | C | 27100 | 59 | 0.22% | 3.62E−04 | 37 | 38 |
| E1_CncE1 | 43 | T | C | 38913 | 82 | 0.21% | 3.60E−05 | 40 | 40 |
| E1_CncE1 | 48 | T | C | 38990 | 84 | 0.21% | 3.01E−05 | 40 | 40 |
| E1_CncE1 | 398 | T | C | 34143 | 65 | 0.19% | 1.19E−03 | 39 | 39 |
| E1_CncE1 | 376 | T | C | 34263 | 63 | 0.18% | 2.10E−03 | 39 | 39 |
| E1_CncE1 | 107 | T | C | 37420 | 61 | 0.16% | 9.81E−03 | 39 | 40 |
| E1_CncE1 | 82 | T | C | 36575 | 13 | 0.04% | 6.99E−04 | 39 | 38 |
| E1_CncE1 | 341 | T | C | 30383 | 7 | 0.02% | 9.51E−05 | 37 | 39 |
| eGFP | 138 | T | C | 3938 | 92 | 2.27% | 2.71E−23 | 34 | 36 |
| eGFP | 144 | T | C | 16111 | 121 | 0.75% | 1.65E−21 | 36 | 38 |
| eGFP | 324 | T | C | 11757 | 89 | 0.75% | 1.12E−16 | 37 | 40 |
| eGFP | 309 | T | C | 10067 | 67 | 0.66% | 7.84E−12 | 36 | 37 |
| eGFP | 313 | T | C | 12803 | 82 | 0.64% | 2.56E−14 | 38 | 39 |
| eGFP | 118 | T | C | 26045 | 157 | 0.60% | 2.12E−24 | 38 | 38 |
| eGFP | 292 | T | C | 11936 | 71 | 0.59% | 1.11E−11 | 37 | 39 |
| eGFP | 100 | T | C | 28833 | 149 | 0.51% | 1.70E−21 | 39 | 39 |
| eGFP | 295 | T | C | 10647 | 55 | 0.51% | 5.61E−09 | 37 | 40 |
| eGFP | 364 | T | C | 15654 | 81 | 0.51% | 1.88E−12 | 39 | 40 |
| eGFP | 121 | T | C | 28428 | 130 | 0.46% | 2.98E−17 | 38 | 39 |
| eGFP | 94 | T | C | 27003 | 122 | 0.45% | 5.83E−16 | 38 | 39 |
| eGFP | 99 | T | C | 30195 | 135 | 0.45% | 1.90E−17 | 39 | 40 |
| eGFP | 331 | T | C | 15219 | 69 | 0.45% | 9.24E−10 | 39 | 40 |
| eGFP | 79 | T | C | 29710 | 131 | 0.44% | 5.04E−17 | 39 | 40 |
| eGFP | 70 | T | C | 27821 | 121 | 0.43% | 9.61E−16 | 39 | 39 |
| eGFP | 397 | T | C | 16730 | 71 | 0.42% | 9.36E−10 | 40 | 40 |
| eGFP | 27 | T | C | 32584 | 128 | 0.39% | 3.93E−15 | 40 | 40 |
| eGFP | 370 | T | C | 16072 | 63 | 0.39% | 4.56E−08 | 40 | 40 |
| eGFP | 67 | T | C | 31871 | 121 | 0.38% | 4.32E−14 | 40 | 40 |
| eGFP | 367 | T | C | 15475 | 59 | 0.38% | 1.24E−07 | 39 | 40 |
| eGFP | 359 | T | C | 15809 | 58 | 0.37% | 1.99E−07 | 40 | 40 |
| eGFP | 133 | T | C | 25639 | 89 | 0.35% | 6.32E−10 | 38 | 39 |
| eGFP | 378 | T | C | 16666 | 58 | 0.35% | 4.71E−07 | 40 | 40 |
| eGFP | 379 | T | C | 16317 | 58 | 0.35% | 4.71E−07 | 39 | 40 |
| eGFP | 401 | T | C | 16270 | 56 | 0.34% | 1.17E−06 | 40 | 40 |
| eGFP | 52 | T | C | 31773 | 101 | 0.32% | 3.64E−10 | 40 | 40 |
| eGFP | 382 | T | C | 16451 | 52 | 0.32% | 6.90E−06 | 40 | 40 |
| eGFP | 85 | T | C | 30887 | 92 | 0.30% | 7.98E−09 | 39 | 40 |
| eGFP | 51 | T | C | 31133 | 84 | 0.27% | 3.92E−07 | 39 | 40 |
| eGFP | 46 | T | C | 28515 | 73 | 0.26% | 4.24E−06 | 39 | 40 |
| eGFP | 403 | T | C | 16689 | 44 | 0.26% | 1.95E−04 | 40 | 40 |
| p21_Cdkn1A | 446 | T | C | 69753 | 554 | 0.79% | 4.90E−95 | 40 | 40 |
| p21_Cdkn1A | 121 | T | C | 50810 | 394 | 0.77% | 2.71E−67 | 37 | 39 |
| p21_Cdkn1A | 125 | T | C | 64576 | 464 | 0.71% | 7.60E−76 | 38 | 38 |
| p21_Cdkn1A | 131 | T | C | 54628 | 337 | 0.61% | 1.45E−51 | 37 | 39 |
| p21_Cdkn1A | 137 | T | C | 61371 | 353 | 0.57% | 1.64E−51 | 37 | 38 |
| p21_Cdkn1A | 356 | T | C | 55558 | 321 | 0.57% | 3.04E−47 | 38 | 39 |
| p21_Cdkn1A | 49 | T | C | 74290 | 352 | 0.47% | 7.58E−45 | 39 | 40 |
| p21_Cdkn1A | 352 | T | C | 59255 | 280 | 0.47% | 5.93E−36 | 38 | 39 |
| p21_Cdkn1A | 374 | T | C | 66137 | 310 | 0.47% | 2.57E−39 | 39 | 40 |
| p21_Cdkn1A | 354 | T | C | 54172 | 244 | 0.45% | 2.24E−30 | 38 | 40 |
| p21_Cdkn1A | 350 | T | C | 60059 | 267 | 0.44% | 1.10E−32 | 38 | 39 |
| p21_Cdkn1A | 132 | T | C | 52222 | 228 | 0.43% | 8.09E−28 | 37 | 38 |
| p21_Cdkn1A | 361 | T | C | 53650 | 231 | 0.43% | 5.01E−28 | 38 | 40 |
| p21_Cdkn1A | 378 | T | C | 62420 | 268 | 0.43% | 4.90E−32 | 39 | 40 |
| p21_Cdkn1A | 347 | T | C | 63647 | 247 | 0.39% | 2.93E−27 | 39 | 39 |
| p21_Cdkn1A | 126 | T | C | 62747 | 238 | 0.38% | 8.02E−26 | 38 | 38 |
| p21_Cdkn1A | 439 | T | C | 70197 | 233 | 0.33% | 5.77E−22 | 40 | 40 |
| p21_Cdkn1A | 436 | T | C | 70167 | 183 | 0.26% | 3.77E−13 | 40 | 40 |

TABLE 4-continued

T-to-C mutation frequencies in amplicon sequences: 50 μM 4sU WITH OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| p21_Cdkn1A | 437 | T | C | 69344 | 180 | 0.26% | 6.38E-13 | 40 | 40 |
| p21_Cdkn1A | 447 | T | C | 69978 | 180 | 0.26% | 1.15E-12 | 40 | 40 |
| p21_Cdkn1A | 434 | T | C | 69618 | 169 | 0.24% | 3.54E-11 | 40 | 40 |
| p21_Cdkn1A | 55 | T | C | 78553 | 185 | 0.23% | 1.64E-11 | 40 | 39 |
| p21_Cdkn1A | 94 | T | C | 73973 | 169 | 0.23% | 4.91E-10 | 39 | 40 |
| p21_Cdkn1A | 114 | T | C | 68785 | 152 | 0.22% | 7.22E-09 | 39 | 39 |
| p21_Cdkn1A | 133 | T | C | 52930 | 88 | 0.17% | 2.00E-03 | 37 | 38 |
| p21_Cdkn1A | 334 | T | C | 47404 | 79 | 0.17% | 2.75E-03 | 37 | 38 |
| p21_Cdkn1A | 32 | T | C | 78470 | 41 | 0.05% | 4.42E-04 | 40 | 40 |
| p21_Cdkn1A | 122 | T | C | 58172 | 15 | 0.03% | 2.03E-07 | 37 | 36 |
| p21_Cdkn1A | 385 | T | C | 64321 | 20 | 0.03% | 7.87E-07 | 39 | 36 |
| p21_Cdkn1A | 457 | T | C | 67935 | 23 | 0.03% | 1.88E-06 | 40 | 40 |
| p21_Cdkn1A | 2 | T | C | 79054 | 18 | 0.02% | 1.34E-10 | 40 | 40 |
| PCNA | 145 | T | C | 15020 | 87 | 0.58% | 7.59E-14 | 34 | 38 |
| PCNA | 438 | T | C | 91470 | 179 | 0.20% | 4.53E-08 | 40 | 40 |
| PCNA | 47 | T | C | 102359 | 173 | 0.17% | 1.09E-05 | 40 | 40 |
| PCNA | 353 | T | C | 80534 | 141 | 0.17% | 2.43E-05 | 38 | 40 |
| PCNA | 426 | T | C | 92806 | 157 | 0.17% | 2.25E-05 | 40 | 40 |
| PCNA | 390 | T | C | 89738 | 140 | 0.16% | 4.53E-04 | 40 | 40 |
| PCNA | 69 | T | C | 108282 | 164 | 0.15% | 4.08E-04 | 40 | 40 |
| PCNA | 136 | T | C | 90575 | 136 | 0.15% | 1.33E-03 | 38 | 39 |
| PCNA | 352 | T | C | 79764 | 117 | 0.15% | 4.01E-03 | 39 | 39 |
| PCNA | 409 | T | C | 87349 | 135 | 0.15% | 7.70E-04 | 40 | 40 |
| PCNA | 46 | T | C | 100116 | 139 | 0.14% | 6.87E-03 | 39 | 40 |
| PCNA | 128 | T | C | 98924 | 58 | 0.06% | 8.49E-04 | 39 | 39 |
| PCNA | 372 | T | C | 91029 | 51 | 0.06% | 4.95E-04 | 40 | 40 |
| PCNA | 374 | T | C | 86805 | 50 | 0.06% | 1.27E-03 | 39 | 40 |
| PCNA | 376 | T | C | 90187 | 51 | 0.06% | 6.42E-04 | 40 | 40 |
| PCNA | 434 | T | C | 91952 | 55 | 0.06% | 1.42E-03 | 40 | 40 |
| PCNA | 83 | T | C | 87098 | 46 | 0.05% | 2.37E-04 | 38 | 39 |
| PCNA | 393 | T | C | 90394 | 42 | 0.05% | 1.78E-05 | 40 | 39 |
| PCNA | 396 | T | C | 89196 | 44 | 0.05% | 5.89E-05 | 39 | 39 |
| PCNA | 425 | T | C | 92247 | 46 | 0.05% | 5.55E-05 | 40 | 40 |
| PCNA | 19 | T | C | 107758 | 42 | 0.04% | 4.96E-08 | 40 | 39 |
| PCNA | 38 | T | C | 97486 | 42 | 0.04% | 1.74E-06 | 39 | 40 |
| PCNA | 54 | T | C | 104403 | 44 | 0.04% | 4.40E-07 | 40 | 40 |
| PCNA | 70 | T | C | 105732 | 41 | 0.04% | 5.81E-08 | 40 | 40 |
| PCNA | 93 | T | C | 99610 | 42 | 0.04% | 8.74E-07 | 39 | 39 |
| PCNA | 96 | T | C | 102093 | 34 | 0.03% | 2.16E-09 | 39 | 40 |

TABLE 5

T-to-C mutation frequencies in amplicon sequences: 100 μM 4sU WITH OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| A2_CcnA2 | 314 | T | C | 17229 | 47 | 0.27% | 1.12E-04 | 34 | 37 |
| A2_CcnA2 | 93 | T | C | 95768 | 154 | 0.16% | 1.11E-04 | 40 | 40 |
| A2_CcnA2 | 77 | T | C | 94703 | 53 | 0.06% | 4.51E-04 | 40 | 40 |
| A2_CcnA2 | 344 | T | C | 81562 | 47 | 0.06% | 1.68E-03 | 39 | 40 |
| A2_CcnA2 | 396 | T | C | 88361 | 51 | 0.06% | 1.07E-03 | 40 | 40 |
| A2_CcnA2 | 22 | T | C | 96154 | 47 | 0.05% | 2.54E-05 | 40 | 40 |
| A2_CcnA2 | 56 | T | C | 97232 | 51 | 0.05% | 9.66E-05 | 40 | 40 |
| A2_CcnA2 | 74 | T | C | 93292 | 49 | 0.05% | 1.38E-04 | 40 | 40 |
| A2_CcnA2 | 328 | T | C | 74174 | 36 | 0.05% | 1.85E-04 | 38 | 38 |
| A2_CcnA2 | 108 | T | C | 90484 | 35 | 0.04% | 4.58E-07 | 40 | 39 |
| B1_CncB1 | 372 | T | C | 78828 | 517 | 0.65% | 2.17E-80 | 40 | 40 |
| B1_CncB1 | 90 | T | C | 82706 | 522 | 0.63% | 2.67E-79 | 40 | 40 |
| B1_CncB1 | 374 | T | C | 79457 | 491 | 0.61% | 3.60E-74 | 40 | 40 |
| B1_CncB1 | 376 | T | C | 78643 | 466 | 0.59% | 2.85E-68 | 40 | 39 |
| B1_CncB1 | 366 | T | C | 78836 | 456 | 0.58% | 6.18E-66 | 40 | 39 |
| B1_CncB1 | 128 | T | C | 80127 | 450 | 0.56% | 5.15E-64 | 39 | 39 |
| B1_CncB1 | 382 | T | C | 78664 | 393 | 0.50% | 1.44E-51 | 40 | 40 |
| B1_CncB1 | 367 | T | C | 79817 | 397 | 0.49% | 5.55E-52 | 40 | 39 |
| B1_CncB1 | 373 | T | C | 79744 | 381 | 0.48% | 1.91E-48 | 40 | 39 |
| B1_CncB1 | 334 | T | C | 74480 | 355 | 0.47% | 1.66E-45 | 39 | 39 |
| B1_CncB1 | 416 | T | C | 81354 | 375 | 0.46% | 1.12E-46 | 40 | 40 |
| B1_CncB1 | 380 | T | C | 77105 | 352 | 0.45% | 1.74E-43 | 39 | 39 |
| B1_CncB1 | 333 | T | C | 73215 | 321 | 0.44% | 1.39E-38 | 39 | 39 |
| B1_CncB1 | 346 | T | C | 74830 | 331 | 0.44% | 7.48E-40 | 39 | 39 |
| B1_CncB1 | 387 | T | C | 79064 | 347 | 0.44% | 1.56E-41 | 40 | 40 |
| B1_CncB1 | 422 | T | C | 78794 | 347 | 0.44% | 1.55E-41 | 40 | 40 |

TABLE 5-continued

T-to-C mutation frequencies in amplicon sequences: 100 µM 4sU WITH OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| B1_CncB1 | 137 | T | C | 72495 | 311 | 0.43% | 6.91E-37 | 39 | 39 |
| B1_CncB1 | 426 | T | C | 79682 | 342 | 0.43% | 4.78E-40 | 40 | 40 |
| B1_CncB1 | 38 | T | C | 83781 | 344 | 0.41% | 8.33E-39 | 40 | 40 |
| B1_CncB1 | 440 | T | C | 81257 | 334 | 0.41% | 5.91E-38 | 40 | 40 |
| B1_CncB1 | 417 | T | C | 81403 | 327 | 0.40% | 1.66E-36 | 40 | 40 |
| B1_CncB1 | 123 | T | C | 78311 | 310 | 0.39% | 3.27E-34 | 39 | 39 |
| B1_CncB1 | 377 | T | C | 79551 | 309 | 0.39% | 1.30E-33 | 40 | 40 |
| B1_CncB1 | 97 | T | C | 79964 | 302 | 0.38% | 8.15E-32 | 40 | 39 |
| B1_CncB1 | 98 | T | C | 79033 | 302 | 0.38% | 3.39E-32 | 40 | 40 |
| B1_CncB1 | 103 | T | C | 79125 | 304 | 0.38% | 1.34E-32 | 39 | 39 |
| B1_CncB1 | 116 | T | C | 80234 | 307 | 0.38% | 8.06E-33 | 39 | 39 |
| B1_CncB1 | 328 | T | C | 62391 | 237 | 0.38% | 1.28E-25 | 37 | 37 |
| B1_CncB1 | 345 | T | C | 77092 | 292 | 0.38% | 5.97E-31 | 39 | 39 |
| B1_CncB1 | 60 | T | C | 83848 | 310 | 0.37% | 6.58E-32 | 40 | 40 |
| B1_CncB1 | 129 | T | C | 77324 | 283 | 0.36% | 3.71E-29 | 39 | 38 |
| B1_CncB1 | 50 | T | C | 83021 | 295 | 0.35% | 2.51E-29 | 40 | 40 |
| B1_CncB1 | 61 | T | C | 84477 | 294 | 0.35% | 8.91E-29 | 40 | 40 |
| B1_CncB1 | 62 | T | C | 85160 | 299 | 0.35% | 2.17E-29 | 40 | 40 |
| B1_CncB1 | 330 | T | C | 71978 | 252 | 0.35% | 6.66E-25 | 39 | 39 |
| B1_CncB1 | 348 | T | C | 77510 | 270 | 0.35% | 1.30E-26 | 39 | 39 |
| B1_CncB1 | 43 | T | C | 85102 | 278 | 0.33% | 2.14E-25 | 40 | 40 |
| B1_CncB1 | 358 | T | C | 74562 | 247 | 0.33% | 2.95E-23 | 39 | 39 |
| B1_CncB1 | 396 | T | C | 78642 | 257 | 0.33% | 8.54E-24 | 40 | 40 |
| B1_CncB1 | 117 | T | C | 80847 | 261 | 0.32% | 1.50E-23 | 39 | 39 |
| B1_CncB1 | 341 | T | C | 73130 | 238 | 0.32% | 6.66E-22 | 39 | 39 |
| B1_CncB1 | 353 | T | C | 77394 | 251 | 0.32% | 5.26E-23 | 39 | 39 |
| B1_CncB1 | 451 | T | C | 81093 | 256 | 0.31% | 1.25E-22 | 40 | 40 |
| B1_CncB1 | 113 | T | C | 82500 | 249 | 0.30% | 4.74E-21 | 40 | 40 |
| B1_CncB1 | 369 | T | C | 79995 | 238 | 0.30% | 1.06E-19 | 40 | 39 |
| B1_CncB1 | 421 | T | C | 80248 | 245 | 0.30% | 5.99E-21 | 40 | 40 |
| B1_CncB1 | 436 | T | C | 80004 | 237 | 0.30% | 1.59E-19 | 40 | 40 |
| B1_CncB1 | 54 | T | C | 82820 | 238 | 0.29% | 8.06E-19 | 40 | 40 |
| B1_CncB1 | 72 | T | C | 81138 | 240 | 0.29% | 9.36E-20 | 40 | 40 |
| B1_CncB1 | 89 | T | C | 83776 | 246 | 0.29% | 6.41E-20 | 40 | 40 |
| B1_CncB1 | 349 | T | C | 78521 | 225 | 0.29% | 5.15E-18 | 39 | 39 |
| B1_CncB1 | 356 | T | C | 76090 | 225 | 0.29% | 1.33E-18 | 39 | 39 |
| B1_CncB1 | 433 | T | C | 79213 | 230 | 0.29% | 1.36E-18 | 40 | 40 |
| B1_CncB1 | 336 | T | C | 73123 | 204 | 0.28% | 7.82E-16 | 39 | 39 |
| B1_CncB1 | 368 | T | C | 79647 | 221 | 0.28% | 4.82E-17 | 40 | 39 |
| B1_CncB1 | 418 | T | C | 81630 | 233 | 0.28% | 1.56E-18 | 40 | 40 |
| B1_CncB1 | 53 | T | C | 83461 | 222 | 0.27% | 4.05E-16 | 40 | 40 |
| B1_CncB1 | 111 | T | C | 80562 | 221 | 0.27% | 9.15E-17 | 39 | 39 |
| B1_CncB1 | 332 | T | C | 73702 | 203 | 0.27% | 1.16E-15 | 39 | 39 |
| B1_CncB1 | 399 | T | C | 79847 | 219 | 0.27% | 1.98E-16 | 40 | 40 |
| B1_CncB1 | 407 | T | C | 81039 | 220 | 0.27% | 2.53E-16 | 40 | 40 |
| B1_CncB1 | 85 | T | C | 82212 | 213 | 0.26% | 6.53E-15 | 40 | 40 |
| B1_CncB1 | 405 | T | C | 80276 | 206 | 0.26% | 2.69E-14 | 40 | 39 |
| B1_CncB1 | 20 | T | C | 85206 | 210 | 0.25% | 1.09E-13 | 40 | 40 |
| B1_CncB1 | 108 | T | C | 71091 | 176 | 0.25% | 8.76E-12 | 38 | 40 |
| B1_CncB1 | 115 | T | C | 80685 | 204 | 0.25% | 5.62E-14 | 39 | 39 |
| B1_CncB1 | 351 | T | C | 78288 | 197 | 0.25% | 2.30E-13 | 39 | 39 |
| B1_CncB1 | 354 | T | C | 77671 | 198 | 0.25% | 8.94E-14 | 39 | 39 |
| B1_CncB1 | 408 | T | C | 80953 | 201 | 0.25% | 2.95E-13 | 40 | 40 |
| B1_CncB1 | 45 | T | C | 85165 | 204 | 0.24% | 9.10E-13 | 40 | 40 |
| B1_CncB1 | 92 | T | C | 83194 | 201 | 0.24% | 8.87E-13 | 40 | 40 |
| B1_CncB1 | 42 | T | C | 84936 | 193 | 0.23% | 3.90E-11 | 40 | 40 |
| B1_CncB1 | 27 | T | C | 83380 | 185 | 0.22% | 2.06E-10 | 40 | 40 |
| B1_CncB1 | 139 | T | C | 72494 | 163 | 0.22% | 1.35E-09 | 39 | 39 |
| B1_CncB1 | 386 | T | C | 79842 | 180 | 0.22% | 2.47E-10 | 40 | 40 |
| B1_CncB1 | 102 | T | C | 77004 | 165 | 0.21% | 7.65E-09 | 39 | 40 |
| B1_CncB1 | 362 | T | C | 76543 | 164 | 0.21% | 6.63E-09 | 39 | 39 |
| B1_CncB1 | 409 | T | C | 80977 | 169 | 0.21% | 1.33E-08 | 40 | 40 |
| B1_CncB1 | 415 | T | C | 80737 | 173 | 0.21% | 2.41E-09 | 40 | 40 |
| B1_CncB1 | 338 | T | C | 70439 | 142 | 0.20% | 4.21E-07 | 39 | 39 |
| B1_CncB1 | 352 | T | C | 78610 | 160 | 0.20% | 5.62E-08 | 39 | 39 |
| B1_CncB1 | 442 | T | C | 81762 | 153 | 0.19% | 1.44E-06 | 40 | 40 |
| B1_CncB1 | 29 | T | C | 85095 | 153 | 0.18% | 6.10E-06 | 40 | 40 |
| B1_CncB1 | 144 | T | C | 66483 | 116 | 0.17% | 1.28E-04 | 39 | 39 |
| B1_CncB1 | 454 | T | C | 82057 | 31 | 0.04% | 8.58E-07 | 40 | 40 |
| D1_CncD1 | 395 | T | C | 97363 | 1946 | 1.96% | 0.00E+00 | 40 | 40 |
| D1_CncD1 | 393 | T | C | 98529 | 1112 | 1.12% | 6.94E-219 | 40 | 40 |
| D1_CncD1 | 391 | T | C | 98614 | 779 | 0.78% | 1.55E-132 | 40 | 40 |
| D1_CncD1 | 392 | T | C | 98759 | 763 | 0.77% | 1.56E-128 | 40 | 40 |
| D1_CncD1 | 104 | T | C | 49371 | 321 | 0.65% | 1.38E-50 | 35 | 39 |
| D1_CncD1 | 22 | T | C | 99542 | 630 | 0.63% | 1.96E-95 | 40 | 40 |
| D1_CncD1 | 336 | T | C | 95044 | 525 | 0.55% | 1.59E-73 | 40 | 40 |

TABLE 5-continued

T-to-C mutation frequencies in amplicon sequences: 100 μM 4sU WITH OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| D1_CncD1 | 333 | T | C | 94154 | 503 | 0.53% | 5.34E-69 | 40 | 39 |
| D1_CncD1 | 141 | T | C | 55375 | 279 | 0.50% | 1.29E-37 | 36 | 39 |
| D1_CncD1 | 292 | T | C | 87004 | 437 | 0.50% | 1.50E-57 | 39 | 39 |
| D1_CncD1 | 332 | T | C | 93820 | 472 | 0.50% | 5.26E-62 | 40 | 40 |
| D1_CncD1 | 386 | T | C | 98938 | 472 | 0.47% | 1.19E-59 | 40 | 40 |
| D1_CncD1 | 388 | T | C | 99215 | 466 | 0.47% | 2.46E-58 | 40 | 40 |
| D1_CncD1 | 45 | T | C | 100510 | 452 | 0.45% | 7.54E-55 | 40 | 40 |
| D1_CncD1 | 288 | T | C | 86450 | 370 | 0.43% | 2.03E-43 | 39 | 39 |
| D1_CncD1 | 359 | T | C | 98567 | 419 | 0.42% | 1.11E-48 | 40 | 39 |
| D1_CncD1 | 361 | T | C | 92043 | 383 | 0.41% | 1.23E-43 | 38 | 40 |
| D1_CncD1 | 44 | T | C | 101406 | 409 | 0.40% | 2.35E-45 | 40 | 40 |
| D1_CncD1 | 61 | T | C | 98337 | 395 | 0.40% | 1.12E-43 | 40 | 40 |
| D1_CncD1 | 62 | T | C | 99170 | 391 | 0.39% | 1.85E-42 | 40 | 40 |
| D1_CncD1 | 327 | T | C | 95762 | 374 | 0.39% | 3.54E-40 | 40 | 40 |
| D1_CncD1 | 26 | T | C | 100436 | 382 | 0.38% | 3.02E-40 | 40 | 40 |
| D1_CncD1 | 357 | T | C | 97772 | 374 | 0.38% | 2.10E-39 | 40 | 40 |
| D1_CncD1 | 142 | T | C | 66115 | 247 | 0.37% | 4.16E-26 | 36 | 37 |
| D1_CncD1 | 340 | T | C | 95946 | 357 | 0.37% | 9.21E-37 | 40 | 40 |
| D1_CncD1 | 355 | T | C | 97953 | 363 | 0.37% | 3.31E-37 | 40 | 40 |
| D1_CncD1 | 27 | T | C | 101288 | 366 | 0.36% | 1.08E-36 | 40 | 40 |
| D1_CncD1 | 287 | T | C | 86092 | 310 | 0.36% | 3.58E-31 | 39 | 39 |
| D1_CncD1 | 99 | T | C | 49973 | 174 | 0.35% | 1.37E-17 | 34 | 40 |
| D1_CncD1 | 320 | T | C | 94227 | 327 | 0.35% | 1.29E-31 | 40 | 39 |
| D1_CncD1 | 329 | T | C | 95300 | 334 | 0.35% | 1.29E-32 | 40 | 40 |
| D1_CncD1 | 358 | T | C | 97616 | 343 | 0.35% | 1.20E-33 | 40 | 40 |
| D1_CncD1 | 25 | T | C | 97970 | 335 | 0.34% | 9.34E-32 | 40 | 40 |
| D1_CncD1 | 295 | T | C | 85496 | 289 | 0.34% | 1.81E-27 | 39 | 39 |
| D1_CncD1 | 33 | T | C | 101789 | 342 | 0.33% | 1.02E-31 | 40 | 40 |
| D1_CncD1 | 87 | T | C | 95763 | 321 | 0.33% | 8.76E-30 | 39 | 40 |
| D1_CncD1 | 116 | T | C | 84032 | 276 | 0.33% | 2.35E-25 | 39 | 39 |
| D1_CncD1 | 371 | T | C | 97125 | 317 | 0.33% | 1.06E-28 | 40 | 40 |
| D1_CncD1 | 143 | T | C | 72349 | 233 | 0.32% | 2.66E-21 | 37 | 38 |
| D1_CncD1 | 276 | T | C | 79921 | 256 | 0.32% | 5.94E-23 | 39 | 38 |
| D1_CncD1 | 325 | T | C | 95335 | 302 | 0.32% | 1.41E-26 | 40 | 40 |
| D1_CncD1 | 377 | T | C | 97538 | 302 | 0.31% | 6.10E-26 | 40 | 40 |
| D1_CncD1 | 49 | T | C | 102259 | 303 | 0.30% | 1.38E-24 | 40 | 40 |
| D1_CncD1 | 346 | T | C | 95760 | 293 | 0.30% | 1.25E-24 | 40 | 40 |
| D1_CncD1 | 35 | T | C | 101126 | 288 | 0.28% | 2.88E-22 | 40 | 40 |
| D1_CncD1 | 294 | T | C | 85101 | 236 | 0.28% | 6.51E-18 | 39 | 38 |
| D1_CncD1 | 334 | T | C | 95321 | 271 | 0.28% | 4.63E-21 | 40 | 39 |
| D1_CncD1 | 362 | T | C | 99917 | 277 | 0.28% | 1.12E-20 | 39 | 40 |
| D1_CncD1 | 63 | T | C | 99857 | 268 | 0.27% | 3.56E-19 | 40 | 40 |
| D1_CncD1 | 82 | T | C | 93696 | 252 | 0.27% | 2.10E-18 | 39 | 40 |
| D1_CncD1 | 282 | T | C | 87534 | 237 | 0.27% | 1.57E-17 | 39 | 39 |
| D1_CncD1 | 48 | T | C | 102022 | 270 | 0.26% | 5.65E-19 | 40 | 40 |
| D1_CncD1 | 93 | T | C | 82287 | 211 | 0.26% | 1.37E-14 | 38 | 40 |
| D1_CncD1 | 39 | T | C | 99180 | 251 | 0.25% | 1.10E-16 | 40 | 40 |
| D1_CncD1 | 106 | T | C | 65615 | 167 | 0.25% | 7.55E-12 | 35 | 39 |
| D1_CncD1 | 283 | T | C | 87887 | 223 | 0.25% | 5.41E-15 | 39 | 39 |
| D1_CncD1 | 296 | T | C | 83532 | 212 | 0.25% | 1.70E-14 | 38 | 39 |
| D1_CncD1 | 309 | T | C | 93779 | 224 | 0.24% | 1.04E-13 | 40 | 39 |
| D1_CncD1 | 311 | T | C | 95064 | 230 | 0.24% | 2.18E-14 | 40 | 39 |
| D1_CncD1 | 107 | T | C | 78258 | 169 | 0.22% | 3.40E-09 | 36 | 38 |
| D1_CncD1 | 108 | T | C | 85602 | 186 | 0.22% | 3.88E-10 | 38 | 39 |
| D1_CncD1 | 313 | T | C | 95131 | 206 | 0.22% | 6.92E-11 | 40 | 39 |
| D1_CncD1 | 339 | T | C | 96506 | 206 | 0.21% | 1.10E-10 | 40 | 39 |
| D1_CncD1 | 374 | T | C | 97112 | 208 | 0.21% | 9.25E-11 | 40 | 40 |
| D1_CncD1 | 126 | T | C | 80799 | 162 | 0.20% | 7.22E-08 | 38 | 39 |
| D1_CncD1 | 272 | T | C | 82259 | 169 | 0.20% | 2.06E-08 | 38 | 38 |
| D1_CncD1 | 310 | T | C | 95070 | 189 | 0.20% | 1.26E-08 | 40 | 40 |
| D1_CncD1 | 74 | T | C | 99005 | 190 | 0.19% | 4.63E-08 | 40 | 39 |
| D1_CncD1 | 273 | T | C | 83610 | 157 | 0.19% | 1.01E-06 | 38 | 38 |
| D1_CncD1 | 285 | T | C | 81655 | 156 | 0.19% | 6.20E-07 | 39 | 39 |
| D1_CncD1 | 120 | T | C | 86563 | 152 | 0.18% | 1.11E-05 | 39 | 40 |
| D1_CncD1 | 274 | T | C | 84396 | 142 | 0.17% | 6.86E-05 | 38 | 38 |
| D1_CncD1 | 312 | T | C | 94754 | 159 | 0.17% | 2.59E-05 | 40 | 39 |
| D1_CncD1 | 47 | T | C | 100560 | 149 | 0.15% | 1.14E-03 | 40 | 40 |
| D1_CncD1 | 353 | T | C | 97016 | 145 | 0.15% | 1.22E-03 | 40 | 40 |
| D1_CncD1 | 72 | T | C | 89037 | 128 | 0.14% | 4.84E-03 | 38 | 40 |
| E1_CncE1 | 363 | T | C | 41790 | 452 | 1.07% | 1.29E-88 | 37 | 39 |
| E1_CncE1 | 346 | T | C | 45613 | 424 | 0.92% | 2.60E-78 | 37 | 38 |
| E1_CncE1 | 364 | T | C | 42721 | 392 | 0.91% | 3.44E-72 | 37 | 39 |
| E1_CncE1 | 343 | T | C | 47248 | 429 | 0.90% | 6.94E-79 | 37 | 38 |
| E1_CncE1 | 341 | T | C | 45214 | 370 | 0.81% | 3.43E-65 | 37 | 38 |
| E1_CncE1 | 431 | T | C | 54861 | 425 | 0.77% | 1.83E-72 | 39 | 40 |
| E1_CncE1 | 351 | T | C | 41880 | 307 | 0.73% | 2.28E-51 | 37 | 38 |

TABLE 5-continued

T-to-C mutation frequencies in amplicon sequences: 100 µM 4sU WITH OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| E1_CncE1 | 347 | T | C | 43852 | 293 | 0.66% | 9.69E−47 | 37 | 39 |
| E1_CncE1 | 450 | T | C | 56575 | 366 | 0.64% | 2.29E−57 | 40 | 40 |
| E1_CncE1 | 367 | T | C | 46176 | 292 | 0.63% | 2.40E−45 | 38 | 39 |
| E1_CncE1 | 22 | T | C | 74541 | 444 | 0.59% | 8.08E−66 | 40 | 40 |
| E1_CncE1 | 362 | T | C | 39173 | 231 | 0.59% | 9.13E−35 | 37 | 39 |
| E1_CncE1 | 344 | T | C | 45782 | 247 | 0.54% | 8.06E−35 | 37 | 38 |
| E1_CncE1 | 380 | T | C | 52345 | 275 | 0.52% | 3.46E−38 | 39 | 39 |
| E1_CncE1 | 423 | T | C | 55074 | 278 | 0.50% | 2.15E−37 | 40 | 40 |
| E1_CncE1 | 79 | T | C | 70831 | 328 | 0.46% | 5.66E−41 | 40 | 40 |
| E1_CncE1 | 107 | T | C | 70044 | 323 | 0.46% | 2.45E−40 | 39 | 40 |
| E1_CncE1 | 357 | T | C | 44467 | 197 | 0.44% | 1.17E−24 | 37 | 39 |
| E1_CncE1 | 366 | T | C | 46986 | 210 | 0.44% | 3.88E−26 | 38 | 39 |
| E1_CncE1 | 365 | T | C | 45357 | 198 | 0.43% | 1.95E−24 | 38 | 39 |
| E1_CncE1 | 43 | T | C | 72976 | 307 | 0.42% | 1.27E−35 | 40 | 40 |
| E1_CncE1 | 368 | T | C | 49895 | 203 | 0.41% | 2.13E−23 | 38 | 40 |
| E1_CncE1 | 385 | T | C | 52735 | 204 | 0.39% | 8.30E−23 | 39 | 40 |
| E1_CncE1 | 410 | T | C | 52957 | 204 | 0.38% | 2.03E−22 | 39 | 40 |
| E1_CncE1 | 143 | T | C | 46070 | 169 | 0.37% | 4.72E−18 | 37 | 39 |
| E1_CncE1 | 339 | T | C | 44425 | 165 | 0.37% | 5.31E−18 | 37 | 37 |
| E1_CncE1 | 355 | T | C | 42165 | 157 | 0.37% | 3.74E−17 | 37 | 38 |
| E1_CncE1 | 47 | T | C | 72031 | 258 | 0.36% | 4.54E−26 | 40 | 40 |
| E1_CncE1 | 124 | T | C | 62050 | 225 | 0.36% | 3.13E−23 | 39 | 39 |
| E1_CncE1 | 444 | T | C | 55633 | 199 | 0.36% | 1.14E−20 | 40 | 39 |
| E1_CncE1 | 52 | T | C | 73417 | 247 | 0.34% | 1.35E−23 | 40 | 40 |
| E1_CncE1 | 48 | T | C | 73233 | 244 | 0.33% | 4.99E−23 | 40 | 40 |
| E1_CncE1 | 86 | T | C | 69462 | 218 | 0.31% | 1.66E−19 | 39 | 39 |
| E1_CncE1 | 340 | T | C | 45971 | 144 | 0.31% | 2.79E−13 | 37 | 37 |
| E1_CncE1 | 361 | T | C | 39897 | 125 | 0.31% | 1.05E−11 | 37 | 39 |
| E1_CncE1 | 426 | T | C | 55705 | 173 | 0.31% | 9.96E−16 | 40 | 40 |
| E1_CncE1 | 104 | T | C | 70783 | 211 | 0.30% | 6.28E−18 | 39 | 40 |
| E1_CncE1 | 109 | T | C | 68917 | 205 | 0.30% | 3.64E−17 | 39 | 40 |
| E1_CncE1 | 342 | T | C | 46651 | 137 | 0.29% | 5.10E−12 | 37 | 38 |
| E1_CncE1 | 445 | T | C | 55742 | 159 | 0.28% | 3.16E−13 | 40 | 40 |
| E1_CncE1 | 102 | T | C | 67403 | 172 | 0.25% | 3.83E−12 | 39 | 39 |
| E1_CncE1 | 49 | T | C | 73597 | 167 | 0.23% | 5.81E−10 | 40 | 40 |
| E1_CncE1 | 101 | T | C | 68007 | 149 | 0.22% | 1.93E−08 | 39 | 40 |
| E1_CncE1 | 414 | T | C | 54547 | 122 | 0.22% | 1.56E−07 | 40 | 39 |
| E1_CncE1 | 417 | T | C | 49757 | 108 | 0.22% | 1.40E−06 | 39 | 39 |
| E1_CncE1 | 95 | T | C | 71106 | 152 | 0.21% | 2.99E−08 | 40 | 40 |
| E1_CncE1 | 82 | T | C | 68220 | 134 | 0.20% | 1.96E−06 | 39 | 39 |
| E1_CncE1 | 84 | T | C | 66965 | 134 | 0.20% | 1.30E−06 | 39 | 40 |
| E1_CncE1 | 438 | T | C | 55220 | 108 | 0.20% | 1.98E−05 | 40 | 40 |
| E1_CncE1 | 121 | T | C | 61080 | 116 | 0.19% | 2.13E−05 | 38 | 39 |
| E1_CncE1 | 42 | T | C | 73589 | 132 | 0.18% | 2.25E−05 | 40 | 40 |
| E1_CncE1 | 81 | T | C | 66904 | 117 | 0.17% | 1.39E−04 | 39 | 39 |
| E1_CncE1 | 354 | T | C | 38412 | 65 | 0.17% | 5.01E−03 | 36 | 37 |
| E1_CncE1 | 337 | T | C | 44874 | 73 | 0.16% | 4.65E−03 | 37 | 38 |
| E1_CncE1 | 372 | T | C | 47793 | 12 | 0.03% | 2.55E−06 | 38 | 39 |
| eGFP | 138 | T | C | 11247 | 392 | 3.35% | 2.09E−102 | 34 | 37 |
| eGFP | 144 | T | C | 43588 | 485 | 1.10% | 8.39E−96 | 36 | 38 |
| eGFP | 309 | T | C | 59302 | 599 | 1% | 2.54E−114 | 36 | 37 |
| eGFP | 364 | T | C | 89343 | 688 | 0.76% | 1.31E−115 | 39 | 40 |
| eGFP | 292 | T | C | 68120 | 469 | 0.68% | 3.01E−75 | 37 | 39 |
| eGFP | 99 | T | C | 81558 | 543 | 0.66% | 6.54E−85 | 39 | 39 |
| eGFP | 397 | T | C | 95732 | 614 | 0.64% | 6.92E−94 | 40 | 40 |
| eGFP | 118 | T | C | 70225 | 429 | 0.61% | 1.76E−64 | 38 | 39 |
| eGFP | 94 | T | C | 73976 | 450 | 0.60% | 3.10E−67 | 38 | 39 |
| eGFP | 79 | T | C | 80186 | 475 | 0.59% | 7.70E−70 | 39 | 40 |
| eGFP | 100 | T | C | 78041 | 458 | 0.58% | 6.16E−67 | 39 | 39 |
| eGFP | 313 | T | C | 72954 | 411 | 0.56% | 1.19E−58 | 38 | 39 |
| eGFP | 359 | T | C | 89973 | 507 | 0.56% | 5.69E−72 | 39 | 40 |
| eGFP | 367 | T | C | 89034 | 501 | 0.56% | 4.17E−71 | 39 | 40 |
| eGFP | 27 | T | C | 87812 | 487 | 0.55% | 2.14E−68 | 40 | 40 |
| eGFP | 85 | T | C | 82806 | 429 | 0.52% | 1.06E−57 | 39 | 40 |
| eGFP | 379 | T | C | 93181 | 468 | 0.50% | 1.36E−61 | 39 | 40 |
| eGFP | 52 | T | C | 85476 | 414 | 0.48% | 2.18E−53 | 40 | 39 |
| eGFP | 295 | T | C | 60319 | 289 | 0.48% | 1.80E−37 | 37 | 39 |
| eGFP | 324 | T | C | 65847 | 308 | 0.47% | 7.01E−39 | 37 | 39 |
| eGFP | 70 | T | C | 74903 | 345 | 0.46% | 7.26E−43 | 39 | 40 |
| eGFP | 401 | T | C | 93388 | 421 | 0.45% | 2.86E−51 | 40 | 40 |
| eGFP | 67 | T | C | 85624 | 377 | 0.44% | 6.64E−45 | 40 | 40 |
| eGFP | 121 | T | C | 76820 | 343 | 0.44% | 1.50E−41 | 38 | 39 |
| eGFP | 370 | T | C | 91983 | 406 | 0.44% | 1.72E−48 | 39 | 40 |
| eGFP | 331 | T | C | 86965 | 380 | 0.43% | 4.12E−45 | 39 | 39 |
| eGFP | 46 | T | C | 76930 | 324 | 0.42% | 1.61E−37 | 39 | 40 |
| eGFP | 378 | T | C | 95654 | 382 | 0.40% | 8.28E−42 | 40 | 40 |

TABLE 5-continued

T-to-C mutation frequencies in amplicon sequences: 100 μM 4sU WITH OsO$_4$/NH$_4$Cl treatment

| NAME | POS | REF | ALT | REFdepth | ALTdepth | mutFREQ | PVAL | avgREFBASEQUAL | avgALTBASEQUAL |
|---|---|---|---|---|---|---|---|---|---|
| eGFP | 51 | T | C | 83619 | 317 | 0.38% | 1.11E-33 | 39 | 40 |
| eGFP | 373 | T | C | 93015 | 353 | 0.38% | 4.27E-37 | 39 | 40 |
| eGFP | 133 | T | C | 68982 | 259 | 0.37% | 2.25E-27 | 38 | 39 |
| eGFP | 403 | T | C | 96164 | 334 | 0.35% | 2.92E-32 | 40 | 40 |
| eGFP | 289 | T | C | 62623 | 123 | 0.20% | 4.24E-06 | 37 | 39 |
| eGFP | 382 | T | C | 95594 | 191 | 0.20% | 6.99E-09 | 40 | 39 |
| p21_Cdkn1A | 337 | T | C | 80352 | 632 | 0.78% | 4.52E-108 | 38 | 39 |
| p21_Cdkn1A | 406 | T | C | 86866 | 560 | 0.64% | 4.19E-86 | 38 | 40 |
| p21_Cdkn1A | 445 | T | C | 101457 | 628 | 0.62% | 7.74E-94 | 40 | 40 |
| p21_Cdkn1A | 132 | T | C | 70606 | 303 | 0.43% | 4.81E-36 | 37 | 38 |
| p21_Cdkn1A | 137 | T | C | 79008 | 306 | 0.39% | 5.27E-33 | 37 | 38 |
| p21_Cdkn1A | 383 | T | C | 95273 | 370 | 0.39% | 9.36E-40 | 39 | 39 |
| p21_Cdkn1A | 356 | T | C | 80366 | 299 | 0.37% | 3.24E-31 | 38 | 39 |
| p21_Cdkn1A | 393 | T | C | 95468 | 344 | 0.36% | 1.46E-34 | 39 | 40 |
| p21_Cdkn1A | 37 | T | C | 98156 | 345 | 0.35% | 1.12E-33 | 40 | 40 |
| p21_Cdkn1A | 55 | T | C | 97872 | 323 | 0.33% | 1.73E-29 | 40 | 40 |
| p21_Cdkn1A | 361 | T | C | 75978 | 248 | 0.33% | 8.90E-23 | 38 | 39 |
| p21_Cdkn1A | 126 | T | C | 84531 | 265 | 0.31% | 2.55E-23 | 38 | 39 |
| p21_Cdkn1A | 334 | T | C | 68262 | 213 | 0.31% | 6.56E-19 | 37 | 38 |
| p21_Cdkn1A | 351 | T | C | 86950 | 272 | 0.31% | 1.21E-23 | 38 | 39 |
| p21_Cdkn1A | 94 | T | C | 93018 | 245 | 0.26% | 2.98E-17 | 40 | 40 |
| p21_Cdkn1A | 110 | T | C | 87513 | 223 | 0.25% | 3.04E-15 | 39 | 37 |
| p21_Cdkn1A | 51 | T | C | 95691 | 229 | 0.24% | 3.10E-14 | 40 | 40 |
| p21_Cdkn1A | 34 | T | C | 99260 | 229 | 0.23% | 2.52E-13 | 40 | 40 |
| p21_Cdkn1A | 24 | T | C | 97942 | 216 | 0.22% | 1.14E-11 | 40 | 40 |
| p21_Cdkn1A | 101 | T | C | 92249 | 194 | 0.21% | 7.70E-10 | 39 | 39 |
| p21_Cdkn1A | 384 | T | C | 96193 | 202 | 0.21% | 3.84E-10 | 39 | 39 |
| p21_Cdkn1A | 446 | T | C | 101812 | 211 | 0.21% | 3.40E-10 | 40 | 40 |
| p21_Cdkn1A | 81 | T | C | 96623 | 188 | 0.19% | 2.52E-08 | 40 | 40 |
| p21_Cdkn1A | 441 | T | C | 101908 | 199 | 0.19% | 1.17E-08 | 40 | 40 |
| p21_Cdkn1A | 349 | T | C | 87700 | 149 | 0.17% | 3.24E-05 | 38 | 39 |
| p21_Cdkn1A | 454 | T | C | 98186 | 164 | 0.17% | 2.69E-05 | 40 | 39 |
| p21_Cdkn1A | 21 | T | C | 92046 | 145 | 0.16% | 3.46E-04 | 39 | 40 |
| p21_Cdkn1A | 30 | T | C | 92126 | 145 | 0.16% | 3.46E-04 | 40 | 40 |
| p21_Cdkn1A | 121 | T | C | 66654 | 108 | 0.16% | 8.94E-04 | 37 | 39 |
| p21_Cdkn1A | 377 | T | C | 94805 | 139 | 0.15% | 1.91E-03 | 39 | 39 |
| p21_Cdkn1A | 443 | T | C | 101265 | 157 | 0.15% | 2.93E-04 | 40 | 40 |
| p21_Cdkn1A | 122 | T | C | 76409 | 110 | 0.14% | 7.62E-03 | 37 | 38 |
| p21_Cdkn1A | 354 | T | C | 77695 | 112 | 0.14% | 6.56E-03 | 38 | 39 |
| p21_Cdkn1A | 369 | T | C | 95885 | 138 | 0.14% | 3.60E-03 | 39 | 39 |
| p21_Cdkn1A | 371 | T | C | 91625 | 133 | 0.14% | 3.00E-03 | 39 | 40 |
| p21_Cdkn1A | 439 | T | C | 102587 | 142 | 0.14% | 6.16E-03 | 40 | 40 |
| p21_Cdkn1A | 447 | T | C | 102338 | 140 | 0.14% | 8.57E-03 | 40 | 40 |
| p21_Cdkn1A | 98 | T | C | 92522 | 46 | 0.05% | 5.55E-05 | 39 | 39 |
| p21_Cdkn1A | 125 | T | C | 84971 | 46 | 0.05% | 4.14E-04 | 38 | 39 |
| p21_Cdkn1A | 385 | T | C | 92755 | 21 | 0.02% | 4.29E-12 | 39 | 37 |
| p21_Cdkn1A | 2 | T | C | 98566 | 13 | 0.01% | 1.31E-17 | 40 | 39 |
| p21_Cdkn1A | 76 | T | C | 91679 | 13 | 0.01% | 6.89E-16 | 39 | 41 |
| PCNA | 145 | T | C | 14886 | 71 | 0.47% | 1.15E-10 | 34 | 37 |
| PCNA | 28 | T | C | 115567 | 204 | 0.18% | 3.50E-07 | 40 | 40 |
| PCNA | 55 | T | C | 111925 | 178 | 0.16% | 6.29E-05 | 40 | 40 |
| PCNA | 116 | T | C | 105438 | 167 | 0.16% | 1.01E-04 | 39 | 39 |
| PCNA | 136 | T | C | 97744 | 135 | 0.14% | 7.45E-03 | 39 | 39 |
| PCNA | 417 | T | C | 108604 | 156 | 0.14% | 1.86E-03 | 40 | 40 |
| PCNA | 437 | T | C | 109297 | 153 | 0.14% | 3.87E-03 | 40 | 40 |
| PCNA | 48 | T | C | 112569 | 66 | 0.06% | 3.48E-04 | 40 | 39 |
| PCNA | 126 | T | C | 105637 | 60 | 0.06% | 2.85E-04 | 39 | 39 |
| PCNA | 350 | T | C | 96124 | 53 | 0.06% | 2.67E-04 | 39 | 38 |
| PCNA | 360 | T | C | 104568 | 64 | 0.06% | 1.25E-03 | 39 | 39 |
| PCNA | 374 | T | C | 104724 | 59 | 0.06% | 2.63E-04 | 39 | 40 |
| PCNA | 39 | T | C | 106732 | 58 | 0.05% | 1.10E-04 | 39 | 40 |
| PCNA | 70 | T | C | 113545 | 62 | 0.05% | 7.07E-05 | 40 | 40 |
| PCNA | 93 | T | C | 107360 | 58 | 0.05% | 8.38E-05 | 39 | 40 |
| PCNA | 124 | T | C | 105294 | 51 | 0.05% | 9.13E-06 | 39 | 39 |
| PCNA | 54 | T | C | 111442 | 48 | 0.04% | 3.15E-07 | 40 | 40 |
| PCNA | 118 | T | C | 109419 | 47 | 0.04% | 3.73E-07 | 39 | 39 |
| PCNA | 372 | T | C | 109919 | 48 | 0.04% | 6.20E-07 | 40 | 39 |
| PCNA | 401 | T | C | 109966 | 47 | 0.04% | 2.65E-07 | 40 | 39 |
| PCNA | 91 | T | C | 109896 | 32 | 0.03% | 2.48E-11 | 40 | 39 |

TABLE 6

A-, C-, and G-to-N mutation frequencies in amplicon sequences: no 4sU labeling, no $OsO_4/NH_4Cl$ treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| A2_CcnA2 | 119 | A | G | 97523 | 43 | 0.04% | 2.89E−06 | 39 | 37 |
| A2_CcnA2 | 418 | A | G | 104975 | 44 | 0.04% | 3.10E−07 | 40 | 39 |
| A2_CcnA2 | 41 | A | C | 106184 | 36 | 0.03% | 1.67E−09 | 40 | 37 |
| A2_CcnA2 | 67 | G | C | 103754 | 36 | 0.03% | 5.61E−09 | 40 | 37 |
| A2_CcnA2 | 340 | A | C | 99131 | 31 | 0.03% | 8.80E−10 | 39 | 37 |
| A2_CcnA2 | 362 | A | C | 98117 | 26 | 0.03% | 2.48E−11 | 39 | 38 |
| A2_CcnA2 | 3 | A | C | 107942 | 21 | 0.02% | 2.20E−15 | 40 | 40 |
| A2_CcnA2 | 4 | G | A | 107321 | 19 | 0.02% | 2.22E−16 | 40 | 39 |
| A2_CcnA2 | 102 | A | G | 102414 | 16 | 0.02% | 8.13E−17 | 40 | 38 |
| A2_CcnA2 | 121 | C | A | 98370 | 20 | 0.02% | 7.56E−14 | 39 | 37 |
| A2_CcnA2 | 133 | C | A | 97430 | 22 | 0.02% | 9.82E−13 | 39 | 34 |
| A2_CcnA2 | 325 | G | T | 91136 | 18 | 0.02% | 3.14E−13 | 39 | 36 |
| A2_CcnA2 | 338 | A | G | 99162 | 22 | 0.02% | 3.65E−13 | 39 | 39 |
| A2_CcnA2 | 369 | C | G | 103095 | 16 | 0.02% | 4.69E−17 | 40 | 38 |
| A2_CcnA2 | 392 | A | G | 100171 | 20 | 0.02% | 2.71E−14 | 39 | 38 |
| A2_CcnA2 | 398 | C | T | 105584 | 17 | 0.02% | 5.63E−17 | 40 | 40 |
| A2_CcnA2 | 400 | C | A | 103971 | 17 | 0.02% | 1.67E−16 | 40 | 40 |
| A2_CcnA2 | 1 | C | T | 107483 | 11 | 0.01% | 3.13E−21 | 40 | 39 |
| A2_CcnA2 | 7 | G | T | 107700 | 16 | 0.01% | 5.12E−18 | 40 | 40 |
| A2_CcnA2 | 13 | G | T | 108084 | 13 | 0.01% | 4.10E−20 | 40 | 40 |
| A2_CcnA2 | 29 | C | T | 107409 | 11 | 0.01% | 3.13E−21 | 40 | 40 |
| A2_CcnA2 | 42 | C | T | 107144 | 14 | 0.01% | 3.20E−19 | 40 | 41 |
| A2_CcnA2 | 58 | C | T | 105474 | 12 | 0.01% | 5.09E−20 | 40 | 39 |
| A2_CcnA2 | 88 | C | A | 102680 | 12 | 0.01% | 2.95E−19 | 40 | 40 |
| A2_CcnA2 | 122 | A | G | 98643 | 10 | 0.01% | 1.30E−19 | 39 | 37 |
| A2_CcnA2 | 131 | C | T | 100021 | 11 | 0.01% | 2.00E−19 | 39 | 38 |
| A2_CcnA2 | 132 | C | T | 97688 | 12 | 0.01% | 5.39E−18 | 39 | 39 |
| A2_CcnA2 | 135 | A | C | 91583 | 13 | 0.01% | 6.89E−18 | 39 | 35 |
| A2_CcnA2 | 138 | C | A | 96093 | 10 | 0.01% | 4.29E−19 | 39 | 37 |
| A2_CcnA2 | 317 | G | C | 89718 | 13 | 0.01% | 2.12E−15 | 39 | 34 |
| A2_CcnA2 | 318 | A | G | 84363 | 11 | 0.01% | 2.22E−15 | 38 | 36 |
| A2_CcnA2 | 319 | A | C | 82072 | 9 | 0.01% | 3.49E−16 | 38 | 37 |
| A2_CcnA2 | 322 | A | G | 84505 | 11 | 0.01% | 2.22E−15 | 38 | 35 |
| A2_CcnA2 | 327 | A | G | 95029 | 10 | 0.01% | 7.78E−19 | 38 | 38 |
| A2_CcnA2 | 329 | A | G | 87304 | 10 | 0.01% | 8.79E−17 | 38 | 35 |
| A2_CcnA2 | 331 | A | G | 72518 | 10 | 0.01% | 5.05E−13 | 37 | 35 |
| A2_CcnA2 | 333 | C | T | 99377 | 13 | 0.01% | 7.37E−18 | 39 | 36 |
| A2_CcnA2 | 343 | C | G | 101435 | 11 | 0.01% | 1.11E−19 | 39 | 36 |
| A2_CcnA2 | 374 | C | A | 104164 | 12 | 0.01% | 9.15E−20 | 40 | 39 |
| A2_CcnA2 | 388 | C | A | 100567 | 11 | 0.01% | 2.00E−19 | 39 | 40 |
| A2_CcnA2 | 391 | C | T | 103785 | 14 | 0.01% | 3.13E−18 | 40 | 39 |
| A2_CcnA2 | 394 | C | A | 105701 | 13 | 0.01% | 2.34E−19 | 40 | 39 |
| A2_CcnA2 | 407 | C | T | 106456 | 14 | 0.01% | 5.67E−19 | 40 | 40 |
| A2_CcnA2 | 439 | C | A | 108005 | 12 | 0.01% | 8.71E−21 | 40 | 40 |
| A2_CcnA2 | 451 | C | A | 108552 | 12 | 0.01% | 8.72E−21 | 40 | 40 |
| B1_CncB1 | 94 | A | G | 98140 | 49 | 0.05% | 3.24E−05 | 39 | 37 |
| B1_CncB1 | 432 | A | G | 99799 | 51 | 0.05% | 5.46E−05 | 40 | 39 |
| B1_CncB1 | 383 | G | C | 101113 | 38 | 0.04% | 4.37E−08 | 40 | 38 |
| B1_CncB1 | 41 | A | C | 104232 | 31 | 0.03% | 1.01E−10 | 40 | 38 |
| B1_CncB1 | 67 | A | G | 104762 | 35 | 0.03% | 1.91E−09 | 40 | 36 |
| B1_CncB1 | 119 | C | G | 100562 | 29 | 0.03% | 1.22E−10 | 39 | 37 |
| B1_CncB1 | 126 | A | G | 103135 | 36 | 0.03% | 5.61E−09 | 39 | 36 |
| B1_CncB1 | 135 | C | A | 86856 | 23 | 0.03% | 4.74E−10 | 39 | 34 |
| B1_CncB1 | 331 | G | T | 89799 | 30 | 0.03% | 2.82E−08 | 39 | 33 |
| B1_CncB1 | 379 | A | C | 102188 | 30 | 0.03% | 1.11E−10 | 40 | 37 |
| B1_CncB1 | 406 | A | C | 102599 | 34 | 0.03% | 2.17E−09 | 40 | 36 |
| B1_CncB1 | 47 | C | A | 105454 | 24 | 0.02% | 1.38E−13 | 40 | 40 |
| B1_CncB1 | 142 | C | A | 88214 | 15 | 0.02% | 4.76E−14 | 39 | 35 |
| B1_CncB1 | 340 | C | T | 91828 | 17 | 0.02% | 1.02E−13 | 39 | 39 |
| B1_CncB1 | 342 | G | T | 92136 | 18 | 0.02% | 1.87E−13 | 39 | 34 |
| B1_CncB1 | 350 | G | T | 97733 | 19 | 0.02% | 4.25E−14 | 39 | 34 |
| B1_CncB1 | 357 | C | A | 94279 | 18 | 0.02% | 6.61E−14 | 39 | 36 |
| B1_CncB1 | 365 | C | T | 97077 | 18 | 0.02% | 1.37E−14 | 39 | 39 |
| B1_CncB1 | 431 | C | A | 102336 | 22 | 0.02% | 8.17E−14 | 40 | 41 |
| B1_CncB1 | 471 | A | G | 103486 | 25 | 0.02% | 9.53E−13 | 40 | 40 |
| B1_CncB1 | 13 | G | T | 106805 | 12 | 0.01% | 2.83E−20 | 40 | 39 |
| B1_CncB1 | 24 | C | A | 106282 | 11 | 0.01% | 5.69E−21 | 40 | 40 |
| B1_CncB1 | 26 | C | T | 105856 | 14 | 0.01% | 1.00E−18 | 40 | 40 |
| B1_CncB1 | 59 | A | G | 106223 | 14 | 0.01% | 5.67E−19 | 40 | 40 |
| B1_CncB1 | 68 | A | C | 102366 | 13 | 0.01% | 1.32E−18 | 40 | 40 |
| B1_CncB1 | 70 | G | A | 102822 | 12 | 0.01% | 2.95E−19 | 40 | 39 |
| B1_CncB1 | 109 | A | G | 96134 | 13 | 0.01% | 4.08E−17 | 39 | 39 |
| B1_CncB1 | 118 | A | C | 98950 | 12 | 0.01% | 3.02E−18 | 39 | 35 |
| B1_CncB1 | 133 | A | C | 90986 | 10 | 0.01% | 1.51E−17 | 39 | 32 |
| B1_CncB1 | 410 | G | T | 102758 | 12 | 0.01% | 2.95E−19 | 40 | 39 |

TABLE 6-continued

A-, C-, and G-to-N mutation frequencies in amplicon sequences: no 4sU labeling, no OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| B1_CncB1 | 424 | C | A | 102305 | 15 | 0.01% | 2.18E−17 | 40 | 40 |
| B1_CncB1 | 444 | A | G | 103483 | 11 | 0.01% | 3.39E−20 | 40 | 41 |
| B1_CncB1 | 452 | C | A | 103531 | 13 | 0.01% | 7.41E−19 | 40 | 41 |
| D1_CncD1 | 271 | G | T | 96668 | 39 | 0.04% | 4.99E−07 | 37 | 35 |
| D1_CncD1 | 410 | C | A | 138903 | 54 | 0.04% | 5.66E−10 | 40 | 40 |
| D1_CncD1 | 290 | G | C | 119791 | 30 | 0.03% | 4.71E−14 | 39 | 36 |
| D1_CncD1 | 293 | G | T | 121714 | 31 | 0.03% | 4.53E−14 | 39 | 35 |
| D1_CncD1 | 322 | A | C | 134301 | 42 | 0.03% | 1.05E−12 | 40 | 37 |
| D1_CncD1 | 375 | C | G | 134819 | 46 | 0.03% | 1.77E−11 | 40 | 38 |
| D1_CncD1 | 407 | C | A | 137673 | 41 | 0.03% | 1.35E−13 | 40 | 40 |
| D1_CncD1 | 1 | G | T | 143738 | 32 | 0.02% | 2.90E−18 | 40 | 40 |
| D1_CncD1 | 3 | G | T | 144750 | 25 | 0.02% | 7.80E−22 | 40 | 39 |
| D1_CncD1 | 19 | G | T | 144112 | 24 | 0.02% | 2.29E−22 | 40 | 41 |
| D1_CncD1 | 67 | G | C | 140986 | 27 | 0.02% | 3.93E−20 | 40 | 36 |
| D1_CncD1 | 90 | C | G | 138632 | 23 | 0.02% | 1.70E−21 | 40 | 36 |
| D1_CncD1 | 300 | A | G | 114315 | 28 | 0.02% | 8.07E−14 | 39 | 37 |
| D1_CncD1 | 326 | A | C | 134117 | 31 | 0.02% | 8.98E−17 | 40 | 37 |
| D1_CncD1 | 349 | A | G | 134671 | 32 | 0.02% | 2.35E−16 | 40 | 36 |
| D1_CncD1 | 401 | C | A | 137692 | 24 | 0.02% | 9.86E−21 | 40 | 40 |
| D1_CncD1 | 405 | C | A | 136818 | 31 | 0.02% | 3.37E−17 | 40 | 40 |
| D1_CncD1 | 408 | C | A | 137986 | 26 | 0.02% | 6.05E−20 | 40 | 40 |
| D1_CncD1 | 409 | C | A | 138495 | 31 | 0.02% | 1.26E−17 | 40 | 39 |
| D1_CncD1 | 5 | G | T | 144734 | 16 | 0.01% | 3.03E−27 | 40 | 40 |
| D1_CncD1 | 8 | G | T | 146575 | 18 | 0.01% | 2.07E−26 | 40 | 40 |
| D1_CncD1 | 94 | G | C | 140189 | 19 | 0.01% | 2.77E−24 | 39 | 34 |
| D1_CncD1 | 96 | A | G | 111901 | 16 | 0.01% | 5.48E−19 | 37 | 36 |
| D1_CncD1 | 97 | G | C | 138840 | 16 | 0.01% | 1.03E−25 | 39 | 35 |
| D1_CncD1 | 110 | G | T | 140797 | 17 | 0.01% | 1.48E−25 | 39 | 39 |
| D1_CncD1 | 127 | C | T | 126453 | 13 | 0.01% | 1.01E−24 | 39 | 38 |
| D1_CncD1 | 135 | A | G | 115810 | 14 | 0.01% | 3.18E−21 | 37 | 38 |
| D1_CncD1 | 136 | A | G | 121357 | 14 | 0.01% | 9.65E−23 | 37 | 38 |
| D1_CncD1 | 138 | A | G | 114484 | 16 | 0.01% | 1.01E−19 | 38 | 35 |
| D1_CncD1 | 277 | A | G | 103068 | 11 | 0.01% | 3.39E−20 | 38 | 36 |
| D1_CncD1 | 280 | G | T | 109785 | 16 | 0.01% | 1.68E−18 | 38 | 36 |
| D1_CncD1 | 281 | G | T | 116786 | 14 | 0.01% | 1.78E−21 | 39 | 35 |
| D1_CncD1 | 291 | A | G | 118299 | 15 | 0.01% | 2.49E−21 | 39 | 36 |
| D1_CncD1 | 297 | C | G | 118945 | 13 | 0.01% | 1.17E−22 | 39 | 37 |
| D1_CncD1 | 305 | A | G | 123924 | 13 | 0.01% | 6.05E−24 | 39 | 38 |
| D1_CncD1 | 317 | C | A | 129268 | 14 | 0.01% | 8.70E−25 | 39 | 39 |
| D1_CncD1 | 319 | C | G | 124848 | 17 | 0.01% | 1.44E−21 | 39 | 38 |
| D1_CncD1 | 364 | C | T | 134524 | 16 | 0.01% | 1.06E−24 | 40 | 40 |
| E1_CncE1 | 473 | A | G | 44259 | 92 | 0.21% | 2.32E−05 | 39 | 40 |
| E1_CncE1 | 4 | A | G | 48735 | 23 | 0.05% | 2.03E−03 | 40 | 40 |
| E1_CncE1 | 94 | A | G | 46527 | 20 | 0.04% | 9.26E−04 | 40 | 36 |
| E1_CncE1 | 28 | C | T | 48670 | 13 | 0.03% | 3.81E−06 | 40 | 40 |
| E1_CncE1 | 62 | C | T | 47963 | 14 | 0.03% | 1.35E−05 | 40 | 39 |
| E1_CncE1 | 91 | A | G | 47104 | 16 | 0.03% | 5.82E−05 | 40 | 39 |
| E1_CncE1 | 97 | G | C | 47401 | 14 | 0.03% | 1.35E−05 | 40 | 38 |
| E1_CncE1 | 105 | C | G | 47139 | 15 | 0.03% | 2.87E−05 | 39 | 37 |
| E1_CncE1 | 353 | C | T | 37039 | 11 | 0.03% | 1.11E−04 | 37 | 35 |
| E1_CncE1 | 356 | A | C | 35847 | 11 | 0.03% | 2.67E−04 | 37 | 39 |
| E1_CncE1 | 370 | A | C | 42583 | 11 | 0.03% | 1.12E−05 | 39 | 36 |
| E1_CncE1 | 408 | A | G | 43442 | 13 | 0.03% | 3.65E−05 | 40 | 38 |
| E1_CncE1 | 440 | C | T | 44967 | 14 | 0.03% | 5.00E−05 | 40 | 40 |
| E1_CncE1 | 469 | C | A | 46060 | 13 | 0.03% | 9.53E−06 | 40 | 41 |
| E1_CncE1 | 12 | G | T | 48302 | 11 | 0.02% | 6.16E−07 | 40 | 41 |
| E1_CncE1 | 56 | C | T | 47726 | 8 | 0.02% | 4.00E−08 | 40 | 40 |
| E1_CncE1 | 67 | C | G | 47140 | 10 | 0.02% | 3.73E−07 | 40 | 36 |
| E1_CncE1 | 90 | C | G | 47687 | 9 | 0.02% | 1.28E−07 | 40 | 36 |
| E1_CncE1 | 125 | C | A | 44817 | 7 | 0.02% | 6.01E−08 | 39 | 36 |
| E1_CncE1 | 126 | A | C | 40021 | 10 | 0.02% | 1.19E−05 | 38 | 35 |
| E1_CncE1 | 144 | A | C | 30741 | 5 | 0.02% | 1.11E−05 | 37 | 36 |
| E1_CncE1 | 145 | A | G | 24051 | 6 | 0.02% | 7.13E−04 | 36 | 34 |
| E1_CncE1 | 331 | G | T | 30704 | 5 | 0.02% | 1.11E−05 | 37 | 36 |
| E1_CncE1 | 336 | G | T | 34161 | 7 | 0.02% | 1.26E−05 | 37 | 37 |
| E1_CncE1 | 348 | G | T | 34050 | 6 | 0.02% | 4.16E−06 | 36 | 35 |
| E1_CncE1 | 350 | A | G | 25822 | 6 | 0.02% | 4.37E−04 | 36 | 35 |
| E1_CncE1 | 378 | G | C | 43293 | 10 | 0.02% | 2.76E−06 | 39 | 37 |
| E1_CncE1 | 387 | C | T | 43687 | 10 | 0.02% | 2.76E−06 | 39 | 40 |
| E1_CncE1 | 412 | C | T | 44255 | 11 | 0.02% | 4.32E−06 | 40 | 39 |
| E1_CncE1 | 428 | C | T | 43992 | 8 | 0.02% | 2.01E−07 | 39 | 41 |
| E1_CncE1 | 434 | A | C | 44841 | 8 | 0.02% | 2.01E−07 | 40 | 37 |
| E1_CncE1 | 459 | C | A | 43349 | 9 | 0.02% | 1.01E−06 | 39 | 39 |
| E1_CncE1 | 13 | C | T | 48447 | 5 | 0.01% | 3.51E−10 | 40 | 41 |
| E1_CncE1 | 15 | C | T | 48648 | 5 | 0.01% | 3.51E−10 | 40 | 41 |

TABLE 6-continued

A-, C-, and G-to-N mutation frequencies in amplicon sequences: no 4sU labeling, no OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| E1_CncE1 | 41 | C | G | 47845 | 6 | 0.01% | 2.88E−09 | 40 | 36 |
| E1_CncE1 | 68 | A | G | 46734 | 5 | 0.01% | 1.15E−09 | 40 | 36 |
| E1_CncE1 | 130 | C | A | 45729 | 6 | 0.01% | 9.09E−09 | 39 | 38 |
| E1_CncE1 | 133 | C | G | 44662 | 5 | 0.01% | 3.77E−09 | 39 | 35 |
| E1_CncE1 | 138 | A | C | 32891 | 4 | 0.01% | 9.65E−07 | 37 | 34 |
| E1_CncE1 | 139 | G | T | 38331 | 5 | 0.01% | 1.24E−07 | 38 | 38 |
| E1_CncE1 | 332 | C | T | 25551 | 3 | 0.01% | 1.37E−05 | 36 | 39 |
| E1_CncE1 | 334 | A | C | 16281 | 2 | 0.01% | 6.54E−04 | 35 | 34 |
| E1_CncE1 | 345 | A | G | 33646 | 5 | 0.01% | 2.12E−06 | 37 | 33 |
| E1_CncE1 | 411 | G | A | 44794 | 6 | 0.01% | 1.61E−08 | 40 | 41 |
| E1_CncE1 | 456 | A | T | 28296 | 3 | 0.01% | 2.31E−06 | 36 | 32 |
| E1_CncE1 | 457 | C | A | 42352 | 5 | 0.01% | 1.22E−08 | 39 | 36 |
| E1_CncE1 | 461 | C | A | 44541 | 6 | 0.01% | 1.61E−08 | 40 | 39 |
| E1_CncE1 | 471 | A | T | 45156 | 5 | 0.01% | 2.09E−09 | 40 | 41 |
| E1_CncE1 | 472 | A | G | 44436 | 5 | 0.01% | 3.77E−09 | 39 | 37 |
| E1_CncE1 | 474 | C | A | 46050 | 6 | 0.01% | 5.12E−09 | 40 | 35 |
| eGFP | 97 | A | T | 39970 | 158 | 0.39% | 3.98E−18 | 38 | 40 |
| eGFP | 96 | G | T | 44984 | 155 | 0.34% | 1.12E−15 | 39 | 40 |
| eGFP | 91 | G | C | 44445 | 134 | 0.30% | 4.33E−12 | 39 | 39 |
| eGFP | 424 | A | G | 43067 | 75 | 0.17% | 2.05E−03 | 40 | 40 |
| eGFP | 2 | C | T | 47869 | 20 | 0.04% | 6.51E−04 | 40 | 40 |
| eGFP | 15 | G | T | 47335 | 20 | 0.04% | 6.51E−04 | 40 | 39 |
| eGFP | 291 | C | A | 36227 | 14 | 0.04% | 1.30E−03 | 38 | 35 |
| eGFP | 298 | C | A | 38448 | 16 | 0.04% | 1.91E−03 | 39 | 37 |
| eGFP | 323 | G | C | 37573 | 15 | 0.04% | 1.59E−03 | 38 | 37 |
| eGFP | 109 | A | C | 31446 | 10 | 0.03% | 7.23E−04 | 38 | 33 |
| eGFP | 135 | G | A | 40932 | 12 | 0.03% | 6.35E−05 | 38 | 37 |
| eGFP | 142 | A | G | 26949 | 7 | 0.03% | 6.57E−04 | 36 | 38 |
| eGFP | 307 | A | C | 26035 | 8 | 0.03% | 1.46E−03 | 36 | 32 |
| eGFP | 315 | A | G | 27619 | 8 | 0.03% | 9.36E−04 | 37 | 36 |
| eGFP | 361 | A | G | 40589 | 14 | 0.03% | 2.67E−04 | 39 | 37 |
| eGFP | 414 | G | A | 42908 | 15 | 0.03% | 2.29E−04 | 40 | 40 |
| eGFP | 427 | A | G | 42553 | 11 | 0.03% | 1.12E−05 | 40 | 40 |
| eGFP | 14 | G | T | 47624 | 10 | 0.02% | 3.73E−07 | 40 | 41 |
| eGFP | 41 | C | G | 46237 | 9 | 0.02% | 2.15E−07 | 40 | 36 |
| eGFP | 90 | G | C | 45713 | 8 | 0.02% | 1.18E−07 | 39 | 36 |
| eGFP | 93 | A | G | 40622 | 8 | 0.02% | 1.64E−06 | 39 | 41 |
| eGFP | 102 | A | G | 42272 | 7 | 0.02% | 1.80E−07 | 39 | 39 |
| eGFP | 115 | A | C | 35194 | 6 | 0.02% | 2.42E−06 | 38 | 33 |
| eGFP | 126 | C | G | 43551 | 9 | 0.02% | 1.01E−06 | 39 | 38 |
| eGFP | 129 | A | G | 36577 | 6 | 0.02% | 1.41E−06 | 38 | 41 |
| eGFP | 136 | A | C | 27737 | 6 | 0.02% | 1.61E−04 | 37 | 32 |
| eGFP | 137 | G | C | 39645 | 7 | 0.02% | 9.10E−07 | 38 | 38 |
| eGFP | 143 | C | A | 37251 | 6 | 0.02% | 8.13E−07 | 37 | 35 |
| eGFP | 287 | C | T | 37138 | 9 | 0.02% | 2.02E−05 | 39 | 37 |
| eGFP | 288 | G | A | 34670 | 8 | 0.02% | 3.42E−05 | 38 | 38 |
| eGFP | 293 | G | A | 35390 | 6 | 0.02% | 2.42E−06 | 39 | 37 |
| eGFP | 297 | C | A | 38749 | 8 | 0.02% | 4.60E−06 | 39 | 39 |
| eGFP | 299 | C | A | 38710 | 6 | 0.02% | 4.68E−07 | 39 | 38 |
| eGFP | 300 | G | A | 35847 | 6 | 0.02% | 2.42E−06 | 38 | 36 |
| eGFP | 302 | C | T | 38114 | 8 | 0.02% | 4.60E−06 | 38 | 36 |
| eGFP | 303 | A | C | 30170 | 5 | 0.02% | 1.11E−05 | 37 | 37 |
| eGFP | 322 | A | C | 32459 | 5 | 0.02% | 3.69E−06 | 38 | 34 |
| eGFP | 334 | G | C | 41425 | 10 | 0.02% | 7.33E−06 | 40 | 35 |
| eGFP | 338 | A | G | 36547 | 7 | 0.02% | 4.46E−06 | 38 | 38 |
| eGFP | 339 | G | A | 36719 | 6 | 0.02% | 1.41E−06 | 38 | 39 |
| eGFP | 340 | A | G | 26556 | 4 | 0.02% | 2.96E−05 | 37 | 34 |
| eGFP | 345 | A | G | 35362 | 7 | 0.02% | 7.51E−06 | 38 | 39 |
| eGFP | 349 | A | G | 37206 | 8 | 0.02% | 7.64E−06 | 39 | 38 |
| eGFP | 1 | C | G | 47405 | 5 | 0.01% | 6.37E−10 | 40 | 39 |
| eGFP | 18 | G | T | 46744 | 6 | 0.01% | 5.12E−09 | 40 | 39 |
| eGFP | 26 | C | T | 47102 | 6 | 0.01% | 2.88E−09 | 40 | 41 |
| eGFP | 28 | A | G | 46890 | 5 | 0.01% | 1.15E−09 | 40 | 36 |
| eGFP | 30 | A | G | 47533 | 6 | 0.01% | 2.88E−09 | 40 | 38 |
| eGFP | 31 | A | G | 47053 | 6 | 0.01% | 2.88E−09 | 40 | 38 |
| eGFP | 33 | A | G | 46452 | 5 | 0.01% | 1.15E−09 | 40 | 38 |
| eGFP | 37 | G | C | 46082 | 6 | 0.01% | 5.12E−09 | 40 | 40 |
| eGFP | 42 | G | A | 46501 | 5 | 0.01% | 1.15E−09 | 40 | 41 |
| eGFP | 44 | G | A | 46144 | 5 | 0.01% | 1.15E−09 | 40 | 39 |
| eGFP | 48 | A | G | 45022 | 6 | 0.01% | 9.09E−09 | 39 | 36 |
| eGFP | 68 | G | C | 45501 | 5 | 0.01% | 2.09E−09 | 40 | 37 |
| eGFP | 82 | A | G | 40958 | 5 | 0.01% | 3.91E−08 | 39 | 39 |
| eGFP | 88 | A | G | 40777 | 5 | 0.01% | 3.91E−08 | 39 | 41 |
| eGFP | 117 | A | C | 38724 | 5 | 0.01% | 1.24E−07 | 38 | 33 |
| eGFP | 124 | G | A | 42874 | 5 | 0.01% | 1.22E−08 | 39 | 35 |

TABLE 6-continued

A-, C-, and G-to-N mutation frequencies in amplicon sequences: no 4sU labeling, no OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| eGFP | 140 | C | G | 31619 | 4 | 0.01% | 1.72E−06 | 35 | 38 |
| eGFP | 284 | C | G | 35925 | 5 | 0.01% | 6.87E−07 | 39 | 41 |
| eGFP | 311 | C | G | 39287 | 4 | 0.01% | 1.54E−08 | 39 | 36 |
| eGFP | 312 | C | G | 37355 | 4 | 0.01% | 5.09E−08 | 38 | 34 |
| eGFP | 314 | G | A | 35601 | 4 | 0.01% | 1.67E−07 | 38 | 36 |
| eGFP | 321 | C | A | 39129 | 4 | 0.01% | 1.54E−08 | 39 | 38 |
| eGFP | 326 | C | T | 41161 | 6 | 0.01% | 8.79E−08 | 40 | 37 |
| eGFP | 336 | A | G | 40160 | 5 | 0.01% | 3.91E−08 | 39 | 40 |
| eGFP | 358 | A | G | 39430 | 5 | 0.01% | 6.98E−08 | 39 | 39 |
| eGFP | 375 | G | T | 42226 | 5 | 0.01% | 1.22E−08 | 40 | 41 |
| eGFP | 399 | A | G | 39225 | 4 | 0.01% | 1.54E−08 | 39 | 39 |
| eGFP | 415 | A | G | 42745 | 6 | 0.01% | 5.01E−08 | 40 | 38 |
| eGFP | 423 | A | G | 42877 | 6 | 0.01% | 5.01E−08 | 40 | 41 |
| p21_Cdkn1A | 433 | C | T | 87152 | 49 | 0.06% | 7.06E−04 | 40 | 40 |
| p21_Cdkn1A | 41 | G | C | 82423 | 40 | 0.05% | 8.94E−05 | 40 | 38 |
| p21_Cdkn1A | 363 | C | A | 83915 | 43 | 0.05% | 2.31E−04 | 40 | 39 |
| p21_Cdkn1A | 97 | C | G | 80879 | 34 | 0.04% | 9.73E−06 | 40 | 37 |
| p21_Cdkn1A | 105 | C | G | 82184 | 30 | 0.04% | 4.62E−07 | 39 | 39 |
| p21_Cdkn1A | 119 | A | G | 60171 | 23 | 0.04% | 2.97E−05 | 38 | 38 |
| p21_Cdkn1A | 396 | A | G | 77457 | 33 | 0.04% | 1.64E−05 | 39 | 37 |
| p21_Cdkn1A | 438 | C | T | 87374 | 32 | 0.04% | 2.33E−07 | 40 | 40 |
| p21_Cdkn1A | 138 | A | C | 58243 | 17 | 0.03% | 1.08E−06 | 37 | 33 |
| p21_Cdkn1A | 141 | A | C | 54847 | 15 | 0.03% | 1.30E−06 | 37 | 33 |
| p21_Cdkn1A | 144 | G | A | 65540 | 17 | 0.03% | 4.44E−08 | 39 | 37 |
| p21_Cdkn1A | 332 | C | T | 74324 | 23 | 0.03% | 1.00E−07 | 38 | 38 |
| p21_Cdkn1A | 345 | A | G | 68002 | 20 | 0.03% | 1.37E−07 | 38 | 34 |
| p21_Cdkn1A | 355 | C | T | 81626 | 22 | 0.03% | 2.01E−09 | 39 | 38 |
| p21_Cdkn1A | 370 | G | C | 83000 | 23 | 0.03% | 1.87E−09 | 39 | 37 |
| p21_Cdkn1A | 372 | C | T | 84114 | 25 | 0.03% | 6.02E−09 | 40 | 39 |
| p21_Cdkn1A | 4 | G | T | 84578 | 14 | 0.02% | 1.21E−13 | 40 | 39 |
| p21_Cdkn1A | 20 | G | T | 84091 | 19 | 0.02% | 3.07E−11 | 40 | 39 |
| p21_Cdkn1A | 64 | G | A | 80791 | 16 | 0.02% | 1.02E−11 | 39 | 40 |
| p21_Cdkn1A | 67 | A | G | 80581 | 18 | 0.02% | 8.21E−11 | 40 | 36 |
| p21_Cdkn1A | 82 | C | T | 82174 | 14 | 0.02% | 3.57E−13 | 40 | 40 |
| p21_Cdkn1A | 103 | C | A | 81126 | 16 | 0.02% | 6.11E−12 | 40 | 40 |
| p21_Cdkn1A | 104 | A | C | 75617 | 12 | 0.02% | 1.34E−12 | 39 | 33 |
| p21_Cdkn1A | 116 | C | T | 80121 | 15 | 0.02% | 3.36E−11 | 39 | 37 |
| p21_Cdkn1A | 124 | A | C | 63329 | 12 | 0.02% | 8.38E−10 | 37 | 34 |
| p21_Cdkn1A | 130 | C | T | 74051 | 12 | 0.02% | 2.31E−12 | 38 | 39 |
| p21_Cdkn1A | 135 | A | C | 54696 | 12 | 0.02% | 8.41E−08 | 37 | 34 |
| p21_Cdkn1A | 142 | G | T | 62756 | 11 | 0.02% | 4.50E−10 | 38 | 37 |
| p21_Cdkn1A | 346 | C | T | 81763 | 18 | 0.02% | 5.00E−11 | 39 | 39 |
| p21_Cdkn1A | 373 | C | A | 85957 | 17 | 0.02% | 2.32E−12 | 40 | 38 |
| p21_Cdkn1A | 382 | G | T | 83769 | 20 | 0.02% | 1.31E−10 | 40 | 39 |
| p21_Cdkn1A | 8 | G | T | 84796 | 10 | 0.01% | 5.08E−16 | 39 | 39 |
| p21_Cdkn1A | 10 | G | T | 84608 | 9 | 0.01% | 1.07E−16 | 40 | 40 |
| p21_Cdkn1A | 91 | A | C | 76005 | 8 | 0.01% | 2.47E−15 | 39 | 33 |
| p21_Cdkn1A | 109 | A | C | 74271 | 8 | 0.01% | 8.12E−15 | 39 | 32 |
| p21_Cdkn1A | 127 | G | C | 69788 | 7 | 0.01% | 3.17E−14 | 38 | 33 |
| p21_Cdkn1A | 139 | G | C | 62650 | 7 | 0.01% | 2.03E−12 | 38 | 36 |
| p21_Cdkn1A | 331 | A | C | 61728 | 8 | 0.01% | 1.60E−11 | 37 | 38 |
| p21_Cdkn1A | 333 | A | C | 63628 | 7 | 0.01% | 1.12E−12 | 38 | 39 |
| p21_Cdkn1A | 381 | C | G | 86089 | 11 | 0.01% | 7.06E−16 | 40 | 36 |
| p21_Cdkn1A | 399 | G | A | 85205 | 12 | 0.01% | 5.14E−15 | 40 | 39 |
| p21_Cdkn1A | 467 | C | A | 88316 | 11 | 0.01% | 2.23E−16 | 40 | 41 |
| PCNA | 41 | A | C | 109905 | 46 | 0.04% | 2.22E−07 | 40 | 38 |
| PCNA | 97 | A | G | 111297 | 47 | 0.04% | 1.87E−07 | 40 | 37 |
| PCNA | 373 | G | C | 105015 | 45 | 0.04% | 5.25E−07 | 40 | 38 |
| PCNA | 67 | A | C | 112062 | 29 | 0.03% | 5.14E−13 | 40 | 37 |
| PCNA | 94 | A | G | 104270 | 30 | 0.03% | 4.60E−11 | 39 | 37 |
| PCNA | 105 | C | G | 107996 | 30 | 0.03% | 7.64E−12 | 40 | 39 |
| PCNA | 143 | C | A | 98596 | 29 | 0.03% | 2.95E−10 | 39 | 34 |
| PCNA | 346 | A | C | 68936 | 23 | 0.03% | 1.25E−06 | 36 | 33 |
| PCNA | 362 | A | C | 95726 | 33 | 0.03% | 1.89E−08 | 39 | 38 |
| PCNA | 130 | C | T | 105877 | 23 | 0.02% | 5.08E−14 | 39 | 38 |
| PCNA | 131 | C | G | 100725 | 25 | 0.02% | 3.99E−12 | 39 | 34 |
| PCNA | 139 | C | A | 98909 | 22 | 0.02% | 5.99E−13 | 39 | 37 |
| PCNA | 351 | C | T | 98868 | 15 | 0.02% | 2.01E−16 | 39 | 39 |
| PCNA | 377 | G | C | 106662 | 22 | 0.02% | 1.09E−14 | 40 | 38 |
| PCNA | 400 | G | C | 108304 | 21 | 0.02% | 1.31E−15 | 40 | 36 |
| PCNA | 411 | C | T | 106397 | 17 | 0.02% | 3.26E−17 | 40 | 40 |
| PCNA | 22 | A | G | 114140 | 14 | 0.01% | 5.69E−21 | 40 | 40 |
| PCNA | 30 | A | G | 113261 | 13 | 0.01% | 2.21E−21 | 40 | 40 |
| PCNA | 59 | C | T | 114257 | 17 | 0.01% | 3.95E−19 | 40 | 40 |
| PCNA | 81 | A | G | 109428 | 11 | 0.01% | 9.48E−22 | 40 | 39 |

TABLE 6-continued

A-, C-, and G-to-N mutation frequencies in amplicon sequences: no 4sU labeling, no OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| PCNA | 82 | G | T | 112412 | 13 | 0.01% | 3.98E−21 | 40 | 40 |
| PCNA | 104 | C | T | 111681 | 13 | 0.01% | 7.13E−21 | 40 | 39 |
| PCNA | 120 | C | A | 107076 | 13 | 0.01% | 7.33E−20 | 39 | 35 |
| PCNA | 129 | G | A | 106688 | 14 | 0.01% | 5.67E−19 | 39 | 38 |
| PCNA | 323 | A | G | 65378 | 8 | 0.01% | 1.60E−12 | 37 | 33 |
| PCNA | 324 | A | C | 59302 | 7 | 0.01% | 1.18E−11 | 36 | 38 |
| PCNA | 334 | A | C | 89451 | 9 | 0.01% | 5.41E−18 | 38 | 34 |
| PCNA | 335 | A | G | 89194 | 11 | 0.01% | 1.25E−16 | 38 | 35 |
| PCNA | 345 | C | T | 93281 | 11 | 0.01% | 1.22E−17 | 38 | 39 |
| PCNA | 363 | C | T | 100390 | 15 | 0.01% | 6.64E−17 | 39 | 39 |
| PCNA | 399 | A | C | 106035 | 14 | 0.01% | 5.67E−19 | 40 | 37 |
| PCNA | 421 | A | G | 106215 | 12 | 0.01% | 2.83E−20 | 40 | 40 |
| PCNA | 422 | C | A | 104886 | 11 | 0.01% | 1.87E−20 | 40 | 39 |

TABLE 7

A-, C-, and G-to-N mutation frequencies in amplicon sequences: 100 μ 4sU labeling, no OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| A2_CcnA2 | 12 | A | T | 90491 | 42 | 0.05% | 1.78E−05 | 40 | 32 |
| A2_CcnA2 | 39 | C | G | 88037 | 34 | 0.04% | 5.37E−07 | 40 | 35 |
| A2_CcnA2 | 67 | G | C | 67434 | 30 | 0.04% | 1.09E−04 | 38 | 39 |
| A2_CcnA2 | 88 | C | G | 88302 | 39 | 0.04% | 8.11E−06 | 40 | 38 |
| A2_CcnA2 | 338 | A | C | 75186 | 28 | 0.04% | 2.00E−06 | 40 | 37 |
| A2_CcnA2 | 392 | A | G | 64352 | 25 | 0.04% | 2.15E−05 | 38 | 37 |
| A2_CcnA2 | 419 | A | G | 78256 | 33 | 0.04% | 1.16E−05 | 40 | 37 |
| A2_CcnA2 | 422 | A | G | 79260 | 29 | 0.04% | 7.92E−07 | 40 | 35 |
| A2_CcnA2 | 37 | A | C | 87566 | 24 | 0.03% | 7.01E−10 | 40 | 35 |
| A2_CcnA2 | 117 | A | G | 83084 | 23 | 0.03% | 1.87E−09 | 39 | 36 |
| A2_CcnA2 | 121 | C | G | 83913 | 26 | 0.03% | 1.99E−08 | 39 | 37 |
| A2_CcnA2 | 371 | A | C | 77485 | 22 | 0.03% | 1.23E−08 | 40 | 38 |
| A2_CcnA2 | 374 | C | T | 70338 | 19 | 0.03% | 2.46E−08 | 38 | 36 |
| A2_CcnA2 | 420 | G | C | 78609 | 21 | 0.03% | 3.41E−09 | 40 | 34 |
| A2_CcnA2 | 3 | A | C | 90501 | 17 | 0.02% | 1.73E−13 | 40 | 39 |
| A2_CcnA2 | 4 | G | A | 91010 | 14 | 0.02% | 2.62E−15 | 40 | 40 |
| A2_CcnA2 | 13 | G | T | 90248 | 21 | 0.02% | 1.14E−11 | 40 | 40 |
| A2_CcnA2 | 85 | G | C | 86715 | 19 | 0.02% | 1.14E−11 | 39 | 37 |
| A2_CcnA2 | 91 | A | G | 87850 | 21 | 0.02% | 4.89E−11 | 40 | 35 |
| A2_CcnA2 | 104 | C | A | 87790 | 21 | 0.02% | 4.89E−11 | 40 | 40 |
| A2_CcnA2 | 107 | C | G | 85117 | 17 | 0.02% | 2.32E−12 | 39 | 36 |
| A2_CcnA2 | 122 | A | G | 82274 | 16 | 0.02% | 3.64E−12 | 39 | 35 |
| A2_CcnA2 | 144 | G | A | 75155 | 12 | 0.02% | 1.34E−12 | 38 | 38 |
| A2_CcnA2 | 145 | C | T | 72242 | 12 | 0.02% | 6.88E−12 | 38 | 40 |
| A2_CcnA2 | 316 | C | A | 62341 | 13 | 0.02% | 4.16E−09 | 37 | 40 |
| A2_CcnA2 | 317 | G | A | 67368 | 13 | 0.02% | 3.17E−10 | 39 | 40 |
| A2_CcnA2 | 337 | G | C | 72946 | 11 | 0.02% | 1.93E−12 | 39 | 34 |
| A2_CcnA2 | 355 | C | T | 76273 | 18 | 0.02% | 5.84E−10 | 39 | 38 |
| A2_CcnA2 | 364 | C | T | 65596 | 11 | 0.02% | 8.96E−11 | 38 | 36 |
| A2_CcnA2 | 454 | C | A | 80114 | 14 | 0.02% | 1.05E−12 | 40 | 39 |
| A2_CcnA2 | 7 | G | T | 90412 | 13 | 0.01% | 1.21E−15 | 40 | 41 |
| A2_CcnA2 | 10 | G | T | 91376 | 13 | 0.01% | 6.89E−16 | 40 | 40 |
| A2_CcnA2 | 15 | G | T | 88867 | 11 | 0.01% | 2.23E−16 | 40 | 41 |
| A2_CcnA2 | 19 | G | T | 91331 | 12 | 0.01% | 1.70E−16 | 40 | 40 |
| A2_CcnA2 | 35 | A | C | 76251 | 8 | 0.01% | 2.47E−15 | 39 | 32 |
| A2_CcnA2 | 42 | C | T | 90194 | 13 | 0.01% | 1.21E−15 | 40 | 40 |
| A2_CcnA2 | 82 | A | G | 88565 | 9 | 0.01% | 9.85E−18 | 40 | 39 |
| A2_CcnA2 | 118 | A | G | 72338 | 10 | 0.01% | 5.05E−13 | 38 | 39 |
| A2_CcnA2 | 131 | C | A | 80172 | 11 | 0.01% | 2.17E−14 | 38 | 38 |
| A2_CcnA2 | 132 | C | G | 59336 | 6 | 0.01% | 2.45E−12 | 37 | 39 |
| A2_CcnA2 | 135 | A | C | 61315 | 8 | 0.01% | 1.60E−11 | 37 | 37 |
| A2_CcnA2 | 138 | C | T | 78849 | 8 | 0.01% | 7.50E−16 | 38 | 41 |
| A2_CcnA2 | 315 | A | C | 66677 | 9 | 0.01% | 3.78E−12 | 38 | 39 |
| A2_CcnA2 | 318 | A | T | 71933 | 9 | 0.01% | 2.16E−13 | 39 | 38 |
| A2_CcnA2 | 319 | A | C | 68508 | 7 | 0.01% | 5.76E−14 | 39 | 36 |
| A2_CcnA2 | 331 | A | T | 66726 | 7 | 0.01% | 1.90E−13 | 39 | 39 |
| A2_CcnA2 | 334 | A | T | 68784 | 7 | 0.01% | 5.76E−14 | 38 | 39 |
| A2_CcnA2 | 339 | A | G | 71879 | 9 | 0.01% | 2.16E−13 | 39 | 39 |
| A2_CcnA2 | 349 | C | T | 76557 | 11 | 0.01% | 2.08E−13 | 40 | 37 |
| A2_CcnA2 | 350 | C | A | 75345 | 9 | 0.01% | 2.12E−14 | 39 | 39 |
| A2_CcnA2 | 357 | C | A | 77272 | 11 | 0.01% | 1.18E−13 | 40 | 40 |

TABLE 7-continued

A-, C-, and G-to-N mutation frequencies in amplicon sequences: 100 μ 4sU labeling, no OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| A2_CcnA2 | 363 | C | A | 75963 | 10 | 0.01% | 9.16E−14 | 39 | 40 |
| A2_CcnA2 | 370 | C | T | 77593 | 8 | 0.01% | 1.36E−15 | 40 | 39 |
| A2_CcnA2 | 375 | C | T | 76525 | 8 | 0.01% | 2.47E−15 | 39 | 40 |
| A2_CcnA2 | 381 | C | T | 75137 | 11 | 0.01% | 3.64E−13 | 39 | 39 |
| A2_CcnA2 | 388 | C | T | 75077 | 8 | 0.01% | 4.48E−15 | 38 | 38 |
| A2_CcnA2 | 394 | C | T | 77096 | 8 | 0.01% | 1.36E−15 | 39 | 41 |
| A2_CcnA2 | 398 | C | T | 78472 | 9 | 0.01% | 3.68E−15 | 40 | 39 |
| A2_CcnA2 | 403 | C | A | 69757 | 9 | 0.01% | 6.82E−13 | 38 | 39 |
| A2_CcnA2 | 407 | C | A | 77471 | 9 | 0.01% | 6.61E−15 | 39 | 41 |
| A2_CcnA2 | 424 | A | G | 79883 | 8 | 0.01% | 4.12E−16 | 40 | 40 |
| A2_CcnA2 | 439 | C | A | 79431 | 10 | 0.01% | 9.23E−15 | 40 | 40 |
| A2_CcnA2 | 449 | C | A | 79998 | 10 | 0.01% | 5.18E−15 | 40 | 41 |
| A2_CcnA2 | 456 | C | A | 79483 | 10 | 0.01% | 9.23E−15 | 40 | 39 |
| B1_CncB1 | 381 | A | C | 144866 | 90 | 0.06% | 2.51E−04 | 40 | 37 |
| B1_CncB1 | 40 | A | C | 153787 | 60 | 0.04% | 7.35E−11 | 40 | 35 |
| B1_CncB1 | 77 | C | A | 150111 | 58 | 0.04% | 6.93E−11 | 40 | 38 |
| B1_CncB1 | 88 | C | G | 152064 | 68 | 0.04% | 7.32E−09 | 40 | 37 |
| B1_CncB1 | 96 | C | T | 146404 | 55 | 0.04% | 5.17E−11 | 39 | 39 |
| B1_CncB1 | 100 | A | G | 110463 | 46 | 0.04% | 1.56E−07 | 38 | 36 |
| B1_CncB1 | 121 | A | G | 145399 | 60 | 0.04% | 1.31E−09 | 40 | 36 |
| B1_CncB1 | 385 | G | C | 144121 | 64 | 0.04% | 1.45E−08 | 40 | 38 |
| B1_CncB1 | 122 | A | G | 138713 | 47 | 0.03% | 6.95E−12 | 39 | 37 |
| B1_CncB1 | 145 | C | A | 102984 | 27 | 0.03% | 5.84E−12 | 37 | 38 |
| B1_CncB1 | 371 | C | G | 139141 | 35 | 0.03% | 3.52E−16 | 39 | 39 |
| B1_CncB1 | 383 | G | C | 142677 | 46 | 0.03% | 6.68E−13 | 39 | 36 |
| B1_CncB1 | 406 | A | G | 143721 | 48 | 0.03% | 1.81E−12 | 39 | 37 |
| B1_CncB1 | 434 | A | C | 131975 | 41 | 0.03% | 1.17E−12 | 39 | 34 |
| B1_CncB1 | 471 | A | G | 147782 | 50 | 0.03% | 1.40E−11 | 40 | 40 |
| B1_CncB1 | 21 | C | T | 151707 | 33 | 0.02% | 1.51E−19 | 40 | 39 |
| B1_CncB1 | 31 | C | T | 152908 | 23 | 0.02% | 7.92E−25 | 40 | 40 |
| B1_CncB1 | 39 | G | A | 148672 | 26 | 0.02% | 3.07E−22 | 40 | 32 |
| B1_CncB1 | 55 | C | T | 150856 | 29 | 0.02% | 3.48E−21 | 40 | 39 |
| B1_CncB1 | 65 | C | T | 150655 | 30 | 0.02% | 1.05E−20 | 40 | 40 |
| B1_CncB1 | 67 | A | C | 149688 | 37 | 0.02% | 1.93E−17 | 39 | 37 |
| B1_CncB1 | 71 | C | T | 148348 | 28 | 0.02% | 3.18E−21 | 39 | 40 |
| B1_CncB1 | 91 | G | T | 151365 | 34 | 0.02% | 4.14E−19 | 40 | 40 |
| B1_CncB1 | 110 | C | T | 141562 | 32 | 0.02% | 7.78E−18 | 39 | 39 |
| B1_CncB1 | 126 | A | G | 146852 | 27 | 0.02% | 2.88E−21 | 40 | 37 |
| B1_CncB1 | 135 | C | A | 108713 | 20 | 0.02% | 4.22E−16 | 38 | 37 |
| B1_CncB1 | 142 | C | G | 116452 | 26 | 0.02% | 4.45E−15 | 38 | 38 |
| B1_CncB1 | 329 | A | T | 100521 | 19 | 0.02% | 8.93E−15 | 36 | 38 |
| B1_CncB1 | 350 | G | T | 135444 | 22 | 0.02% | 2.47E−21 | 39 | 36 |
| B1_CncB1 | 375 | A | G | 145129 | 26 | 0.02% | 1.51E−21 | 40 | 39 |
| B1_CncB1 | 388 | A | G | 143637 | 24 | 0.02% | 3.93E−22 | 39 | 38 |
| B1_CncB1 | 389 | C | T | 140288 | 25 | 0.02% | 6.58E−21 | 39 | 40 |
| B1_CncB1 | 435 | C | G | 143841 | 24 | 0.02% | 3.93E−22 | 40 | 34 |
| B1_CncB1 | 437 | G | T | 146335 | 33 | 0.02% | 1.80E−18 | 40 | 39 |
| B1_CncB1 | 445 | G | T | 142182 | 35 | 0.02% | 8.49E−17 | 39 | 38 |
| B1_CncB1 | 452 | C | A | 148495 | 23 | 0.02% | 7.22E−24 | 40 | 40 |
| B1_CncB1 | 460 | A | G | 147813 | 30 | 0.02% | 4.88E−20 | 40 | 36 |
| B1_CncB1 | 13 | G | C | 153109 | 20 | 0.01% | 7.05E−27 | 40 | 37 |
| B1_CncB1 | 18 | G | T | 154290 | 16 | 0.01% | 8.10E−30 | 40 | 41 |
| B1_CncB1 | 35 | A | C | 126097 | 16 | 0.01% | 1.09E−22 | 39 | 32 |
| B1_CncB1 | 37 | C | G | 153166 | 17 | 0.01% | 7.41E−29 | 40 | 33 |
| B1_CncB1 | 76 | G | A | 151733 | 20 | 0.01% | 2.21E−26 | 40 | 39 |
| B1_CncB1 | 136 | A | G | 129694 | 19 | 0.01% | 1.35E−21 | 38 | 39 |
| B1_CncB1 | 138 | G | A | 135163 | 15 | 0.01% | 1.24E−25 | 39 | 38 |
| B1_CncB1 | 141 | C | A | 134881 | 18 | 0.01% | 2.02E−23 | 39 | 38 |
| B1_CncB1 | 331 | G | C | 107917 | 16 | 0.01% | 5.12E−18 | 37 | 36 |
| B1_CncB1 | 343 | G | T | 126541 | 17 | 0.01% | 4.61E−22 | 38 | 38 |
| B1_CncB1 | 361 | C | A | 130273 | 14 | 0.01% | 4.81E−25 | 38 | 38 |
| B1_CncB1 | 438 | C | T | 144245 | 18 | 0.01% | 6.57E−26 | 40 | 39 |
| B1_CncB1 | 447 | C | T | 144703 | 18 | 0.01% | 6.57E−26 | 40 | 39 |
| B1_CncB1 | 472 | G | A | 148624 | 19 | 0.01% | 2.88E−26 | 40 | 39 |
| D1_CncD1 | 38 | A | G | 162422 | 98 | 0.06% | 4.30E−05 | 40 | 34 |
| D1_CncD1 | 324 | A | C | 138219 | 81 | 0.06% | 7.08E−05 | 40 | 38 |
| D1_CncD1 | 40 | G | C | 165486 | 76 | 0.05% | 4.88E−09 | 40 | 34 |
| D1_CncD1 | 328 | A | C | 138865 | 63 | 0.05% | 6.42E−08 | 40 | 38 |
| D1_CncD1 | 67 | G | C | 143797 | 54 | 0.04% | 8.76E−11 | 38 | 39 |
| D1_CncD1 | 376 | A | G | 138754 | 58 | 0.04% | 5.22E−09 | 40 | 35 |
| D1_CncD1 | 316 | A | C | 118332 | 32 | 0.03% | 4.35E−13 | 38 | 35 |
| D1_CncD1 | 326 | A | C | 136576 | 47 | 0.03% | 1.55E−11 | 39 | 37 |
| D1_CncD1 | 349 | A | G | 137102 | 39 | 0.03% | 2.75E−14 | 39 | 37 |
| D1_CncD1 | 403 | A | G | 136420 | 36 | 0.03% | 3.47E−15 | 39 | 36 |
| D1_CncD1 | 3 | G | T | 165798 | 29 | 0.02% | 1.30E−24 | 40 | 39 |

TABLE 7-continued

A-, C-, and G-to-N mutation frequencies in amplicon sequences: 100 µ 4sU labeling, no OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| D1_CncD1 | 8 | G | T | 167609 | 32 | 0.02% | 1.49E−23 | 40 | 40 |
| D1_CncD1 | 36 | C | T | 164310 | 26 | 0.02% | 5.36E−26 | 40 | 41 |
| D1_CncD1 | 85 | G | A | 160075 | 34 | 0.02% | 4.69E−21 | 39 | 37 |
| D1_CncD1 | 90 | C | G | 160691 | 36 | 0.02% | 3.62E−20 | 40 | 36 |
| D1_CncD1 | 91 | A | G | 153432 | 24 | 0.02% | 1.69E−24 | 39 | 38 |
| D1_CncD1 | 145 | C | A | 124043 | 19 | 0.02% | 2.17E−20 | 37 | 37 |
| D1_CncD1 | 280 | G | T | 98070 | 24 | 0.02% | 4.11E−12 | 37 | 37 |
| D1_CncD1 | 299 | C | A | 117379 | 20 | 0.02% | 3.51E−18 | 39 | 37 |
| D1_CncD1 | 331 | A | C | 135572 | 29 | 0.02% | 7.34E−18 | 40 | 36 |
| D1_CncD1 | 379 | A | G | 137701 | 30 | 0.02% | 7.54E−18 | 40 | 36 |
| D1_CncD1 | 401 | C | A | 138536 | 26 | 0.02% | 6.05E−20 | 40 | 39 |
| D1_CncD1 | 405 | C | A | 140836 | 31 | 0.02% | 4.69E−18 | 39 | 38 |
| D1_CncD1 | 407 | C | A | 140875 | 30 | 0.02% | 1.68E−18 | 40 | 40 |
| D1_CncD1 | 408 | C | A | 140392 | 27 | 0.02% | 6.61E−20 | 40 | 40 |
| D1_CncD1 | 409 | C | A | 141231 | 30 | 0.02% | 1.02E−18 | 40 | 39 |
| D1_CncD1 | 410 | C | A | 141849 | 33 | 0.02% | 2.07E−17 | 40 | 40 |
| D1_CncD1 | 1 | G | T | 165712 | 19 | 0.01% | 1.51E−30 | 40 | 39 |
| D1_CncD1 | 15 | A | C | 166358 | 24 | 0.01% | 1.25E−27 | 40 | 36 |
| D1_CncD1 | 19 | G | T | 167771 | 24 | 0.01% | 7.14E−28 | 40 | 40 |
| D1_CncD1 | 37 | C | G | 164988 | 19 | 0.01% | 1.50E−30 | 40 | 32 |
| D1_CncD1 | 65 | A | G | 162143 | 20 | 0.01% | 3.98E−29 | 40 | 39 |
| D1_CncD1 | 76 | G | T | 163676 | 17 | 0.01% | 1.98E−31 | 40 | 40 |
| D1_CncD1 | 109 | G | T | 158642 | 18 | 0.01% | 1.90E−29 | 39 | 39 |
| D1_CncD1 | 121 | G | T | 157557 | 17 | 0.01% | 6.98E−30 | 39 | 39 |
| D1_CncD1 | 122 | C | T | 148536 | 20 | 0.01% | 1.22E−25 | 39 | 37 |
| D1_CncD1 | 123 | C | T | 148707 | 17 | 0.01% | 1.40E−27 | 39 | 36 |
| D1_CncD1 | 129 | A | G | 131890 | 18 | 0.01% | 1.11E−22 | 38 | 39 |
| D1_CncD1 | 135 | A | G | 139164 | 16 | 0.01% | 5.72E−26 | 39 | 37 |
| D1_CncD1 | 137 | A | C | 140670 | 16 | 0.01% | 3.18E−26 | 39 | 39 |
| D1_CncD1 | 278 | A | C | 104743 | 12 | 0.01% | 9.15E−20 | 37 | 38 |
| D1_CncD1 | 293 | G | T | 118367 | 14 | 0.01% | 5.56E−22 | 39 | 35 |
| D1_CncD1 | 319 | C | A | 126146 | 13 | 0.01% | 1.01E−24 | 39 | 38 |
| D1_CncD1 | 364 | C | T | 134143 | 16 | 0.01% | 1.06E−24 | 39 | 40 |
| E1_CncE1 | 473 | A | G | 65088 | 184 | 0.28% | 1.13E−14 | 40 | 40 |
| E1_CncE1 | 92 | A | G | 66273 | 36 | 0.05% | 1.93E−03 | 39 | 39 |
| E1_CncE1 | 373 | A | C | 51282 | 24 | 0.05% | 1.22E−03 | 37 | 36 |
| E1_CncE1 | 383 | A | C | 63973 | 33 | 0.05% | 1.07E−03 | 39 | 37 |
| E1_CncE1 | 39 | A | G | 68980 | 30 | 0.04% | 5.52E−05 | 40 | 34 |
| E1_CncE1 | 90 | C | G | 68485 | 29 | 0.04% | 4.64E−05 | 40 | 37 |
| E1_CncE1 | 100 | C | T | 63764 | 25 | 0.04% | 3.12E−05 | 39 | 38 |
| E1_CncE1 | 404 | C | T | 49675 | 18 | 0.04% | 9.67E−05 | 35 | 36 |
| E1_CncE1 | 436 | G | C | 63839 | 25 | 0.04% | 3.12E−05 | 40 | 33 |
| E1_CncE1 | 13 | C | T | 70257 | 20 | 0.03% | 5.63E−08 | 40 | 38 |
| E1_CncE1 | 88 | A | G | 63560 | 17 | 0.03% | 1.12E−07 | 39 | 36 |
| E1_CncE1 | 358 | A | C | 46038 | 15 | 0.03% | 4.40E−06 | 37 | 36 |
| E1_CncE1 | 370 | A | C | 57737 | 20 | 0.03% | 1.45E−05 | 38 | 39 |
| E1_CncE1 | 375 | G | C | 47832 | 12 | 0.03% | 2.55E−06 | 37 | 37 |
| E1_CncE1 | 408 | A | G | 56870 | 16 | 0.03% | 1.19E−06 | 38 | 37 |
| E1_CncE1 | 435 | A | G | 63214 | 22 | 0.03% | 4.87E−06 | 39 | 34 |
| E1_CncE1 | 469 | C | A | 65644 | 20 | 0.03% | 5.11E−07 | 40 | 40 |
| E1_CncE1 | 15 | C | T | 69767 | 14 | 0.02% | 3.37E−10 | 40 | 41 |
| E1_CncE1 | 36 | G | C | 68198 | 11 | 0.02% | 1.75E−11 | 39 | 39 |
| E1_CncE1 | 37 | A | C | 65104 | 12 | 0.02% | 2.93E−10 | 39 | 36 |
| E1_CncE1 | 40 | G | C | 69224 | 15 | 0.02% | 9.59E−10 | 40 | 38 |
| E1_CncE1 | 85 | C | A | 66251 | 11 | 0.02% | 5.21E−11 | 39 | 35 |
| E1_CncE1 | 91 | A | G | 67868 | 12 | 0.02% | 1.01E−10 | 40 | 39 |
| E1_CncE1 | 97 | G | T | 67481 | 11 | 0.02% | 3.02E−11 | 40 | 39 |
| E1_CncE1 | 129 | C | A | 63902 | 10 | 0.02% | 7.68E−11 | 39 | 38 |
| E1_CncE1 | 134 | A | C | 31951 | 6 | 0.02% | 2.05E−05 | 37 | 34 |
| E1_CncE1 | 139 | G | T | 55878 | 10 | 0.02% | 5.82E−09 | 38 | 38 |
| E1_CncE1 | 349 | A | G | 44498 | 8 | 0.02% | 2.01E−07 | 37 | 35 |
| E1_CncE1 | 457 | C | A | 61428 | 11 | 0.02% | 7.67E−10 | 39 | 39 |
| E1_CncE1 | 460 | C | G | 58909 | 9 | 0.02% | 3.37E−10 | 38 | 36 |
| E1_CncE1 | 461 | C | A | 62653 | 14 | 0.02% | 1.15E−08 | 39 | 40 |
| E1_CncE1 | 462 | A | G | 65512 | 14 | 0.02% | 2.57E−09 | 40 | 38 |
| E1_CncE1 | 474 | G | A | 66046 | 15 | 0.02% | 4.27E−09 | 40 | 37 |
| E1_CncE1 | 12 | G | A | 70109 | 8 | 0.01% | 8.61E−14 | 40 | 37 |
| E1_CncE1 | 26 | G | A | 66774 | 8 | 0.01% | 8.93E−13 | 39 | 39 |
| E1_CncE1 | 76 | C | T | 68346 | 8 | 0.01% | 2.78E−13 | 40 | 41 |
| E1_CncE1 | 115 | C | C | 63035 | 7 | 0.01% | 1.12E−12 | 39 | 36 |
| E1_CncE1 | 125 | C | G | 65007 | 7 | 0.01% | 3.44E−13 | 39 | 39 |
| E1_CncE1 | 142 | G | A | 59561 | 6 | 0.01% | 2.45E−12 | 39 | 40 |
| E1_CncE1 | 145 | A | G | 52509 | 6 | 0.01% | 1.56E−10 | 38 | 36 |
| E1_CncE1 | 330 | G | T | 51827 | 6 | 0.01% | 2.81E−10 | 37 | 35 |
| E1_CncE1 | 331 | G | C | 45851 | 5 | 0.01% | 2.09E−09 | 36 | 33 |

TABLE 7-continued

A-, C-, and G-to-N mutation frequencies in amplicon sequences: 100 μ 4sU labeling, no OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| E1_CncE1 | 332 | C | T | 38937 | 5 | 0.01% | 1.24E−07 | 36 | 40 |
| E1_CncE1 | 334 | A | T | 45737 | 6 | 0.01% | 9.09E−09 | 37 | 40 |
| E1_CncE1 | 335 | A | C | 46392 | 6 | 0.01% | 5.12E−09 | 37 | 37 |
| E1_CncE1 | 336 | G | T | 53280 | 6 | 0.01% | 8.68E−11 | 38 | 35 |
| E1_CncE1 | 345 | A | T | 52521 | 6 | 0.01% | 1.56E−10 | 38 | 36 |
| E1_CncE1 | 394 | C | A | 58625 | 7 | 0.01% | 2.11E−11 | 39 | 38 |
| E1_CncE1 | 420 | C | A | 53896 | 8 | 0.01% | 1.48E−09 | 38 | 41 |
| E1_CncE1 | 447 | A | C | 19055 | 2 | 0.01% | 1.10E−04 | 36 | 34 |
| E1_CncE1 | 454 | G | C | 50669 | 6 | 0.01% | 5.04E−10 | 37 | 38 |
| E1_CncE1 | 459 | C | A | 63400 | 8 | 0.01% | 5.08E−12 | 39 | 40 |
| eGFP | 97 | A | T | 86904 | 512 | 0.59% | 9.95E−75 | 38 | 40 |
| eGFP | 96 | G | T | 96112 | 513 | 0.53% | 2.86E−70 | 39 | 40 |
| eGFP | 91 | G | C | 96698 | 445 | 0.46% | 1.13E−54 | 39 | 40 |
| eGFP | 424 | A | G | 82010 | 171 | 0.21% | 1.11E−08 | 40 | 40 |
| eGFP | 1 | C | T | 102856 | 182 | 0.18% | 1.65E−06 | 40 | 39 |
| eGFP | 3 | A | C | 102193 | 168 | 0.16% | 3.49E−05 | 40 | 40 |
| eGFP | 2 | C | T | 103090 | 160 | 0.15% | 2.63E−04 | 40 | 40 |
| eGFP | 352 | A | G | 76563 | 43 | 0.06% | 1.59E−03 | 39 | 40 |
| eGFP | 384 | A | G | 75415 | 42 | 0.06% | 1.46E−03 | 39 | 40 |
| eGFP | 33 | A | G | 80189 | 43 | 0.05% | 5.40E−04 | 38 | 38 |
| eGFP | 73 | A | G | 99084 | 48 | 0.05% | 1.56E−05 | 39 | 39 |
| eGFP | 76 | G | A | 99739 | 47 | 0.05% | 1.00E−05 | 40 | 39 |
| eGFP | 92 | C | G | 99322 | 52 | 0.05% | 8.08E−05 | 40 | 38 |
| eGFP | 117 | A | G | 84844 | 46 | 0.05% | 5.44E−04 | 38 | 38 |
| eGFP | 129 | A | G | 74280 | 38 | 0.05% | 4.28E−04 | 38 | 39 |
| eGFP | 290 | G | A | 70811 | 32 | 0.05% | 1.06E−04 | 39 | 38 |
| eGFP | 304 | A | G | 61338 | 31 | 0.05% | 1.15E−03 | 37 | 39 |
| eGFP | 340 | A | G | 58964 | 27 | 0.05% | 5.06E−04 | 37 | 38 |
| eGFP | 346 | A | G | 67444 | 35 | 0.05% | 9.93E−04 | 38 | 39 |
| eGFP | 416 | G | A | 82280 | 43 | 0.05% | 3.08E−04 | 40 | 36 |
| eGFP | 12 | A | T | 101680 | 44 | 0.04% | 1.24E−06 | 40 | 34 |
| eGFP | 38 | C | G | 100398 | 39 | 0.04% | 1.15E−07 | 40 | 34 |
| eGFP | 63 | A | G | 92857 | 38 | 0.04% | 1.21E−06 | 39 | 38 |
| eGFP | 115 | A | G | 80133 | 34 | 0.04% | 9.73E−06 | 38 | 39 |
| eGFP | 139 | A | G | 66591 | 26 | 0.04% | 1.82E−05 | 36 | 36 |
| eGFP | 140 | C | G | 84359 | 31 | 0.04% | 3.98E−07 | 37 | 39 |
| eGFP | 287 | C | A | 68196 | 24 | 0.04% | 2.45E−06 | 38 | 39 |
| eGFP | 293 | G | C | 67462 | 24 | 0.04% | 3.65E−06 | 39 | 39 |
| eGFP | 294 | C | A | 64032 | 26 | 0.04% | 3.81E−05 | 39 | 36 |
| eGFP | 298 | C | A | 70533 | 27 | 0.04% | 7.34E−06 | 39 | 39 |
| eGFP | 307 | A | G | 58438 | 22 | 0.04% | 3.49E−05 | 37 | 39 |
| eGFP | 310 | A | G | 52213 | 21 | 0.04% | 1.85E−04 | 37 | 38 |
| eGFP | 315 | A | G | 66381 | 26 | 0.04% | 1.82E−05 | 39 | 38 |
| eGFP | 323 | G | C | 71531 | 27 | 0.04% | 5.02E−06 | 39 | 37 |
| eGFP | 336 | A | C | 78805 | 29 | 0.04% | 1.17E−06 | 39 | 37 |
| eGFP | 337 | A | G | 76057 | 32 | 0.04% | 1.37E−05 | 39 | 39 |
| eGFP | 338 | A | G | 71691 | 26 | 0.04% | 2.71E−06 | 39 | 38 |
| eGFP | 358 | A | G | 73848 | 27 | 0.04% | 2.33E−06 | 38 | 38 |
| eGFP | 361 | A | G | 73864 | 31 | 0.04% | 2.31E−05 | 39 | 37 |
| eGFP | 414 | G | A | 80997 | 30 | 0.04% | 6.81E−07 | 40 | 40 |
| eGFP | 18 | G | T | 100429 | 26 | 0.03% | 9.79E−12 | 40 | 40 |
| eGFP | 43 | A | G | 93519 | 24 | 0.03% | 4.39E−11 | 39 | 40 |
| eGFP | 49 | A | G | 68494 | 22 | 0.03% | 6.20E−07 | 38 | 39 |
| eGFP | 87 | A | G | 94600 | 29 | 0.03% | 1.68E−09 | 39 | 39 |
| eGFP | 106 | A | G | 89023 | 24 | 0.03% | 2.81E−10 | 39 | 40 |
| eGFP | 127 | A | G | 73577 | 22 | 0.03% | 7.25E−08 | 38 | 40 |
| eGFP | 135 | G | A | 89290 | 25 | 0.03% | 6.50E−10 | 39 | 39 |
| eGFP | 136 | A | G | 57037 | 17 | 0.03% | 1.69E−06 | 37 | 38 |
| eGFP | 137 | G | C | 86064 | 24 | 0.03% | 1.10E−09 | 38 | 38 |
| eGFP | 142 | A | G | 73094 | 19 | 0.03% | 6.11E−09 | 37 | 37 |
| eGFP | 291 | C | A | 68197 | 20 | 0.03% | 1.37E−07 | 38 | 39 |
| eGFP | 318 | A | G | 47135 | 16 | 0.03% | 5.82E−05 | 36 | 39 |
| eGFP | 345 | A | G | 71929 | 18 | 0.03% | 6.42E−09 | 38 | 39 |
| eGFP | 351 | A | G | 74710 | 22 | 0.03% | 4.68E−08 | 39 | 40 |
| eGFP | 390 | G | C | 80258 | 26 | 0.03% | 7.07E−08 | 40 | 33 |
| eGFP | 396 | A | G | 79792 | 23 | 0.03% | 1.13E−08 | 39 | 39 |
| eGFP | 399 | A | G | 73061 | 19 | 0.03% | 6.11E−09 | 38 | 39 |
| eGFP | 14 | G | T | 102593 | 19 | 0.02% | 3.13E−15 | 40 | 40 |
| eGFP | 16 | A | C | 101784 | 18 | 0.02% | 1.65E−15 | 40 | 32 |
| eGFP | 24 | A | G | 97284 | 20 | 0.02% | 1.26E−13 | 40 | 40 |
| eGFP | 25 | A | G | 87154 | 19 | 0.02% | 6.90E−12 | 39 | 40 |
| eGFP | 31 | A | G | 83119 | 17 | 0.02% | 6.46E−12 | 39 | 39 |
| eGFP | 34 | C | T | 99838 | 15 | 0.02% | 1.16E−16 | 39 | 38 |
| eGFP | 37 | G | T | 99731 | 18 | 0.02% | 4.78E−15 | 40 | 38 |
| eGFP | 40 | C | A | 99281 | 19 | 0.02% | 1.50E−14 | 39 | 33 |

TABLE 7-continued

A-, C-, and G-to-N mutation frequencies in amplicon sequences: 100 µ 4sU labeling, no OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| eGFP | 61 | A | G | 89054 | 21 | 0.02% | 1.86E−11 | 39 | 38 |
| eGFP | 65 | C | A | 98224 | 20 | 0.02% | 7.56E−14 | 39 | 39 |
| eGFP | 66 | C | A | 100682 | 17 | 0.02% | 8.49E−16 | 40 | 39 |
| eGFP | 72 | A | G | 82074 | 18 | 0.02% | 3.04E−11 | 37 | 39 |
| eGFP | 82 | A | G | 86259 | 20 | 0.02% | 3.06E−11 | 38 | 39 |
| eGFP | 89 | G | A | 96424 | 18 | 0.02% | 2.32E−14 | 39 | 38 |
| eGFP | 93 | A | G | 93807 | 16 | 0.02% | 1.09E−14 | 39 | 40 |
| eGFP | 109 | A | G | 82209 | 18 | 0.02% | 3.04E−11 | 38 | 40 |
| eGFP | 114 | A | G | 91839 | 21 | 0.02% | 7.01E−12 | 39 | 40 |
| eGFP | 124 | G | A | 90756 | 21 | 0.02% | 1.14E−11 | 39 | 36 |
| eGFP | 134 | G | A | 91642 | 14 | 0.02% | 2.62E−15 | 39 | 36 |
| eGFP | 143 | C | G | 91944 | 16 | 0.02% | 3.18E−14 | 39 | 37 |
| eGFP | 145 | A | C | 64112 | 10 | 0.02% | 4.43E−11 | 36 | 35 |
| eGFP | 288 | G | A | 66828 | 14 | 0.02% | 1.55E−09 | 38 | 38 |
| eGFP | 296 | G | C | 67476 | 15 | 0.02% | 2.60E−09 | 39 | 38 |
| eGFP | 299 | C | A | 74108 | 13 | 0.02% | 7.87E−12 | 39 | 38 |
| eGFP | 300 | G | A | 71489 | 16 | 0.02% | 9.68E−10 | 39 | 38 |
| eGFP | 306 | C | A | 71297 | 13 | 0.02% | 3.89E−11 | 38 | 39 |
| eGFP | 322 | A | G | 68515 | 11 | 0.02% | 1.75E−11 | 39 | 39 |
| eGFP | 333 | A | G | 72127 | 14 | 0.02% | 7.14E−11 | 39 | 38 |
| eGFP | 339 | G | A | 72067 | 16 | 0.02% | 5.89E−10 | 38 | 37 |
| eGFP | 342 | C | A | 71975 | 11 | 0.02% | 3.37E−12 | 38 | 37 |
| eGFP | 343 | C | T | 70629 | 16 | 0.02% | 1.59E−09 | 38 | 35 |
| eGFP | 348 | G | A | 77400 | 12 | 0.02% | 4.46E−13 | 39 | 40 |
| eGFP | 349 | A | G | 70834 | 17 | 0.02% | 4.13E−09 | 39 | 39 |
| eGFP | 376 | A | G | 77503 | 15 | 0.02% | 1.61E−11 | 39 | 37 |
| eGFP | 388 | C | G | 78504 | 19 | 0.02% | 5.70E−10 | 39 | 35 |
| eGFP | 389 | C | T | 75026 | 16 | 0.02% | 1.31E−11 | 39 | 38 |
| eGFP | 391 | C | G | 80079 | 14 | 0.02% | 1.05E−12 | 40 | 33 |
| eGFP | 415 | A | G | 81719 | 20 | 0.02% | 3.43E−10 | 40 | 36 |
| eGFP | 423 | A | G | 81971 | 15 | 0.02% | 1.99E−12 | 40 | 40 |
| eGFP | 427 | A | G | 81118 | 18 | 0.02% | 5.00E−11 | 40 | 40 |
| eGFP | 15 | G | C | 99092 | 13 | 0.01% | 7.37E−18 | 40 | 37 |
| eGFP | 28 | A | G | 91354 | 10 | 0.01% | 8.34E−18 | 38 | 40 |
| eGFP | 30 | A | G | 100357 | 11 | 0.01% | 2.00E−19 | 40 | 40 |
| eGFP | 39 | G | A | 94283 | 13 | 0.01% | 1.27E−16 | 39 | 35 |
| eGFP | 56 | G | T | 95069 | 11 | 0.01% | 3.79E−18 | 39 | 40 |
| eGFP | 71 | G | A | 92814 | 11 | 0.01% | 2.19E−17 | 38 | 36 |
| eGFP | 78 | A | G | 95693 | 10 | 0.01% | 7.78E−19 | 40 | 38 |
| eGFP | 101 | C | T | 96992 | 12 | 0.01% | 5.39E−18 | 39 | 37 |
| eGFP | 103 | A | G | 92817 | 13 | 0.01% | 3.93E−16 | 39 | 38 |
| eGFP | 112 | G | A | 94088 | 14 | 0.01% | 4.95E−16 | 39 | 38 |
| eGFP | 122 | G | C | 92745 | 13 | 0.01% | 3.93E−16 | 39 | 35 |
| eGFP | 123 | G | T | 90482 | 10 | 0.01% | 1.51E−17 | 39 | 38 |
| eGFP | 126 | C | A | 92748 | 12 | 0.01% | 9.60E−17 | 39 | 35 |
| eGFP | 302 | C | T | 73425 | 9 | 0.01% | 6.79E−14 | 39 | 36 |
| eGFP | 308 | C | T | 66266 | 7 | 0.01% | 1.90E−13 | 37 | 37 |
| eGFP | 317 | C | T | 71216 | 9 | 0.01% | 2.16E−13 | 38 | 38 |
| eGFP | 341 | C | T | 75139 | 11 | 0.01% | 3.64E−13 | 39 | 39 |
| eGFP | 371 | G | A | 80314 | 12 | 0.01% | 8.46E−14 | 40 | 40 |
| eGFP | 392 | C | G | 80310 | 10 | 0.01% | 5.18E−15 | 40 | 39 |
| eGFP | 393 | G | A | 81533 | 11 | 0.01% | 1.23E−14 | 40 | 39 |
| p21_Cdkn1A | 40 | G | C | 70603 | 29 | 0.04% | 2.29E−05 | 39 | 34 |
| p21_Cdkn1A | 142 | G | T | 52751 | 21 | 0.04% | 1.85E−04 | 38 | 39 |
| p21_Cdkn1A | 4 | G | T | 73556 | 25 | 0.03% | 6.35E−07 | 40 | 40 |
| p21_Cdkn1A | 67 | A | C | 66518 | 19 | 0.03% | 1.51E−07 | 39 | 38 |
| p21_Cdkn1A | 107 | C | G | 67744 | 19 | 0.03% | 9.62E−08 | 39 | 38 |
| p21_Cdkn1A | 117 | C | G | 64846 | 20 | 0.03% | 7.87E−07 | 39 | 37 |
| p21_Cdkn1A | 129 | A | C | 35436 | 12 | 0.03% | 5.42E−04 | 37 | 32 |
| p21_Cdkn1A | 341 | C | G | 66122 | 18 | 0.03% | 6.61E−08 | 39 | 37 |
| p21_Cdkn1A | 346 | C | G | 67944 | 21 | 0.03% | 4.57E−07 | 39 | 40 |
| p21_Cdkn1A | 370 | G | C | 70495 | 24 | 0.03% | 1.09E−06 | 39 | 37 |
| p21_Cdkn1A | 375 | G | C | 66233 | 23 | 0.03% | 2.83E−06 | 39 | 38 |
| p21_Cdkn1A | 438 | C | G | 74327 | 26 | 0.03% | 8.27E−07 | 40 | 37 |
| p21_Cdkn1A | 463 | A | C | 71804 | 20 | 0.03% | 3.59E−08 | 39 | 33 |
| p21_Cdkn1A | 8 | G | T | 72689 | 11 | 0.02% | 1.93E−12 | 39 | 39 |
| p21_Cdkn1A | 9 | G | T | 73113 | 13 | 0.02% | 1.34E−11 | 40 | 40 |
| p21_Cdkn1A | 39 | G | C | 68379 | 14 | 0.02% | 5.62E−10 | 39 | 33 |
| p21_Cdkn1A | 57 | G | T | 71411 | 15 | 0.02% | 3.50E−10 | 40 | 39 |
| p21_Cdkn1A | 77 | C | G | 70521 | 13 | 0.02% | 6.59E−11 | 40 | 36 |
| p21_Cdkn1A | 85 | C | A | 68765 | 15 | 0.02% | 1.58E−09 | 39 | 35 |
| p21_Cdkn1A | 100 | A | C | 45313 | 8 | 0.02% | 1.18E−07 | 38 | 33 |
| p21_Cdkn1A | 119 | A | C | 55369 | 13 | 0.02% | 1.36E−07 | 38 | 34 |
| p21_Cdkn1A | 124 | A | C | 56360 | 11 | 0.02% | 1.06E−08 | 38 | 32 |
| p21_Cdkn1A | 127 | G | C | 58762 | 14 | 0.02% | 8.17E−08 | 38 | 33 |

TABLE 7-continued

A-, C-, and G-to-N mutation frequencies in amplicon sequences: 100 μ 4sU labeling, no OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| p21_Cdkn1A | 134 | G | T | 53122 | 12 | 0.02% | 1.38E−07 | 38 | 35 |
| p21_Cdkn1A | 140 | C | G | 61190 | 11 | 0.02% | 7.67E−10 | 38 | 36 |
| p21_Cdkn1A | 143 | C | A | 61817 | 12 | 0.02% | 2.38E−09 | 38 | 35 |
| p21_Cdkn1A | 330 | A | T | 63822 | 12 | 0.02% | 8.38E−10 | 39 | 38 |
| p21_Cdkn1A | 331 | A | C | 57584 | 12 | 0.02% | 1.85E−08 | 38 | 38 |
| p21_Cdkn1A | 333 | A | T | 59379 | 9 | 0.02% | 1.94E−10 | 38 | 39 |
| p21_Cdkn1A | 335 | A | T | 62560 | 13 | 0.02% | 4.16E−09 | 39 | 37 |
| p21_Cdkn1A | 338 | G | T | 59823 | 9 | 0.02% | 1.94E−10 | 39 | 39 |
| p21_Cdkn1A | 339 | G | T | 61435 | 13 | 0.02% | 6.90E−09 | 39 | 39 |
| p21_Cdkn1A | 340 | C | A | 65915 | 14 | 0.02% | 2.57E−09 | 39 | 38 |
| p21_Cdkn1A | 345 | A | G | 62526 | 11 | 0.02% | 4.50E−10 | 38 | 38 |
| p21_Cdkn1A | 348 | G | C | 64941 | 10 | 0.02% | 4.43E−11 | 38 | 38 |
| p21_Cdkn1A | 358 | G | C | 66114 | 15 | 0.02% | 4.27E−09 | 39 | 38 |
| p21_Cdkn1A | 368 | G | C | 71745 | 13 | 0.02% | 3.89E−11 | 40 | 35 |
| p21_Cdkn1A | 390 | A | G | 64336 | 16 | 0.02% | 2.91E−08 | 38 | 37 |
| p21_Cdkn1A | 458 | C | A | 72557 | 11 | 0.02% | 1.93E−12 | 39 | 39 |
| p21_Cdkn1A | 460 | C | G | 73417 | 16 | 0.02% | 3.58E−10 | 40 | 34 |
| p21_Cdkn1A | 462 | C | G | 73491 | 12 | 0.02% | 4.00E−12 | 39 | 37 |
| p21_Cdkn1A | 20 | G | T | 72140 | 8 | 0.01% | 2.65E−14 | 40 | 39 |
| p21_Cdkn1A | 27 | C | T | 65817 | 7 | 0.01% | 3.44E−13 | 39 | 38 |
| p21_Cdkn1A | 38 | G | C | 70993 | 8 | 0.01% | 4.78E−14 | 40 | 34 |
| p21_Cdkn1A | 88 | G | T | 69297 | 9 | 0.01% | 6.82E−13 | 39 | 37 |
| p21_Cdkn1A | 91 | A | G | 67343 | 9 | 0.01% | 2.14E−12 | 39 | 39 |
| p21_Cdkn1A | 138 | A | G | 55203 | 6 | 0.01% | 2.66E−11 | 38 | 39 |
| p21_Cdkn1A | 144 | G | A | 56488 | 6 | 0.01% | 1.47E−11 | 39 | 38 |
| p21_Cdkn1A | 332 | C | T | 62499 | 9 | 0.01% | 3.63E−11 | 38 | 39 |
| p21_Cdkn1A | 344 | G | T | 64795 | 9 | 0.01% | 1.18E−11 | 39 | 37 |
| p21_Cdkn1A | 353 | C | A | 67943 | 10 | 0.01% | 8.38E−12 | 39 | 36 |
| p21_Cdkn1A | 407 | C | A | 66220 | 9 | 0.01% | 3.78E−12 | 38 | 39 |
| p21_Cdkn1A | 459 | C | A | 73097 | 9 | 0.01% | 6.79E−14 | 39 | 37 |
| PCNA | 105 | C | G | 178080 | 101 | 0.06% | 2.33E−06 | 39 | 38 |
| PCNA | 12 | A | T | 188422 | 98 | 0.05% | 5.57E−08 | 40 | 32 |
| PCNA | 341 | A | C | 104039 | 56 | 0.05% | 9.10E−05 | 36 | 33 |
| PCNA | 427 | A | G | 174742 | 79 | 0.05% | 1.11E−09 | 40 | 36 |
| PCNA | 40 | G | C | 191594 | 75 | 0.04% | 3.77E−13 | 39 | 36 |
| PCNA | 121 | A | G | 178549 | 66 | 0.04% | 2.27E−13 | 39 | 37 |
| PCNA | 322 | G | A | 84818 | 30 | 0.04% | 2.11E−07 | 36 | 33 |
| PCNA | 362 | A | C | 151818 | 64 | 0.04% | 1.36E−09 | 38 | 36 |
| PCNA | 379 | A | C | 174281 | 74 | 0.04% | 9.14E−11 | 40 | 38 |
| PCNA | 429 | A | C | 173034 | 68 | 0.04% | 4.86E−12 | 40 | 34 |
| PCNA | 67 | A | C | 184262 | 64 | 0.03% | 6.05E−15 | 39 | 38 |
| PCNA | 88 | C | G | 189896 | 55 | 0.03% | 1.05E−18 | 40 | 36 |
| PCNA | 131 | C | A | 165053 | 47 | 0.03% | 6.97E−17 | 38 | 38 |
| PCNA | 139 | C | G | 169530 | 45 | 0.03% | 2.13E−18 | 39 | 39 |
| PCNA | 324 | A | T | 106797 | 31 | 0.03% | 4.21E−11 | 37 | 39 |
| PCNA | 333 | C | A | 133775 | 45 | 0.03% | 1.35E−11 | 38 | 33 |
| PCNA | 346 | A | G | 117804 | 40 | 0.03% | 2.94E−10 | 37 | 37 |
| PCNA | 377 | G | C | 171276 | 54 | 0.03% | 1.16E−15 | 39 | 37 |
| PCNA | 428 | A | C | 170042 | 43 | 0.03% | 2.27E−19 | 39 | 35 |
| PCNA | 455 | G | A | 174164 | 50 | 0.03% | 1.45E−17 | 40 | 32 |
| PCNA | 13 | G | C | 192828 | 32 | 0.02% | 2.57E−29 | 40 | 35 |
| PCNA | 15 | A | C | 189743 | 30 | 0.02% | 1.05E−29 | 39 | 37 |
| PCNA | 37 | G | C | 193709 | 39 | 0.02% | 5.22E−26 | 40 | 35 |
| PCNA | 127 | A | C | 170201 | 30 | 0.02% | 3.00E−25 | 39 | 40 |
| PCNA | 130 | C | T | 175444 | 38 | 0.02% | 1.61E−22 | 39 | 39 |
| PCNA | 142 | C | A | 165679 | 29 | 0.02% | 1.30E−24 | 38 | 38 |
| PCNA | 334 | A | G | 145834 | 26 | 0.02% | 1.51E−21 | 38 | 39 |
| PCNA | 337 | A | C | 141344 | 22 | 0.02% | 9.26E−23 | 38 | 38 |
| PCNA | 345 | C | A | 147343 | 24 | 0.02% | 4.49E−23 | 38 | 37 |
| PCNA | 349 | C | A | 151680 | 24 | 0.02% | 5.06E−24 | 38 | 37 |
| PCNA | 387 | C | A | 170703 | 27 | 0.02% | 7.26E−27 | 40 | 39 |
| PCNA | 411 | C | T | 166072 | 36 | 0.02% | 1.84E−21 | 39 | 39 |
| PCNA | 430 | A | G | 173198 | 41 | 0.02% | 8.44E−21 | 40 | 35 |
| PCNA | 17 | G | C | 193273 | 23 | 0.01% | 5.87E−35 | 39 | 37 |
| PCNA | 22 | A | G | 192655 | 25 | 0.01% | 2.08E−33 | 40 | 40 |
| PCNA | 31 | A | G | 169752 | 23 | 0.01% | 5.74E−29 | 39 | 37 |
| PCNA | 36 | A | C | 187646 | 21 | 0.01% | 8.68E−35 | 40 | 38 |
| PCNA | 66 | G | A | 188425 | 25 | 0.01% | 2.04E−32 | 40 | 40 |
| PCNA | 72 | C | T | 177089 | 25 | 0.01% | 1.03E−29 | 39 | 39 |
| PCNA | 85 | C | G | 187534 | 24 | 0.01% | 8.43E−33 | 39 | 37 |
| PCNA | 122 | C | A | 181971 | 26 | 0.01% | 4.33E−30 | 39 | 39 |
| PCNA | 129 | G | T | 182945 | 24 | 0.01% | 1.47E−31 | 40 | 39 |
| PCNA | 140 | A | G | 169929 | 22 | 0.01% | 1.36E−29 | 39 | 38 |
| PCNA | 141 | G | A | 170785 | 20 | 0.01% | 3.83E−31 | 39 | 39 |
| PCNA | 143 | C | A | 174326 | 21 | 0.01% | 1.73E−31 | 39 | 38 |

TABLE 7-continued

A-, C-, and G-to-N mutation frequencies in amplicon sequences: 100 µ 4sU labeling, no OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| PCNA | 323 | A | C | 113580 | 17 | 0.01% | 6.88E−19 | 37 | 38 |
| PCNA | 328 | C | T | 132314 | 18 | 0.01% | 6.30E−23 | 37 | 37 |
| PCNA | 332 | A | C | 154014 | 21 | 0.01% | 1.67E−26 | 38 | 40 |
| PCNA | 335 | A | G | 148126 | 16 | 0.01% | 2.86E−28 | 38 | 39 |
| PCNA | 336 | A | T | 139413 | 16 | 0.01% | 5.72E−26 | 38 | 38 |
| PCNA | 340 | C | T | 143840 | 17 | 0.01% | 2.59E−26 | 38 | 37 |
| PCNA | 342 | C | T | 141762 | 15 | 0.01% | 3.58E−27 | 38 | 37 |
| PCNA | 344 | C | T | 110197 | 14 | 0.01% | 5.72E−20 | 37 | 38 |
| PCNA | 375 | C | T | 166798 | 17 | 0.01% | 3.32E−32 | 39 | 40 |
| PCNA | 389 | C | A | 167870 | 20 | 0.01% | 2.19E−30 | 39 | 40 |
| PCNA | 443 | C | T | 169230 | 18 | 0.01% | 2.89E−32 | 40 | 40 |

TABLE 8

A-, C-, and G-to-N mutation frequencies in amplicon sequences: 50 µ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| A2_CcnA2 | 29 | C | T | 101085 | 60 | 0.06% | 7.66E−04 | 40 | 40 |
| A2_CcnA2 | 45 | C | T | 100966 | 58 | 0.06% | 4.04E−04 | 40 | 40 |
| A2_CcnA2 | 350 | C | T | 85274 | 44 | 0.05% | 1.93E−04 | 39 | 39 |
| A2_CcnA2 | 381 | C | T | 85531 | 46 | 0.05% | 4.14E−04 | 39 | 39 |
| A2_CcnA2 | 391 | C | T | 85435 | 40 | 0.05% | 3.49E−05 | 40 | 40 |
| A2_CcnA2 | 394 | C | T | 87232 | 44 | 0.05% | 1.07E−04 | 40 | 40 |
| 2_CcnA2 | 24 | C | T | 100641 | 41 | 0.04% | 3.59E−07 | 40 | 40 |
| A2_CcnA2 | 119 | A | G | 91835 | 38 | 0.04% | 1.72E−06 | 39 | 38 |
| A2_CcnA2 | 133 | C | T | 91730 | 37 | 0.04% | 9.95E−07 | 39 | 39 |
| A2_CcnA2 | 145 | C | T | 80096 | 29 | 0.04% | 5.36E−07 | 38 | 38 |
| A2_CcnA2 | 323 | C | T | 77322 | 30 | 0.04% | 3.12E−06 | 39 | 39 |
| A2_CcnA2 | 333 | C | T | 82442 | 32 | 0.04% | 1.56E−06 | 39 | 37 |
| A2_CcnA2 | 357 | C | T | 86338 | 33 | 0.04% | 6.28E−07 | 40 | 40 |
| A2_CcnA2 | 369 | C | T | 84996 | 35 | 0.04% | 2.85E−06 | 40 | 38 |
| A2_CcnA2 | 386 | C | T | 83770 | 37 | 0.04% | 1.61E−05 | 39 | 39 |
| A2_CcnA2 | 400 | C | T | 85598 | 34 | 0.04% | 1.63E−06 | 40 | 40 |
| A2_CcnA2 | 418 | A | G | 86519 | 38 | 0.04% | 9.66E−06 | 40 | 38 |
| A2_CcnA2 | 41 | A | G | 100072 | 31 | 0.03% | 5.74E−10 | 40 | 38 |
| A2_CcnA2 | 44 | C | T | 101794 | 35 | 0.03% | 6.43E−09 | 40 | 40 |
| A2_CcnA2 | 67 | G | C | 97523 | 31 | 0.03% | 2.06E−09 | 40 | 37 |
| A2_CcnA2 | 88 | C | T | 96603 | 26 | 0.03% | 6.23E−11 | 40 | 40 |
| A2_CcnA2 | 132 | C | T | 91695 | 27 | 0.03% | 1.33E−09 | 39 | 39 |
| A2_CcnA2 | 316 | C | T | 76073 | 22 | 0.03% | 1.93E−08 | 39 | 37 |
| A2_CcnA2 | 332 | C | T | 82036 | 27 | 0.03% | 6.25E−08 | 39 | 37 |
| A2_CcnA2 | 355 | C | T | 85696 | 26 | 0.03% | 8.41E−09 | 39 | 40 |
| A2_CcnA2 | 363 | C | T | 85614 | 24 | 0.03% | 1.73E−09 | 40 | 40 |
| A2_CcnA2 | 378 | C | T | 86778 | 24 | 0.03% | 1.10E−09 | 40 | 39 |
| A2_CcnA2 | 403 | C | T | 87679 | 25 | 0.03% | 1.60E−09 | 40 | 39 |
| A2_CcnA2 | 407 | C | T | 87607 | 28 | 0.03% | 1.58E−08 | 40 | 40 |
| A2_CcnA2 | 451 | C | A | 89309 | 26 | 0.03% | 1.46E−09 | 40 | 40 |
| A2_CcnA2 | 4 | G | T | 101156 | 19 | 0.02% | 5.29E−15 | 40 | 41 |
| A2_CcnA2 | 7 | G | T | 101489 | 17 | 0.02% | 4.95E−16 | 40 | 41 |
| A2_CcnA2 | 15 | G | T | 101050 | 19 | 0.02% | 5.29E−15 | 40 | 40 |
| A2_CcnA2 | 42 | C | T | 100911 | 25 | 0.02% | 3.99E−12 | 40 | 40 |
| A2_CcnA2 | 52 | C | T | 100201 | 21 | 0.02% | 7.91E−14 | 40 | 40 |
| A2_CcnA2 | 87 | C | T | 97404 | 18 | 0.02% | 1.37E−14 | 40 | 40 |
| A2_CcnA2 | 92 | C | T | 99672 | 21 | 0.02% | 1.31E−13 | 40 | 40 |
| A2_CcnA2 | 99 | C | T | 98407 | 15 | 0.02% | 2.01E−16 | 40 | 40 |
| A2_CcnA2 | 104 | C | T | 98649 | 19 | 0.02% | 2.53E−14 | 40 | 39 |
| A2_CcnA2 | 107 | C | T | 97491 | 24 | 0.02% | 6.63E−12 | 40 | 40 |
| A2_CcnA2 | 110 | C | T | 95109 | 22 | 0.02% | 2.62E−12 | 40 | 39 |
| A2_CcnA2 | 142 | C | T | 89047 | 16 | 0.02% | 9.22E−14 | 39 | 37 |
| A2_CcnA2 | 334 | C | T | 81721 | 16 | 0.02% | 6.11E−12 | 39 | 39 |
| A2_CcnA2 | 340 | A | C | 81909 | 19 | 0.02% | 1.34E−10 | 39 | 38 |
| A2_CcnA2 | 349 | C | T | 85552 | 20 | 0.02% | 4.98E−11 | 39 | 39 |
| A2_CcnA2 | 362 | A | C | 80815 | 20 | 0.02% | 5.52E−10 | 39 | 37 |
| A2_CcnA2 | 367 | C | T | 84866 | 19 | 0.02% | 3.07E−11 | 40 | 40 |
| A2_CcnA2 | 370 | C | T | 85922 | 20 | 0.02% | 4.98E−11 | 40 | 40 |
| A2_CcnA2 | 374 | C | T | 85818 | 19 | 0.02% | 1.87E−11 | 40 | 39 |
| A2_CcnA2 | 375 | C | T | 86069 | 20 | 0.02% | 3.06E−11 | 39 | 39 |
| A2_CcnA2 | 388 | C | T | 83334 | 13 | 0.02% | 5.92E−14 | 39 | 40 |
| A2_CcnA2 | 389 | C | T | 84723 | 21 | 0.02% | 2.05E−10 | 39 | 40 |
| A2_CcnA2 | 392 | A | C | 82591 | 20 | 0.02% | 2.12E−10 | 39 | 38 |

TABLE 8-continued

A-, C-, and G-to-N mutation frequencies in amplicon sequences: 50 μ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| A2_CcnA2 | 431 | C | T | 88207 | 22 | 0.02% | 7.66E−11 | 40 | 40 |
| A2_CcnA2 | 439 | C | A | 88806 | 20 | 0.02% | 1.15E−11 | 40 | 40 |
| A2_CcnA2 | 449 | C | A | 88437 | 22 | 0.02% | 7.66E−11 | 40 | 40 |
| A2_CcnA2 | 454 | C | A | 89317 | 20 | 0.02% | 7.00E−12 | 40 | 40 |
| A2_CcnA2 | 10 | G | T | 101410 | 14 | 0.01% | 9.73E−18 | 40 | 40 |
| A2_CcnA2 | 13 | G | T | 101717 | 13 | 0.01% | 2.34E−18 | 40 | 41 |
| A2_CcnA2 | 34 | G | T | 99965 | 10 | 0.01% | 7.15E−20 | 40 | 40 |
| A2_CcnA2 | 38 | C | T | 100563 | 15 | 0.01% | 6.64E−17 | 40 | 40 |
| A2_CcnA2 | 39 | C | T | 99957 | 13 | 0.01% | 7.37E−18 | 40 | 39 |
| A2_CcnA2 | 68 | A | C | 94259 | 13 | 0.01% | 1.27E−16 | 39 | 38 |
| A2_CcnA2 | 115 | G | A | 96932 | 11 | 0.01% | 2.11E−18 | 39 | 40 |
| A2_CcnA2 | 127 | C | T | 93178 | 10 | 0.01% | 2.55E−18 | 39 | 39 |
| A2_CcnA2 | 130 | A | C | 92107 | 10 | 0.01% | 4.62E−18 | 39 | 36 |
| A2_CcnA2 | 137 | A | C | 84434 | 12 | 0.01% | 9.02E−15 | 39 | 33 |
| A2_CcnA2 | 317 | G | C | 74759 | 9 | 0.01% | 3.80E−14 | 39 | 35 |
| A2_CcnA2 | 322 | A | G | 70429 | 8 | 0.01% | 8.61E−14 | 38 | 37 |
| A2_CcnA2 | 329 | A | G | 71999 | 10 | 0.01% | 5.05E−13 | 37 | 39 |
| A2_CcnA2 | 331 | A | T | 59430 | 6 | 0.01% | 2.45E−12 | 37 | 38 |
| A2_CcnA2 | 338 | A | G | 82158 | 9 | 0.01% | 3.49E−16 | 39 | 39 |
| A2_CcnA2 | 343 | C | T | 83917 | 11 | 0.01% | 3.94E−15 | 39 | 39 |
| A2_CcnA2 | 397 | G | T | 87980 | 11 | 0.01% | 3.97E−16 | 40 | 41 |
| A2_CcnA2 | 416 | A | G | 88663 | 10 | 0.01% | 4.89E−17 | 40 | 40 |
| A2_CcnA2 | 453 | C | A | 89250 | 13 | 0.01% | 2.12E−15 | 40 | 40 |
| A2_CcnA2 | 456 | C | A | 88489 | 12 | 0.01% | 9.40E−16 | 40 | 40 |
| B1_CncB1 | 24 | C | T | 108045 | 63 | 0.06% | 3.58E−04 | 40 | 40 |
| B1_CncB1 | 65 | C | T | 106473 | 59 | 0.06% | 1.56E−04 | 40 | 40 |
| B1_CncB1 | 66 | C | T | 104822 | 62 | 0.06% | 6.91E−04 | 40 | 40 |
| B1_CncB1 | 389 | C | T | 96124 | 56 | 0.06% | 7.35E−04 | 40 | 40 |
| B1_CncB1 | 135 | C | T | 88411 | 41 | 0.05% | 2.12E−05 | 39 | 38 |
| B1_CncB1 | 432 | A | G | 94725 | 43 | 0.05% | 7.79E−06 | 40 | 39 |
| B1_CncB1 | 462 | C | A | 98472 | 51 | 0.05% | 7.27E−05 | 40 | 40 |
| B1_CncB1 | 465 | C | A | 99099 | 48 | 0.05% | 1.56E−05 | 40 | 40 |
| B1_CncB1 | 41 | A | G | 105874 | 43 | 0.04% | 1.80E−07 | 40 | 37 |
| B1_CncB1 | 47 | C | T | 107247 | 43 | 0.04% | 8.78E−08 | 40 | 40 |
| B1_CncB1 | 68 | A | G | 103941 | 38 | 0.04% | 2.03E−08 | 40 | 39 |
| B1_CncB1 | 94 | A | G | 99380 | 44 | 0.04% | 2.42E−06 | 39 | 37 |
| B1_CncB1 | 119 | C | G | 102496 | 42 | 0.04% | 3.04E−07 | 40 | 38 |
| B1_CncB1 | 347 | C | T | 88976 | 40 | 0.04% | 9.51E−06 | 39 | 38 |
| B1_CncB1 | 447 | C | T | 97309 | 38 | 0.04% | 1.96E−07 | 40 | 40 |
| B1_CncB1 | 468 | C | A | 99025 | 37 | 0.04% | 5.08E−08 | 40 | 40 |
| B1_CncB1 | 471 | A | G | 98039 | 36 | 0.04% | 4.01E−08 | 40 | 40 |
| B1_CncB1 | 9 | G | T | 108711 | 28 | 0.03% | 1.37E−12 | 40 | 40 |
| B1_CncB1 | 18 | G | T | 107816 | 35 | 0.03% | 5.53E−10 | 40 | 40 |
| B1_CncB1 | 25 | A | G | 106857 | 27 | 0.03% | 1.44E−12 | 40 | 40 |
| B1_CncB1 | 26 | C | T | 107549 | 28 | 0.03% | 2.19E−12 | 40 | 41 |
| B1_CncB1 | 126 | A | G | 104611 | 28 | 0.03% | 8.75E−12 | 39 | 39 |
| B1_CncB1 | 357 | A | G | 89779 | 29 | 0.03% | 1.40E−08 | 39 | 38 |
| B1_CncB1 | 379 | A | C | 96563 | 30 | 0.03% | 1.51E−09 | 40 | 38 |
| B1_CncB1 | 383 | G | C | 95480 | 28 | 0.03% | 5.02E−10 | 40 | 38 |
| B1_CncB1 | 413 | A | G | 94556 | 28 | 0.03% | 7.79E−10 | 40 | 40 |
| B1_CncB1 | 438 | C | T | 97050 | 33 | 0.03% | 8.40E−09 | 40 | 40 |
| B1_CncB1 | 446 | C | T | 96926 | 30 | 0.03% | 1.51E−09 | 40 | 40 |
| B1_CncB1 | 13 | G | T | 108571 | 23 | 0.02% | 1.13E−14 | 40 | 40 |
| B1_CncB1 | 23 | G | C | 107712 | 21 | 0.02% | 2.20E−15 | 40 | 40 |
| B1_CncB1 | 31 | C | T | 107883 | 22 | 0.02% | 6.53E−15 | 40 | 40 |
| B1_CncB1 | 37 | C | T | 106772 | 19 | 0.02% | 3.78E−16 | 40 | 40 |
| B1_CncB1 | 49 | C | T | 106517 | 17 | 0.02% | 3.26E−17 | 40 | 40 |
| B1_CncB1 | 52 | G | T | 106909 | 20 | 0.02% | 1.21E−15 | 40 | 40 |
| B1_CncB1 | 55 | C | T | 105971 | 20 | 0.02% | 2.03E−15 | 40 | 39 |
| B1_CncB1 | 56 | A | G | 105739 | 24 | 0.02% | 1.38E−13 | 40 | 39 |
| B1_CncB1 | 67 | A | G | 106404 | 17 | 0.02% | 3.26E−17 | 40 | 35 |
| B1_CncB1 | 71 | C | G | 103991 | 19 | 0.02% | 1.09E−15 | 39 | 39 |
| B1_CncB1 | 96 | C | T | 103909 | 19 | 0.02% | 1.85E−15 | 40 | 38 |
| B1_CncB1 | 132 | C | T | 96946 | 22 | 0.02% | 1.61E−12 | 39 | 39 |
| B1_CncB1 | 133 | A | C | 92940 | 15 | 0.02% | 5.44E−15 | 39 | 33 |
| B1_CncB1 | 134 | C | T | 98174 | 15 | 0.02% | 2.01E−16 | 39 | 39 |
| B1_CncB1 | 142 | C | A | 90159 | 15 | 0.02% | 1.61E−14 | 39 | 34 |
| B1_CncB1 | 331 | G | T | 85758 | 20 | 0.02% | 4.98E−11 | 39 | 34 |
| B1_CncB1 | 350 | G | T | 92775 | 22 | 0.02% | 1.13E−11 | 39 | 35 |
| B1_CncB1 | 360 | C | T | 91321 | 14 | 0.02% | 2.62E−15 | 39 | 40 |
| B1_CncB1 | 406 | A | C | 96976 | 18 | 0.02% | 2.32E−14 | 40 | 37 |
| B1_CncB1 | 410 | G | C | 96868 | 17 | 0.02% | 7.25E−15 | 40 | 40 |
| B1_CncB1 | 420 | C | T | 97731 | 16 | 0.02% | 1.25E−15 | 40 | 40 |
| B1_CncB1 | 431 | C | T | 96920 | 23 | 0.02% | 4.21E−12 | 40 | 40 |
| B1_CncB1 | 439 | A | G | 98216 | 24 | 0.02% | 4.11E−12 | 40 | 40 |

TABLE 8-continued

A-, C-, and G-to-N mutation frequencies in amplicon sequences: 50 μ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| B1_CncB1 | 441 | G | T | 98389 | 24 | 0.02% | 4.11E−12 | 40 | 40 |
| B1_CncB1 | 445 | G | T | 97717 | 23 | 0.02% | 2.60E−12 | 40 | 40 |
| B1_CncB1 | 469 | A | C | 98961 | 22 | 0.02% | 5.99E−13 | 40 | 40 |
| B1_CncB1 | 472 | G | A | 98498 | 15 | 0.02% | 2.01E−16 | 40 | 39 |
| B1_CncB1 | 6 | G | T | 108332 | 14 | 0.01% | 1.81E−19 | 40 | 41 |
| B1_CncB1 | 99 | G | T | 103886 | 13 | 0.01% | 7.41E−19 | 39 | 40 |
| B1_CncB1 | 335 | A | T | 85443 | 9 | 0.01% | 5.89E−17 | 39 | 37 |
| B1_CncB1 | 342 | A | T | 88071 | 11 | 0.01% | 2.23E−16 | 39 | 35 |
| B1_CncB1 | 363 | G | T | 91388 | 13 | 0.01% | 6.89E−16 | 39 | 33 |
| B1_CncB1 | 392 | A | G | 95216 | 13 | 0.01% | 7.20E−17 | 40 | 40 |
| B1_CncB1 | 443 | A | G | 98308 | 11 | 0.01% | 6.52E−19 | 40 | 38 |
| D1_CncD1 | 271 | G | T | 81803 | 38 | 0.05% | 5.00E−05 | 37 | 36 |
| D1_CncD1 | 43 | C | T | 131694 | 50 | 0.04% | 7.25E−10 | 40 | 40 |
| D1_CncD1 | 122 | C | T | 123476 | 51 | 0.04% | 2.36E−08 | 39 | 38 |
| D1_CncD1 | 290 | G | C | 98550 | 38 | 0.04% | 1.35E−07 | 39 | 37 |
| D1_CncD1 | 322 | A | C | 109913 | 42 | 0.04% | 2.36E−08 | 40 | 37 |
| D1_CncD1 | 382 | C | T | 109455 | 43 | 0.04% | 4.23E−08 | 40 | 40 |
| D1_CncD1 | 37 | C | T | 130009 | 44 | 0.03% | 2.30E−11 | 40 | 40 |
| D1_CncD1 | 51 | C | T | 132356 | 36 | 0.03% | 2.18E−14 | 40 | 40 |
| D1_CncD1 | 55 | C | T | 130935 | 37 | 0.03% | 1.23E−13 | 40 | 39 |
| D1_CncD1 | 299 | C | T | 98787 | 25 | 0.03% | 1.03E−11 | 39 | 38 |
| D1_CncD1 | 300 | A | G | 94534 | 26 | 0.03% | 1.55E−10 | 39 | 36 |
| D1_CncD1 | 317 | C | T | 105872 | 28 | 0.03% | 5.52E−12 | 39 | 40 |
| D1_CncD1 | 319 | C | T | 102498 | 26 | 0.03% | 3.84E−12 | 39 | 39 |
| D1_CncD1 | 326 | A | C | 109600 | 30 | 0.03% | 4.86E−12 | 40 | 37 |
| D1_CncD1 | 375 | C | G | 110202 | 37 | 0.03% | 6.51E−10 | 40 | 38 |
| D1_CncD1 | 67 | G | C | 129319 | 26 | 0.02% | 6.38E−18 | 40 | 37 |
| D1_CncD1 | 81 | C | T | 128059 | 24 | 0.02% | 1.15E−18 | 40 | 39 |
| D1_CncD1 | 90 | C | T | 127230 | 29 | 0.02% | 3.88E−16 | 40 | 37 |
| D1_CncD1 | 94 | G | C | 128862 | 27 | 0.02% | 3.09E−17 | 39 | 36 |
| D1_CncD1 | 96 | A | G | 101641 | 16 | 0.02% | 1.41E−16 | 37 | 36 |
| D1_CncD1 | 97 | G | C | 127268 | 21 | 0.02% | 5.44E−20 | 39 | 35 |
| D1_CncD1 | 112 | A | G | 114572 | 22 | 0.02% | 1.78E−16 | 39 | 38 |
| D1_CncD1 | 118 | C | T | 122156 | 19 | 0.02% | 6.55E−20 | 39 | 39 |
| D1_CncD1 | 123 | C | T | 120339 | 30 | 0.02% | 2.94E−14 | 39 | 39 |
| D1_CncD1 | 127 | C | T | 115844 | 24 | 0.02% | 9.39E−16 | 39 | 37 |
| D1_CncD1 | 129 | A | G | 108137 | 21 | 0.02% | 1.31E−15 | 38 | 37 |
| D1_CncD1 | 131 | A | G | 101627 | 24 | 0.02% | 9.71E−13 | 37 | 38 |
| D1_CncD1 | 138 | A | G | 104607 | 22 | 0.02% | 2.99E−14 | 38 | 34 |
| D1_CncD1 | 145 | C | A | 72671 | 14 | 0.02% | 7.14E−11 | 36 | 34 |
| D1_CncD1 | 280 | G | T | 90960 | 20 | 0.02% | 4.26E−12 | 39 | 36 |
| D1_CncD1 | 291 | A | G | 97781 | 15 | 0.02% | 3.50E−16 | 39 | 35 |
| D1_CncD1 | 293 | G | T | 99854 | 21 | 0.02% | 1.31E−13 | 39 | 33 |
| D1_CncD1 | 297 | C | T | 98530 | 22 | 0.02% | 5.99E−13 | 39 | 40 |
| D1_CncD1 | 302 | C | T | 100529 | 16 | 0.02% | 2.44E−16 | 39 | 39 |
| D1_CncD1 | 304 | G | T | 106085 | 22 | 0.02% | 1.09E−14 | 39 | 38 |
| D1_CncD1 | 328 | A | G | 109321 | 19 | 0.02% | 7.64E−17 | 40 | 39 |
| D1_CncD1 | 349 | A | G | 109993 | 20 | 0.02% | 1.47E−16 | 40 | 38 |
| D1_CncD1 | 18 | G | T | 133233 | 16 | 0.01% | 1.90E−24 | 40 | 39 |
| D1_CncD1 | 19 | G | T | 132381 | 19 | 0.01% | 2.53E−22 | 40 | 40 |
| D1_CncD1 | 36 | C | T | 131085 | 14 | 0.01% | 2.66E−25 | 40 | 40 |
| D1_CncD1 | 56 | A | G | 129476 | 13 | 0.01% | 1.69E−25 | 40 | 40 |
| D1_CncD1 | 73 | G | T | 127801 | 18 | 0.01% | 1.06E−21 | 39 | 38 |
| D1_CncD1 | 76 | G | T | 130489 | 19 | 0.01% | 7.74E−22 | 40 | 39 |
| D1_CncD1 | 79 | C | T | 127094 | 14 | 0.01% | 2.84E−24 | 40 | 40 |
| D1_CncD1 | 92 | G | A | 129831 | 15 | 0.01% | 4.21E−24 | 39 | 39 |
| D1_CncD1 | 121 | G | T | 126740 | 17 | 0.01% | 4.61E−22 | 39 | 37 |
| D1_CncD1 | 134 | A | G | 102932 | 13 | 0.01% | 1.32E−18 | 37 | 39 |
| D1_CncD1 | 135 | A | C | 105117 | 11 | 0.01% | 1.03E−20 | 37 | 37 |
| D1_CncD1 | 137 | A | C | 106946 | 14 | 0.01% | 5.67E−19 | 37 | 36 |
| D1_CncD1 | 277 | A | G | 86860 | 9 | 0.01% | 3.25E−17 | 38 | 35 |
| D1_CncD1 | 278 | A | C | 89354 | 13 | 0.01% | 2.12E−15 | 38 | 37 |
| D1_CncD1 | 279 | G | T | 92578 | 10 | 0.01% | 4.62E−18 | 39 | 36 |
| D1_CncD1 | 301 | C | T | 97333 | 14 | 0.01% | 9.26E−17 | 39 | 37 |
| D1_CncD1 | 314 | A | G | 105132 | 14 | 0.01% | 1.00E−18 | 39 | 38 |
| D1_CncD1 | 321 | A | G | 111193 | 14 | 0.01% | 3.22E−20 | 40 | 40 |
| D1_CncD1 | 330 | A | G | 104837 | 13 | 0.01% | 4.16E−19 | 40 | 38 |
| D1_CncD1 | 337 | A | G | 110188 | 14 | 0.01% | 5.72E−20 | 40 | 39 |
| D1_CncD1 | 345 | C | T | 106511 | 13 | 0.01% | 1.31E−19 | 39 | 40 |
| D1_CncD1 | 348 | A | G | 110689 | 12 | 0.01% | 2.68E−21 | 40 | 37 |
| D1_CncD1 | 370 | A | G | 109945 | 11 | 0.01% | 9.48E−22 | 40 | 39 |
| E1_CncE1 | 473 | A | G | 36428 | 80 | 0.22% | 2.66E−05 | 39 | 40 |
| E1_CncE1 | 412 | C | T | 36711 | 68 | 0.18% | 1.10E−03 | 40 | 40 |
| E1_CncE1 | 3 | G | T | 39995 | 70 | 0.17% | 2.71E−03 | 40 | 40 |
| E1_CncE1 | 13 | C | T | 39828 | 16 | 0.04% | 1.33E−03 | 40 | 40 |

TABLE 8-continued

A-, C-, and G-to-N mutation frequencies in amplicon sequences: 50 μ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| E1_CncE1 | 15 | C | T | 40040 | 12 | 0.03% | 6.35E−05 | 40 | 41 |
| E1_CncE1 | 105 | C | G | 38688 | 10 | 0.03% | 3.07E−05 | 39 | 38 |
| E1_CncE1 | 126 | A | G | 33229 | 9 | 0.03% | 1.35E−04 | 38 | 36 |
| E1_CncE1 | 138 | A | C | 26812 | 7 | 0.03% | 6.57E−04 | 37 | 34 |
| E1_CncE1 | 335 | A | C | 19564 | 5 | 0.03% | 3.30E−03 | 36 | 35 |
| E1_CncE1 | 356 | A | C | 31205 | 10 | 0.03% | 7.23E−04 | 38 | 38 |
| E1_CncE1 | 370 | A | C | 35587 | 10 | 0.03% | 1.23E−04 | 39 | 38 |
| E1_CncE1 | 434 | A | G | 37358 | 11 | 0.03% | 1.11E−04 | 40 | 37 |
| E1_CncE1 | 41 | C | G | 39355 | 7 | 0.02% | 9.10E−07 | 40 | 34 |
| E1_CncE1 | 67 | C | G | 38785 | 6 | 0.02% | 4.68E−07 | 40 | 39 |
| E1_CncE1 | 97 | G | C | 38938 | 7 | 0.02% | 1.55E−06 | 40 | 36 |
| E1_CncE1 | 334 | A | G | 17408 | 4 | 0.02% | 3.59E−03 | 36 | 41 |
| E1_CncE1 | 336 | G | T | 29661 | 5 | 0.02% | 1.92E−05 | 38 | 35 |
| E1_CncE1 | 350 | A | G | 23694 | 4 | 0.02% | 1.55E−04 | 36 | 33 |
| E1_CncE1 | 425 | C | T | 36964 | 7 | 0.02% | 4.46E−06 | 40 | 39 |
| E1_CncE1 | 474 | G | A | 38002 | 9 | 0.02% | 1.24E−05 | 40 | 36 |
| E1_CncE1 | 50 | G | T | 39302 | 4 | 0.01% | 1.54E−08 | 40 | 41 |
| E1_CncE1 | 125 | C | A | 37033 | 4 | 0.01% | 5.09E−08 | 39 | 33 |
| E1_CncE1 | 130 | C | G | 37711 | 4 | 0.01% | 5.09E−08 | 39 | 38 |
| E1_CncE1 | 142 | G | A | 33531 | 4 | 0.01% | 5.39E−07 | 39 | 38 |
| E1_CncE1 | 348 | G | C | 29550 | 4 | 0.01% | 5.44E−06 | 37 | 37 |
| E1_CncE1 | 359 | G | C | 36130 | 4 | 0.01% | 9.22E−08 | 39 | 36 |
| E1_CncE1 | 459 | C | A | 36086 | 4 | 0.01% | 9.22E−08 | 39 | 41 |
| E1_CncE1 | 460 | C | T | 36980 | 4 | 0.01% | 9.22E−08 | 40 | 36 |
| E1_CncE1 | 461 | C | A | 37035 | 5 | 0.01% | 2.20E−07 | 40 | 41 |
| E1_CncE1 | 471 | A | T | 37232 | 4 | 0.01% | 5.09E−08 | 40 | 38 |
| eGFP | 425 | G | A | 17324 | 56 | 0.32% | 2.58E−06 | 40 | 40 |
| eGFP | 141 | A | G | 18416 | 44 | 0.24% | 6.44E−06 | 36 | 38 |
| eGFP | 97 | A | T | 28703 | 62 | 0.22% | 2.17E−04 | 39 | 40 |
| eGFP | 96 | G | T | 31907 | 61 | 0.19% | 1.15E−03 | 39 | 40 |
| eGFP | 136 | A | G | 20242 | 39 | 0.19% | 9.13E−03 | 37 | 39 |
| eGFP | 31 | A | G | 33013 | 61 | 0.18% | 2.52E−03 | 40 | 40 |
| eGFP | 91 | G | C | 31354 | 56 | 0.18% | 4.81E−03 | 39 | 39 |
| eGFP | 21 | G | A | 32739 | 12 | 0.04% | 1.82E−03 | 40 | 39 |
| eGFP | 49 | A | G | 31052 | 12 | 0.04% | 2.69E−03 | 39 | 40 |
| eGFP | 61 | A | G | 30693 | 11 | 0.04% | 2.16E−03 | 39 | 40 |
| eGFP | 119 | C | G | 30288 | 11 | 0.04% | 2.16E−03 | 38 | 38 |
| eGFP | 47 | G | A | 31680 | 8 | 0.03% | 1.46E−04 | 39 | 39 |
| eGFP | 68 | G | A | 32010 | 10 | 0.03% | 4.69E−04 | 40 | 39 |
| eGFP | 69 | G | A | 32238 | 11 | 0.03% | 9.54E−04 | 40 | 38 |
| eGFP | 122 | G | A | 30636 | 10 | 0.03% | 1.11E−03 | 39 | 38 |
| eGFP | 128 | C | T | 29850 | 9 | 0.03% | 8.26E−04 | 39 | 36 |
| eGFP | 129 | A | C | 26078 | 7 | 0.03% | 6.57E−04 | 38 | 35 |
| eGFP | 1 | C | T | 33108 | 8 | 0.02% | 5.59E−05 | 39 | 36 |
| eGFP | 22 | G | A | 32235 | 8 | 0.02% | 9.07E−05 | 40 | 41 |
| eGFP | 25 | A | G | 33112 | 8 | 0.02% | 5.59E−05 | 40 | 41 |
| eGFP | 26 | C | T | 33113 | 7 | 0.02% | 2.10E−05 | 40 | 39 |
| eGFP | 29 | C | T | 33539 | 6 | 0.02% | 7.11E−06 | 40 | 40 |
| eGFP | 32 | G | A | 32612 | 5 | 0.02% | 3.69E−06 | 40 | 41 |
| eGFP | 35 | C | T | 33069 | 7 | 0.02% | 2.10E−05 | 40 | 40 |
| eGFP | 37 | G | T | 32457 | 8 | 0.02% | 9.07E−05 | 40 | 41 |
| eGFP | 41 | C | G | 32651 | 5 | 0.02% | 3.69E−06 | 40 | 39 |
| eGFP | 42 | G | A | 32725 | 7 | 0.02% | 3.50E−05 | 40 | 37 |
| eGFP | 50 | G | A | 32592 | 7 | 0.02% | 3.50E−05 | 40 | 38 |
| eGFP | 53 | C | T | 32825 | 7 | 0.02% | 3.50E−05 | 40 | 41 |
| eGFP | 58 | G | A | 31674 | 5 | 0.02% | 6.42E−06 | 40 | 40 |
| eGFP | 64 | C | T | 32752 | 7 | 0.02% | 3.50E−05 | 40 | 39 |
| eGFP | 65 | C | A | 32424 | 5 | 0.02% | 3.69E−06 | 40 | 41 |
| eGFP | 71 | G | A | 29617 | 6 | 0.02% | 5.82E−05 | 38 | 39 |
| eGFP | 72 | A | G | 30584 | 7 | 0.02% | 9.51E−05 | 39 | 39 |
| eGFP | 74 | C | A | 32906 | 7 | 0.02% | 3.50E−05 | 40 | 40 |
| eGFP | 77 | C | T | 33234 | 7 | 0.02% | 2.10E−05 | 40 | 40 |
| eGFP | 81 | G | A | 32360 | 7 | 0.02% | 3.50E−05 | 40 | 39 |
| eGFP | 86 | G | A | 32217 | 5 | 0.02% | 3.69E−06 | 40 | 38 |
| eGFP | 90 | G | C | 32315 | 5 | 0.02% | 3.69E−06 | 39 | 39 |
| eGFP | 95 | C | T | 30548 | 7 | 0.02% | 9.51E−05 | 39 | 39 |
| eGFP | 104 | G | A | 31988 | 5 | 0.02% | 6.42E−06 | 39 | 39 |
| eGFP | 115 | A | G | 25454 | 6 | 0.02% | 4.37E−04 | 38 | 40 |
| eGFP | 116 | C | T | 29976 | 7 | 0.02% | 1.56E−04 | 39 | 35 |
| eGFP | 123 | G | A | 29690 | 6 | 0.02% | 5.82E−05 | 39 | 38 |
| eGFP | 126 | C | G | 30587 | 6 | 0.02% | 3.46E−05 | 39 | 36 |
| eGFP | 137 | G | C | 28236 | 5 | 0.02% | 3.29E−05 | 38 | 37 |
| eGFP | 140 | C | G | 22367 | 5 | 0.02% | 7.55E−04 | 36 | 38 |
| eGFP | 287 | C | T | 15189 | 3 | 0.02% | 3.76E−03 | 39 | 35 |
| eGFP | 299 | C | G | 15715 | 3 | 0.02% | 3.76E−03 | 39 | 39 |

TABLE 8-continued

A-, C-, and G-to-N mutation frequencies in amplicon sequences: 50 μ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| eGFP | 316 | G | A | 15015 | 3 | 0.02% | 3.76E−03 | 38 | 35 |
| eGFP | 325 | C | T | 16421 | 3 | 0.02% | 2.21E−03 | 40 | 41 |
| eGFP | 336 | A | G | 16200 | 3 | 0.02% | 2.21E−03 | 39 | 41 |
| eGFP | 357 | G | A | 16036 | 3 | 0.02% | 2.21E−03 | 38 | 39 |
| eGFP | 404 | C | T | 17016 | 4 | 0.02% | 3.59E−03 | 40 | 41 |
| eGFP | 412 | A | T | 16846 | 3 | 0.02% | 2.21E−03 | 40 | 41 |
| eGFP | 2 | C | G | 33662 | 5 | 0.01% | 2.12E−06 | 40 | 40 |
| eGFP | 39 | G | C | 32703 | 4 | 0.01% | 9.65E−07 | 40 | 41 |
| eGFP | 45 | G | A | 31798 | 4 | 0.01% | 1.72E−06 | 40 | 41 |
| eGFP | 92 | C | A | 32148 | 4 | 0.01% | 9.65E−07 | 40 | 36 |
| eGFP | 284 | C | A | 14677 | 2 | 0.01% | 2.09E−03 | 39 | 39 |
| eGFP | 294 | C | G | 14385 | 2 | 0.01% | 2.09E−03 | 38 | 32 |
| eGFP | 314 | G | T | 14349 | 2 | 0.01% | 2.09E−03 | 38 | 32 |
| eGFP | 319 | C | T | 16442 | 2 | 0.01% | 6.54E−04 | 39 | 37 |
| eGFP | 323 | G | A | 15126 | 2 | 0.01% | 1.17E−03 | 38 | 41 |
| eGFP | 327 | G | A | 16462 | 2 | 0.01% | 6.54E−04 | 40 | 34 |
| eGFP | 328 | C | G | 16367 | 2 | 0.01% | 6.54E−04 | 39 | 32 |
| eGFP | 329 | C | T | 16427 | 2 | 0.01% | 6.54E−04 | 39 | 36 |
| eGFP | 348 | G | A | 16328 | 2 | 0.01% | 6.54E−04 | 39 | 36 |
| eGFP | 350 | G | A | 16008 | 2 | 0.01% | 6.54E−04 | 39 | 34 |
| eGFP | 353 | G | A | 16559 | 2 | 0.01% | 6.54E−04 | 40 | 37 |
| eGFP | 356 | C | T | 16537 | 2 | 0.01% | 6.54E−04 | 39 | 41 |
| eGFP | 360 | C | T | 16467 | 2 | 0.01% | 6.54E−04 | 40 | 41 |
| eGFP | 371 | G | A | 16711 | 2 | 0.01% | 6.54E−04 | 40 | 39 |
| eGFP | 398 | C | G | 16651 | 2 | 0.01% | 6.54E−04 | 40 | 41 |
| eGFP | 411 | G | A | 17124 | 2 | 0.01% | 3.63E−04 | 40 | 41 |
| eGFP | 424 | A | C | 17249 | 2 | 0.01% | 3.63E−04 | 40 | 41 |
| p21_Cdkn1A | 54 | C | A | 77218 | 158 | 0.20% | 6.70E−08 | 40 | 40 |
| p21_Cdkn1A | 112 | C | T | 74933 | 142 | 0.19% | 3.13E−06 | 40 | 39 |
| p21_Cdkn1A | 143 | C | T | 65226 | 104 | 0.16% | 1.66E−03 | 38 | 36 |
| p21_Cdkn1A | 403 | A | C | 53513 | 88 | 0.16% | 2.00E−03 | 37 | 39 |
| p21_Cdkn1A | 60 | G | T | 76689 | 109 | 0.14% | 9.16E−03 | 40 | 40 |
| p21_Cdkn1A | 41 | G | C | 77403 | 43 | 0.06% | 1.22E−03 | 40 | 38 |
| p21_Cdkn1A | 97 | C | G | 75942 | 40 | 0.05% | 7.04E−04 | 40 | 37 |
| p21_Cdkn1A | 119 | A | G | 55575 | 26 | 0.05% | 8.41E−04 | 38 | 38 |
| p21_Cdkn1A | 89 | C | T | 75866 | 27 | 0.04% | 1.07E−06 | 40 | 40 |
| p21_Cdkn1A | 138 | A | C | 53714 | 20 | 0.04% | 7.05E−05 | 37 | 33 |
| p21_Cdkn1A | 345 | A | G | 55921 | 22 | 0.04% | 1.08E−04 | 38 | 34 |
| p21_Cdkn1A | 105 | C | G | 77027 | 26 | 0.03% | 2.45E−07 | 39 | 37 |
| p21_Cdkn1A | 124 | A | C | 58754 | 19 | 0.03% | 4.86E−06 | 37 | 34 |
| p21_Cdkn1A | 135 | A | C | 49981 | 13 | 0.03% | 2.39E−06 | 37 | 33 |
| p21_Cdkn1A | 141 | A | C | 50501 | 14 | 0.03% | 3.51E−06 | 37 | 33 |
| p21_Cdkn1A | 370 | G | C | 67153 | 20 | 0.03% | 2.14E−07 | 39 | 38 |
| p21_Cdkn1A | 67 | A | G | 75669 | 16 | 0.02% | 1.31E−10 | 40 | 36 |
| p21_Cdkn1A | 68 | C | G | 77861 | 17 | 0.02% | 1.34E−10 | 40 | 38 |
| p21_Cdkn1A | 104 | A | C | 70705 | 11 | 0.02% | 5.84E−12 | 39 | 33 |
| p21_Cdkn1A | 116 | C | G | 75437 | 13 | 0.02% | 4.60E−12 | 39 | 36 |
| p21_Cdkn1A | 142 | G | C | 58400 | 11 | 0.02% | 3.74E−09 | 38 | 35 |
| p21_Cdkn1A | 4 | C | T | 79565 | 8 | 0.01% | 4.12E−16 | 40 | 40 |
| p21_Cdkn1A | 8 | G | T | 79621 | 10 | 0.01% | 9.23E−15 | 39 | 39 |
| p21_Cdkn1A | 9 | G | T | 79439 | 11 | 0.01% | 3.83E−14 | 40 | 37 |
| p21_Cdkn1A | 91 | A | C | 71342 | 8 | 0.01% | 4.78E−14 | 39 | 32 |
| p21_Cdkn1A | 333 | A | C | 49792 | 7 | 0.01% | 3.70E−09 | 37 | 33 |
| p21_Cdkn1A | 338 | G | T | 59944 | 8 | 0.01% | 5.03E−11 | 39 | 39 |
| p21_Cdkn1A | 451 | A | G | 68856 | 7 | 0.01% | 5.76E−14 | 40 | 41 |
| p21_Cdkn1A | 467 | C | A | 71372 | 9 | 0.01% | 2.16E−13 | 40 | 41 |
| PCNA | 120 | C | T | 101656 | 60 | 0.06% | 7.66E−04 | 39 | 39 |
| PCNA | 122 | C | T | 101725 | 51 | 0.05% | 3.04E−05 | 39 | 39 |
| PCNA | 340 | C | T | 75202 | 40 | 0.05% | 7.04E−04 | 37 | 37 |
| PCNA | 342 | C | T | 82515 | 43 | 0.05% | 3.08E−04 | 39 | 38 |
| PCNA | 389 | C | T | 91777 | 49 | 0.05% | 2.42E−04 | 40 | 40 |
| PCNA | 436 | C | T | 92547 | 43 | 0.05% | 1.49E−05 | 40 | 40 |
| PCNA | 77 | C | T | 107763 | 40 | 0.04% | 1.50E−08 | 40 | 40 |
| PCNA | 85 | C | T | 104343 | 40 | 0.04% | 4.68E−08 | 39 | 39 |
| PCNA | 97 | A | G | 105449 | 40 | 0.04% | 3.21E−08 | 40 | 38 |
| PCNA | 105 | C | G | 102130 | 44 | 0.04% | 8.78E−07 | 40 | 38 |
| PCNA | 351 | C | A | 86317 | 34 | 0.04% | 1.13E−06 | 39 | 39 |
| PCNA | 362 | A | C | 84597 | 31 | 0.04% | 3.98E−07 | 39 | 38 |
| PCNA | 373 | G | C | 91223 | 37 | 0.04% | 9.95E−07 | 40 | 38 |
| PCNA | 422 | C | T | 90997 | 32 | 0.04% | 4.82E−08 | 40 | 40 |
| PCNA | 41 | A | C | 103554 | 36 | 0.03% | 5.61E−09 | 40 | 38 |
| PCNA | 59 | C | T | 108078 | 29 | 0.03% | 3.28E−12 | 40 | 40 |
| PCNA | 72 | C | T | 105299 | 30 | 0.03% | 2.95E−11 | 40 | 40 |
| PCNA | 94 | A | G | 98756 | 27 | 0.03% | 5.82E−11 | 39 | 37 |
| PCNA | 104 | C | T | 105605 | 31 | 0.03% | 6.55E−11 | 40 | 40 |

TABLE 8-continued

A-, C-, and G-to-N mutation frequencies in amplicon sequences: 50 µ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| PCNA | 130 | C | T | 100440 | 31 | 0.03% | 5.74E−10 | 39 | 39 |
| PCNA | 137 | C | T | 93552 | 27 | 0.03% | 5.50E−10 | 39 | 38 |
| PCNA | 139 | C | T | 94253 | 32 | 0.03% | 1.44E−08 | 39 | 38 |
| PCNA | 324 | A | T | 52355 | 14 | 0.03% | 1.40E−06 | 37 | 37 |
| PCNA | 333 | C | T | 82495 | 22 | 0.03% | 1.27E−09 | 39 | 36 |
| PCNA | 346 | A | C | 61810 | 17 | 0.03% | 2.81E−07 | 37 | 33 |
| PCNA | 354 | C | T | 85765 | 24 | 0.03% | 1.73E−09 | 39 | 38 |
| PCNA | 363 | C | T | 88288 | 24 | 0.03% | 4.44E−10 | 39 | 39 |
| PCNA | 375 | C | T | 90442 | 29 | 0.03% | 9.19E−09 | 40 | 39 |
| PCNA | 445 | C | T | 93120 | 30 | 0.03% | 5.36E−09 | 40 | 41 |
| PCNA | 21 | C | T | 107406 | 22 | 0.02% | 6.53E−15 | 40 | 41 |
| PCNA | 25 | C | T | 108939 | 21 | 0.02% | 1.31E−15 | 40 | 41 |
| PCNA | 62 | C | T | 108653 | 25 | 0.02% | 8.46E−14 | 40 | 40 |
| PCNA | 67 | A | C | 105691 | 18 | 0.02% | 1.95E−16 | 40 | 36 |
| PCNA | 71 | C | T | 105541 | 25 | 0.02% | 3.63E−13 | 39 | 40 |
| PCNA | 92 | G | A | 105950 | 17 | 0.02% | 5.63E−17 | 40 | 39 |
| PCNA | 132 | G | T | 97807 | 24 | 0.02% | 6.63E−12 | 39 | 40 |
| PCNA | 142 | C | T | 97562 | 17 | 0.02% | 4.25E−15 | 39 | 37 |
| PCNA | 143 | C | A | 93580 | 22 | 0.02% | 6.94E−12 | 39 | 32 |
| PCNA | 328 | C | T | 75774 | 12 | 0.02% | 1.34E−11 | 38 | 38 |
| PCNA | 335 | A | G | 77701 | 12 | 0.02% | 4.46E−13 | 38 | 38 |
| PCNA | 339 | C | T | 81898 | 14 | 0.02% | 6.12E−13 | 38 | 37 |
| PCNA | 344 | C | T | 82817 | 13 | 0.02% | 1.03E−13 | 39 | 38 |
| PCNA | 345 | C | T | 82113 | 17 | 0.02% | 1.08E−11 | 38 | 38 |
| PCNA | 357 | C | T | 88674 | 17 | 0.02% | 4.91E−13 | 40 | 40 |
| PCNA | 365 | C | T | 89116 | 22 | 0.02% | 4.76E−11 | 39 | 40 |
| PCNA | 400 | G | C | 93711 | 15 | 0.02% | 3.15E−15 | 40 | 37 |
| PCNA | 424 | C | T | 93695 | 16 | 0.02% | 1.09E−14 | 40 | 40 |
| PCNA | 427 | A | G | 93194 | 14 | 0.02% | 8.64E−16 | 40 | 40 |
| PCNA | 433 | C | T | 93427 | 19 | 0.02% | 3.33E−13 | 40 | 41 |
| PCNA | 440 | G | T | 92008 | 17 | 0.02% | 6.04E−14 | 40 | 40 |
| PCNA | 82 | G | T | 106264 | 11 | 0.01% | 5.69E−21 | 40 | 40 |
| PCNA | 90 | G | T | 105112 | 15 | 0.01% | 4.06E−18 | 40 | 40 |
| PCNA | 111 | G | T | 103931 | 11 | 0.01% | 3.39E−20 | 39 | 40 |
| PCNA | 119 | G | T | 103084 | 14 | 0.01% | 3.13E−18 | 39 | 39 |
| PCNA | 131 | C | G | 95583 | 13 | 0.01% | 7.20E−17 | 39 | 34 |
| PCNA | 135 | A | C | 82860 | 11 | 0.01% | 6.97E−15 | 38 | 32 |
| PCNA | 140 | A | G | 88600 | 10 | 0.01% | 4.89E−17 | 39 | 38 |
| PCNA | 322 | G | T | 55098 | 8 | 0.01% | 4.83E−10 | 37 | 38 |
| PCNA | 323 | A | G | 58163 | 7 | 0.01% | 2.11E−11 | 37 | 33 |
| PCNA | 334 | A | G | 78594 | 9 | 0.01% | 3.68E−15 | 38 | 39 |
| PCNA | 337 | A | C | 62456 | 7 | 0.01% | 2.03E−12 | 37 | 37 |
| PCNA | 338 | G | T | 79957 | 11 | 0.01% | 3.83E−14 | 39 | 35 |
| PCNA | 367 | C | T | 89503 | 11 | 0.01% | 1.25E−16 | 40 | 40 |
| PCNA | 377 | G | C | 92611 | 12 | 0.01% | 9.60E−17 | 40 | 37 |
| PCNA | 386 | C | T | 91447 | 11 | 0.01% | 3.91E−17 | 40 | 39 |
| PCNA | 395 | G | T | 92545 | 13 | 0.01% | 3.93E−16 | 40 | 39 |
| PCNA | 399 | A | C | 92134 | 10 | 0.01% | 4.62E−18 | 40 | 36 |
| PCNA | 406 | A | G | 90321 | 11 | 0.01% | 7.00E−17 | 40 | 40 |
| PCNA | 410 | G | T | 91070 | 12 | 0.01% | 1.70E−16 | 40 | 40 |
| PCNA | 421 | A | G | 91935 | 10 | 0.01% | 8.34E−18 | 40 | 40 |
| PCNA | 439 | G | A | 91870 | 10 | 0.01% | 8.34E−18 | 40 | 39 |
| PCNA | 443 | C | A | 91582 | 10 | 0.01% | 8.34E−18 | 40 | 40 |

TABLE 9

A-, C-, and G-to-N mutation frequencies in amplicon sequences: 100 µ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| A2_CcnA2 | 350 | C | T | 87589 | 40 | 0.05% | 1.83E−05 | 39 | 39 |
| A2_CcnA2 | 391 | C | T | 87904 | 40 | 0.05% | 1.83E−05 | 40 | 39 |
| A2_CcnA2 | 394 | C | T | 89485 | 46 | 0.05% | 1.34E−04 | 40 | 39 |
| A2_CcnA2 | 29 | C | T | 98082 | 35 | 0.04% | 2.12E−08 | 40 | 41 |
| A2_CcnA2 | 133 | C | T | 89154 | 35 | 0.04% | 6.64E−07 | 39 | 40 |
| A2_CcnA2 | 142 | C | T | 86716 | 34 | 0.04% | 1.13E−06 | 39 | 38 |
| A2_CcnA2 | 386 | C | T | 86020 | 38 | 0.04% | 9.66E−06 | 39 | 40 |
| A2_CcnA2 | 398 | C | T | 89498 | 40 | 0.04% | 9.51E−06 | 40 | 40 |
| A2_CcnA2 | 418 | A | G | 89399 | 38 | 0.04% | 3.46E−06 | 40 | 38 |
| A2_CcnA2 | 10 | G | T | 98221 | 25 | 0.03% | 1.03E−11 | 40 | 40 |
| A2_CcnA2 | 41 | A | C | 97159 | 32 | 0.03% | 4.20E−09 | 40 | 37 |
| A2_CcnA2 | 45 | C | T | 97565 | 28 | 0.03% | 2.07E−10 | 40 | 40 |

TABLE 9-continued

A-, C-, and G-to-N mutation frequencies in amplicon sequences: 100 μ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| A2_CcnA2 | 67 | G | C | 94824 | 24 | 0.03% | 2.74E−11 | 40 | 37 |
| A2_CcnA2 | 104 | C | T | 95609 | 24 | 0.03% | 1.71E−11 | 40 | 40 |
| A2_CcnA2 | 119 | A | G | 89321 | 29 | 0.03% | 1.40E−08 | 39 | 36 |
| A2_CcnA2 | 131 | C | T | 91625 | 28 | 0.03% | 2.87E−09 | 39 | 40 |
| A2_CcnA2 | 138 | C | T | 88660 | 30 | 0.03% | 4.24E−08 | 39 | 38 |
| A2_CcnA2 | 316 | C | T | 77731 | 26 | 0.03% | 2.45E−07 | 39 | 39 |
| A2_CcnA2 | 323 | C | T | 78895 | 26 | 0.03% | 1.62E−07 | 39 | 40 |
| A2_CcnA2 | 333 | C | T | 84451 | 28 | 0.03% | 5.50E−08 | 39 | 38 |
| A2_CcnA2 | 334 | C | T | 83884 | 25 | 0.03% | 9.32E−09 | 39 | 39 |
| A2_CcnA2 | 357 | C | T | 88891 | 29 | 0.03% | 2.12E−08 | 40 | 39 |
| A2_CcnA2 | 362 | A | C | 83867 | 26 | 0.03% | 1.99E−08 | 39 | 37 |
| A2_CcnA2 | 363 | C | T | 87741 | 30 | 0.03% | 6.35E−08 | 40 | 40 |
| A2_CcnA2 | 4 | G | T | 97999 | 17 | 0.02% | 2.49E−15 | 40 | 40 |
| A2_CcnA2 | 7 | G | T | 98166 | 18 | 0.02% | 8.11E−15 | 40 | 40 |
| A2_CcnA2 | 13 | G | T | 98534 | 24 | 0.02% | 4.11E−12 | 40 | 40 |
| A2_CcnA2 | 15 | G | T | 97946 | 16 | 0.02% | 1.25E−15 | 40 | 39 |
| A2_CcnA2 | 24 | C | T | 97538 | 22 | 0.02% | 9.82E−13 | 40 | 40 |
| A2_CcnA2 | 38 | C | T | 97407 | 18 | 0.02% | 1.37E−14 | 40 | 40 |
| A2_CcnA2 | 39 | C | T | 96723 | 20 | 0.02% | 2.09E−13 | 40 | 39 |
| A2_CcnA2 | 42 | C | T | 97786 | 23 | 0.02% | 2.60E−12 | 40 | 40 |
| A2_CcnA2 | 44 | C | T | 98467 | 17 | 0.02% | 2.49E−15 | 40 | 41 |
| A2_CcnA2 | 52 | C | T | 97108 | 22 | 0.02% | 9.82E−13 | 40 | 40 |
| A2_CcnA2 | 58 | C | T | 96191 | 22 | 0.02% | 1.61E−12 | 40 | 40 |
| A2_CcnA2 | 102 | A | G | 93640 | 15 | 0.02% | 3.15E−15 | 40 | 38 |
| A2_CcnA2 | 110 | C | T | 92305 | 14 | 0.02% | 1.51E−15 | 40 | 40 |
| A2_CcnA2 | 121 | C | A | 90335 | 16 | 0.02% | 5.42E−14 | 39 | 35 |
| A2_CcnA2 | 123 | G | T | 92280 | 14 | 0.02% | 1.51E−15 | 39 | 39 |
| A2_CcnA2 | 127 | C | T | 90486 | 16 | 0.02% | 5.42E−14 | 39 | 38 |
| A2_CcnA2 | 132 | C | T | 89217 | 15 | 0.02% | 2.77E−14 | 39 | 39 |
| A2_CcnA2 | 315 | A | G | 70437 | 13 | 0.02% | 6.59E−11 | 38 | 38 |
| A2_CcnA2 | 332 | C | T | 83790 | 14 | 0.02% | 2.08E−13 | 39 | 37 |
| A2_CcnA2 | 340 | A | C | 84644 | 20 | 0.02% | 8.09E−11 | 39 | 38 |
| A2_CcnA2 | 343 | C | T | 86089 | 14 | 0.02% | 4.08E−14 | 39 | 39 |
| A2_CcnA2 | 355 | C | T | 88046 | 18 | 0.02% | 1.47E−12 | 39 | 39 |
| A2_CcnA2 | 364 | C | T | 87931 | 18 | 0.02% | 2.44E−12 | 39 | 40 |
| A2_CcnA2 | 369 | C | T | 87129 | 20 | 0.02% | 1.87E−11 | 40 | 40 |
| A2_CcnA2 | 374 | C | T | 88068 | 18 | 0.02% | 1.47E−12 | 40 | 39 |
| A2_CcnA2 | 375 | C | T | 88489 | 19 | 0.02% | 4.18E−12 | 39 | 39 |
| A2_CcnA2 | 378 | C | T | 89068 | 19 | 0.02% | 2.53E−12 | 40 | 39 |
| A2_CcnA2 | 381 | C | T | 88166 | 20 | 0.02% | 1.15E−11 | 40 | 39 |
| A2_CcnA2 | 388 | C | T | 85483 | 13 | 0.02% | 1.96E−14 | 39 | 40 |
| A2_CcnA2 | 389 | C | T | 87209 | 14 | 0.02% | 2.36E−14 | 39 | 40 |
| A2_CcnA2 | 392 | A | G | 85375 | 19 | 0.02% | 1.87E−11 | 40 | 39 |
| A2_CcnA2 | 403 | C | T | 90073 | 16 | 0.02% | 5.42E−14 | 40 | 40 |
| A2_CcnA2 | 407 | C | T | 90013 | 22 | 0.02% | 2.95E−11 | 40 | 40 |
| A2_CcnA2 | 431 | C | T | 90735 | 22 | 0.02% | 2.95E−11 | 40 | 40 |
| A2_CcnA2 | 50 | A | G | 97588 | 13 | 0.01% | 2.31E−17 | 40 | 39 |
| A2_CcnA2 | 68 | A | C | 91781 | 10 | 0.01% | 8.34E−18 | 39 | 37 |
| A2_CcnA2 | 73 | C | T | 94943 | 11 | 0.01% | 6.81E−18 | 40 | 39 |
| A2_CcnA2 | 82 | A | G | 97605 | 11 | 0.01% | 1.17E−18 | 40 | 39 |
| A2_CcnA2 | 84 | A | G | 95658 | 10 | 0.01% | 7.78E−19 | 40 | 40 |
| A2_CcnA2 | 87 | C | T | 94196 | 13 | 0.01% | 1.27E−16 | 40 | 40 |
| A2_CcnA2 | 88 | C | A | 93595 | 13 | 0.01% | 2.23E−16 | 40 | 40 |
| A2_CcnA2 | 97 | G | C | 94988 | 11 | 0.01% | 6.81E−18 | 40 | 39 |
| A2_CcnA2 | 99 | C | T | 95480 | 10 | 0.01% | 7.78E−19 | 40 | 40 |
| A2_CcnA2 | 113 | C | T | 94557 | 13 | 0.01% | 1.27E−16 | 40 | 39 |
| A2_CcnA2 | 135 | A | C | 83988 | 9 | 0.01% | 1.93E−16 | 39 | 35 |
| A2_CcnA2 | 145 | C | A | 78166 | 11 | 0.01% | 6.74E−14 | 38 | 36 |
| A2_CcnA2 | 317 | G | C | 76499 | 11 | 0.01% | 2.08E−13 | 39 | 34 |
| A2_CcnA2 | 319 | A | C | 70955 | 8 | 0.01% | 8.61E−14 | 38 | 38 |
| A2_CcnA2 | 325 | G | T | 77579 | 8 | 0.01% | 1.36E−15 | 39 | 36 |
| A2_CcnA2 | 327 | A | G | 81231 | 9 | 0.01% | 6.30E−16 | 39 | 37 |
| A2_CcnA2 | 329 | A | C | 75026 | 8 | 0.01% | 4.48E−15 | 38 | 39 |
| A2_CcnA2 | 336 | G | T | 82843 | 11 | 0.01% | 6.97E−15 | 39 | 36 |
| A2_CcnA2 | 337 | G | T | 85012 | 9 | 0.01% | 5.89E−17 | 39 | 38 |
| A2_CcnA2 | 349 | C | T | 87688 | 10 | 0.01% | 8.79E−17 | 39 | 38 |
| A2_CcnA2 | 370 | C | T | 88558 | 13 | 0.01% | 3.70E−15 | 40 | 40 |
| A2_CcnA2 | 415 | G | T | 90446 | 10 | 0.01% | 1.51E−17 | 40 | 39 |
| A2_CcnA2 | 433 | A | G | 90639 | 12 | 0.01% | 3.01E−16 | 40 | 40 |
| B1_CncB1 | 432 | A | G | 79444 | 40 | 0.05% | 2.22E−04 | 40 | 39 |
| B1_CncB1 | 447 | C | T | 81188 | 43 | 0.05% | 4.08E−04 | 40 | 40 |
| B1_CncB1 | 24 | C | T | 84948 | 36 | 0.04% | 6.90E−06 | 40 | 40 |
| B1_CncB1 | 28 | C | T | 84486 | 33 | 0.04% | 1.33E−06 | 40 | 40 |
| B1_CncB1 | 47 | C | T | 84485 | 32 | 0.04% | 7.35E−07 | 40 | 39 |
| B1_CncB1 | 88 | C | T | 83388 | 30 | 0.04% | 3.13E−07 | 40 | 39 |
| B1_CncB1 | 94 | A | G | 78861 | 28 | 0.04% | 6.21E−07 | 39 | 39 |

TABLE 9-continued

A-, C-, and G-to-N mutation frequencies in amplicon sequences: 100 μ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| B1_CncB1 | 119 | C | G | 80850 | 30 | 0.04% | 1.00E−06 | 40 | 38 |
| B1_CncB1 | 41 | A | C | 83508 | 27 | 0.03% | 4.12E−08 | 40 | 38 |
| B1_CncB1 | 66 | C | T | 82667 | 23 | 0.03% | 2.95E−09 | 40 | 39 |
| B1_CncB1 | 67 | A | G | 83839 | 24 | 0.03% | 4.24E−09 | 40 | 37 |
| B1_CncB1 | 70 | G | T | 82500 | 22 | 0.03% | 1.27E−09 | 40 | 39 |
| B1_CncB1 | 126 | A | G | 82728 | 28 | 0.03% | 1.25E−07 | 39 | 37 |
| B1_CncB1 | 135 | C | T | 70379 | 24 | 0.03% | 1.09E−06 | 39 | 40 |
| B1_CncB1 | 142 | C | T | 71170 | 21 | 0.03% | 8.01E−08 | 39 | 39 |
| B1_CncB1 | 145 | C | T | 63547 | 18 | 0.03% | 2.58E−07 | 38 | 40 |
| B1_CncB1 | 337 | A | G | 69550 | 20 | 0.03% | 8.81E−08 | 39 | 39 |
| B1_CncB1 | 340 | C | T | 73202 | 25 | 0.03% | 6.35E−07 | 39 | 39 |
| B1_CncB1 | 357 | A | C | 74947 | 19 | 0.03% | 3.82E−09 | 39 | 36 |
| B1_CncB1 | 379 | A | C | 80948 | 27 | 0.03% | 1.43E−07 | 40 | 37 |
| B1_CncB1 | 383 | G | C | 79926 | 20 | 0.03% | 8.87E−10 | 40 | 36 |
| B1_CncB1 | 395 | G | T | 80360 | 21 | 0.03% | 1.35E−09 | 40 | 39 |
| B1_CncB1 | 420 | C | T | 81549 | 21 | 0.03% | 8.46E−10 | 40 | 40 |
| B1_CncB1 | 9 | G | T | 85406 | 18 | 0.02% | 6.73E−12 | 40 | 39 |
| B1_CncB1 | 18 | G | T | 84890 | 17 | 0.02% | 3.87E−12 | 40 | 41 |
| B1_CncB1 | 34 | C | T | 85244 | 19 | 0.02% | 1.87E−11 | 40 | 39 |
| B1_CncB1 | 49 | C | T | 83852 | 14 | 0.02% | 2.08E−13 | 40 | 39 |
| B1_CncB1 | 68 | A | G | 82143 | 18 | 0.02% | 3.04E−11 | 40 | 39 |
| B1_CncB1 | 114 | A | G | 78805 | 17 | 0.02% | 8.11E−11 | 39 | 39 |
| B1_CncB1 | 131 | G | T | 75479 | 15 | 0.02% | 4.53E−11 | 39 | 38 |
| B1_CncB1 | 141 | C | T | 74626 | 14 | 0.02% | 2.51E−11 | 39 | 40 |
| B1_CncB1 | 350 | G | T | 77600 | 13 | 0.02% | 1.57E−12 | 39 | 34 |
| B1_CncB1 | 371 | C | A | 79271 | 18 | 0.02% | 1.34E−10 | 40 | 40 |
| B1_CncB1 | 394 | G | A | 80467 | 14 | 0.02% | 1.05E−12 | 40 | 40 |
| B1_CncB1 | 402 | A | G | 76885 | 16 | 0.02% | 7.91E−11 | 39 | 38 |
| B1_CncB1 | 404 | G | A | 81357 | 15 | 0.02% | 1.99E−12 | 40 | 40 |
| B1_CncB1 | 406 | A | G | 81527 | 17 | 0.02% | 1.79E−11 | 40 | 36 |
| B1_CncB1 | 452 | C | T | 81776 | 20 | 0.02% | 3.43E−10 | 40 | 40 |
| B1_CncB1 | 13 | G | T | 85242 | 10 | 0.01% | 2.83E−16 | 40 | 41 |
| B1_CncB1 | 95 | A | G | 81199 | 12 | 0.01% | 4.84E−14 | 40 | 40 |
| B1_CncB1 | 101 | G | T | 82160 | 12 | 0.01% | 2.77E−14 | 39 | 38 |
| B1_CncB1 | 143 | A | C | 66325 | 7 | 0.01% | 1.90E−13 | 38 | 34 |
| B1_CncB1 | 342 | G | T | 73133 | 9 | 0.01% | 6.79E−14 | 39 | 33 |
| B1_CncB1 | 443 | A | G | 82265 | 11 | 0.01% | 6.97E−15 | 40 | 38 |
| D1_CncD1 | 271 | G | T | 71690 | 34 | 0.05% | 1.94E−04 | 37 | 37 |
| D1_CncD1 | 280 | G | T | 79973 | 40 | 0.05% | 1.64E−04 | 39 | 37 |
| D1_CncD1 | 51 | C | T | 102462 | 36 | 0.04% | 8.36E−09 | 40 | 40 |
| D1_CncD1 | 364 | C | T | 96421 | 38 | 0.04% | 2.84E−07 | 40 | 40 |
| D1_CncD1 | 43 | C | T | 101861 | 35 | 0.03% | 6.43E−09 | 40 | 40 |
| D1_CncD1 | 73 | G | T | 99432 | 33 | 0.03% | 3.71E−09 | 39 | 39 |
| D1_CncD1 | 118 | C | T | 94805 | 30 | 0.03% | 3.52E−09 | 39 | 39 |
| D1_CncD1 | 123 | C | T | 91961 | 23 | 0.03% | 4.59E−11 | 39 | 39 |
| D1_CncD1 | 127 | C | T | 90095 | 25 | 0.03% | 4.14E−10 | 39 | 38 |
| D1_CncD1 | 290 | G | C | 87104 | 25 | 0.03% | 1.59E−09 | 39 | 37 |
| D1_CncD1 | 293 | G | T | 88203 | 28 | 0.03% | 1.03E−08 | 39 | 37 |
| D1_CncD1 | 297 | C | T | 86440 | 27 | 0.03% | 1.16E−08 | 39 | 39 |
| D1_CncD1 | 299 | C | T | 86813 | 29 | 0.03% | 4.83E−08 | 39 | 39 |
| D1_CncD1 | 319 | C | T | 89888 | 28 | 0.03% | 6.76E−09 | 39 | 40 |
| D1_CncD1 | 322 | A | C | 97030 | 29 | 0.03% | 4.57E−10 | 40 | 36 |
| D1_CncD1 | 326 | A | C | 96727 | 27 | 0.03% | 1.44E−10 | 40 | 37 |
| D1_CncD1 | 383 | C | T | 96127 | 29 | 0.03% | 7.06E−10 | 40 | 40 |
| D1_CncD1 | 394 | A | G | 99539 | 28 | 0.03% | 8.48E−11 | 40 | 40 |
| D1_CncD1 | 8 | G | T | 104215 | 24 | 0.02% | 2.25E−13 | 40 | 40 |
| D1_CncD1 | 37 | C | T | 100778 | 17 | 0.02% | 8.49E−16 | 40 | 40 |
| D1_CncD1 | 50 | G | T | 102712 | 18 | 0.02% | 9.71E−16 | 40 | 40 |
| D1_CncD1 | 55 | C | T | 101456 | 17 | 0.02% | 4.95E−16 | 40 | 40 |
| D1_CncD1 | 67 | G | C | 100393 | 24 | 0.02% | 1.57E−12 | 40 | 39 |
| D1_CncD1 | 78 | C | T | 99997 | 17 | 0.02% | 8.49E−16 | 40 | 40 |
| D1_CncD1 | 90 | C | T | 98813 | 22 | 0.02% | 5.99E−13 | 40 | 37 |
| D1_CncD1 | 96 | A | G | 80689 | 15 | 0.02% | 3.36E−12 | 37 | 39 |
| D1_CncD1 | 119 | G | T | 99936 | 15 | 0.02% | 1.16E−16 | 40 | 38 |
| D1_CncD1 | 122 | C | T | 95514 | 15 | 0.02% | 1.05E−15 | 39 | 38 |
| D1_CncD1 | 129 | A | G | 85569 | 18 | 0.02% | 6.73E−12 | 38 | 37 |
| D1_CncD1 | 132 | A | G | 83247 | 13 | 0.02% | 5.92E−14 | 38 | 36 |
| D1_CncD1 | 135 | A | G | 83172 | 13 | 0.02% | 5.92E−14 | 38 | 39 |
| D1_CncD1 | 138 | A | G | 82337 | 16 | 0.02% | 3.64E−12 | 38 | 36 |
| D1_CncD1 | 144 | G | A | 88195 | 16 | 0.02% | 1.57E−13 | 37 | 38 |
| D1_CncD1 | 277 | A | C | 76058 | 19 | 0.02% | 1.48E−09 | 38 | 38 |
| D1_CncD1 | 278 | A | C | 78683 | 17 | 0.02% | 8.11E−11 | 38 | 39 |
| D1_CncD1 | 281 | G | T | 84406 | 21 | 0.02% | 2.05E−10 | 39 | 36 |
| D1_CncD1 | 286 | C | T | 83808 | 19 | 0.02% | 5.02E−11 | 39 | 38 |
| D1_CncD1 | 300 | A | G | 83414 | 18 | 0.02% | 1.84E−11 | 39 | 37 |
| D1_CncD1 | 302 | C | T | 88452 | 18 | 0.02% | 1.47E−12 | 39 | 40 |

TABLE 9-continued

A-, C-, and G-to-N mutation frequencies in amplicon sequences: 100 μ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| D1_CncD1 | 305 | A | G | 90256 | 16 | 0.02% | 5.42E-14 | 39 | 35 |
| D1_CncD1 | 335 | A | G | 97803 | 18 | 0.02% | 1.37E-14 | 40 | 39 |
| D1_CncD1 | 349 | A | G | 97138 | 23 | 0.02% | 2.60E-12 | 40 | 37 |
| D1_CncD1 | 369 | G | A | 97574 | 24 | 0.02% | 6.63E-12 | 40 | 39 |
| D1_CncD1 | 382 | C | T | 96054 | 21 | 0.02% | 5.91E-13 | 40 | 40 |
| D1_CncD1 | 410 | C | A | 99960 | 22 | 0.02% | 3.65E-13 | 40 | 40 |
| D1_CncD1 | 1 | G | T | 103335 | 12 | 0.01% | 1.64E-19 | 40 | 40 |
| D1_CncD1 | 53 | A | G | 100474 | 11 | 0.01% | 2.00E-19 | 40 | 39 |
| D1_CncD1 | 65 | A | G | 99254 | 12 | 0.01% | 1.69E-18 | 40 | 41 |
| D1_CncD1 | 68 | C | T | 99275 | 11 | 0.01% | 3.61E-19 | 40 | 38 |
| D1_CncD1 | 76 | G | T | 101352 | 11 | 0.01% | 1.11E-19 | 40 | 40 |
| D1_CncD1 | 79 | C | T | 98596 | 13 | 0.01% | 1.31E-17 | 40 | 39 |
| D1_CncD1 | 85 | G | T | 101912 | 12 | 0.01% | 5.28E-19 | 40 | 39 |
| D1_CncD1 | 94 | G | C | 99809 | 13 | 0.01% | 7.37E-18 | 39 | 35 |
| D1_CncD1 | 97 | G | C | 99232 | 11 | 0.01% | 3.61E-19 | 39 | 37 |
| D1_CncD1 | 112 | A | G | 90289 | 10 | 0.01% | 1.51E-17 | 39 | 35 |
| D1_CncD1 | 137 | A | G | 84620 | 12 | 0.01% | 9.02E-15 | 37 | 37 |
| D1_CncD1 | 145 | C | G | 57797 | 8 | 0.01% | 1.57E-10 | 36 | 38 |
| D1_CncD1 | 279 | G | T | 81488 | 12 | 0.01% | 4.84E-14 | 39 | 38 |
| D1_CncD1 | 284 | A | C | 87948 | 13 | 0.01% | 6.46E-15 | 39 | 39 |
| D1_CncD1 | 317 | C | T | 92965 | 12 | 0.01% | 9.60E-17 | 39 | 39 |
| D1_CncD1 | 345 | C | T | 93633 | 14 | 0.01% | 8.64E-16 | 39 | 40 |
| D1_CncD1 | 360 | A | G | 97817 | 14 | 0.01% | 9.26E-17 | 40 | 41 |
| D1_CncD1 | 363 | G | T | 97240 | 12 | 0.01% | 5.39E-18 | 40 | 40 |
| D1_CncD1 | 370 | A | G | 97303 | 13 | 0.01% | 2.31E-17 | 40 | 40 |
| D1_CncD1 | 376 | A | G | 99085 | 11 | 0.01% | 3.61E-19 | 40 | 38 |
| D1_CncD1 | 405 | C | A | 98087 | 11 | 0.01% | 6.52E-19 | 40 | 41 |
| E1_CncE1 | 24 | C | T | 75199 | 134 | 0.18% | 2.68E-05 | 40 | 40 |
| E1_CncE1 | 134 | A | C | 52012 | 25 | 0.05% | 1.39E-03 | 38 | 33 |
| E1_CncE1 | 350 | A | T | 34821 | 13 | 0.04% | 1.54E-03 | 36 | 36 |
| E1_CncE1 | 378 | G | C | 54175 | 20 | 0.04% | 4.78E-05 | 39 | 37 |
| E1_CncE1 | 434 | A | G | 56421 | 22 | 0.04% | 7.44E-05 | 40 | 38 |
| E1_CncE1 | 440 | C | T | 56255 | 25 | 0.04% | 3.74E-04 | 40 | 40 |
| E1_CncE1 | 9 | G | T | 75276 | 22 | 0.03% | 3.01E-08 | 40 | 40 |
| E1_CncE1 | 12 | G | T | 74531 | 21 | 0.03% | 2.11E-08 | 40 | 40 |
| E1_CncE1 | 105 | C | G | 72520 | 24 | 0.03% | 4.81E-07 | 40 | 37 |
| E1_CncE1 | 122 | C | G | 69105 | 22 | 0.03% | 4.06E-07 | 39 | 40 |
| E1_CncE1 | 123 | C | A | 70585 | 23 | 0.03% | 5.47E-07 | 39 | 41 |
| E1_CncE1 | 126 | A | G | 63147 | 16 | 0.03% | 4.68E-08 | 39 | 38 |
| E1_CncE1 | 130 | C | A | 70797 | 23 | 0.03% | 5.47E-07 | 40 | 40 |
| E1_CncE1 | 356 | A | C | 46718 | 14 | 0.03% | 2.10E-05 | 38 | 37 |
| E1_CncE1 | 408 | A | C | 54732 | 15 | 0.03% | 1.30E-06 | 40 | 37 |
| E1_CncE1 | 1 | C | T | 74699 | 12 | 0.02% | 2.32E-12 | 40 | 40 |
| E1_CncE1 | 3 | G | T | 75076 | 17 | 0.02% | 3.61E-10 | 40 | 40 |
| E1_CncE1 | 67 | C | G | 72581 | 12 | 0.02% | 6.88E-12 | 40 | 38 |
| E1_CncE1 | 90 | C | G | 73303 | 12 | 0.02% | 3.99E-12 | 40 | 37 |
| E1_CncE1 | 94 | A | C | 71205 | 13 | 0.02% | 3.89E-11 | 39 | 35 |
| E1_CncE1 | 145 | A | G | 39007 | 6 | 0.02% | 2.69E-07 | 36 | 37 |
| E1_CncE1 | 334 | A | G | 24115 | 5 | 0.02% | 2.72E-04 | 36 | 37 |
| E1_CncE1 | 335 | A | C | 28469 | 7 | 0.02% | 2.53E-04 | 36 | 33 |
| E1_CncE1 | 345 | A | G | 43889 | 7 | 0.02% | 1.04E-07 | 37 | 35 |
| E1_CncE1 | 375 | G | C | 54167 | 11 | 0.02% | 2.99E-08 | 39 | 39 |
| E1_CncE1 | 456 | A | T | 36909 | 6 | 0.02% | 1.41E-06 | 37 | 32 |
| E1_CncE1 | 473 | A | G | 56398 | 11 | 0.02% | 1.06E-08 | 39 | 39 |
| E1_CncE1 | 4 | A | G | 75051 | 8 | 0.01% | 4.48E-15 | 40 | 39 |
| E1_CncE1 | 6 | G | T | 75312 | 9 | 0.01% | 2.12E-14 | 40 | 40 |
| E1_CncE1 | 41 | C | G | 73764 | 11 | 0.01% | 1.11E-12 | 40 | 34 |
| E1_CncE1 | 68 | A | G | 72284 | 8 | 0.01% | 2.65E-14 | 40 | 37 |
| E1_CncE1 | 119 | G | C | 68359 | 9 | 0.01% | 1.21E-12 | 39 | 37 |
| E1_CncE1 | 142 | G | A | 63637 | 7 | 0.01% | 1.12E-12 | 39 | 39 |
| E1_CncE1 | 331 | G | T | 40838 | 5 | 0.01% | 3.91E-08 | 37 | 37 |
| E1_CncE1 | 336 | G | C | 44480 | 5 | 0.01% | 3.77E-09 | 38 | 35 |
| E1_CncE1 | 348 | G | T | 44690 | 5 | 0.01% | 3.77E-09 | 37 | 35 |
| E1_CncE1 | 359 | G | T | 54708 | 6 | 0.01% | 4.81E-11 | 39 | 35 |
| E1_CncE1 | 370 | A | C | 53860 | 8 | 0.01% | 1.48E-09 | 39 | 37 |
| E1_CncE1 | 393 | C | T | 52850 | 6 | 0.01% | 1.56E-10 | 39 | 41 |
| E1_CncE1 | 428 | C | T | 55157 | 7 | 0.01% | 1.20E-10 | 39 | 41 |
| eGFP | 96 | G | T | 85709 | 832 | 0.96% | 4.32E-155 | 39 | 40 |
| eGFP | 91 | G | C | 84681 | 800 | 0.94% | 1.64E-147 | 39 | 40 |
| eGFP | 136 | A | G | 55222 | 167 | 0.30% | 1.22E-14 | 37 | 39 |
| eGFP | 141 | A | G | 51064 | 145 | 0.28% | 5.92E-12 | 36 | 38 |
| eGFP | 139 | A | G | 28797 | 71 | 0.25% | 8.98E-06 | 34 | 35 |
| eGFP | 340 | A | G | 62957 | 140 | 0.22% | 3.30E-08 | 37 | 39 |
| eGFP | 145 | A | G | 28555 | 58 | 0.20% | 7.96E-04 | 35 | 37 |
| eGFP | 310 | A | G | 57104 | 112 | 0.20% | 1.39E-05 | 36 | 39 |
| eGFP | 338 | A | G | 85244 | 167 | 0.20% | 1.30E-07 | 38 | 39 |

TABLE 9-continued

A-, C-, and G-to-N mutation frequencies in amplicon sequences: 100 μ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| eGFP | 78 | A | G | 82782 | 158 | 0.19% | 5.20E−07 | 39 | 40 |
| eGFP | 103 | A | G | 77038 | 149 | 0.19% | 9.45E−07 | 38 | 39 |
| eGFP | 43 | A | G | 83026 | 144 | 0.17% | 3.07E−05 | 39 | 39 |
| eGFP | 48 | A | G | 85730 | 142 | 0.17% | 9.30E−05 | 39 | 40 |
| eGFP | 117 | A | G | 74669 | 125 | 0.17% | 1.82E−04 | 38 | 39 |
| eGFP | 142 | A | G | 54321 | 95 | 0.17% | 4.88E−04 | 37 | 38 |
| eGFP | 303 | A | G | 70804 | 119 | 0.17% | 2.23E−04 | 37 | 37 |
| eGFP | 345 | A | G | 83694 | 142 | 0.17% | 5.02E−05 | 38 | 39 |
| eGFP | 82 | A | G | 78762 | 125 | 0.16% | 5.91E−04 | 39 | 39 |
| eGFP | 88 | A | G | 78716 | 123 | 0.16% | 9.14E−04 | 39 | 39 |
| eGFP | 130 | A | G | 61660 | 101 | 0.16% | 1.04E−03 | 37 | 38 |
| eGFP | 396 | A | G | 98088 | 158 | 0.16% | 1.06E−04 | 40 | 40 |
| eGFP | 93 | A | G | 78202 | 114 | 0.15% | 5.65E−03 | 39 | 40 |
| eGFP | 106 | A | G | 74063 | 110 | 0.15% | 4.82E−03 | 38 | 39 |
| eGFP | 349 | A | G | 87266 | 134 | 0.15% | 9.47E−04 | 39 | 39 |
| eGFP | 102 | A | G | 81147 | 117 | 0.14% | 6.31E−03 | 39 | 39 |
| eGFP | 363 | A | G | 91042 | 131 | 0.14% | 4.33E−03 | 39 | 39 |
| eGFP | 15 | G | T | 89627 | 46 | 0.05% | 1.34E−04 | 40 | 39 |
| eGFP | 60 | G | A | 86322 | 42 | 0.05% | 6.23E−05 | 40 | 40 |
| eGFP | 72 | A | G | 82455 | 38 | 0.05% | 3.62E−05 | 39 | 39 |
| eGFP | 115 | A | G | 69358 | 34 | 0.05% | 3.62E−04 | 38 | 38 |
| eGFP | 286 | C | A | 81831 | 38 | 0.05% | 5.00E−05 | 39 | 38 |
| eGFP | 318 | A | C | 64101 | 31 | 0.05% | 4.60E−04 | 37 | 34 |
| eGFP | 413 | C | A | 98673 | 51 | 0.05% | 7.27E−05 | 40 | 39 |
| eGFP | 422 | C | A | 100363 | 46 | 0.05% | 4.58E−06 | 40 | 40 |
| eGFP | 86 | G | A | 86705 | 36 | 0.04% | 3.43E−06 | 40 | 38 |
| eGFP | 127 | A | G | 67966 | 27 | 0.04% | 2.24E−05 | 38 | 38 |
| eGFP | 296 | G | C | 86886 | 35 | 0.04% | 1.99E−06 | 39 | 38 |
| eGFP | 300 | G | C | 83523 | 31 | 0.04% | 5.85E−07 | 38 | 37 |
| eGFP | 323 | G | C | 87040 | 32 | 0.04% | 2.33E−07 | 38 | 37 |
| eGFP | 344 | C | T | 93502 | 34 | 0.04% | 7.95E−08 | 39 | 39 |
| eGFP | 417 | C | A | 100215 | 44 | 0.04% | 1.73E−06 | 40 | 40 |
| eGFP | 14 | G | T | 89986 | 24 | 0.03% | 1.77E−10 | 40 | 39 |
| eGFP | 21 | G | A | 88106 | 26 | 0.03% | 2.27E−09 | 40 | 40 |
| eGFP | 33 | A | G | 88249 | 26 | 0.03% | 2.27E−09 | 40 | 39 |
| eGFP | 42 | G | A | 88155 | 23 | 0.03% | 1.88E−10 | 40 | 39 |
| eGFP | 64 | C | T | 87983 | 28 | 0.03% | 1.03E−08 | 40 | 38 |
| eGFP | 74 | C | T | 88250 | 23 | 0.03% | 1.88E−10 | 40 | 38 |
| eGFP | 90 | G | A | 87018 | 28 | 0.03% | 1.58E−08 | 39 | 39 |
| eGFP | 109 | A | C | 61886 | 16 | 0.03% | 1.20E−07 | 38 | 33 |
| eGFP | 119 | C | G | 81707 | 26 | 0.03% | 4.64E−08 | 38 | 36 |
| eGFP | 284 | C | G | 84034 | 26 | 0.03% | 1.29E−08 | 39 | 39 |
| eGFP | 285 | C | A | 82435 | 24 | 0.03% | 6.62E−09 | 39 | 38 |
| eGFP | 287 | C | T | 86443 | 30 | 0.03% | 9.50E−08 | 39 | 38 |
| eGFP | 293 | G | C | 81938 | 21 | 0.03% | 8.46E−10 | 39 | 36 |
| eGFP | 294 | C | A | 81796 | 22 | 0.03% | 2.01E−09 | 38 | 36 |
| eGFP | 297 | C | G | 90020 | 23 | 0.03% | 7.35E−11 | 39 | 38 |
| eGFP | 301 | A | C | 77139 | 21 | 0.03% | 5.39E−09 | 37 | 39 |
| eGFP | 334 | G | C | 96225 | 29 | 0.03% | 7.06E−10 | 40 | 37 |
| eGFP | 335 | C | T | 95248 | 28 | 0.03% | 5.02E−10 | 39 | 39 |
| eGFP | 339 | G | A | 85990 | 25 | 0.03% | 2.49E−09 | 38 | 35 |
| eGFP | 356 | C | T | 94823 | 26 | 0.03% | 1.55E−10 | 39 | 39 |
| eGFP | 371 | G | A | 96765 | 27 | 0.03% | 1.44E−10 | 40 | 39 |
| eGFP | 389 | C | T | 96773 | 26 | 0.03% | 6.23E−11 | 40 | 40 |
| eGFP | 393 | G | A | 97756 | 28 | 0.03% | 2.07E−10 | 40 | 40 |
| eGFP | 398 | C | T | 95496 | 25 | 0.03% | 4.17E−11 | 40 | 40 |
| eGFP | 408 | A | G | 100235 | 30 | 0.03% | 2.68E−10 | 40 | 40 |
| eGFP | 18 | G | T | 88492 | 15 | 0.02% | 4.76E−14 | 40 | 39 |
| eGFP | 22 | G | A | 86906 | 18 | 0.02% | 4.06E−12 | 40 | 40 |
| eGFP | 29 | C | T | 90080 | 20 | 0.02% | 4.26E−12 | 40 | 40 |
| eGFP | 32 | G | A | 87836 | 18 | 0.02% | 2.44E−12 | 40 | 40 |
| eGFP | 36 | C | T | 88590 | 21 | 0.02% | 3.02E−11 | 40 | 40 |
| eGFP | 37 | G | A | 87453 | 16 | 0.02% | 2.66E−13 | 40 | 39 |
| eGFP | 39 | G | A | 87822 | 15 | 0.02% | 8.15E−14 | 40 | 39 |
| eGFP | 40 | C | A | 87195 | 18 | 0.02% | 2.44E−12 | 40 | 40 |
| eGFP | 41 | C | G | 87208 | 15 | 0.02% | 8.15E−14 | 40 | 37 |
| eGFP | 50 | G | A | 87987 | 18 | 0.02% | 1.47E−12 | 40 | 40 |
| eGFP | 53 | C | T | 88034 | 14 | 0.02% | 1.37E−14 | 40 | 40 |
| eGFP | 68 | G | A | 86270 | 14 | 0.02% | 4.08E−14 | 40 | 37 |
| eGFP | 101 | C | T | 86344 | 21 | 0.02% | 7.91E−11 | 39 | 39 |
| eGFP | 105 | G | A | 86250 | 17 | 0.02% | 1.38E−12 | 39 | 38 |
| eGFP | 111 | G | A | 85573 | 21 | 0.02% | 1.28E−10 | 39 | 39 |
| eGFP | 112 | G | A | 83671 | 19 | 0.02% | 5.02E−11 | 39 | 38 |
| eGFP | 131 | G | A | 77740 | 13 | 0.02% | 1.57E−12 | 38 | 38 |
| eGFP | 134 | G | A | 79559 | 12 | 0.02% | 1.47E−13 | 38 | 36 |
| eGFP | 135 | G | A | 79427 | 17 | 0.02% | 4.91E−11 | 39 | 37 |

TABLE 9-continued

A-, C-, and G-to-N mutation frequencies in amplicon sequences: 100 μ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| eGFP | 137 | G | C | 77014 | 14 | 0.02% | 5.17E-12 | 38 | 40 |
| eGFP | 140 | C | G | 61195 | 12 | 0.02% | 2.38E-09 | 36 | 36 |
| eGFP | 288 | G | C | 80085 | 13 | 0.02% | 3.07E-13 | 38 | 36 |
| eGFP | 298 | C | G | 89668 | 21 | 0.02% | 1.86E-11 | 39 | 40 |
| eGFP | 307 | A | C | 61860 | 12 | 0.02% | 2.38E-09 | 36 | 33 |
| eGFP | 312 | C | T | 86695 | 17 | 0.02% | 1.38E-12 | 38 | 36 |
| eGFP | 316 | G | A | 87500 | 20 | 0.02% | 1.87E-11 | 39 | 35 |
| eGFP | 326 | C | T | 95539 | 23 | 0.02% | 6.81E-12 | 40 | 38 |
| eGFP | 355 | G | A | 95076 | 19 | 0.02% | 1.19E-13 | 39 | 39 |
| eGFP | 368 | C | T | 94433 | 19 | 0.02% | 1.99E-13 | 40 | 39 |
| eGFP | 369 | C | G | 95506 | 17 | 0.02% | 1.23E-14 | 40 | 39 |
| eGFP | 385 | C | T | 95939 | 20 | 0.02% | 3.47E-13 | 40 | 40 |
| eGFP | 387 | G | A | 97629 | 17 | 0.02% | 4.25E-15 | 40 | 40 |
| eGFP | 402 | C | T | 96588 | 19 | 0.02% | 7.12E-14 | 40 | 40 |
| eGFP | 425 | G | T | 101085 | 16 | 0.02% | 1.41E-16 | 40 | 40 |
| eGFP | 1 | C | T | 89553 | 9 | 0.01% | 5.41E-18 | 40 | 41 |
| eGFP | 38 | C | T | 88929 | 9 | 0.01% | 9.85E-18 | 40 | 41 |
| eGFP | 59 | C | T | 87626 | 10 | 0.01% | 8.79E-17 | 40 | 37 |
| eGFP | 66 | C | T | 88484 | 13 | 0.01% | 3.70E-15 | 40 | 39 |
| eGFP | 77 | C | A | 88980 | 9 | 0.01% | 9.85E-18 | 40 | 39 |
| eGFP | 80 | C | T | 85795 | 11 | 0.01% | 1.25E-15 | 39 | 39 |
| eGFP | 81 | G | A | 86862 | 12 | 0.01% | 2.92E-15 | 40 | 39 |
| eGFP | 84 | C | A | 87643 | 12 | 0.01% | 1.66E-15 | 40 | 36 |
| eGFP | 108 | G | A | 84419 | 12 | 0.01% | 9.02E-15 | 39 | 38 |
| eGFP | 124 | C | A | 82588 | 10 | 0.01% | 1.63E-15 | 39 | 37 |
| eGFP | 126 | C | G | 82801 | 12 | 0.01% | 2.77E-14 | 39 | 39 |
| eGFP | 128 | C | A | 80699 | 11 | 0.01% | 2.17E-14 | 39 | 37 |
| eGFP | 129 | A | C | 71170 | 9 | 0.01% | 2.16E-13 | 38 | 40 |
| eGFP | 283 | G | C | 46656 | 5 | 0.01% | 1.15E-09 | 37 | 35 |
| eGFP | 291 | C | A | 84101 | 9 | 0.01% | 1.07E-16 | 38 | 35 |
| eGFP | 302 | C | T | 88874 | 13 | 0.01% | 3.70E-15 | 38 | 35 |
| eGFP | 306 | C | T | 88046 | 11 | 0.01% | 2.23E-16 | 38 | 38 |
| eGFP | 311 | C | A | 91164 | 10 | 0.01% | 8.34E-18 | 39 | 34 |
| eGFP | 314 | G | A | 83255 | 10 | 0.01% | 9.10E-16 | 38 | 37 |
| eGFP | 320 | C | A | 93762 | 11 | 0.01% | 1.22E-17 | 39 | 39 |
| eGFP | 321 | C | T | 91383 | 13 | 0.01% | 6.89E-16 | 39 | 40 |
| eGFP | 332 | G | A | 93738 | 13 | 0.01% | 2.23E-16 | 39 | 40 |
| eGFP | 341 | C | T | 96704 | 11 | 0.01% | 2.11E-18 | 40 | 38 |
| eGFP | 347 | C | T | 97040 | 11 | 0.01% | 1.17E-18 | 39 | 39 |
| eGFP | 348 | G | A | 94231 | 11 | 0.01% | 6.81E-18 | 39 | 39 |
| eGFP | 350 | G | A | 92219 | 13 | 0.01% | 3.93E-16 | 39 | 39 |
| eGFP | 353 | G | A | 95058 | 14 | 0.01% | 2.84E-16 | 40 | 39 |
| eGFP | 360 | C | T | 94427 | 12 | 0.01% | 3.04E-17 | 40 | 38 |
| eGFP | 362 | C | G | 96062 | 14 | 0.01% | 1.62E-16 | 39 | 40 |
| eGFP | 365 | G | A | 95969 | 14 | 0.01% | 2.84E-16 | 40 | 39 |
| eGFP | 372 | C | T | 95730 | 14 | 0.01% | 2.84E-16 | 40 | 41 |
| eGFP | 375 | G | A | 97913 | 14 | 0.01% | 9.26E-17 | 40 | 40 |
| eGFP | 377 | G | A | 98890 | 14 | 0.01% | 5.28E-17 | 40 | 39 |
| eGFP | 380 | C | T | 95817 | 12 | 0.01% | 1.71E-17 | 40 | 38 |
| eGFP | 386 | C | T | 96470 | 10 | 0.01% | 4.29E-19 | 40 | 40 |
| eGFP | 394 | G | A | 98265 | 10 | 0.01% | 1.30E-19 | 40 | 40 |
| eGFP | 395 | G | A | 98335 | 11 | 0.01% | 6.52E-19 | 40 | 41 |
| eGFP | 407 | C | T | 97381 | 11 | 0.01% | 1.17E-18 | 40 | 41 |
| p21_Cdkn1A | 31 | A | G | 97394 | 256 | 0.26% | 5.33E-18 | 40 | 40 |
| p21_Cdkn1A | 438 | C | T | 102154 | 255 | 0.25% | 1.42E-16 | 40 | 40 |
| p21_Cdkn1A | 85 | C | T | 95772 | 231 | 0.24% | 2.64E-14 | 40 | 39 |
| p21_Cdkn1A | 50 | C | T | 95539 | 201 | 0.21% | 3.35E-10 | 40 | 40 |
| p21_Cdkn1A | 357 | C | T | 97973 | 200 | 0.20% | 1.69E-09 | 39 | 39 |
| p21_Cdkn1A | 123 | C | T | 89610 | 168 | 0.19% | 4.65E-07 | 39 | 37 |
| p21_Cdkn1A | 422 | C | T | 100156 | 175 | 0.17% | 3.53E-06 | 40 | 40 |
| p21_Cdkn1A | 41 | G | C | 96478 | 48 | 0.05% | 3.88E-05 | 40 | 37 |
| p21_Cdkn1A | 105 | C | G | 96107 | 46 | 0.05% | 1.64E-05 | 39 | 38 |
| p21_Cdkn1A | 119 | A | C | 72294 | 36 | 0.05% | 3.41E-04 | 38 | 35 |
| p21_Cdkn1A | 448 | C | T | 100688 | 49 | 0.05% | 1.77E-05 | 40 | 40 |
| p21_Cdkn1A | 67 | A | G | 95023 | 34 | 0.04% | 3.63E-08 | 40 | 36 |
| p21_Cdkn1A | 97 | C | G | 95095 | 35 | 0.04% | 6.86E-08 | 40 | 37 |
| p21_Cdkn1A | 345 | A | G | 80912 | 31 | 0.04% | 1.83E-06 | 38 | 34 |
| p21_Cdkn1A | 135 | A | C | 65390 | 17 | 0.03% | 4.44E-08 | 37 | 33 |
| p21_Cdkn1A | 370 | G | C | 97118 | 28 | 0.03% | 2.07E-10 | 39 | 38 |
| p21_Cdkn1A | 116 | C | G | 93794 | 23 | 0.02% | 1.78E-11 | 39 | 38 |
| p21_Cdkn1A | 124 | A | C | 76053 | 18 | 0.02% | 5.84E-10 | 38 | 33 |
| p21_Cdkn1A | 138 | A | C | 69895 | 16 | 0.02% | 2.59E-09 | 37 | 34 |
| p21_Cdkn1A | 141 | A | C | 65589 | 15 | 0.02% | 6.99E-09 | 38 | 33 |
| p21_Cdkn1A | 142 | G | T | 75346 | 14 | 0.02% | 1.49E-11 | 38 | 39 |
| p21_Cdkn1A | 339 | G | T | 91653 | 16 | 0.02% | 3.18E-14 | 39 | 36 |
| p21_Cdkn1A | 341 | C | G | 93773 | 19 | 0.02% | 3.33E-13 | 39 | 39 |

TABLE 9-continued

A-, C-, and G-to-N mutation frequencies in amplicon sequences: 100 μ 4sU labeling with OsO$_4$/NH$_4$Cl treatment.

| NAME | POS | REF | ALT | REFdepth | ALTdepth | mutFREQ | PVAL | avgREFBASEQUAL | avgALTBASEQUAL |
|---|---|---|---|---|---|---|---|---|---|
| p21_Cdkn1A | 8 | G | T | 99272 | 10 | 0.01% | 7.15E−20 | 39 | 39 |
| p21_Cdkn1A | 68 | C | G | 97390 | 10 | 0.01% | 2.36E−19 | 40 | 37 |
| p21_Cdkn1A | 143 | C | A | 82605 | 9 | 0.01% | 3.49E−16 | 38 | 37 |
| p21_Cdkn1A | 333 | A | C | 72148 | 10 | 0.01% | 5.05E−13 | 37 | 37 |
| p21_Cdkn1A | 335 | A | T | 70892 | 10 | 0.01% | 1.56E−12 | 37 | 38 |
| p21_Cdkn1A | 343 | G | C | 89035 | 9 | 0.01% | 5.41E−18 | 39 | 38 |
| p21_Cdkn1A | 346 | C | G | 96393 | 12 | 0.01% | 9.61E−18 | 39 | 40 |
| p21_Cdkn1A | 348 | G | C | 92357 | 10 | 0.01% | 4.62E−18 | 39 | 39 |
| p21_Cdkn1A | 359 | G | C | 93955 | 11 | 0.01% | 1.22E−17 | 39 | 37 |
| p21_Cdkn1A | 381 | C | T | 100475 | 14 | 0.01% | 1.71E−17 | 40 | 38 |
| PCNA | 373 | G | C | 109556 | 61 | 0.06% | 1.43E−04 | 40 | 39 |
| PCNA | 411 | C | T | 110084 | 61 | 0.06% | 1.10E−04 | 40 | 39 |
| PCNA | 137 | C | T | 100626 | 50 | 0.05% | 2.71E−05 | 39 | 38 |
| PCNA | 139 | C | T | 101419 | 47 | 0.05% | 5.30E−06 | 39 | 40 |
| PCNA | 143 | C | T | 100920 | 48 | 0.05% | 1.14E−05 | 39 | 38 |
| PCNA | 339 | C | T | 97737 | 53 | 0.05% | 2.04E−04 | 38 | 38 |
| PCNA | 21 | C | T | 115277 | 47 | 0.04% | 4.57E−08 | 40 | 40 |
| PCNA | 41 | A | C | 112162 | 47 | 0.04% | 1.32E−07 | 40 | 38 |
| PCNA | 77 | C | T | 115823 | 48 | 0.04% | 7.87E−08 | 40 | 39 |
| PCNA | 105 | C | G | 109796 | 44 | 0.04% | 7.46E−08 | 40 | 36 |
| PCNA | 130 | C | T | 107955 | 42 | 0.04% | 4.96E−08 | 39 | 39 |
| PCNA | 328 | C | T | 90965 | 34 | 0.04% | 2.52E−07 | 38 | 37 |
| PCNA | 345 | C | T | 98875 | 40 | 0.04% | 4.23E−07 | 38 | 37 |
| PCNA | 59 | C | T | 116042 | 36 | 0.03% | 2.58E−11 | 40 | 39 |
| PCNA | 62 | C | T | 116566 | 30 | 0.03% | 1.93E−13 | 40 | 40 |
| PCNA | 68 | A | G | 114358 | 29 | 0.03% | 2.01E−13 | 40 | 39 |
| PCNA | 97 | A | G | 113234 | 34 | 0.03% | 2.05E−11 | 40 | 36 |
| PCNA | 120 | C | T | 109094 | 35 | 0.03% | 2.40E−10 | 39 | 40 |
| PCNA | 125 | A | G | 105947 | 27 | 0.03% | 2.30E−12 | 39 | 39 |
| PCNA | 355 | A | G | 102093 | 29 | 0.03% | 5.00E−11 | 39 | 39 |
| PCNA | 362 | A | C | 101722 | 34 | 0.03% | 3.26E−09 | 39 | 38 |
| PCNA | 375 | C | T | 107919 | 33 | 0.03% | 1.28E−10 | 40 | 39 |
| PCNA | 400 | G | C | 112166 | 30 | 0.03% | 1.23E−12 | 40 | 36 |
| PCNA | 436 | C | T | 110720 | 33 | 0.03% | 3.50E−11 | 40 | 40 |
| PCNA | 441 | C | T | 109271 | 35 | 0.03% | 2.40E−10 | 40 | 40 |
| PCNA | 443 | C | T | 109264 | 28 | 0.03% | 8.60E−13 | 40 | 40 |
| PCNA | 35 | A | G | 116979 | 21 | 0.02% | 1.16E−17 | 40 | 40 |
| PCNA | 53 | G | T | 116368 | 21 | 0.02% | 1.98E−17 | 40 | 40 |
| PCNA | 66 | G | A | 114962 | 18 | 0.02% | 1.46E−18 | 40 | 38 |
| PCNA | 67 | A | G | 113964 | 28 | 0.02% | 1.30E−13 | 40 | 35 |
| PCNA | 72 | C | T | 113051 | 23 | 0.02% | 8.93E−16 | 40 | 39 |
| PCNA | 94 | A | G | 106637 | 26 | 0.02% | 5.76E−13 | 39 | 36 |
| PCNA | 108 | C | T | 108311 | 23 | 0.02% | 1.13E−14 | 39 | 39 |
| PCNA | 122 | C | T | 109485 | 18 | 0.02% | 2.24E−17 | 39 | 38 |
| PCNA | 131 | C | T | 102490 | 21 | 0.02% | 2.86E−14 | 39 | 39 |
| PCNA | 142 | C | T | 105275 | 25 | 0.02% | 3.63E−13 | 39 | 38 |
| PCNA | 337 | A | G | 78107 | 14 | 0.02% | 3.04E−12 | 37 | 38 |
| PCNA | 340 | C | T | 90538 | 16 | 0.02% | 5.42E−14 | 37 | 38 |
| PCNA | 342 | C | T | 98872 | 23 | 0.02% | 1.60E−12 | 39 | 39 |
| PCNA | 344 | C | T | 98799 | 16 | 0.02% | 7.26E−16 | 39 | 38 |
| PCNA | 346 | A | C | 76137 | 17 | 0.02% | 2.20E−10 | 37 | 34 |
| PCNA | 357 | C | T | 106241 | 22 | 0.02% | 1.09E−14 | 40 | 38 |
| PCNA | 363 | C | T | 104980 | 20 | 0.02% | 2.03E−15 | 39 | 38 |
| PCNA | 367 | C | T | 107577 | 19 | 0.02% | 2.22E−16 | 40 | 39 |
| PCNA | 377 | G | C | 110677 | 25 | 0.02% | 3.17E−14 | 40 | 38 |
| PCNA | 422 | C | T | 108127 | 23 | 0.02% | 1.13E−14 | 40 | 41 |
| PCNA | 433 | C | T | 111563 | 23 | 0.02% | 2.48E−15 | 40 | 40 |
| PCNA | 445 | C | T | 111456 | 22 | 0.02% | 8.40E−16 | 40 | 40 |
| PCNA | 25 | C | T | 116978 | 14 | 0.01% | 1.78E−21 | 40 | 40 |
| PCNA | 43 | G | T | 115832 | 16 | 0.01% | 5.77E−20 | 40 | 40 |
| PCNA | 71 | C | T | 113523 | 15 | 0.01% | 4.37E−20 | 39 | 40 |
| PCNA | 85 | C | T | 112049 | 15 | 0.01% | 7.73E−20 | 39 | 40 |
| PCNA | 87 | G | T | 114545 | 17 | 0.01% | 3.95E−19 | 40 | 40 |
| PCNA | 90 | G | T | 113094 | 12 | 0.01% | 4.52E−22 | 40 | 39 |
| PCNA | 100 | G | T | 113583 | 14 | 0.01% | 1.01E−20 | 40 | 39 |
| PCNA | 129 | G | T | 108967 | 12 | 0.01% | 8.72E−21 | 39 | 39 |
| PCNA | 324 | A | G | 67041 | 9 | 0.01% | 2.14E−12 | 37 | 35 |
| PCNA | 335 | A | G | 94858 | 12 | 0.01% | 3.05E−17 | 38 | 37 |
| PCNA | 336 | A | G | 87500 | 13 | 0.01% | 6.46E−15 | 38 | 38 |
| PCNA | 379 | A | T | 110012 | 12 | 0.01% | 2.68E−21 | 40 | 40 |
| PCNA | 389 | C | T | 109930 | 13 | 0.01% | 2.29E−20 | 40 | 40 |
| PCNA | 424 | C | T | 111523 | 12 | 0.01% | 1.48E−21 | 40 | 40 |
| PCNA | 430 | A | G | 109255 | 13 | 0.01% | 2.29E−20 | 40 | 39 |

FIG. 21B shows the results of the TUC-seq gene expression analyses for eGFP and the endogenous, and stably expressed gene, proliferating cell nuclear antigen (PCNA). In eGFP, multiple U positions were mutated to C, and these had median mutation frequencies of 0.42% (50 µM 4sU) and 0.48% (100 µM 4sU) in the OsO$_4$-converted samples (FIG. 21B). By contrast, in PCNA amplicons, U-to-C conversion rates were considerably lower with median values of 0.06% for both labeling conditions (FIG. 21B). In control experiments, unlabeled, and labeled but not OsO$_4$-treated samples showed median mutation frequencies of 0.02% for eGFP and PCNA. Only the eGFP amplicon derived from labeled but not OsO$_4$-treated RNA exhibited a slightly higher median mutation frequency of 0.17% . Statistical analysis confirmed that both the number of converted Us and the mutation frequencies were significantly lower in unlabeled than in the labeled samples (Chi-square test,)$p<10^{-10}$. Likewise, numbers of affected nucleotides and mutation frequencies of A, C and G to N were low regardless of the conditions used and significantly different from U-to-C mutation frequencies in the labeled samples (Chi-square test, $p<10^{-10}$, FIG. 21B), indicating that overall mutation rates are low and that elevated U-to-C occurrence is caused by OsO$_4$-mediated conversion of U to C in 4sU-labeled transcripts. The increased 4sU levels detected by osmium conversion therefore suggest enhanced transcription of eGFP compared to PCNA.

Figure 22:
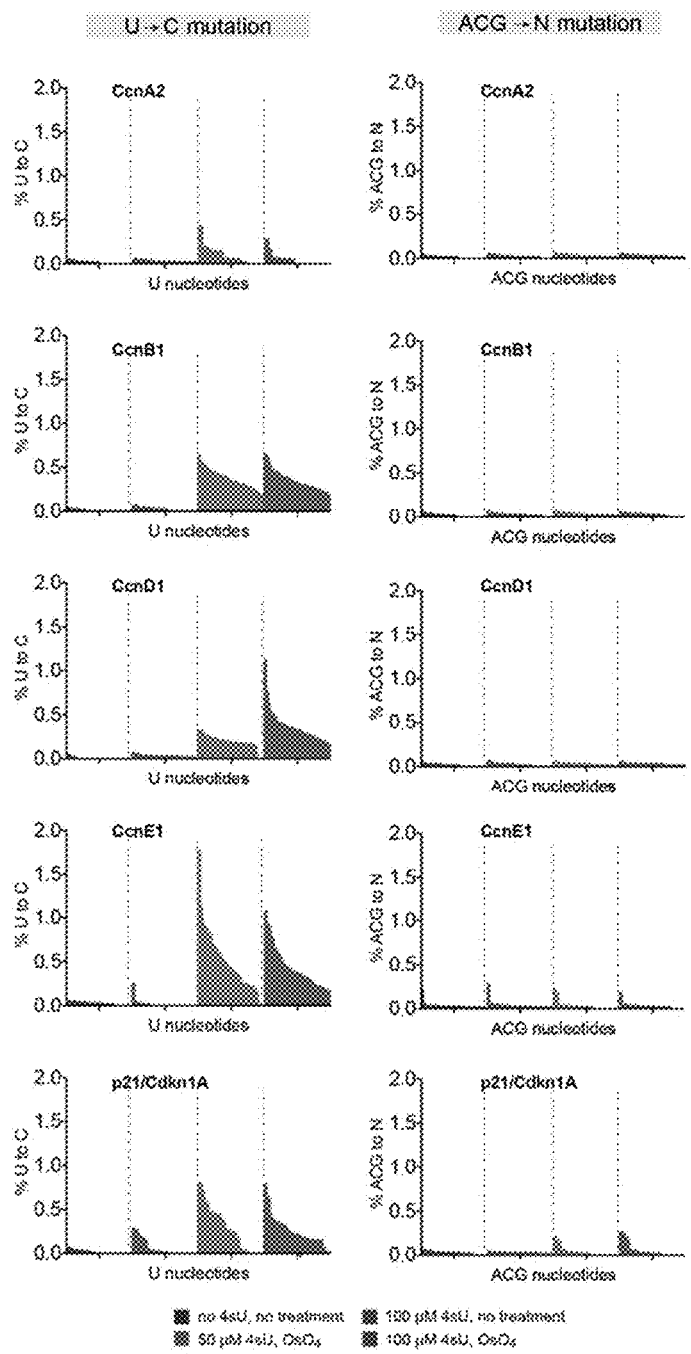
FIG. 22: U-to-C mutation frequencies in amplicon sequences indicate successful incorporation and conversion of 4sU in HEK293 cell transcripts. Left graphs: U-to-C mutation frequencies for individual U positions in amplicon sequencing reads of the indicated transcripts. Each U position for which a C exchange was observed is shown as a vertical line and the four different labeling conditions (see legend) were combined into one graph. Due to random incorporation of 4sU during labeling, different numbers of U nucleotides were converted in the different conditions. Converted Us are ordered according to their mutation frequency in a descending manner. Right graphs: Background mutation frequencies of A, C and G into any nucleotide (ACG>N) are shown in the same manner as described for the graphs on the left.

Next, transcription of five cell cycle related genes, cyclins A2, B1, D1, E1 (CcnA2, CcnB1, CcnD1, CcnE1) and p21/Cdkn1A, were examined in 4sU-pulse labeled and unlabeled cells (FIG. 22). These experiments indicated clear differences in new transcription between the different cyclins: median U-to-C conversion frequencies in labeled (50 mM 4sU) and OsO$_4$-treated samples were highest for CcnE1 (0.43%), followed by p21/Cdnk1A (0.38%), CcnB1 (0.34%), CcnD1 (0.19%) and CcnA2 (0.10%) (FIG. 22). Of note, conversion frequencies were similar for both 4sU concentrations used for labeling and significantly higher than in the corresponding control samples (Chi-Square test, $p<10^{-10}$; FIG. 22).

Figure 23:
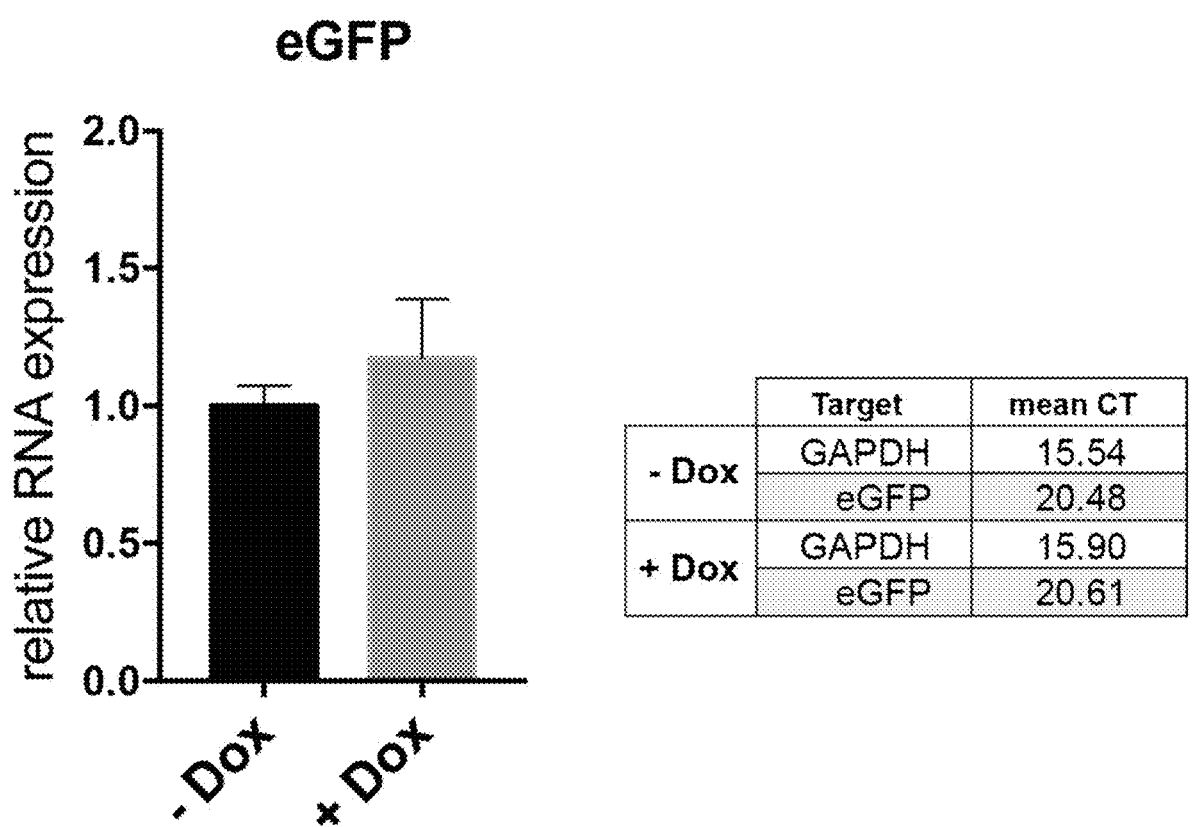
FIG. 23: eGFP is expressed from the Dox-inducible CMV promoter even in the absence of doxycycline. qRT-PCR was performed on RNA from untreated HEK293 cells and cells treated with doxycycline (Dox) for 30 min. Values were normalized against the internal reference gene GAPDH. The table shows the mean CT values of the qPCR reactions for an estimate of the abundance of eGFP.

To obtain a more direct estimate of the relative contribution of new transcription to the existing pool of transcripts, the fraction of sequencing reads bearing at least one U-to-C conversion relative to the pool of unlabeled transcripts was calculated for the sample labeled with 50 µM 4sU and treated with OsO$_4$/NH$_4$Cl. The values were corrected for background U-to-C mutation rates using the reads from the unlabeled sample. This analysis revealed that for PCNA, new transcripts amounted to 1.6% of all sequences, while new eGFP transcripts represented 5.0% of eGFP sequences (FIG. 21C; Table 10). The relatively weak contribution of newly synthesized eGFP transcripts to the total pool of eGFP transcripts was unexpected considering that transgenic eGFP transcription in the cell is supposed to be suppressed until induction by Dox. Reverse-transcription real-time PCR (RT-qPCR) of non-induced and induced cells, however, confirmed a considerable pool of eGFP transcripts even in the absence of Dox indicating that the promoter is quite leaky (FIG. 23). This result together with the short labeling time of nascent eGFP transcripts (30 minutes after Dox addition), explains why labeled transcripts are not the major species in the eGFP pool.

TABLE 10

Amplicon fragments with >1 U-to-C conversion

| Amplicon Name | Treatment | Total Fragments | Thio converted Fragments | Unconverted Fragments | THIO converted fragment Frequency (%) | Mean number of UtoC conversion OnFragments |
|---|---|---|---|---|---|---|
| B1_CcnB1 | no4sU | 215940 | 736 | 214855 | 0.340835417 | 2.830825272 |
| A2_CcnA2 | no4sU | 220357 | 564 | 219500 | 0.255948302 | 3.405112411 |
| D1_CcnD1 | no4sU | 289095 | 881 | 287644 | 0.304744115 | 3.027810443 |
| PCNA | no4sU | 229185 | 990 | 227825 | 0.31965443 | 4,271,097576 |
| p21_Cdkn1A | no4sU | 175983 | 785 | 174907 | 0.446065813 | 3.721246624 |
| E1_CcnE1 | no4sU | 96678 | 454 | 96104 | 0.469600116 | 5.854195815 |
| eGFP | no4sU | 93351 | 351 | 92556 | 0.376000257 | 8.346547578 |
| B1_CcnB1 | 50 uM 4sU + OSO$_4$ | 211665 | 18505 | 192810 | 8.742588524 | 3.623885777 |
| A2_CcnA2 | 50 uM 4sU + OSO$_4$ | 194258 | 4561 | 189404 | 2.347908452 | 3.633974874 |
| D1_CcnD1 | 50 uM 4sU + OSO$_4$ | 251328 | 11689 | 239141 | 4.650894449 | 3406370425 |
| PCNA | 50 uM 4sU + OSO$_4$ | 207780 | 5206 | 202.256 | 2.5055347 | 3.83345267 |
| p21_Cdkn1A | 50 uM 4sU + OSO$_4$ | 153478 | 5706 | 147501 | 3.717796687 | 3.945026954 |
| E1_CcnE1 | 50 uM 4sU + OSO$_4$ | 79639 | 6990 | 72.531 | 8.777106694 | 4.576882031 |
| eGFP | 50 uM 4sU + OSO$_4$ | 52244 | 2646 | 49420 | 5.064696424 | 6.468369539 |
| B1_CcnB1 | 100 uM 4sU + OsO$_4$ | 171437 | 11475 | 159.736 | 6.693420907 | 4.518613917 |
| A2_CcnA2 | 100 uM 4sU + OsO$_4$ | 193641 | 3481 | 189898 | 1.797656488 | 4.146518299 |
| D1_CcnD1 | 100 uM 4sU + OsO$_4$ | 206576 | 14210 | 191,954 | 6.878824258 | 4.373755222 |
| PCNA | 100 uM 4sU + OsO$_4$ | 234785 | 4858 | 229564 | 2.069127074 | 4.441642528 |
| p21_Cdkn1A | 100 uM 4sU + OsO$_4$ | 206044 | 7973 | 197,727 | 3.869561841 | 3756333011 |
| E1_CcnE1 | 100 uM 4sU + OsO$_4$ | 135362 | 8615 | 126581 | 6.364415419 | 5.26085213 |
| eGFP | 100 uM 4sU + OsO$_4$ | 195972 | 11508 | 183,950 | 5.872267467 | 7.117189077 |

The same analysis was applied to the endogenous cell cycle-related transcripts showing strongest transcription for CcnB1 and CcnE1 with 6.2% new transcripts, while CcnD1, p21/Cdkn1A and CcnA2 appeared to be more weakly transcribed with 4.9%, 3.6% and 1.6% new transcripts, respectively (FIG. 21C, Table 10). This conclusion is based on the assumption that the contribution of RNA decay within the labeling period is negligible. Cyclin mRNA half-life has been estimated to range from 2 to 4.5 h in mouse fibroblast cells (Penelova et al., 2005). Therefore, mRNA decay likely plays a minor role in the 1 h labeling period examined here.

Taken together, these experiments demonstrate that $OsO_4$/$NH_4Cl$ mediated conversion of thiolated uridines allows for direct sequencing-based analysis of metabolically labeled or naturally modified RNA. The high selectivity and specificity of the osmium reaction, combined with nearly quantitative yields, make TUC-seq a promising new method to study the cellular dynamics of various types of RNA. The method provides even more advantages than current methods given the very low number of processing steps. It is important to note that the $OsO_4$/$NH_4Cl$ mediated 4sU-to-C conversion is a clean and mild reaction that otherwise leaves the RNA intact; it does not result in unwanted modification of canonical nucleobases nor in unwanted (e.g. hydrolyzed or alkylated) 4sU byproducts. Therefore, interference with any downstream processing steps, such as reverse transcription, that might cause biased results can be excluded. For the examples shown here, PCR-based sequencing methods were used, but clearly this approach is amenable for direct RNA-seq methods, and it is expected that RNA-seq of $OsO_4$-treated samples (TUC-seq) will find a broad field of applications. TUC-seq enables the simultaneous and accurate quantification of labeled and unlabeled RNA. Together with properly designed pulse and pulse-chase labeling conditions, it will greatly facilitate transcriptome-wide analyses of RNA synthesis and decay rates or of RNA processing events. Moreover, the method will be highly useful for the identification of novel sites of endogenous 4sU incorporation in the RNA of any organism.

Example 4

Conversion of 4-thiothymidine to 2'-deoxy-5-methylcytidine

Figure 24:
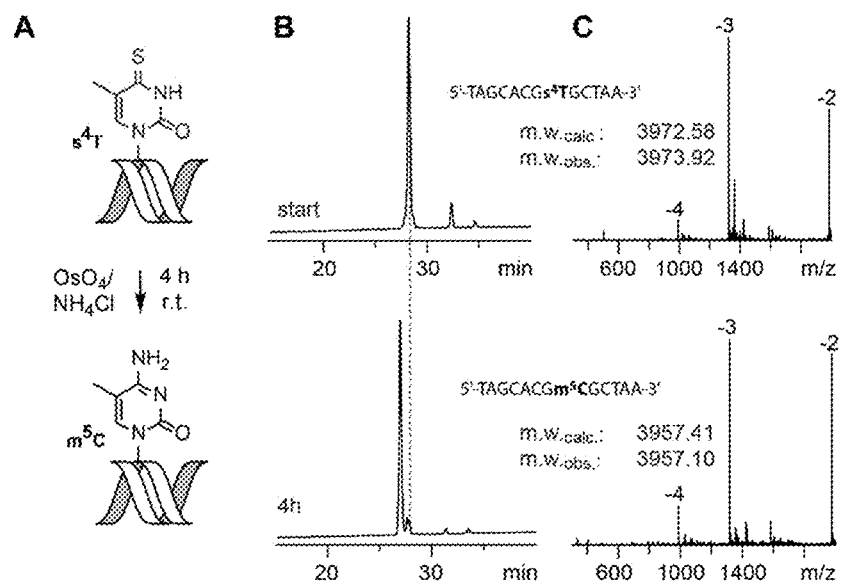
FIG. 24: Transformation of 4sT-to-m$^5$C in the 13 nt reverse complementary DNA oligo CR042. (A) Chemical structures of the reaction; conditions: 0.45 mM OsO$_4$, 180 mM NH$_4$Cl (pH=8.88), 4 h, r.t.; (B) anion-exchange chromatograms of the oligonucleotide before treatment and after 4 h; (C) corresponding LC-ESI mass spectra (5'-TAG-CACG4sT GCTAA-3' (SEQ ID NO: 23); 5'-TAG-CACGm5CGCTAA-3' (SEQ ID NO: 24)).

Beyond the incorporation of 4-thiouridine in RNA, other thiolated nucleotides may be used for metabolic labeling of nucleic acids. Another thiolated nucleotide which may be used for metabolic labeling of nucleic acids is 4-thiothymidine (4sT). Nucleic acids in which 4-thiothymidine has been incorporated can be treated as above. $OsO_4$ treatment will transform the 4sT to 2'-deoxy-5-methylcytidine ($m^5C$ (FIG. 24A). As proof of concept, a 13 bp oligo having an internal 4sT (SEQ ID NO: 23) was treated with $OsO_4$ and $NH_4Cl$. This reaction transformed the 4sT to $m^5C$, thereby completing the conversion (SEQ ID NO: 24). This conversion was confirmed by anion-exchange chromatography and LC-ESI, as shown in FIG. 24. Incorporation and conversion of 4-thiothymidine and the subsequent detection of $m^5C$ indicates that the methods presented herein can be used to detect other thiolated nucleotides in nucleic acids, specifically in DNA.

Example 5

Figure 25:
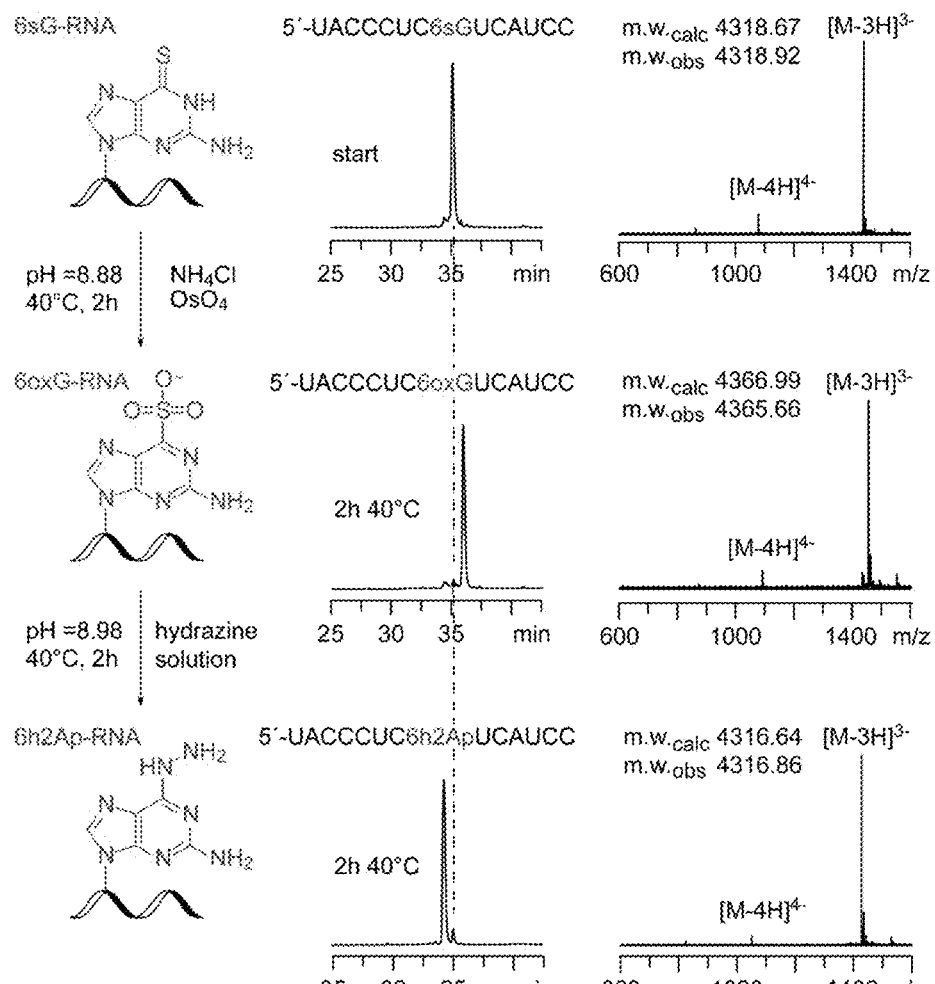
FIG. 25: Transformation of 6sG to 6-hydrazino-2-aminopurine in RNA and DNA. (Left) Shown are the chemical structures and reaction conditions for the conversion of 6sG-to-6h2AP. (Center) Ion exchange traces of the indicated oligonucleotides. (Right) Mass spectra of the indicated oligonucleotides. (UACCCUC6sGUCAUCC=SEQ ID NO: 28; UACCCUC6oxGUCAUCC=SEQ ID NO: 29; UACCCUC6h2ApUCAUCC=SEQ ID NO: 30).

Conversion of 6-thioguanosine (6sG) to 6'-hydrazino-2-aminopurine-ribonucleoside (6h2AP) in RNA Additional metabolic labeling techniques may find use in sequencing and assessing RNA dynamics. The availability of additional modified nucleosides which can be chemically converted into other nucleosides will enable double labeling strategies to more accurately distinguish between synthesis and decay rates in RNA. Another strategy for metabolic labeling includes pulse-labeling of cells with 6sG. 6sG can be oxidized by treatment with $OsO_4$/$NH_4Cl$ as above, thereby generating 6oxG (FIG. 25). This 6oxG product may then be treated with hydrazine to convert 6oxG to 6'-hydrazino-2-aminopurine (6h2AP) (FIG. 25).

In order to test these reactions on synthesized RNA, 1 nmol of RNA containing 6sG was mixed with $NH_4Cl$ buffer (2 µL, 2M, pH=8.88), and $OsO_4$ solution (10 µL, 1 mM) was added to give final concentrations of 0.45 mM ($OsO_4$ and 180 mM $NH_4Cl$ in a volume of 22 µL. The mixture was incubated for 2 hours at 40° C., and then transferred to Vivaspin® 500 (MWCO 3000, PES) centrifugal concentrator columns (Sartorius, Gottingen, Germany) and washed twice with 400 µL of water. Following washing, the RNA was lyophilized and dissolved in water. This product, as well as its ion exchange trace and mass spectra, can be seen in the middle of FIG. 25. Hydrazine buffer (5 µL, 1.5 M, pH=8.98) was added to the RNA to give a final concentration of 375 mM hydrazine in a total volume of 20 µL. The solution was again incubated for 2 hours at 40° C. and purified. The product, as well as a representative ion exchange trace and mass spectra, can be seen at the bottom of FIG. 25.

Pulse labeling with two different thiolated nucleotides may be used to further understand the dynamics of nucleic acid synthesis and decay. One method includes pulse labeling with 6sG for 30-60 minutes. Following labeling, excess 6sG can be washed and 4sU may be added during the chase period. After the chase period, the RNA is extracted and subjected to $OsO_4$/$NH_4Cl$ treatment. This treatment converts 4sU to C, as above, and oxidizes 6sG, producing 6oxG (FIG. 25). The converted RNA harboring the 6oxG is then treated with hydrazine, as in FIG. 25, to convert the 6oxG groups to 6'-hydrazino-2-aminopurine (6h2AP) which will be read as adenosine during sequencing.

Sequencing of these converted RNAs will reveal four distinct groups of RNAs. The first group is the unlabeled RNA, which will have no conversions, characterizing the pool of preexisting RNA. The second group is RNA that was labeled by 6sG only, and thus resulted in G-to-A mutations, indicating that this RNA was synthesized during the pulse labeling period. The third group of RNAs are those that are synthesized during the chase labeling period and are characterized by both 6sG and 4sU labeling and will thus have G-to-A and U-to-C mutations. The fourth group is RNA which has been labeled by 4sU only, and thus comprises U-to-C mutations, and corresponds to RNA which was synthesized late during the chase period, when the 6sG from the prior labeling step has been completely incorporated. The group that contains only the G-to-A mutations may be used then to accurately determine RNA decay rates, since it can be unequivocally separated from RNA that is synthesized during the chase period.

The data provided herein illustrate methods and provide compositions for the metabolic labeling of nucleic acids and subsequent detection of these labeled nucleic acids. These methods are particularly advantageous as they allow for direct sequencing of nucleic acids, rather than requiring a separation or enrichment steps, thus saving time and preventing human error. These methods also allow for greatly improved determination of in vivo rates of synthesis and decay of nucleic acids.

Example 6

Comparison Between TUC-Seq and TimeLapse-Seq

The following studies were performed in order to evaluate the performances of TUC-Seq in comparison with Time-Lapse-Seq. Both methods are based on similar chemistry (oxidative-nucleophilic-aromatic substitution of 4-thiouridine), however, the reagents and the end products of TUC-Seq and TimeLapse-Seq are different.

Specifically, in TUC-Seq the conversion of 4-thiouridine (4sU) is achieved by oxidation by $OsO_4$ in the presence of a nucleophilic agent (e.g. $NH_3$ added as $NH_4Cl$). This treatment results in the generation of bona fide cytidine (C). By contrast, The TimeLapse-Seq method converts 4sU into cytidine analogues by treating 4sU-labeled RNA with $NaIO4$, followed by a treatment with a nucleophilic agent (e.g. TFEA) and sodium acetate resulting in the generation of tri-fluorethylcytidine.

In the studies described below two different short RNA oligos (EN-RNA-63; 5'-G(4sU)CAUA-3' and EN-RNA-64; 5'-GU(4sU)ACU-3'), each containing a single 4sU modification, were treated according to the TUC-Seq method and according to the TimeLapse-Seq method. The products of the two reactions were analyzed with anion exchange HPLC (AE-HPLC; using Dionex DNAPac PA-100 column (4 mm×250 mm) at 80° C.; injection: 200 pmol of crude RNA in 100 µL of $H_2O$; flow rate: 1 mL/min;; eluent A: 25 mM Tris·HCl (pH 8.0), 6 M urea; eluent B: Tris·HCl (25 mM) (pH 8.0), $NaClO4$ (0.5 M), urea (6 M); gradient: 0-60% B in A within 45 min and UV detection at 260 and 320 nm.) and ESI-MS and results were compared.

FIG. 26A and B clearly show that in both RNA oligos 4sU is efficiently converted into C after $OsO_4$/$NH_4Cl$ treatment. HPLC data show that a single clearly shifted peak is present in the chromatogram after $OsO_4$/$NH_4Cl$, indicating a complete conversion of 4sU to C. A decrease in the AE-HPLC retention time is observed when 4sU is converted into C. The ESI-MS data unequivocally confirm the expected molecular weight (of 1835.1 mass units) of the transformed oligo.

Figure 26C:
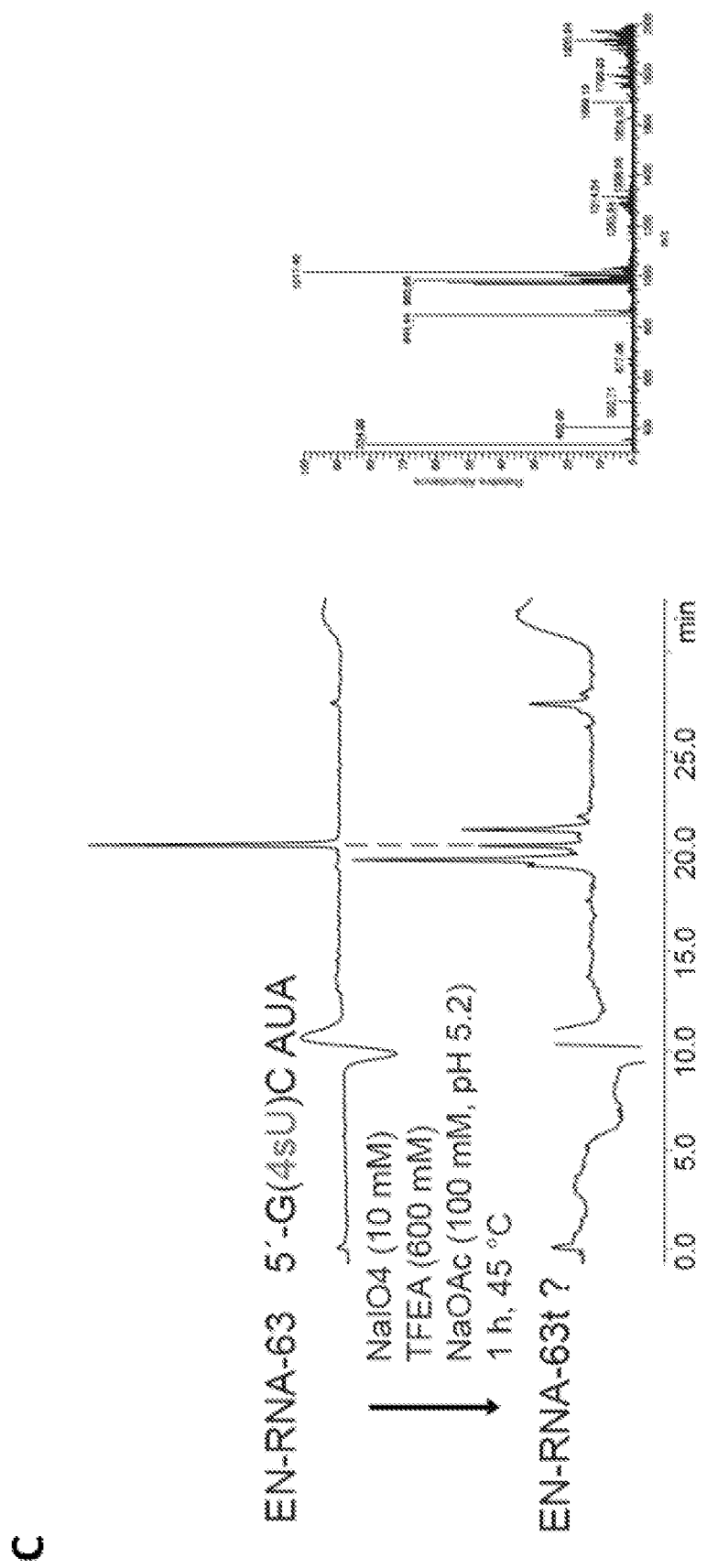
Figure 26D:

FIG. 26C and D show, in contrast, that in both RNA oligos 4sUs are only partially converted into other nucleotides after $NaIO_4$/TFEA/Na-acetate (NaOAc) treatment according to the TimeLapse protocol (Schofield et al., 2018, incorporated herein by reference). As reported in Schofield et al., 2018 HPLC data confirmed that 4sU is not completely converted during TimeLapse-Seq treatment since a peak corresponding to the 4sU-containing oligo is still visible in both, FIG. 26C and D, after the treatment. Moreover, at least 3 additional distinct peaks (corresponding to three distinct side products with unique elution times) are visible in the chromatogram. The presence of multiple reaction products is also visible in the ESI-MS data.

Example 7

$OsO_4$ Meditated Conversion of 4sU into C

Figure 27:
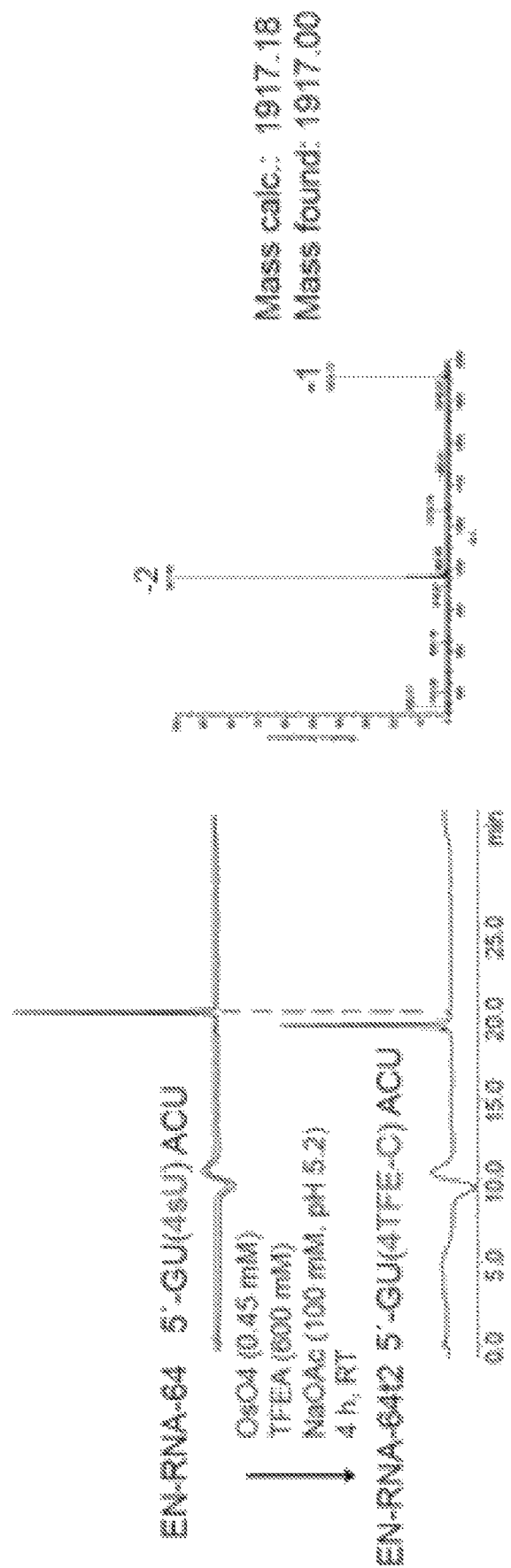
FIG. 27: HPLC analysis shows that when NH$_4$Cl is substituted with TFEA (600 mM) in TUC-Seq, the reaction results in a complete conversion of 4sU into tri-fluorethyl-cytidine.

The aim of the studies in this example was to define which step of the oxidative-nucleophilic-aromatic substitution reaction is most important for complete conversion of 4sU into C (analogues). Here, we changed the nucleophile molecule used in TUC-Seq, leaving the oxidant agent and the reaction conditions unchanged. FIG. 27 shows that when $NH_4Cl$ is substituted with TFEA (600 mM) in TUC-Seq, the reaction results in a complete conversion of 4sU into tri-fluorethylcytidine. The complete conversion of 4sU into the C analogues by $OsO_4$ with TFEA as the nucleophile was quite surprising. These data indicate that $NH_4Cl$ could be substituted with other nucleophiles in TUC-Seq without affecting the performances of the method. $OsO_4$ is a key oxidizing agent in the conversion of 4sU into C (FIG. 27).

Example 8

Analysis of RNA Integrity after TUC-Seq and TimeLapse-Seq Reactions

Figure 28:
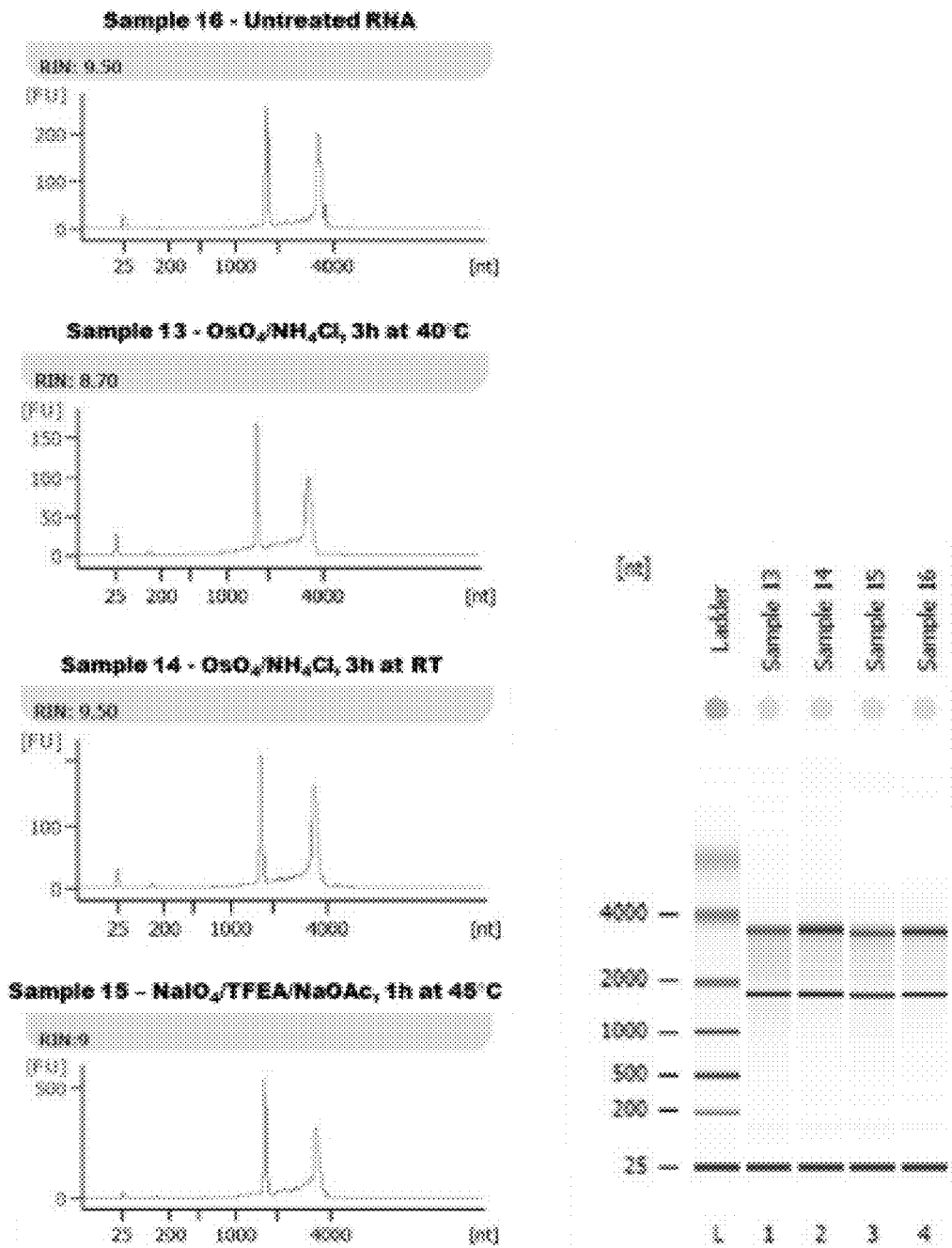
FIG. 28: An HPLC analysis showing that RNA quality is not affected by TUC-Seq and by TimeLapse-Seq treatments.

This study was performed to examine if the TUC-Seq or TimeLapse-seq methods alter the RNA quality. Total RNA was isolated from HEK293 cells and treated either with TUC-seq conditions or with TimeLapse-Seq conditions. RNA quality was analyzed by Agilent Bioanalyzer. Results shown in FIG. 28 demonstrate that that RNA quality is not affected by TUC-Seq and by TimeLapse-Seq treatments.

Example 9

TUC-Seq: Model for Single-Cell Sequencing

This study tested if TUC-Seq methodology is applicable to single-cell RNA sequencing. In order to avoid losing RNA from a single cell and streamlining the workflow it is important to couple cell lysis, reverse transcription and library amplification omitting any purification step during this process.

In the first experiment (FIG. 29) results showed that TUC-Seq conditions (the presence of $OsO_4$ and a relatively high concentration of $NH_4Cl$) are compatible with the activities of reverse transcriptase and Taq polymerase. 1.5 µg total isolated RNA was dissolved in 10 µl cell Lysis Buffer (containing 0.2% Triton-X-100, 0.455 mM $OsO_4$, and 182 mM $NH_4Cl$) and cDNA synthesis was performed immediately using Promega GoScript Kit according to manufacturer's instructions. 2 µl of cDNA was used in PCR to amplify GAPDH transcript.

Figure 29:
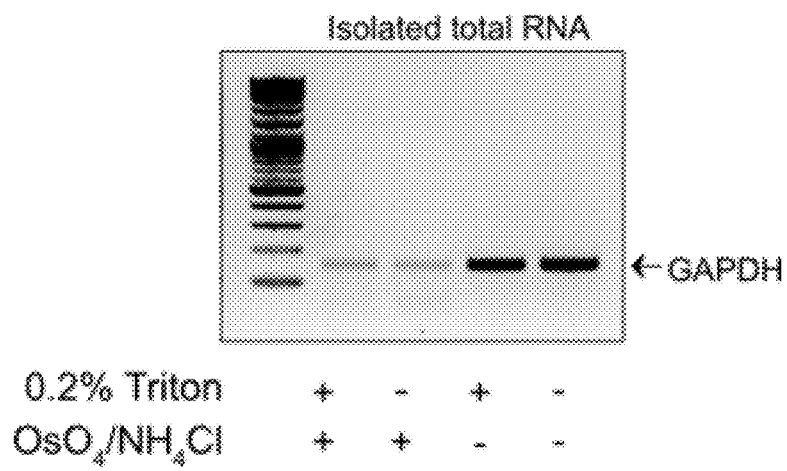
FIG. 29: An agarose gel analysis showing that TUC-Seq treatment is compatible with cell lysis or RT-PCR.

FIG. 29 shows: lane 1: 2-log DNA ladder (NEB); lane 2: cDNA synthesis and PCR in the presence of Triton and $OsO_4$/$NH_4Cl$; lane 3: Reaction in the presence of $OsO_4$/$NH_4Cl$ but absence of Triton; lane 4: Reaction in the presence of Triton but absence of $OsO_4$/$NH_4Cl$; and lane 5: control reaction without Triton and $OsO_4$/$NH_4Cl$. Thus, FIG. 29 lanes 2 and 3 show that the presence of $OsO_4$/$NH_4Cl$ in the cDNA synthesis reaction reduces the efficiency but does not prevent the reaction indicating that the TUC-seq treatment can be combined with conditions of single-cell sequencing library preparation.

Figure 30:
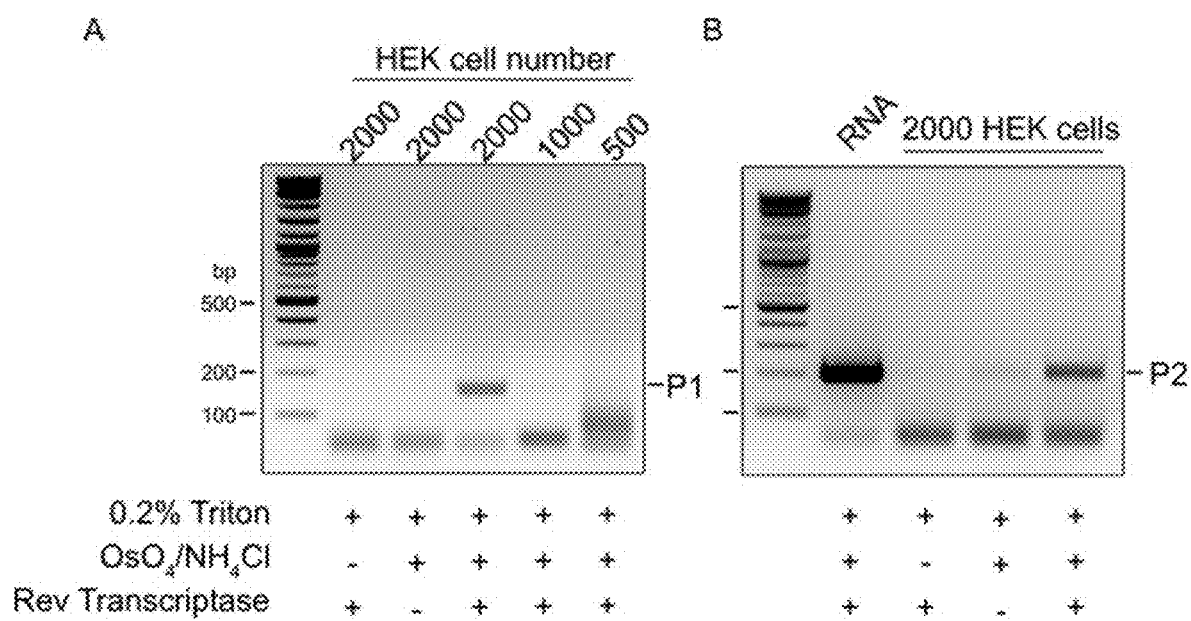
FIG. 30: An agarose gel analysis showing that TUC-Seq treatment is compatible with cell lysis or RT-PCR.

A second experiment was also performed to support the compatibility of single-cell sequencing with TUC-Seq (FIG. 30). In this experiment, a model was used in which different numbers of HEK293 cells (i.e. 2000, 1000, 500) were collected and resuspended in 10 µl Lysis Buffer (containing 0.2% Triton-X-100). Cells were incubated at 40° C. for 3 h in the presence or absence of 0.455 mM $OsO_4$ and 182 mM $NH_4Cl$ in order to allow 4sU to C conversion, then centrifuged at 700×g for 5 min at RT. Supernatant was then transferred into a PCR tube and cDNA synthesis conditions were applied in the presence or absence of reverse transcriptase (Promega) using Promega GoScript Kit according to manufacturer's instructions. 2 µl of cDNA was used in PCR to amplify two different fragments (P1, P2) of the GAPDH transcript. The primers used to amplify these regions allow to amplify cDNA, but not genomic DNA.

FIG. 30 shows a reproduction of an agarose gel showing the results. In FIG. 30A, amplification of the GAPDH P1 fragment is shown. Lanes are as follows: lane 1: 2-log DNA ladder (NEB); lane 2: Control reaction in which $OsO_4$/$NH_4Cl$ treatment was omitted, but reverse transcription was performed; lane 3: Reaction in which $OsO_4$/$NH_4Cl$ treatment was performed, but reverse transcriptase enzyme was not added during the reverse transcription step; lane 4: Reaction in which $OsO_4$/$NH_4Cl$ treatment and reverse transcription were performed with 2000 cells; lanes 5 and 6: Reactions in which $OsO_4$/$NH_4Cl$ treatment and reverse transcription were performed with 1000 and 500 cells respectively. FIG. 30B shows amplification of the GAPDH fragment P2. Lanes were: lane 1: 2-log DNA ladder (NEB); lane 2: control reaction in with HEK293 $OsO_4$/$NH_4Cl$-treated RNA was used for cDNA synthesis and PCR; lane 3: PCR reaction from lysate of 2000 HEK293 cells untreated with $OsO_4$/$NH_4Cl$ and reverse transcribed; lane 4: PCR reaction from lysate of 2000 HEK293 cells treated with $OsO_4$/$NH_4Cl$ but not reverse transcribed; lane 5: PCR reaction from lysate of 2000 HEK293 cells treated with $OsO_4$/$NH_4Cl$ and reverse transcribed.

FIG. 30A lane 4 and FIG. 30B lane 5 indicate that reverse transcription and PCR steps work efficiently even in the presence of $OsO_4$ and $NH_4Cl$ (TUC-Seq conditions). A clear band of the expected size (152 bp for P1 and 197 bp for P2) is visible for the GAPDH amplicon in these lanes. Unexpectedly, FIG. 30A lane 2, and FIG. 30B lane 3 show no GAPDH amplification, suggesting that the cells are not lysed efficiently in 0.2% Triton X-100. The lysis is however achieved after $OsO_4$/$NH_4Cl$ treatment (FIG. 30A lane 4 and FIG. 30B lane 5), suggesting that TUC-Seq conditions promote cell lysis. Decreasing the cell input to 1000 or 500 weakens or eliminates the PCR signal (FIG. 30A, lanes 5 and 6) indicating that the amount of input is rate limiting in this experimental protocol. In conclusion, these data indicate not only that reverse transcription and PCR reaction are compatible with the presence of $OsO_4$ and $NH_4Cl$ in the reaction, but also that $OsO_4$/$NH_4Cl$ treatment increases cell lysis, which is a key aspect in single-cell sequencing. Thus, the results in FIG. 30 strongly support the compatibility of single-cell sequencing library preparation with TUC-Seq.

Example 10

Compatibility of $OsO_4$/$NH_4Cl$ Treatment with Guanidinium Thiocyanate-Based RNA Isolation This study was carried out in order to evaluate the efficiency of $OsO_4$/$NH_4Cl$ treatment in converting 4sU into C during the RNA isolation from biological material using guanidinium thiocyanate (one of the main components of TRIzol, TRI Reagent®, and analogue reagents commonly used for RNA isolation). $OsO_4$/$NH_4Cl$ treatment was performed on 4sU-labeled EN-RNA-64 in standard conditions, and in the presence of guanidinium thiocyanate at a concentration of 0.2 mM and 0.9 mM (FIG. 31).

Figure 31:
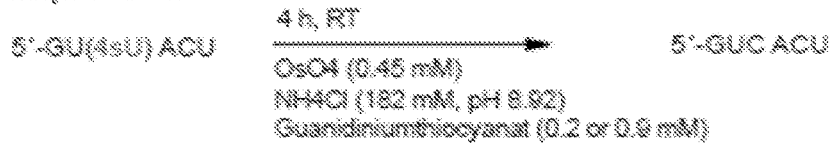
FIG. 31: An HPLC analysis showing that TUC-Seq treatment is effective even in the presence of chaotropic lysis reagents.
Figure 31:
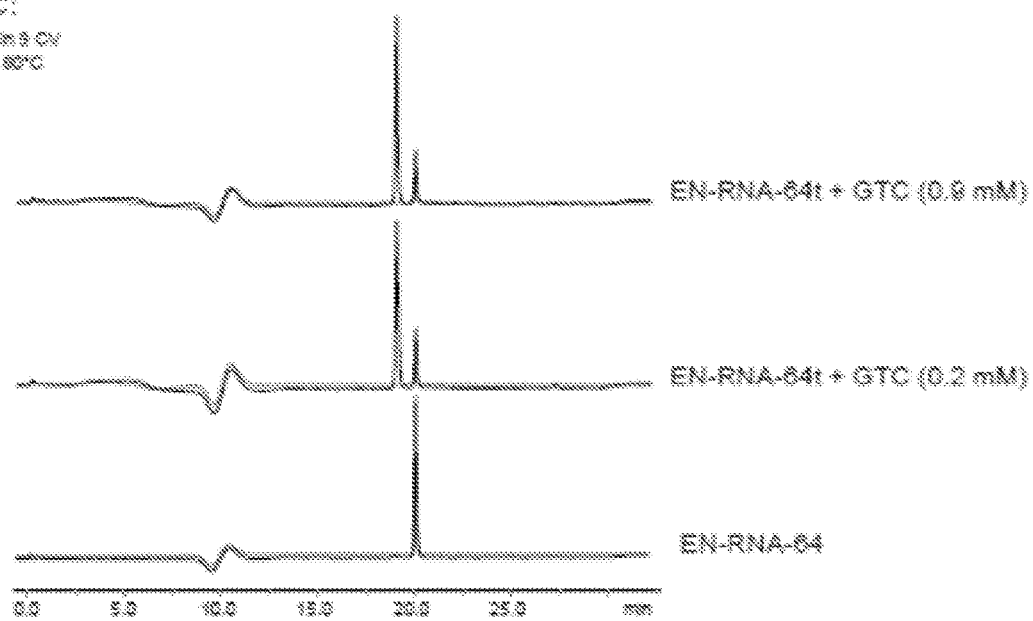
Figure 31:
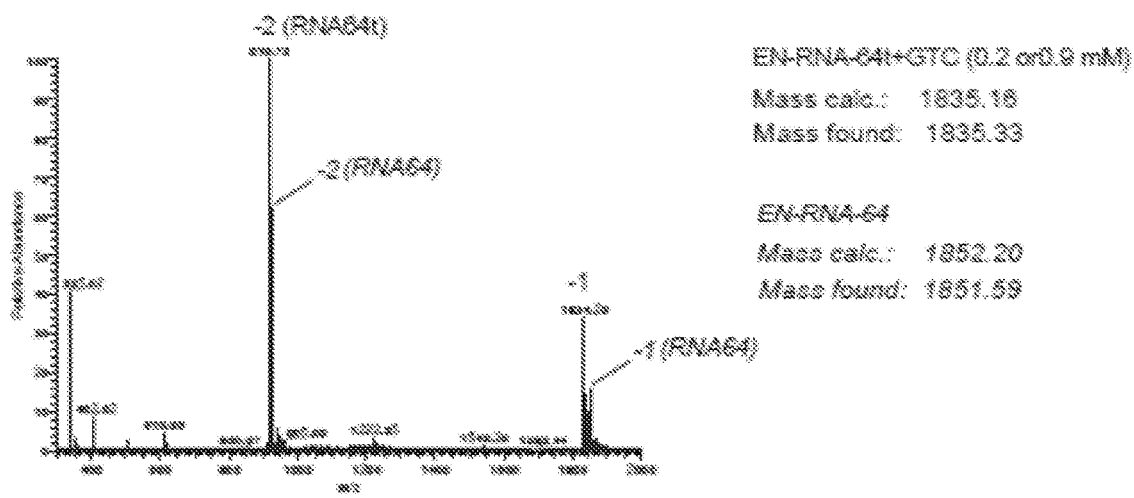

Studies shown in FIG. 31 (both AE-HPLC and ESI-MS data) indicate that $OsO_4$/$NH_4Cl$ treatment is still able to convert 4sU into C in presence of guanidinium thiocyanate, however the efficiency of the reaction is decreased when guanidinium thiocyanate is added to the reaction. The TUC-Seq reaction efficiency is not further decreased when the concentration of guanidinium thiocyanate added to the reaction is increased from 0.2 to 0.9 mM, suggesting that 4sU to C conversion is still possible at higher guanidinium thiocyanate concentration.

All of the devices and methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adams et al., *Tetrahedron Letters*, 35: 765-768, 1994.
Balagopal et al., *Biochim. Biophys. Acta Gene Regul. Mech.*, 1819: 593-603, 2012.
Barrass et al., *Genome Biol.*, 16: 282, 2015.
Burger et al., *RNA Biol.*, 10: 1623-1630, 2013.
Burow et al., *Neural Dev.*, 10: 11, 2015.
Burton, *Biochem. J.*, 104:686-694, 1967.
Ĉavužić and Liu, *Biomolecules*, 7: 27, 2017.
Cleary et al., *Nat. Biotechnol.*, 23: 232-237, 2005.
Dodt et al., *Biology*, 1: 895-905, 2012.
Dolken et al., *RNA*, 14: 1959-1972, 2008.
Duffy et al., *Mol. Cell*, 59: 858-866, 2015.
Fuchs et al., *Genome biol.*, 15: R69, 2014.
Glatter et al., *Molecular Systems Biology*, 5: 237, 2009.
Koboldt et al., *Genome Research*, 22: 568-576, 2012.
Kan et al., *RNA*, 23 :473-482, 2017.
Langmead et al., *Genome Biology*, 10: R25, 2009.
Lindenbaum, *Figshare*, 2015.
Machnicka et al., *RNA Biol.*, 11: 1619-1629, 2014.
Martin and Coller, *Mol. Cell*, 59: 716-717, 2015.
McGregor et al., *Nucleic Acids Research*, 24: 3173-3180, 1996.
Melvin et al., *Eur. J Biochem.*, 92: 373-379, 1978.
Miller et al., *Nat. Methods*, 6 439-441.
Neymotin et al., *RNA*, 20:1645-1652, 2014.
Russo et al., *Methods*, 120: 39-48, 2017.
Penelova et al., *FEBS J.*, 272: 5217-5229, 2005.
Pérez-Ortín et al., *J. Mol. Biol.* 425: 3750-3775, 2013.
Serebryany and Beigelman, *Tetrahedron Letters*, 43: 1983-1985, 2002.
Tani and Akimitsu, *RNA Biol.*, 9: 1233-1238, 2012.
Wang et al., *Cell*, 161: 1388-1399, 2015.
Windhager et al., *Genome Res.*, 22: 2031-2042, 2012.
Zeiner et al., *Methods Mol. Biol.*, 419:135-146, 2008.
Zhang et al., *Cell Rep.*, 15: 611-624, 2016.

What is claimed is:

1. A method for determining the presence of a thiolated nucleotide in a nucleic acid-containing sample comprising:
   (a) providing a nucleic acid-containing sample;
   (b) treating the nucleic acid-containing sample with osmium tetroxide and ammonium chloride to convert the thiolated nucleotide; and
   (c) detecting the presence of a converted nucleotide in the nucleic acid-containing sample.

2. The method of claim 1, wherein the nucleic acid-containing sample comprises RNA.

3. The method of claim 2, wherein the thiolated nucleotide is 4-thiouridine.

4. The method of claim 3, wherein 4-thiouridine is converted to cytidine.

5. The method of claim 2, wherein the thiolated nucleotide is 6-thioguanosine.

6. The method of claim 5, wherein the 6-thioguanosine is converted to 6-hydrazino-2aminopurine-ribonuceloside (6h2Ap).

7. The method of claim 2, wherein the RNA is total RNA.

8. The method of claim 2, wherein the RNA is tRNA, rRNA, siRNA, shRNA or miRNA.

9. The method of claim 2, wherein the RNA is mRNA.

10. The method of claim 1, wherein the nucleic acid-containing sample comprises DNA and RNA.

11. The method of claim 1, wherein the nucleic acid-containing sample is synthetic.

12. The method of claim 1, wherein the nucleic acid-containing sample is isolated from an organism.

13. The method of claim 12, wherein the nucleic acid-containing sample is isolated from a eukaryotic organism.

14. The method of claim 13, wherein the eukaryotic organism is mammalian.

15. The method of claim 14 wherein the organism is human.

16. A method for detecting the presence of 4-thiouridine in a bacterial tRNA comprising:
   (a) isolating total RNA from the bacteria;
   (b) treating at least a portion of the isolated total RNA with osmium tetroxide and ammonium chloride to convert 4-thiouridine to cytidine;
   (c) amplifying the tRNA of interest; and
   (d) detecting the presence or absence of cytosine at the position of a 4-thiouridine in the amplified tRNA of interest.

17. The method of claim 16, wherein the bacteria are metabolically labeled prior to step (a).

18. The method of claim 16, wherein the method does not comprise biotinylating the isolated total RNA.

19. A method for metabolic labelling of a nucleic acid-containing sample in a cell culture comprising:
   (a) pulse-labeling a cell culture with a thiolated nucleotide;
   (b) isolating a nucleic acid-containing sample from the cell culture;
   (c) treating the nucleic acid-containing sample with osmium tetroxide and ammonium chloride to convert the thiolated nucleotide incorporated into the nucleic acid-containing sample into a converted nucleotide;
   (d) detecting the converted nucleic acid-containing sample; and
   (e) determining the quantity of converted nucleotides in the converted nucleic acid-containing sample.

20. The method of claim 19, wherein detecting is by sequencing.

* * * * *